US012460191B2

(12) United States Patent
Frisch et al.

(10) Patent No.: US 12,460,191 B2
(45) Date of Patent: Nov. 4, 2025

(54) CAS9 VARIANTS AND METHODS OF USE

(71) Applicant: DANISCO US INC., Palo Alto, CA (US)

(72) Inventors: Ryan L Frisch, Newark, DE (US); Hongxian He, Wilmington, DE (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 18/456,663

(22) Filed: Aug. 28, 2023

(65) Prior Publication Data

US 2024/0018497 A1 Jan. 18, 2024

Related U.S. Application Data

(62) Division of application No. 16/772,910, filed as application No. PCT/US2018/064955 on Dec. 11, 2018, now Pat. No. 11,781,125.

(60) Provisional application No. 62/599,176, filed on Dec. 15, 2017.

(51) Int. Cl.

| | |
|---|---|
| ***C12N 9/22*** | (2006.01) |
| ***C12N 15/113*** | (2010.01) |
| ***C12N 15/70*** | (2006.01) |
| ***C12N 15/75*** | (2006.01) |
| ***C12N 15/80*** | (2006.01) |

(52) U.S. Cl.

CPC .............. *C12N 9/22* (2013.01); *C12N 15/113* (2013.01); *C12N 15/70* (2013.01); *C12N 15/75* (2013.01); *C12N 15/80* (2013.01); *C12N 2310/20* (2017.05); *C12N 2800/101* (2013.01); *C12N 2800/80* (2013.01)

(58) Field of Classification Search

CPC ........ C12N 9/22; C12N 15/113; C12N 15/70; C12N 15/75; C12N 15/80; C12N 2310/20; C12N 2800/101; C12N 2800/80; C12N 15/102; C12N 15/8213; C12Y 301/00

See application file for complete search history.

(56) References Cited

FOREIGN PATENT DOCUMENTS

| | | | |
|---|---|---|---|
| WO | 20170154714 | A1 | 9/2017 |
| WO | 2018183808 | A1 | 10/2018 |

OTHER PUBLICATIONS

Whisstock et al. Quaterly Reviews of Biophysics, 2003, "Prediction of protein function from protein sequence and structure", 36(3): 307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

Jeffrey M. Spencer et al., Deep mutational scanning of *S. pyogenes* Cas9 reveals important functional domains, Scientific Reports, Dec. 1, 2017, pp. 1-13, vol. 7, No. 1.

Hiroshi Nishimasu et al., Crystal Structure of Cas9 in Complex with Guide RNA and Target DNA, Cell, Feb. 1, 2014, pp. 935-949, vol. 156, No. 5.

Martin Jinek et al., A Programmable Dual-RNA-Guided DNA Endonuclease in Adaptive Bacterial Immunity, Science, Aug. 17, 2012, pp. 816-821, vol. 337, No. 6096.

Rimantas Sapranauskas et al., The *Streptococcus thermophilus* CRISPR/Cas system provides immunity in *Escherichia coli,* Nucleic Acids Research, Aug. 3, 2011, pp. 9275-9282, vol. 39, No. 21.

International Search Report—PCT/US2018/064955—mailed Feb. 27, 2019.

* cited by examiner

*Primary Examiner* — Iqbal H Chowdhury

(57) ABSTRACT

Compositions and methods are provided for variant Cas systems and elements comprising such systems, including, but not limiting to, Cas endonuclease variants, guide polynucleotide/Cas endonuclease complexes comprising Cas endonuclease variants, as well as guide polynucleotides and guide RNA elements that can interact with Cas endonuclease variants. Compositions and methods are provided for genome modification of a target sequence in the genome of a cell. The methods and compositions employ a guide polynucleotide/Cas endonuclease system comprising a Cas9 endonuclease variant to provide an effective system for modifying or altering target sequences within the genome of a cell or organism.

9 Claims, 3 Drawing Sheets

Specification includes a Sequence Listing.

SEQUENCE LISTING

```
Sequence total quantity: 157
SEQ ID NO: 1            moltype = AA  length = 1368
FEATURE                 Location/Qualifiers
source                  1..1368
                        mol_type = protein
                        organism = Streptococcus pyogenes
SEQUENCE: 1
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 2            moltype = DNA  length = 5056
FEATURE                 Location/Qualifiers
misc_feature            1..5056
                        note = Bacillus codon optimized Cas9
source                  1..5056
                        mol_type = other DNA
                        organism = synthetic construct
SEQUENCE: 2
aattcctcca ttttcttctg ctatcaaaat aacagactcg tgattttcca aacgagcttt  60
caaaaaagcc tctgcccctt gcaaatcgga tgcctgtcta taaaattccc gatattggtt  120
aaacagcggc gcaatggcgg ccgcatctga tgtctttgct tggcgaatgt tcatcttatt  180
tcttcctccc tctcaataat tttttcattc tatccctttt ctgtaaagtt tatttttcag  240
aatactttta tcatcatgct ttgaaaaaat atcacgataa tatccattgt tctcacggaa  300
gcacacgcag gtcatttgaa cgaatttttt cgacaggaat ttgccgggac tcaggagcat  360
ttaacctaaa aaagcatgac atttcagcat aatgaacatt tactcatgtc tattttcgtt  420
cttttctgta tgaaaatagt tatttcgagt ctctacggaa atagcgagag atgatatacc  480
taaatagaga taaaatcatc tcaaaaaaat gggtctacta aaatattatt ccatctatta  540
caataaattc acagaatagt cttttaagta agtctactct gaattttttt aaaaggagag  600
ggtaactagt ggccccaaaa aagaaacgca aggttatgga taaaaaatac agcattggtc  660
tggatatcgg aaccaacagc gttgggtggg cagtaataac agatgaatac aaagtgccgt  720
caaaaaaatt taaggttctg gggaatacag atcgccacag cataaaaaag aatctgattg  780
gggcattgct gtttgattcg ggtgagacag ctgaggccac gcgtctgaaa cgtacagcaa  840
gaagacgtta cacacgtcgt aaaaatcgta tttgctactt acaggaaatt ttttctaacg  900
aaatggccaa ggtagatgat agtttcttcc atcgtctcga agaatctttt ctggttgagg  960
aagataaaaa acacgaacgt caccctatct ttggcaatat cgtggatgaa gtggcctatc  1020
atgaaaaata ccctacgatt tatcatcttc gcaagaagtt ggttgatagt acggacaaag  1080
cggatctgcg tttaatctat cttgcgttag cgcacatgat caaatttcgt ggtcatttct  1140
taattgaagg tgatctgaat cctgataact ctgatgtgga caaattgttt atacaattag  1200
tgcaaaccta taatcagctg ttcgaggaaa accccattaa tgcctctgga gttgatgcca  1260
```

-continued

```
aagcgatttt aagcgcgaga ctttctaagt cccggcgtct ggagaatctg atcgcccagt  1320
taccagggga aaagaaaaat ggtctgtttg gtaatctgat tgccctcagt ctggggctta  1380
ccccgaactt caaatccaat tttgacctgg ctgaggacgc aaagctgcag ctgagcaaag  1440
atacttatga tgatgacctc gacaatctgc tcgcccagat tggtgaccaa tatgcggatc  1500
tgtttctggc agcgaagaat ctttcggatg ctatcttgct gtcggatatt ctgcgtgtta  1560
ataccgaaat caccaaagcg cctctgtctg caagtatgat caagagatac gacgagcacc  1620
accaggacct gactcttctt aaggcactgg tacgccaaca gcttccggag aaatacaaag  1680
aaatattctt cgaccagtcc aagaatggtt acgcgggcta catcgatggt ggtgcatcac  1740
aggaagagtt ctataaattt attaaaccaa tccttgagaa aatggatggc acggaagagt  1800
tacttgttaa acttaaccgc gaagacttgc ttagaaagca acgtacattc gacaacggct  1860
ccatcccaca ccagattcat ttaggtgaac ttcacgccat cttgcgcaga caagaagatt  1920
tctatccctt cttaaaagac aatcgggaga aaatcgagaa gatcctgacg ttccgcattc  1980
cctattatgt cggtcccctg gcacgtggta attctcggtt tgcctggatg acgcgcaaaa  2040
gtgaggaaac catcacccct tggaactttg aagaagtcgt ggataaaggt gctagcgcgc  2100
agtcttttat agaaagaatg acgaacttcg ataaaaactt gcccaacgaa aaagtcctgc  2160
ccaagcactc tcttttatat gagtacttta ctgtgtacaa cgaactgact aaagtgaaat  2220
acgttacgga aggtatgcgc aaacctgcct ttcttagtgg cgagcagaaa aaagcaattg  2280
tcgatcttct ctttaaaacg aatcgcaagg taactgtaaa acagctgaag gaagattatt  2340
tcaaaaagat cgaatgcttt gattctgtcg agatctcggg tgtcgaagat cgtttcaacg  2400
cttccttagg gacctatcat gatttgctga agataataaa agacaaagac tttctcgaca  2460
atgaagaaaa tgaagatatt ctggaggata ttgttttgac cttgacctta ttcgaagata  2520
gagagatgat cgaggagcgc ttaaaaacct atgcccacct gtttgatgac aaagtcatga  2580
agcaattaaa gcgccgcaga tatacggggt ggggccgctt gagccgcaag ttgattaacg  2640
gtattagaga caagcagagc ggaaaaacta tcctggattt cctcaaatct gacggatttg  2700
cgaaccgcaa ttttatgcag cttatacatg atgattcgct tacattcaaa gaggatattc  2760
agaaggctca ggtgtctggg caaggtgatt cactccacga acatatagca aatttggccg  2820
gctctcctgc gattaagaag gggatcctgc aaacagttaa agttgtggat gaacttgtaa  2880
aagtaatggg ccgccacaag ccggagaata tcgtgataga aatggcgcgc gagaatcaaa  2940
cgacacaaaa aggtcaaaag aactcaagag agagaatgaa gcgcattgag gaggggataa  3000
aggaacttgg atctcaaatt ctgaaagaac atccagttga aaacactcag ctgcaaaatg  3060
aaaaattgta cctgtactac ctgcagaatg gaagagacat gtacgtggat caggaattgg  3120
atatcaatag actctcggac tatgacgtag atcacattgt ccctcagagc ttcctcaagg  3180
atgattctat agataataaa gtacttacga gatcggacaa aaatcgcggt aaatcggata  3240
acgtcccatc ggaggaagtc gttaaaaaga tgaaaaacta ttggcgtcaa ctgctgaacg  3300
ccaagctgat cacacagcgt aagtttgata atctgactaa agccgaacgc ggtggtctta  3360
gtgaactcga taaagcagga tttataaaac ggcagttagt agaaacgcgc caaattacga  3420
aacacgtggc tcagatcctc gattctagaa tgaatacaaa gtacgatgaa aacgataaac  3480
tgatccgtga agtaaaagtc attaccttaa aatctaaact tgtgtccgat ttccgcaaag  3540
attttcagtt ttacaaggtc cgggaaatca ataactatca ccatgcacat gatgcatatt  3600
taaatgcggt tgtaggcacg gcccttatta agaaataccc taaactcgaa agtgagtttg  3660
tttatgggga ttataaagtg tatgacgttc gcaaaatgat cgcgaaatca gaacaggaaa  3720
tcggtaaggc taccgctaaa tacttttttt attccaacat tatgaatttt tttaagaccg  3780
aaataactct cgcgaatggt gaaatccgta aacggcctct tatagaaacc aatggtgaaa  3840
cgggagaaat cgtttgggat aaaggtcgtg actttgccac cgttcgtaaa gtcctctcaa  3900
tgccgcaagt taacattgtc aagaagacgg aagttcaaac agggggattc tccaaagaat  3960
ctatcctgcc gaagcgtaac agtgataaac ttattgccag aaaaaaagat tgggatccaa  4020
aaaaatacgg aggctttgat tcccctaccg tcgcgtatag tgtgctggtg gttgctaaag  4080
tcgagaaagg gaaaagcaag aaattgaaat cagttaaaga actgctgggt attacaatta  4140
tggaaagatc gtcctttgag aaaaatccga tcgacttttt agaggccaag gggtataagg  4200
aagtgaaaaa agatctcatc atcaaattac cgaagtatag tctttttgag ctggaaaacg  4260
gcagaaaaag aatgctggcc tccgcgggcg agttacagaa gggaaatgag ctggcgctgc  4320
cttccaaata tgttaatttt ctgtaccttg ccagtcatta tgagaaactg aagggcagcc  4380
ccgaagataa cgaacagaaa caattattcg tggaacagca taagcactat ttagatgaaa  4440
ttatagagca aattagtgaa ttttctaagc gcgttatcct cgcggatgct aatttagaca  4500
aagtactgtc agcttataat aaacatcggg ataagccgat tagagaacag gccgaaaata  4560
tcattcattt gtttacctta accaaccttg gagcaccagc tgccttcaaa tatttcgata  4620
ccacaattga tcgtaaacgg tatacaagta caaaagaagt cttggacgca accctcattc  4680
atcaatctat tactggatta tatgagacac gcattgatct ttcacagctg ggcggagaca  4740
agaagaaaaa actgaaactg caccatcatc accatcatca tcaccatcat tgataactcg  4800
agaaagctta cataaaaaac cggccttggc cccgccggtt ttttattatt tttcttcctc  4860
cgcatgttca atccgctcca taatcgacgg atggctccct ctgaaaattt taacgagaaa  4920
cggcgggttg acccggctca gtcccgtaac ggccaagtcc tgaaacgtct caatcgccgc  4980
ttcccggttt ccggtcagct caatgccgta acggtcggcg gcgttttcct gataccggga  5040
gacggcattc gtaatc                                                  5056
```

```
SEQ ID NO: 3          moltype = AA  length = 8
FEATURE               Location/Qualifiers
REGION                1..8
                      note = N-terminal NLS
source                1..8
                      mol_type = protein
                      organism = synthetic construct
SEQUENCE: 3
APKKKRKV                                                           8

SEQ ID NO: 4          moltype = AA  length = 6
FEATURE               Location/Qualifiers
REGION                1..6
                      note = C-terminal NLS
```

```
source                 1..6
                       mol_type = protein
                       organism = synthetic construct
SEQUENCE: 4
KKKKLK                                                        6

SEQ ID NO: 5           moltype = AA  length = 10
FEATURE                Location/Qualifiers
REGION                 1..10
                       note = deca-Histidine tag
source                 1..10
                       mol_type = protein
                       organism = synthetic construct
SEQUENCE: 5
HHHHHHHHHH                                                    10

SEQ ID NO: 6           moltype = DNA  length = 607
FEATURE                Location/Qualifiers
source                 1..607
                       mol_type = unassigned DNA
                       organism = Bacillus subtilis
SEQUENCE: 6
attcctccat tttcttctgc tatcaaaata acagactcgt gattttccaa acgagctttc  60
aaaaaagcct ctgccccttg caaatcggat gcctgtctat aaaattcccg atattggtta  120
aacagcggcg caatggcggc cgcatctgat gtctttgctt ggcgaatgtt catcttattt  180
cttcctccct ctcaataatt ttttcattct atcccttttc tgtaaagttt atttttcaga  240
atacttttat catcatgctt tgaaaaaata tcacgataat atccattgtt ctcacggaag  300
cacacgcagg tcatttgaac gaatttttttc gacaggaatt tgccgggact caggagcatt  360
taacctaaaa aagcatgaca tttcagcata atgaacattt actcatgtct attttcgttc  420
ttttctgtat gaaaatagtt atttcgagtc tctacggaaa tagcgagaga tgatatacct  480
aaatagagat aaaatcatct caaaaaaatg ggtctactaa aatattattc catctattac  540
aataaattca cagaatagtc ttttaagtaa gtctactctg aattttttta aaaggagagg  600
gtaacta                                                       607

SEQ ID NO: 7           moltype = DNA  length = 247
FEATURE                Location/Qualifiers
misc_feature           1..247
                       note = synthesized terminator DNA sequence
source                 1..247
                       mol_type = other DNA
                       organism = synthetic construct
SEQUENCE: 7
acataaaaaa ccggccttgg ccccgccggt tttttattat ttttcttcct ccgcatgttc  60
aatccgctcc ataatcgacg gatggctccc tctgaaaatt ttaacgagaa acggcgggtt  120
gacccggctc agtcccgtaa cggccaagtc ctgaaacgtc tcaatcgccg cttcccggtt  180
tccggtcagc tcaatgccgt aacggtcggc ggcgttttcc tgataccggg agacggcatt  240
cgtaatc                                                       247

SEQ ID NO: 8           moltype = DNA  length = 50
FEATURE                Location/Qualifiers
misc_feature           1..50
                       note = Cas9 forward primer
source                 1..50
                       mol_type = other DNA
                       organism = synthetic construct
SEQUENCE: 8
atatatgagt aaacttggtc tgacagaatt cctccatttt cttctgctat        50

SEQ ID NO: 9           moltype = DNA  length = 35
FEATURE                Location/Qualifiers
misc_feature           1..35
                       note = Cas9 revers primer
source                 1..35
                       mol_type = other DNA
                       organism = synthetic construct
SEQUENCE: 9
tgcggccgcg aattcgatta cgaatgccgt ctccc                        35

SEQ ID NO: 10          moltype = DNA  length = 3290
FEATURE                Location/Qualifiers
misc_feature           1..3290
                       note = plasmid pKB320 backbone
source                 1..3290
                       mol_type = other DNA
                       organism = synthetic construct
SEQUENCE: 10
gaattcgcgg ccgcacgcgt ccatggggat ccccgcgggt cgacctcgag agttacgcta  60
gggataacag ggtaatatag gagctccagt cggcttaaac cagttttcgc tggtgcgaaa  120
aaagagtgtc ttgtgacacc taaattcaaa atctatcggt cagatttata ccgatttgat  180
```

```
tttatatatt cttgaataac atacgccgag ttatcacata aaagcgggaa ccaatcataa  240
aatttaaact tcattgcata atccattaaa ctcttaaatt ctacgattcc ttgttcatca  300
ataaactcaa tcatttcttt aattaattta tatctatctg ttgttgtttt ctttaataat  360
tcattaacat ctacaccgcc ataaactatc atatcttctt tttgatattt aaatttatta  420
ggatcgtcca tgtgaagcat atatctcaca agacctttca cacttcctgc aatctgcgga  480
atagtcgcat tcaattcttc tgttaattat ttttatctgt tcataagatt tattaccctc  540
atacatcact agaatatgat aatgctcttt tttcatccta ccttctgtat cagtatccct  600
atcatgtaat ggagacacta caaattgaat gtgtaactct tttaaatact ctaaccactc  660
ggcttttgct gattctggat ataaaacaaa tgtccaatta cgtcctcttg aatttttctt  720
gttttcagtt tcttttatta cattttcgct catgatataa taacggtgct aatacactta  780
acaaaattta gtcatagata ggcagcatgc cagtgctgtc tatctttttt tgtttaaaat  840
gcaccgtatt cctcctttgc atattttttt attagaatac cggttgcatc tgatttgcta  900
atattatatt tttctttgat tctatttaat atctcatttt cttctgttgt aagtcttaaa  960
gtaacagcaa ctttttttctc ttcttttcta tctacaacta tcactgtacc tcccaacatc  1020
tgttttttttc actttaacat aaaaaacaac cttttaacat taaaaaccca atatttattt  1080
atttgtttgg acaatggaca ctggacacct aggggggagg tcgtagtacc cccctatgtt  1140
ttctccccta aataacccca aaaatctaag aaaaaaagac ctcaaaaagg tctttaatta  1200
acatctcaaa tttcgcattt attccaattt cctttttgcg tgtgatgcga gctcatcggc  1260
tccgtcgata ctatgttata cgccaacttt caaaacaact ttgaaaaagc tgttttctgg  1320
tatttaaggt tttagaatgc aaggaacagt gaattggagt tcgtcttgtt ataattagct  1380
tcttggggta tctttaaata ctgtagaaaa gaggaaggaa ataataaatg gctaaaatga  1440
gaatatcacc ggaattgaaa aaactgatcg aaaaataccg ctgcgtaaaa gatacggaag  1500
gaatgtctcc tgctaaggta tataagctgg tgggagaaaa tgaaaaccta tatttaaaaa  1560
tgacggacag ccggtataaa gggaccacct atgatgtgga acgggaaaag gacatgatgc  1620
tatggctgga aggaaagctg cctgttccaa aggtcctgca ctttgaacgg catgatggct  1680
ggagcaatct gctcatgagt gaggccgatg gcgtcctttg ctcggaagag tatgaagatg  1740
aacaaagccc tgaaaagatt atcgagctgt atgcggagtg catcaggctc tttcactcca  1800
tcgacatatc ggattgtccc tatacgaata gcttagacag ccgcttagcc gaattggatt  1860
acttactgaa taacgatctg gccgatgtgg attgcgaaaa ctgggaagaa gacactccat  1920
ttaaagatcc gcgcgagctg tatgattttt taaagacgga aaagcccgaa gaggaacttg  1980
tcttttccca cggcgacctg ggagacagca acatctttgt gaaagatggc aaagtaagtg  2040
gctttattga tcttgggaga agcggcaggg cggacaagtg gtatgacatt gccttctgcg  2100
tccggtcgat cagggaggat atcggggaag aacagtatgt cgagctattt tttgacttac  2160
tggggatcaa gcctgattgg gagaaaataa aatattatat tttactggat gaattgtttt  2220
agtgactgca gtgagatctg gtaatgactc tctagcttga ggcatcaaat aaaacgaaag  2280
gctcagtcga aagactgggc ctttcgtttt atctgttgtt tgtcggtgaa cgctctcctg  2340
agtaggacaa atccgccgct ctagctaagc agaaggccat cctgacggat ggcctttttg  2400
cgtttctaca aactcttgtt aactctagag ctgcctgccg cgtttcggtg atgaagatct  2460
tcccgatgat taattaattc agaacgctcg gttgccgccg ggcgtttttt atgaagcttc  2520
gttgctggcg tttttccata ggctccgccc ccctgacgag catcacaaaa atcgacgctc  2580
aagtcagagg tggcgaaacc cgacaggact ataaagatac caggcgtttc cccctggaag  2640
ctccctcgtg cgctctcctg ttccgaccct gccgcttacc ggatacctgt ccgcctttct  2700
cccttcggga agcgtggcgc tttctcatag ctcacgctgt aggtatctca gttcggtgta  2760
ggtcgttcgc tccaagctgg gctgtgtgca cgaacccccc gttcagcccg accgctgcgc  2820
cttatccggt aactatcgtc ttgagtccaa cccggtaaga cacgacttat cgccactggc  2880
agcagccact ggtaacagga ttagcagagc gaggtatgta ggcggtgcta cagagttctt  2940
gaagtggtgg cctaactacg gctacactag aaggacagta tttggtatct gcgctctgct  3000
gaagccagtt accttcggaa aaagagttgg tagctcttga tccggcaaac aaaccaccgc  3060
tggtagcggt ggtttttttg tttgcaagca gcagattacg cgcagaaaaa aaggatctca  3120
agaagatcct ttgatctttt ctacggggtc tgacgctcag tggaacgaaa actcacgtta  3180
agggattttg gtcatgagat tatcaaaaag gatcttcacc tagatccttt taaattaaaa  3240
atgaagtttt aaatcaatct aaagtatata tgagtaaact tggtctgaca            3290
```

```
SEQ ID NO: 11           moltype = DNA  length = 4204
FEATURE                 Location/Qualifiers
misc_feature            1..4204
                        note = pKB320 plasmid
source                  1..4204
                        mol_type = other DNA
                        organism = synthetic construct
SEQUENCE: 11
gcggccgcac gcgtccatgg ggatccccgc gggtcgacct cgagagttac gctagggata  60
acagggtaat ataggagctc cagtcggctt aaaccagttt tcgctggtgc gaaaaaagag  120
tgtcttgtga cacctaaatt caaaatctat cggtcagatt tataccgatt tgattttata  180
tattcttgaa taacatacgc cgagttatca cataaaagcg ggaaccaatc ataaaattta  240
aacttcattg cataatccat taaactctta aattctacga ttccttgttc atcaataaac  300
tcaatcattt ctttaattaa tttatatcta tctgttgttg ttttctttaa taattcatta  360
acatctacac cgccataaac tatcatatct tctttttgat atttaaattt attaggatcg  420
tccatgtgaa gcatatatct cacaagacct ttcacacttc ctgcaatctg cggaatagtc  480
gcattcaatt cttctgttaa ttatttttat ctgttcataa gatttattac cctcatacat  540
cactagaata tgataatgct ctttttttcat cctaccttct gtatcagtat ccctatcatg  600
taatggagac actacaaatt gaatgtgtaa ctcttttaaa tactctaacc actcggcttt  660
tgctgattct ggatataaaa caaatgtcca attacgtcct cttgaatttt tcttgttttc  720
agtttctttt attacatttt cgctcatgat ataataacgg tgctaataca cttaacaaaa  780
tttagtcata gataggcagc atgccagtgc tgtctatctt tttttgttta aaatgcaccg  840
tattcctcct ttgcatattt ttttattaga ataccggttg catctgattt gctaatatta  900
tatttttctt tgattctatt taatatctca ttttcttctg ttgtaagtct taaagtaaca  960
gcaacttttt tctcttcttt tctatctaca actatcactg tacctcccaa catctgtttt  1020
tttcacttta acataaaaaa caacctttta acattaaaaa cccaatattt atttatttgt  1080
```

```
ttggacaatg gacactggac acctaggggg gaggtcgtag taccccccta tgttttctcc  1140
cctaaataac cccaaaaatc taagaaaaaa agacctcaaa aaggtcttta attaacatct  1200
caaatttcgc atttattcca atttcctttt tgcgtgtgat gcgagctcat cggctccgtc  1260
gatactatgt tatacgccaa ctttcaaaac aactttgaaa aagctgtttt ctggtattta  1320
aggttttaga atgcaaggaa cagtgaattg gagttcgtct tgttataatt agcttcttgg  1380
ggtatcttta aatactgtag aaaagaggaa ggaaataata aatggctaaa atgagaatat  1440
caccggaatt gaaaaaactg atcgaaaaat accgctgcgt aaaagatacg gaaggaatgt  1500
ctcctgctaa ggtatataag ctggtgggag aaaatgaaaa cctatattta aaaatgacgg  1560
acagccggta taaagggacc acctatgatg tggaacggga aaaggacatg atgctatggc  1620
tggaaggaaa gctgcctgtt ccaaaggtcc tgcactttga acggcatgat ggctggagca  1680
atctgctcat gagtgaggcc gatggcgtcc tttgctcgga agagtatgaa gatgaacaaa  1740
gccctgaaaa gattatcgag ctgtatgcgg agtgcatcag gctctttcac tccatcgaca  1800
tatcggattg tccctatacg aatagcttag acagccgctt agccgaattg gattacttac  1860
tgaataacga tctggccgat gtggattgcg aaaactggga agaagacact ccatttaaag  1920
atccgcgcga gctgtatgat tttttaaaga cggaaaagcc cgaagaggaa cttgtctttt  1980
cccacggcga cctgggagac agcaacatct ttgtgaaaga tggcaaagta agtggcttta  2040
ttgatcttgg gagaagcggc agggcggaca agtggtatga cattgccttc tgcgtccggt  2100
cgatcaggga ggatatcggg gaagaacagt atgtcgagct atttttgac ttactgggga  2160
tcaagcctga ttgggagaaa ataaaatatt atattttact ggatgaattg ttttagtgac  2220
tgcagtgaga tctggtaatg actctctagc ttgaggcatc aaataaaacg aaaggctcag  2280
tcgaaagact gggcctttcg ttttatctgt tgtttgtcgg tgaacgctct cctgagtagg  2340
acaaatccgc cgctctagct aagcagaagg ccatcctgac ggatggcctt tttgcgtttc  2400
tacaaactct tgttaactct agagctgcct gccgcgtttc ggtgatgaag atcttcccga  2460
tgattaatta attcagaacg ctcggttgcc gccgggcgtt ttttatgaag cttcgttgct  2520
ggcgtttttc cataggctcc gcccccctga cgagcatcac aaaaatcgac gctcaagtca  2580
gaggtggcga aacccgacag gactataaag ataccaggcg tttccccctg gaagctccct  2640
cgtgcgctct cctgttccga ccctgccgct taccggatac ctgtccgcct ttctcccttc  2700
gggaagcgtg gcgctttctc atagctcacg ctgtaggtat ctcagttcgg tgtaggtcgt  2760
tcgctccaag ctgggctgtg tgcacgaacc ccccgttcag cccgaccgct gcgccttatc  2820
cggtaactat cgtcttgagt ccaacccggt aagacacgac ttatcgccac tggcagcagc  2880
cactggtaac aggattagca gagcgaggta tgtaggcggt gctacagagt tcttgaagtg  2940
gtggcctaac tacggctaca ctagaaggac agtatttggt atctgcgctc tgctgaagcc  3000
agttaccttc ggaaaaagag ttggtagctc ttgatccggc aaacaaacca ccgctggtag  3060
cggtggtttt tttgtttgca agcagcagat tacgcgcaga aaaaaaggat ctcaagaaga  3120
tcctttgatc ttttctacgg ggtctgacgc tcagtggaac gaaaactcac gttaagggat  3180
tttggtcatg agattatcaa aaaggatctt cacctagatc cttttaaatt aaaaatgaag  3240
ttttaaatca atctaaagta tatatgagta aacttggtct gacagttacc aatgcttaat  3300
cagtgaggca cctatctcag cgatctgtct atttcgttca tccatagttg cctgactccc  3360
cgtcgtgtag ataactacga tacgggaggg cttaccatct ggccccagtg ctgcaatgat  3420
accgcgagac ccacgctcac cggctccaga tttatcagca ataaaccagc cagccggaag  3480
ggccgagcgc agaagtggtc ctgcaacttt atccgcctcc atccagtcta ttaattgttg  3540
ccgggaagct agagtaagta gttcgccagt taatagtttg cgcaacgttg ttgccattgc  3600
tacaggcatc gtggtgtcac gctcgtcgtt tggtatggct tcattcagct ccggttccca  3660
acgatcaagg cgagttacat gatcccccat gttgtgcaaa aaagcggtta gctccttcgg  3720
tcctccgatc gttgtcagaa gtaagttggc cgcagtgtta tcactcatgg ttatggcagc  3780
actgcataat tctcttactg tcatgccatc cgtaagatgc ttttctgtga ctggtgagta  3840
ctcaaccaag tcattctgag aatagtgtat gcggcgaccg agttgctctt gcccggcgtc  3900
aatacgggat aataccgcgc cacatagcag aactttaaaa gtgctcatca ttggaaaacg  3960
ttcttcgggg cgaaaactct caaggatctt accgctgttg agatccagtt cgatgtaacc  4020
cactcgtgca cccaactgat cttcagcatc ttttactttc accagcgttt ctgggtgagc  4080
aaaaacagga aggcaaaatg ccgcaaaaaa gggaataagg gcgacacgga aatgttgaat  4140
actcatactc ttcctttttc aatattattg aagcatttat cagggttatt gtctcatgga  4200
attc                                                                4204

SEQ ID NO: 12          moltype = DNA  length = 35
FEATURE                Location/Qualifiers
misc_feature           1..35
                       note = pKB320 forward primer
source                 1..35
                       mol_type = other DNA
                       organism = synthetic construct
SEQUENCE: 12
gggagacggc attcgtaatc gaattcgcgg ccgca                              35

SEQ ID NO: 13          moltype = DNA  length = 50
FEATURE                Location/Qualifiers
misc_feature           1..50
                       note = pKB320 reverse primer
source                 1..50
                       mol_type = other DNA
                       organism = synthetic construct
SEQUENCE: 13
atagcagaag aaaatggagg aattctgtca gaccaagttt actcatatat              50

SEQ ID NO: 14          moltype = DNA  length = 23
FEATURE                Location/Qualifiers
misc_feature           1..23
                       note = plasmid RSP1
source                 1..23
```

```
                         mol_type = other DNA
                         organism = synthetic construct
SEQUENCE: 14
ccgactggag ctcctatatt acc                                            23

SEQ ID NO: 15            moltype = DNA  length = 20
FEATURE                  Location/Qualifiers
misc_feature             1..20
                         note = plasmid RSP2
source                   1..20
                         mol_type = other DNA
                         organism = synthetic construct
SEQUENCE: 15
gctgtggcga tctgtattcc                                                20

SEQ ID NO: 16            moltype = DNA  length = 22
FEATURE                  Location/Qualifiers
misc_feature             1..22
                         note = plasmid FSP1
source                   1..22
                         mol_type = other DNA
                         organism = synthetic construct
SEQUENCE: 16
gtcttttaag taagtctact ct                                             22

SEQ ID NO: 17            moltype = DNA  length = 20
FEATURE                  Location/Qualifiers
misc_feature             1..20
                         note = plasmid FSP2
source                   1..20
                         mol_type = other DNA
                         organism = synthetic construct
SEQUENCE: 17
ccaaagcgat tttaagcgcg                                                20

SEQ ID NO: 18            moltype = DNA  length = 20
FEATURE                  Location/Qualifiers
misc_feature             1..20
                         note = plasmid FSP3
source                   1..20
                         mol_type = other DNA
                         organism = synthetic construct
SEQUENCE: 18
cctggcacgt ggtaattctc                                                20

SEQ ID NO: 19            moltype = DNA  length = 20
FEATURE                  Location/Qualifiers
misc_feature             1..20
                         note = plasmid FSP4
source                   1..20
                         mol_type = other DNA
                         organism = synthetic construct
SEQUENCE: 19
ggatttcctc aaatctgacg                                                20

SEQ ID NO: 20            moltype = DNA  length = 21
FEATURE                  Location/Qualifiers
misc_feature             1..21
                         note = plasmid FSP5
source                   1..21
                         mol_type = other DNA
                         organism = synthetic construct
SEQUENCE: 20
gtagaaacgc gccaaattac g                                              21

SEQ ID NO: 21            moltype = DNA  length = 20
FEATURE                  Location/Qualifiers
misc_feature             1..20
                         note = plasmid FSP6
source                   1..20
                         mol_type = other DNA
                         organism = synthetic construct
SEQUENCE: 21
gctggtggtt gctaaagtcg                                                20

SEQ ID NO: 22            moltype = DNA  length = 20
FEATURE                  Location/Qualifiers
misc_feature             1..20
                         note = plasmid FSP7
```

```
source                  1..20
                        mol_type = other DNA
                        organism = synthetic construct
SEQUENCE: 22
ggacgcaacc ctcattcatc                                              20

SEQ ID NO: 23           moltype = DNA  length = 20
FEATURE                 Location/Qualifiers
misc_feature            1..20
                        note = plasmid RSP3
source                  1..20
                        mol_type = other DNA
                        organism = synthetic construct
SEQUENCE: 23
caggcatccg atttgcaagg                                              20

SEQ ID NO: 24           moltype = DNA  length = 19
FEATURE                 Location/Qualifiers
misc_feature            1..19
                        note = plasmid FSP8
source                  1..19
                        mol_type = other DNA
                        organism = synthetic construct
SEQUENCE: 24
gcaagcagca gattacgcg                                               19

SEQ ID NO: 25           moltype = DNA  length = 8347
FEATURE                 Location/Qualifiers
misc_feature            1..8347
                        note = plasmid pRF694
source                  1..8347
                        mol_type = other DNA
                        organism = synthetic construct
SEQUENCE: 25
gaattcctcc attttcttct gctatcaaaa taacagactc gtgattttcc aaacgagctt  60
tcaaaaaagc ctctgcccct tgcaaatcgg atgcctgtct ataaaattcc cgatattggt  120
taaacagcgg cgcaatggcg gccgcatctg atgtctttgc ttggcgaatg ttcatcttat  180
ttcttcctcc ctctcaataa ttttttcatt ctatcccttt tctgtaaagt ttatttttca  240
gaatactttt atcatcatgc tttgaaaaaa tatcacgata atatccattg ttctcacgga  300
agcacacgca ggtcatttga acgaattttt tcgacaggaa tttgccggga ctcaggagca  360
tttaacctaa aaaagcatga catttcagca taatgaacat ttactcatgt ctattttcgt  420
tcttttctgt atgaaaatag ttatttcgag tctctacgga aatagcgaga gatgatatac  480
ctaaatagag ataaaatcat ctcaaaaaaa tgggtctact aaaatattat tccatctatt  540
acaataaatt cacagaatag tcttttaagt aagtctactc tgaatttttt taaaaggaga  600
gggtaactag tggccccaaa aaagaaacgc aaggttatgg ataaaaaata cagcattggt  660
ctggatatcg gaaccaacag cgttgggtgg gcagtaataa cagatgaata caaagtgccg  720
tcaaaaaaat ttaaggttct ggggaataca gatcgccaca gcataaaaaa gaatctgatt  780
ggggcattgc tgtttgattc gggtgagaca gctgaggcca cgcgtctgaa acgtacagca  840
agaagacgtt acacacgtcg taaaaatcgt atttgctact tacaggaaat tttttctaac  900
gaaatggcca aggtagatga tagtttcttc catcgtctcg aagaatcttt tctggttgag  960
gaagataaaa aacacgaacg tcaccctatc tttggcaata tcgtggatga agtggcctat  1020
catgaaaaat accctacgat ttatcatctt cgcaagaagt tggttgatag tacggacaaa  1080
gcggatctgc gtttaatcta tcttgcgtta gcgcacatga tcaaatttcg tggtcatttc  1140
ttaattgaag gtgatctgaa tcctgataac tctgatgtgg acaaattgtt tatacaatta  1200
gtgcaaacct ataatcagct gttcgaggaa aaccccatta atgcctctgg agttgatgcc  1260
aaagcgattt taagcgcgag actttctaag tcccggcgtc tggagaatct gatcgcccag  1320
ttaccagggg aaaagaaaaa tggtctgttt ggtaatctga ttgccctcag tctggggctt  1380
accccgaact tcaaatccaa ttttgacctg gctgaggacg caaagctgca gctgagcaaa  1440
gatacttatg atgatgacct cgacaatctg ctcgcccaga ttggtgacca atatgcggat  1500
ctgtttctgg cagcgaagaa tctttcggat gctatcttgc tgtcggatat tctgcgtgtt  1560
aataccgaaa tcaccaaagc gcctctgtct gcaagtatga tcaagagata cgacgagcac  1620
caccaggacc tgactcttct taaggcactg gtacgccaac agcttccgga gaaatacaaa  1680
gaaatattct tcgaccagtc caagaatggt tacgcgggct acatcgatgg tggtgcatca  1740
caggaagagt tctataaatt tattaaacca atccttgaga aaatggatgg cacggaagag  1800
ttacttgtta aacttaaccg cgaagacttg cttagaaagc aacgtacatt cgacaacggc  1860
tccatcccac accagattca tttaggtgaa cttcacgcca tcttgcgcag acaagaagat  1920
ttctatccct tcttaaaaga caatcgggag aaaatcgaga agatcctgac gttccgcatt  1980
ccctattatg tcggtcccct ggcacgtggt aattctcggt ttgcctggat gacgcgcaaa  2040
agtgaggaaa ccatcacccc ttggaacttt gaagaagtcg tggataaagg tgctagcgcg  2100
cagtctttta tagaaagaat gacgaacttc gataaaaact tgcccaacga aaaagtcctg  2160
cccaagcact ctcttttata tgagtacttt actgtgtaca acgaactgac taaagtgaaa  2220
tacgttacgg aaggtatgcg caaacctgcc tttcttagtg gcgagcagaa aaaagcaatt  2280
gtcgatcttc tctttaaaac gaatcgcaag gtaactgtaa aacagctgaa ggaagattat  2340
ttcaaaaaga tcgaatgctt tgattctgtc gagatctcgg gtgtcgaaga tcgtttcaac  2400
gcttccttag ggacctatca tgatttgctg aagataataa aagacaaaga ctttctcgac  2460
aatgaagaaa atgaagatat tctggaggat attgttttga ccttgacctt attcgaagat  2520
agagagatga tcgaggagcg cttaaaaacc tatgcccacc tgtttgatga caaagtcatg  2580
aagcaattaa agcgccgcag atatacgggg tggggccgct tgagccgcaa gttgattaac  2640
ggtattagag acaagcagag cggaaaaact atcctggatt tcctcaaatc tgacggattt  2700
```

```
gcgaaccgca attttatgca gcttatacat gatgattcgc ttacattcaa agaggatatt  2760
cagaaggctc aggtgtctgg gcaaggtgat tcactccacg aacatatagc aaatttggcc  2820
ggctctcctg cgattaagaa ggggatcctg caaacagtta aagttgtgga tgaacttgta  2880
aaagtaatgg gccgccacaa gccggagaat atcgtgatag aaatggcgcg cgagaatcaa  2940
acgacacaaa aaggtcaaaa gaactcaaga gagagaatga agcgcattga ggaggggata  3000
aaggaacttg gatctcaaat tctgaaagaa catccagttg aaaacactca gctgcaaaat  3060
gaaaaattgt acctgtacta cctgcagaat ggaagagaca tgtacgtgga tcaggaattg  3120
gatatcaata gactctcgga ctatgacgta gatcacattg tccctcagag cttcctcaag  3180
gatgattcta tagataataa agtacttacg agatcggaca aaaatcgcgg taaatcggat  3240
aacgtcccat cggaggaagt cgttaaaaag atgaaaaact attggcgtca actgctgaac  3300
gccaagctga tcacacagcg taagtttgat aatctgacta aagccgaacg cggtggtctt  3360
agtgaactcg ataaagcagg atttataaaa cggcagttag tagaaacgcg ccaaattacg  3420
aaacacgtgg ctcagatcct cgattctaga atgaatacaa agtacgatga aaacgataaa  3480
ctgatccgtg aagtaaaagt cattacctta aaatctaaac ttgtgtccga tttccgcaaa  3540
gattttcagt tttacaaggt ccgggaaatc aataactatc accatgcaca tgatgcatat  3600
ttaaatgcgg ttgtaggcac ggcccttatt aagaaatacc ctaaactcga aagtgagttt  3660
gtttatgggg attataaagt gtatgacgtt cgcaaaatga tcgcgaaatc agaacaggaa  3720
atcggtaagg ctaccgctaa atactttttt tattccaaca ttatgaattt ttttaagacc  3780
gaaataactc tcgcgaatgg tgaaatccgt aaacggcctc ttatagaaac caatggtgaa  3840
acgggagaaa tcgtttggga taaaggtcgt gactttgcca ccgttcgtaa agtcctctca  3900
atgccgcaag ttaacattgt caagaagacg gaagttcaaa caggggggatt ctccaaagaa  3960
tctatcctgc cgaagcgtaa cagtgataaa cttattgcca gaaaaaaaga ttgggatcca  4020
aaaaaatacg gaggctttga ttcccctacc gtcgcgtata gtgtgctggt ggttgctaaa  4080
gtcgagaaag ggaaaagcaa gaaattgaaa tcagttaaag aactgctggg tattacaatt  4140
atggaaagat cgtcctttga gaaaaatccg atcgactttt tagaggccaa ggggtataag  4200
gaagtgaaaa aagatctcat catcaaatta ccgaagtata gtctttttga gctggaaaac  4260
ggcagaaaaa gaatgctggc ctccgcgggc gagttacaga agggaaatga gctggcgctg  4320
ccttccaaat atgttaattt tctgtacctt gccagtcatt atgagaaact gaagggcagc  4380
cccgaagata acgaacagaa acaattattc gtggaacagc ataagcacta tttagatgaa  4440
attatagagc aaattagtga attttctaag cgcgttatcc tcgcggatgc taatttagac  4500
aaagtactgt cagcttataa taaacatcgg gataagccga ttagagaaca ggccgaaaat  4560
atcattcatt tgtttacctt aaccaacctt ggagcaccag ctgccttcaa atatttcgat  4620
accacaattg atcgtaaacg gtatacaagt acaaaagaag tcttggacgc aaccctcatt  4680
catcaatcta ttactggatt atatgagaca cgcattgatc tttcacagct gggcggagac  4740
aagaagaaaa aactgaaact gcaccatcat caccatcatc atcaccatca ttgataactc  4800
gagaaagctt acataaaaaa ccggccttgg ccccgccggt tttttattat ttttcttcct  4860
ccgcatgttc aatccgctcc ataatcgacg gatggctccc tctgaaaatt ttaacgagaa  4920
acggcgggtt gacccggctc agtcccgtaa cggccaagtc ctgaaacgtc tcaatcgccg  4980
cttcccggtt tccggtcagc tcaatgccgt aacggtcggc ggcgttttcc tgataccggg  5040
agacggcatt cgtaatcgaa ttcgcggcgg cacgcgtcca tggggatccc cgcgggtcga  5100
cctcgagagt tacgctaggg ataacagggt aatataggag ctccagtcgg cttaaaccag  5160
ttttcgctgg tgcgaaaaaa gagtgtcttg tgacacctaa attcaaaatc tatcggtcag  5220
atttataccg atttgatttt atatattctt gaataacata cgccgagtta tcacataaaa  5280
gcgggaacca atcataaaat ttaaacttca ttgcataatc cattaaactc ttaaattcta  5340
cgattccttg ttcatcaata aactcaatca tttctttaat taatttatat ctatctgttg  5400
ttgttttctt taataattca ttaacatcta caccgccata aactatcata tcttcttttt  5460
gatatttaaa tttattagga tcgtccatgt gaagcatata tctcacaaga cctttcacac  5520
ttcctgcaat ctgcggaata gtcgcattca attcttctgt taattatttt tatctgttca  5580
taagatttat taccctcata catcactaga atatgataat gctctttttt catcctacct  5640
tctgtatcag tatccctatc atgtaatgga gacactacaa attgaatgtg taactctttt  5700
aaatactcta accactcggc ttttgctgat tctggatata aaacaaatgt ccaattacgt  5760
cctcttgaat ttttcttgtt ttcagtttct tttattacat tttcgctcat gatataataa  5820
cggtgctaat acacttaaca aaatttagtc atagataggc agcatgccag tgctgtctat  5880
cttttttttgt ttaaaatgca ccgtattcct cctttgcata ttttttttatt agaataccgg  5940
ttgcatctga tttgctaata ttatattttt ctttgattct atttaatatc tcattttctt  6000
ctgttgtaag tcttaaagta acagcaactt ttttctcttc ttttctatct acaactatca  6060
ctgtacctcc caacatctgt ttttttcact ttaacataaa aaacaacctt ttaacattaa  6120
aaacccaata tttatttatt tgtttggaca atggacactg gacacctagg ggggaggtcg  6180
tagtaccccc ctatgtttc tcccctaaat aaccccaaaa atctaagaaa aaaagacctc  6240
aaaaaggtct ttaattaaca tctcaaattt cgcatttatt ccaatttcct ttttgcgtgt  6300
gatgcgagct catcggctcc gtcgatacta tgttatacgc caactttcaa aacaactttg  6360
aaaaagctgt tttctggtat ttaaggtttt agaatgcaag gaacagtgaa ttggagttcg  6420
tcttgttata attagcttct tggggtatct ttaaatactg tagaaaagag gaaggaaata  6480
ataaatggct aaaatgagaa tatcaccgga attgaaaaaa ctgatcgaaa aataccgctg  6540
cgtaaaagat acggaaggaa tgtctcctgc taaggtatat aagctggtgg gagaaaatga  6600
aaacctatat ttaaaaatga cggacagccg gtataaaggg accacctatg atgtggaacg  6660
ggaaaaggac atgatgctat ggctggaagg aaagctgcct gttccaaagg tcctgcactt  6720
tgaacggcat gatggctgga gcaatctgct catgagtgag gccgatggcg tcctttgctc  6780
ggaagagtat gaagatgaac aaagccctga aaagattatc gagctgtatg cggagtgcat  6840
caggctcttt cactccatcg acatatcgga ttgtccctat acgaatagct tagacagccg  6900
cttagccgaa ttggattact tactgaataa cgatctggcc gatgtggatt gcgaaaactg  6960
ggaagaagac actccattta aagatccgcg cgagctgtat gatttttttaa agacggaaaa  7020
gcccgaagag gaacttgtct tttcccacgg cgacctggga gacagcaaca tctttgtgaa  7080
agatggcaaa gtaagtggct ttattgatct tgggagaagc ggcagggcgg acaagtggta  7140
tgacattgcc ttctgcgtcc ggtcgatcag ggaggatatc ggggaagaac agtatgtcga  7200
gctatttttt gacttactgg ggatcaagcc tgattgggag aaaataaaat attatatttt  7260
actggatgaa ttgttttagt gactgcagtg agatctggta atgactctct agcttgaggc  7320
atcaaataaa acgaaaggct cagtcgaaag actgggcctt tcgttttatc tgttgtttgt  7380
cggtgaacgc tctcctgagt aggacaaatc cgccgctcta gctaagcaga aggccatcct  7440
```

```
gacggatggc ctttttgcgt ttctacaaac tcttgttaac tctagagctg cctgccgcgt  7500
ttcggtgatg aagatcttcc cgatgattaa ttaattcaga acgctcggtt gccgccgggc  7560
gtttttttatg aagcttcgtt gctggcgttt ttccataggc tccgcccccc tgacgagcat  7620
cacaaaaatc gacgctcaag tcagaggtgg cgaaacccga caggactata aagataccag  7680
gcgtttcccc ctggaagctc cctcgtgcgc tctcctgttc cgaccctgcc gcttaccgga  7740
tacctgtccg cctttctccc ttcgggaagc gtggcgcttt ctcatagctc acgctgtagg  7800
tatctcagtt cggtgtaggt cgttcgctcc aagctgggct gtgtgcacga accccccgtt  7860
cagcccgacc gctgcgcctt atccggtaac tatcgtcttg agtccaaccc ggtaagacac  7920
gacttatcgc cactggcagc agccactggt aacaggatta gcagagcgag gtatgtaggc  7980
ggtgctacag agttcttgaa gtggtggcct aactacggct acactagaag gacagtattt  8040
ggtatctgcg ctctgctgaa gccagttacc ttcggaaaaa gagttggtag ctcttgatcc  8100
ggcaaacaaa ccaccgctgg tagcggtggt ttttttgttt gcaagcagca gattacgcgc  8160
agaaaaaaag gatctcaaga agatcctttg atcttttcta cggggtctga cgctcagtgg  8220
aacgaaaact cacgttaagg gattttggtc atgagattat caaaaaggat cttcacctag  8280
atccttttaa attaaaaatg aagttttaaa tcaatctaaa gtatatatga gtaaacttgg  8340
tctgaca                                                            8347

SEQ ID NO: 26          moltype = DNA  length = 9724
FEATURE                Location/Qualifiers
misc_feature           1..9724
                       note = plasmid pRF801
source                 1..9724
                       mol_type = other DNA
                       organism = synthetic construct
SEQUENCE: 26
gggtgaagtg gtcaagacct cactaggcac cttaaaaata gcgcaccctg aagaagattt  60
atttgaggta gcccttgcct acctagcttc caagaaagat atcctaacag cacaagagcg  120
gaaagatgtt ttgttctaca tccagaacaa cctctgctaa aattcctgaa aaattttgca  180
aaaagttgtt gactttatct acaaggtgtg gcataatgtg tggactcgac ttcgaataca  240
tccagtttta gagctagaaa tagcaagtta aaataaggct agtccgttat caacttgaaa  300
aagtggcacc gagtcggtgc gactcctgtt gatagatcca gtaatgacct cagaactcca  360
tctggatttg ttcagaacgc tcggttgccg ccgggcgttt tttattggtg agaatgtcga  420
cctcgagagt tacgctaggg ataacagggt aatataggag ctccagtcgg cttaaaccag  480
ttttcgctgg tgcgaaaaaa gagtgtcttg tgacacctaa attcaaaatc tatcggtcag  540
atttataccg atttgatttt atatattctt gaataacata cgccgagtta tcacataaaa  600
gcgggaacca atcataaaat ttaaacttca ttgcataatc cattaaactc ttaaattcta  660
cgattccttg ttcatcaata aactcaatca tttctttaat taatttatat ctatctgttg  720
ttgttttctt taataattca ttaacatcta caccgccata aactatcata tcttcttttt  780
gatatttaaa tttattagga tcgtccatgt gaagcatata tctcacaaga cctttcacac  840
ttcctgcaat ctgcggaata gtcgcattca attcttctgt taattatttt tatctgttca  900
taagatttat taccctcata catcactaga atatgataat gctctttttt catcctacct  960
tctgtatcag tatccctatc atgtaatgga gacactacaa attgaatgtg taactctttt  1020
aaatactcta accactcggc ttttgctgat tctggatata aaacaaatgt ccaattacgt  1080
cctcttgaat ttttcttgtt ttcagtttct tttattacat tttcgctcat gatataataa  1140
cggtgctaat acacttaaca aaatttagtc atagataggc agcatgccag tgctgtctat  1200
cttttttttgt ttaaaatgca ccgtattcct cctttgcata ttttttttatt agaataccgg  1260
ttgcatctga tttgctaata ttatattttt ctttgattct atttaatatc tcattttctt  1320
ctgttgtaag tcttaaagta acagcaactt ttttctcttc ttttctatct acaactatca  1380
ctgtacctcc caacatctgt ttttttcact ttaacataaa aaacaacctt ttaacattaa  1440
aaacccaata tttatttatt tgtttggaca atggacactg gacacctagg ggggaggtcg  1500
tagtaccccc ctatgttttc tcccctaaat aaccccaaaa atctaagaaa aaaagacctc  1560
aaaaaggtct ttaattaaca tctcaaattt cgcatttatt ccaatttcct ttttgcgtgt  1620
gatgcgagct catcggctcc gtcgatacta tgttatacgc caactttcaa aacaactttg  1680
aaaaagctgt ttctggtat ttaaggtttt agaatgcaag gaacagtgaa ttggagttcg  1740
tcttgttata attagcttct tggggtatct ttaaatactg tagaaaagag gaaggaaata  1800
ataaatggct aaaatgagaa tatcaccgga attgaaaaaa ctgatcgaaa aataccgctg  1860
cgtaaaagat acggaaggaa tgtctcctgc taaggtatat aagctggtgg gagaaaatga  1920
aaacctatat ttaaaaatga cggacagccg gtataaaggg accacctatg atgtggaacg  1980
ggaaaaggac atgatgctat ggctggaagg aaagctgcct gttccaaagg tcctgcactt  2040
tgaacggcat gatggctgga gcaatctgct catgagtgag gccgatggcg tcctttgctc  2100
ggaagagtat gaagatgaac aaagccctga aaagattatc gagctgtatg cggagtgcat  2160
caggctcttt cactccatcg acatatcgga ttgtccctat acgaatagct tagacagccg  2220
cttagccgaa ttggattact tactgaataa cgatctggcc gatgtggatt gcgaaaactg  2280
ggaagaagac actccattta aagatccgcg cgagctgtat gattttttaa agacggaaaa  2340
gcccgaagag gaacttgtct tttcccacgg cgacctggga gacagcaaca tctttgtgaa  2400
agatggcaaa gtaagtggct ttattgatct tgggagaagc ggcagggcgg acaagtggta  2460
tgacattgcc ttctgcgtcc ggtcgatcag ggaggatatc ggggaagaac agtatgtcga  2520
gctatttttt gacttactgg ggatcaagcc tgattgggag aaaataaaat attatatttt  2580
actggatgaa ttgttttagt gactgcagtg agatctggta atgactctct agcttgaggc  2640
atcaaataaa acgaaaggct cagtcgaaag actgggcctt tcgttttatc tgttgtttgt  2700
cggtgaacgc tctcctgagt aggacaaatc cgccgctcta gctaagcaga aggccatcct  2760
gacggatggc ctttttgcgt ttctacaaac tcttgttaac tctagagctg cctgccgcgt  2820
ttcggtgatg aagatcttcc cgatgattaa ttaattcaga acgctcggtt gccgccgggc  2880
gtttttttatg aagcttcgtt gctggcgttt ttccataggc tccgcccccc tgacgagcat  2940
cacaaaaatc gacgctcaag tcagaggtgg cgaaacccga caggactata aagataccag  3000
gcgtttcccc ctggaagctc cctcgtgcgc tctcctgttc cgaccctgcc gcttaccgga  3060
tacctgtccg cctttctccc ttcgggaagc gtggcgcttt ctcatagctc acgctgtagg  3120
tatctcagtt cggtgtaggt cgttcgctcc aagctgggct gtgtgcacga accccccgtt  3180
cagcccgacc gctgcgcctt atccggtaac tatcgtcttg agtccaaccc ggtaagacac  3240
```

```
gacttatcgc cactggcagc agccactggt aacaggatta gcagagcgag gtatgtaggc  3300
ggtgctacag agttcttgaa gtggtggcct aactacggct acactagaag gacagtattt  3360
ggtatctgcg ctctgctgaa gccagttacc ttcggaaaaa gagttggtag ctcttgatcc  3420
ggcaaacaaa ccaccgctgg tagcggtggt ttttttgttt gcaagcagca gattacgcgc  3480
agaaaaaaag gatctcaaga agatcctttg atcttttcta cggggtctga cgctcagtgg  3540
aacgaaaact cacgttaagg gattttggtc atgagattat caaaaaggat cttcacctag  3600
atccttttaa attaaaaatg aagttttaaa tcaatctaaa gtatatatga gtaaacttgg  3660
tctgacaaat ggttctttcc cctgtcctaa acaaaaaacc cgctttattg aaaaagcggg  3720
gctgttttac agacaggtca aataaacgtt tgaaaatgtt catttcaaaa cgcgcggaac  3780
ctccatcttc tcccatccag actatactgt cggcttcgga atcgcaccga atcctgccca  3840
taaaaaggct cgcgggctta gagcgcttgc tcatcaccgc cggtagggaa tttcaccctg  3900
ccccgaagat tgatcttatt tatttttaat actgatatta ttataaatta attgtgaaaa  3960
aatgtacagg tgcaaagctt attgcgctgt tttgggacat cctgcacgat atttcggtaa  4020
actcactttt tccgcatact aaaaaccgca cattcacagt tatttcattt ttaattttcg  4080
tctttccgcg tgaaactcat tgacactctt tatggaatat ggtaaattat cagatattta  4140
tgacgcttat ttaggaggaa atcttacaca gaagctgcgg aacctgaaaa gaattccttt  4200
caggttccgt ttttttagg aattctccct gatctcaagc atctggcggg gataaatccg  4260
ctctcctttc aaatcgttcc attctttgag gcgctgtaca gttacgccca tttttcggc  4320
gatatgatga agcgtatccc ctttccgcac tacatatgta ccggtcttcg attcatcgtc  4380
atgaaggcgg agtgtttggc cggccttgag atttgaatgt ttcaacccgt ttattctcat  4440
gatctcctcg atggatatac cgctatcctt gctgattctc cagagcgtgt cccctttttg  4500
aacggtcacc gcaccgctca ttgtcccggc gttttgataa acgtggatag aattttgccg  4560
gaacgcctcc tcacgaagca ccgtcagcgg attgattgca tatcttttat cttcagtcca  4620
tgaaccgtga tgcatttcaa aatgcaggtg ggttccggtc gatattcgaa ttcctccatt  4680
ttcttctgct atcaaaataa cagactcgtg attttccaaa cgagctttca aaaaagcctc  4740
tgccccttgc aaatcggatg cctgtctata aaattcccga tattggttaa acagcggcgc  4800
aatggcggcc gcatctgatg tctttgcttg gcgaatgttc atcttatttc ttcctccctc  4860
tcaataattt tttcattcta tccctttct gtaaagttta tttttcagaa tacttttatc  4920
atcatgcttt gaaaaaatat cacgataata tccattgttc tcacggaagc acacgcaggt  4980
catttgaacg aattttttcg acaggaattt gccgggactc aggagcattt aacctaaaaa  5040
agcatgacat ttcagcataa tgaacattta ctcatgtcta ttttcgttct tttctgtatg  5100
aaaatagtta tttcgagtct ctacggaaat agcgagagat gatataccta aatagagata  5160
aaatcatctc aaaaaaatgg gtctactaaa atattattcc atctattaca ataaattcac  5220
agaatagtct tttaagtaag tctactctga atttttttaa aaggagaggg taactagtgg  5280
ccccaaaaaa gaaacgcaag gttatggata aaaaatacag cattggtctg gatatcggaa  5340
ccaacagcgt tgggtgggca gtaataacag atgaatacaa agtgccgtca aaaaaattta  5400
aggttctggg gaatacagat cgccacagca taaaaaagaa tctgattggg gcattgctgt  5460
ttgattcggg tgagacagct gaggccacgc gtctgaaacg tacagcaaga agacgttaca  5520
cacgtcgtaa aaatcgtatt tgctacttac aggaaatttt ttctaacgaa atggccaagg  5580
tagatgatag tttcttccat cgtctcgaag aatctttctt ggttgaggaa gataaaaaac  5640
acgaacgtca ccctatcttt ggcaatatcg tggatgaagt ggcctatcat gaaaaatacc  5700
ctacgattta tcatcttcgc aagaagttgg ttgatagtac ggacaaagcg gatctgcgtt  5760
taatctatct tgcgttagcg cacatgatca aatttcgtgg tcatttctta attgaaggtg  5820
atctgaatcc tgataactct gatgtggaca aattgtttat acaattagtg caaacctata  5880
atcagctgtt cgaggaaaac cccattaatg cctctggagt tgatgccaaa gcgattttaa  5940
gcgcgagact ttctaagtcc cggcgtctgg agaatctgat cgcccagtta ccaggggaaa  6000
agaaaaatgg tctgtttggt aatctgattg ccctcagtct ggggcttacc ccgaacttca  6060
aatccaattt tgacctggct gaggacgcaa agctgcagct gagcaaagat acttatgatg  6120
atgacctcga caatctgctc gcccagattg gtgaccaata tgcggatctg tttctggcag  6180
cgaagaatct ttcggatgct atcttgctgt cggatattct gcgtgttaat accgaaatca  6240
ccaaagcgcc tctgtctgca agtatgatca agagatacga cgagcaccac caggacctga  6300
ctcttcttaa ggcactggta cgccaacagc ttccggagaa atacaaagaa atattcttcg  6360
accagtccaa gaatggttac gcgggctaca tcgatggtgg tgcatcacag gaagagttct  6420
ataaatttat taaaccaatc cttgagaaaa tggatggcac ggaagagtta cttgttaaac  6480
ttaaccgcga agacttgctt agaaagcaac gtacattcga caacggctcc atcccacacc  6540
agattcattt aggtgaactt cacgccatct tgcgcagaca agaagatttc tatcccttct  6600
taaaagacaa tcgggagaaa atcgagaaga tcctgacgtt ccgcattccc tattatgtcg  6660
gtcccctggc acgtggtaat tctcggtttg cctggatgac gcgcaaaagt gaggaaacca  6720
tcaccccttg gaactttgaa gaagtcgtgg ataaaggtgc tagcgcgcag tcttttatag  6780
aaagaatgac gaacttcgat aaaaacttgc ccaacgaaaa agtcctgccc aagcactctc  6840
ttttatatga gtactttact gtgtacaacg aactgactaa agtgaaatac gttacggaag  6900
gtatgcgcaa acctgccttt cttagtggcg agcagaaaaa agcaattgtc gatcttctct  6960
ttaaaacgaa tcgcaaggta actgtaaaac agctgaagga agattatttc aaaaagatcg  7020
aatgctttga ttctgtcgag atctcgggtg tcgaagatcg tttcaacgct tccttaggga  7080
cctatcatga tttgctgaag ataataaaag acaaagactt tctcgacaat gaagaaaatg  7140
aagatattct ggaggatatt gttttgacct tgaccttatt cgaagataga gagatgatcg  7200
aggagcgctt aaaaacctat gcccacctgt ttgatgacaa agtcatgaag caattaaagc  7260
gccgcagata tacggggtgg ggccgcttga gccgcaagtt gattaacggt attagagaca  7320
agcagagcgg aaaaactatc ctggatttcc tcaaatctga cggatttgcg aaccgcaatt  7380
ttatgcagct tatacatgat gattcgctta cattcaaaga ggatattcag aaggctcagg  7440
tgtctgggca aggtgattca ctccacgaac atatagcaaa tttggccggc tctcctgcga  7500
ttaagaaggg gatcctgcaa acagttaaag ttgtggatga acttgtaaaa gtaatgggcc  7560
gccacaagcc ggagaatatc gtgatagaaa tggcgcgcga gaatcaaacg acacaaaaag  7620
gtcaaaagaa ctcaagagag agaatgaagc gcattgagga ggggataaag gaacttggat  7680
ctcaaattct gaaagaacat ccagttgaaa acactcagct gcaaaatgaa aaattgtacc  7740
tgtactacct gcagaatgga agagacatgt acgtggatca ggaattggat atcaatagac  7800
tctcggacta tgacgtagat cacattgtcc ctcagagctt cctcaaggat gattctatag  7860
ataataaagt acttacgaga tcggacaaaa atcgcggtaa atcggataac gtcccatcgg  7920
aggaagtcgt taaaaagatg aaaaactatt ggcgtcaact gctgaacgcc aagctgatca  7980
```

```
cacagcgtaa gtttgataat ctgactaaag ccgaacgcgg tggtcttagt gaactcgata  8040
aagcaggatt tataaaacgg cagttagtag aaacgcgcca aattacgaaa cacgtggctc  8100
agatcctcga ttctagaatg aatacaaagt acgatgaaaa cgataaactg atccgtgaag  8160
taaaagtcat taccttaaaa tctaaacttg tgtccgattt ccgcaaagat tttcagtttt  8220
acaaggtccg ggaaatcaat aactatcacc atgcacatga tgcatattta aatgcggttg  8280
taggcacggc ccttattaag aaatacccta aactcgaaag tgagtttgtt tatggggatt  8340
ataaagtgta tgacgttcgc aaaatgatcg cgaaatcaga acaggaaatc ggtaaggcta  8400
ccgctaaata ctttttttat tccaacatta tgaatttttt taagaccgaa ataactctcg  8460
cgaatggtga aatccgtaaa cggcctctta tagaaaccaa tggtgaaacg ggagaaatcg  8520
tttgggataa aggtcgtgac tttgccaccg ttcgtaaagt cctctcaatg ccgcaagtta  8580
acattgtcaa gaagacggaa gttcaaacag gggattctc caaagaatct atcctgccga  8640
agcgtaacag tgataaactt attgccagaa aaaaagattg ggatccaaaa aaatacggag  8700
gctttgattc ccctaccgtc gcgtatagtg tgctggtggt tgctaaagtc gagaaaggga  8760
aaagcaagaa attgaaatca gttaaagaac tgctgggtat tacaattatg gaaagatcgt  8820
cctttgagaa aaatccgatc gactttttag aggccaaggg gtataaggaa gtgaaaaaag  8880
atctcatcat caaattaccg aagtatagtc tttttgagct ggaaaacggc agaaaaagaa  8940
tgctggcctc cgcgggcgag ttacagaagg gaaatgagct ggcgctgcct tccaaatatg  9000
ttaattttct gtaccttgcc agtcattatg agaaactgaa gggcagcccc gaagataacg  9060
aacagaaaca attattcgtg gaacagcata agcactattt agatgaaatt atagagcaaa  9120
ttagtgaatt ttctaagcgc gttatcctcg cggatgctaa tttagacaaa gtactgtcag  9180
cttataataa acatcgggat aagccgatta gagaacaggc cgaaaatatc attcatttgt  9240
ttaccttaac caaccttgga gcaccagctg ccttcaaata tttcgatacc acaattgatc  9300
gtaaacggta tacaagtaca aaagaagtct tggacgcaac cctcattcat caatctatta  9360
ctggattata tgagacacgc attgatcttt cacagctggg cggagacaag aagaaaaaac  9420
tgaaactgca ccatcatcac catcatcatc accatcattg ataactcgag aaagcttaca  9480
taaaaaaccg gccttggccc cgccggtttt ttattatttt tcttcctccg catgttcaat  9540
ccgctccata atcgacggat ggctccctct gaaaatttta acgagaaacg gcgggttgac  9600
ccggctcagt cccgtaacgg ccaagtcctg aaacgtctca atcgccgctt cccggtttcc  9660
ggtcagctca atgccgtaac ggtcggcggc gttttcctga taccgggaga cggcattcgt  9720
aatc                                                               9724

SEQ ID NO: 27          moltype = DNA  length = 9724
FEATURE                Location/Qualifiers
misc_feature           1..9724
                       note = pRF806 plasmid
source                 1..9724
                       mol_type = other DNA
                       organism = synthetic construct
SEQUENCE: 27
gggtgaagtg gtcaagacct cactaggcac cttaaaaata gcgcaccctg aagaagattt  60
atttgaggta gcccttgcct acctagcttc caagaaagat atcctaacag cacaagagcg  120
gaaagatgtt ttgttctaca tccagaacaa cctctgctaa aattcctgaa aaattttgca  180
aaaagttgtt gactttatct acaaggtgtg gcataatgtg tggagatgcc atcagttcct  240
catagtttta gagctagaaa tagcaagtta aaataaggct agtccgttat caacttgaaa  300
aagtggcacc gagtcggtgc gactcctgtt gatagatcca gtaatgacct cagaactcca  360
tctggatttg ttcagaacgc tcggttgccg ccgggcgttt tttattggtg agaatgtcga  420
cctcgagagt tacgctaggg ataacagggt aatataggag ctccagtcgg cttaaaccag  480
ttttcgctgg tgcgaaaaaa gagtgtcttg tgacacctaa attcaaaatc tatcggtcag  540
atttataccg atttgatttt atatattctt gaataacata cgccgagtta tcacataaaa  600
gcgggaacca atcataaaat ttaaacttca ttgcataatc cattaaactc ttaaattcta  660
cgattccttg ttcatcaata aactcaatca tttctttaat taatttatat ctatctgttg  720
ttgttttctt taataattca ttaacatcta caccgccata aactatcata tcttcttttt  780
gatatttaaa tttattagga tcgtccatgt gaagcatata tctcacaaga cctttcacac  840
ttcctgcaat ctgcggaata gtcgcattca attcttctgt taattatttt tatctgttca  900
taagatttat taccctcata catcactaga atatgataat gctctttttt catcctacct  960
tctgtatcag tatccctatc atgtaatgga gacactacaa attgaatgtg taactctttt  1020
aaatactcta accactcggc ttttgctgat tctggatata aaacaaatgt ccaattacgt  1080
cctcttgaat tttttcttgtt ttcagtttct tttattacat tttcgctcat gatataataa  1140
cggtgctaat acacttaaca aaatttagtc atagataggc agcatgccag tgctgtctat  1200
cttttttttgt ttaaaatgca ccgtattcct cctttgcata ttttttttatt agaataccgg  1260
ttgcatctga tttgctaata ttatattttt ctttgattct atttaatatc tcattttctt  1320
ctgttgtaag tcttaaagta acagcaactt ttttctcttc ttttctatct acaactatca  1380
ctgtacctcc caacatctgt ttttttcact ttaacataaa aaacaacctt ttaacattaa  1440
aaacccaata tttatttatt tgtttggaca atggacactg gacacctagg ggggaggtcg  1500
tagtaccccc ctatgtttc tcccctaaat aaccccaaaa atctaagaaa aaaagacctc  1560
aaaaaggtct ttaattaaca tctcaaattt cgcatttatt ccaatttcct ttttgcgtgt  1620
gatgcgagct catcggctcc gtcgatacta tgttatacgc caactttcaa aacaactttg  1680
aaaaagctgt ttctggtat ttaaggtttt agaatgcaag gaacagtgaa ttggagttcg  1740
tcttgttata attagcttct tggggtatct ttaaatactg tagaaaagag gaaggaaata  1800
ataaatggct aaaatgagaa tatcaccgga attgaaaaaa ctgatcgaaa aataccgctg  1860
cgtaaaagat acggaaggaa tgtctcctgc taaggtatat aagctggtgg gagaaaatga  1920
aaacctatat ttaaaaatga cggacagccg gtataaaggg accacctatg atgtggaacg  1980
ggaaaaggac atgatgctat ggctggaagg aaagctgcct gttccaaagg tcctgcactt  2040
tgaacggcat gatggctgga gcaatctgct catgagtgag gccgatggcg tcctttgctc  2100
ggaagagtat gaagatgaac aaagccctga aaagattatc gagctgtatg cggagtgcat  2160
caggctcttt cactccatcg acatatcgga ttgtccctat acgaatagct tagacagccg  2220
cttagccgaa ttggattact tactgaataa cgatctggcc gatgtggatt gcgaaaactg  2280
ggaagaagac actccattta aagatccgcg cgagctgtat gatttttttaa agacggaaaa  2340
gcccgaagag gaacttgtct tttcccacgg cgacctggga gacagcaaca tctttgtgaa  2400
```

-continued

```
agatggcaaa gtaagtggct ttattgatct tgggagaagc ggcagggcgg acaagtggta  2460
tgacattgcc ttctgcgtcc ggtcgatcag ggaggatatc ggggaagaac agtatgtcga  2520
gctatttttt gacttactgg ggatcaagcc tgattgggag aaaataaaat attatatttt  2580
actggatgaa ttgttttagt gactgcagtg agatctggta atgactctct agcttgaggc  2640
atcaaataaa acgaaaggct cagtcgaaag actgggcctt tcgttttatc tgttgtttgt  2700
cggtgaacgc tctcctgagt aggacaaatc cgccgctcta gctaagcaga aggccatcct  2760
gacggatggc ctttttgcgt ttctacaaac tcttgttaac tctagagctg cctgccgcgt  2820
ttcggtgatg aagatcttcc cgatgattaa ttaattcaga acgctcggtt gccgccgggc  2880
gtttttttatg aagcttcgtt gctggcgttt ttccataggc tccgcccccc tgacgagcat  2940
cacaaaaatc gacgctcaag tcagaggtgg cgaaacccga caggactata aagataccag  3000
gcgtttcccc ctggaagctc cctcgtgcgc tctcctgttc cgaccctgcc gcttaccgga  3060
tacctgtccg cctttctccc ttcgggaagc gtggcgcttt ctcatagctc acgctgtagg  3120
tatctcagtt cggtgtaggt cgttcgctcc aagctgggct gtgtgcacga accccccgtt  3180
cagcccgacc gctgcgcctt atccggtaac tatcgtcttg agtccaaccc ggtaagacac  3240
gacttatcgc cactggcagc agccactggt aacaggatta gcagagcgag gtatgtaggc  3300
ggtgctacag agttcttgaa gtggtggcct aactacggct acactagaag gacagtattt  3360
ggtatctgcg ctctgctgaa gccagttacc ttcggaaaaa gagttggtag ctcttgatcc  3420
ggcaaacaaa ccaccgctgg tagcggtggt ttttttgttt gcaagcagca gattacgcgc  3480
agaaaaaaag gatctcaaga agatcctttg atcttttcta cggggtctga cgctcagtgg  3540
aacgaaaact cacgttaagg gattttggtc atgagattat caaaaaggat cttcacctag  3600
atccttttaa attaaaaatg aagttttaaa tcaatctaaa gtatatatga gtaaacttgg  3660
tctgacattg atattcagca ccctgcgcat ttcgaccggg agaacgactc tgccgagctc  3720
atcgattctc cggacaatcc cggtattttt cacgtttgaa aagcctcctt ttctcctttc  3780
tttattgact tttgtcaaca tctttataat aaaagagatc ttcaaatttt ttgttgaaat  3840
actgaatcat ctttccgatc acaagttgtc cgggcctcct ttcgccattt aaaactctgc  3900
tgagtgtcgc cggggatacg ccgatttcaa tggcaagctg atttaaggag agattgtgtt  3960
caatcatgta ctggagaaca aaatctcttt tgatatgaat ctttttttacc atgattactc  4020
ccctttctaa tctcttatgt ttcttttttat ctacattgaa catatacgat ttgttaactt  4080
ttgtcaatac ttttaccatc catatgtttc ctataggcaa tattcgtact aaaatatttt  4140
ataataagag attgcgaggt tttggccata cttctccgcg gcacactctc ctctctatca  4200
ttttcgtctg tttacgatcc tgctgttatt ttatccctta tgttaacttt tgtcaatatt  4260
tttcctgtct aagtatttcc tatagtcaac atttgtatta aaatgttcat atcatgaatt  4320
tgcggggggg atggcgatga caaggttcgg cgagcggctc aaagagctga gggaacaaag  4380
aagcctgtcg gttaatcagc ttgccatgta tgccggtgtg agcgccgcag ccatttccag  4440
agccgcagcc atttccagaa tcgaaaacgg ccaccgcggc gttcccaagc ccgcgacgat  4500
cagaaaattg gccgaggctc tgaaaatgcc gtacgagcag ctcatggata ttgccggtta  4560
tatgagagct gacgagattc gcgaacagcc gcgcggctat gtcacgatgc aggagatcgc  4620
ggccaagcac ggcgtcgaag acctgtggct gtttaaaccc gagaaatgaa ttcctccatt  4680
ttcttctgct atcaaaataa cagactcgtg attttccaaa cgagctttca aaaaagcctc  4740
tgccccttgc aaatcggatg cctgtctata aaattcccga tattggttaa acagcggcgc  4800
aatggcggcc gcatctgatg tctttgcttg gcgaatgttc atcttatttc ttcctccctc  4860
tcaataattt tttcattcta tcccttttct gtaaagttta tttttcagaa tacttttatc  4920
atcatgcttt gaaaaaatat cacgataata tccattgttc tcacggaagc acacgcaggt  4980
catttgaacg aatttttttcg acaggaattt gccgggactc aggagcattt aacctaaaaa  5040
agcatgacat ttcagcataa tgaacattta ctcatgtcta ttttcgttct tttctgtatg  5100
aaaatagtta tttcgagtct ctacggaaat agcgagagat gatataccta aatagagata  5160
aaatcatctc aaaaaaatgg gtctactaaa atattattcc atctattaca ataaattcac  5220
agaatagtct tttaagtaag tctactctga attttttttaa aaggagaggg taactagtgg  5280
ccccaaaaaa gaaacgcaag gttatggata aaaaatacag cattggtctg gatatcggaa  5340
ccaacagcgt tgggtgggca gtaataacag atgaatacaa agtgccgtca aaaaaattta  5400
aggttctggg gaatacagat cgccacagca taaaaaagaa tctgattggg gcattgctgt  5460
ttgattcggg tgagacagct gaggccacgc gtctgaaacg tacagcaaga agacgttaca  5520
cacgtcgtaa aaatcgtatt tgctacttac aggaaatttt ttctaacgaa atggccaagg  5580
tagatgatag tttcttccat cgtctcgaag aatcttttct ggttgaggaa gataaaaaac  5640
acgaacgtca ccctatcttt ggcaatatcg tggatgaagt ggcctatcat gaaaaatacc  5700
ctacgattta tcatcttcgc aagaagttgg ttgatagtac ggacaaagcg gatctgcgtt  5760
taatctatct tgcgttagcg cacatgatca aatttcgtgg tcatttctta attgaaggtg  5820
atctgaatcc tgataactct gatgtggaca aattgtttat acaattagtg caaacctata  5880
atcagctgtt cgaggaaaac cccattaatg cctctggagt tgatgccaaa gcgattttaa  5940
gcgcgagact ttctaagtcc cggcgtctgg agaatctgat cgcccagtta ccaggggaaa  6000
agaaaaatgg tctgtttggt aatctgattg ccctcagtct ggggcttacc ccgaacttca  6060
aatccaattt tgacctggct gaggacgcaa agctgcagct gagcaaagat acttatgatg  6120
atgacctcga caatctgctc gcccagattg gtgaccaata tgcggatctg tttctggcag  6180
cgaagaatct ttcggatgct atcttgctgt cggatattct gcgtgttaat accgaaatca  6240
ccaaagcgcc tctgtctgca agtatgatca agagatacga cgagcaccac caggacctga  6300
ctcttcttaa ggcactggta cgccaacagc ttccggagaa atacaaagaa atattcttcg  6360
accagtccaa gaatggttac gcgggctaca tcgatggtgg tgcatcacag gaagagttct  6420
ataaatttat taaaccaatc cttgagaaaa tggatggcac ggaagagtta cttgttaaac  6480
ttaaccgcga agacttgctt agaaagcaac gtacattcga caacggctcc atcccacacc  6540
agattcattt aggtgaactt cacgccatct tgcgcagaca agaagatttc tatcccttct  6600
taaaagacaa tcgggagaaa atcgagaaga tcctgacgtt ccgcattccc tattatgtcg  6660
gtcccctggc acgtggtaat tctcggtttg cctggatgac gcgcaaaagt gaggaaacca  6720
tcacccottg gaactttgaa gaagtcgtgg ataaaggtgc tagcgcgcag tcttttatag  6780
aaagaatgac gaacttcgat aaaaacttgc ccaacgaaaa agtcctgccc aagcactctc  6840
ttttatatga gtactttact gtgtacaacg aactgactaa agtgaaatac gttacggaag  6900
gtatgcgcaa acctgccttt cttagtggcg agcagaaaaa agcaattgtc gatcttctct  6960
ttaaaacgaa tcgcaaggta actgtaaaac agctgaagga agattatttc aaaaagatcg  7020
aatgctttga ttctgtcgag atctcgggtg tcgaagatcg tttcaacgct tccttaggga  7080
cctatcatga tttgctgaag ataataaaag acaaagactt tctcgacaat gaagaaaatg  7140
```

```
aagatattct ggaggatatt gttttgacct tgaccttatt cgaagataga gagatgatcg  7200
aggagcgctt aaaaacctat gcccacctgt ttgatgacaa agtcatgaag caattaaagc  7260
gccgcagata tacggggtgg ggccgcttga gccgcaagtt gattaacggt attagagaca  7320
agcagagcgg aaaaactatc ctggatttcc tcaaatctga cggatttgcg aaccgcaatt  7380
ttatgcagct tatacatgat gattcgctta cattcaaaga ggatattcag aaggctcagg  7440
tgtctgggca aggtgattca ctccacgaac atatagcaaa tttggccggc tctcctgcga  7500
ttaagaaggg gatcctgcaa acagttaaag ttgtggatga acttgtaaaa gtaatgggcc  7560
gccacaagcc ggagaatatc gtgatagaaa tggcgcgcga gaatcaaacg acacaaaaag  7620
gtcaaaagaa ctcaagagag agaatgaagc gcattgagga ggggataaag gaacttggat  7680
ctcaaattct gaaagaacat ccagttgaaa acactcagct gcaaaatgaa aaattgtacc  7740
tgtactacct gcagaatgga agagacatgt acgtggatca ggaattggat atcaatagac  7800
tctcggacta tgacgtagat cacattgtcc ctcagagctt cctcaaggat gattctatag  7860
ataataaagt acttacgaga tcggacaaaa atcgcggtaa atcggataac gtcccatcgg  7920
aggaagtcgt taaaaagatg aaaaactatt ggcgtcaact gctgaacgcc aagctgatca  7980
cacagcgtaa gtttgataat ctgactaaag ccgaacgcgg tggtcttagt gaactcgata  8040
aagcaggatt tataaaacgg cagttagtag aaacgcgcca aattacgaaa cacgtggctc  8100
agatcctcga ttctagaatg aatacaaagt acgatgaaaa cgataaactg atccgtgaag  8160
taaaagtcat taccttaaaa tctaaacttg tgtccgattt ccgcaaagat tttcagtttt  8220
acaaggtccg ggaaatcaat aactatcacc atgcacatga tgcatattta aatgcggttg  8280
taggcacggc ccttattaag aaatacccta aactcgaaag tgagtttgtt tatggggatt  8340
ataaagtgta tgacgttcgc aaaatgatcg cgaaatcaga acaggaaatc ggtaaggcta  8400
ccgctaaata ctttttttat tccaacatta tgaatttttt taagaccgaa ataactctcg  8460
cgaatggtga aatccgtaaa cggcctctta tagaaaccaa tggtgaaacg ggagaaatcg  8520
tttgggataa aggtcgtgac tttgccaccg ttcgtaaagt cctctcaatg ccgcaagtta  8580
acattgtcaa gaagacggaa gttcaaacag gggggattctc caaagaatct atcctgccga  8640
agcgtaacag tgataaactt attgccagaa aaaaagattg ggatccaaaa aaatacggag  8700
gctttgattc ccctaccgtc gcgtatagtg tgctggtggt tgctaaagtc gagaaaggga  8760
aaagcaagaa attgaaatca gttaaagaac tgctgggtat tacaattatg gaaagatcgt  8820
cctttgagaa aaatccgatc gactttttag aggccaaggg gtataaggaa gtgaaaaaag  8880
atctcatcat caaattaccg aagtatagtc tttttgagct ggaaaacggc agaaaaagaa  8940
tgctggcctc cgcgggcgag ttacagaagg gaaatgagct ggcgctgcct tccaaatatg  9000
ttaattttct gtaccttgcc agtcattatg agaaactgaa gggcagcccc gaagataacg  9060
aacagaaaca attattcgtg gaacagcata agcactattt agatgaaatt atagagcaaa  9120
ttagtgaatt ttctaagcgc gttatcctcg cggatgctaa tttagacaaa gtactgtcag  9180
cttataataa acatcgggat aagccgatta gagaacaggc cgaaaatatc attcatttgt  9240
ttaccttaac caaccttgga gcaccagctg ccttcaaata tttcgatacc acaattgatc  9300
gtaaacggta tacaagtaca aaagaagtct tggacgcaac cctcattcat caatctatta  9360
ctggattata tgagacacgc attgatcttt cacagctggg cggagacaag aagaaaaaac  9420
tgaaactgca ccatcatcac catcatcatc accatcattg ataactcgag aaagcttaca  9480
taaaaaaccg gccttggccc cgccggtttt ttattatttt tcttcctccg catgttcaat  9540
ccgctccata atcgacggat ggctccctct gaaaatttta acgagaaacg gcgggttgac  9600
ccggctcagt cccgtaacgg ccaagtcctg aaacgtctca atcgccgctt cccggtttcc  9660
ggtcagctca atgccgtaac ggtcggcggc gttttcctga taccgggaga cggcattcgt  9720
aatc                                                              9724
```

```
SEQ ID NO: 28           moltype = DNA  length = 20
FEATURE                 Location/Qualifiers
source                  1..20
                        mol_type = unassigned DNA
                        organism = Bacillus licheniformis
SEQUENCE: 28
ctcgacttcg aatacatcca                                             20

SEQ ID NO: 29           moltype = DNA  length = 20
FEATURE                 Location/Qualifiers
source                  1..20
                        mol_type = unassigned DNA
                        organism = Bacillus licheniformis
SEQUENCE: 29
gatgccatca gttcctcata                                             20

SEQ ID NO: 30           moltype = DNA  length = 1578
FEATURE                 Location/Qualifiers
source                  1..1578
                        mol_type = unassigned DNA
                        organism = Bacillus licheniformis
SEQUENCE: 30
atgtttcgag tattggtctc agataaaatg tccagcgacg gcctcaaacc attaatggaa  60
gcagatttta ttgaaattgt agaaaagaat gttgcggaag cggaagacga gcttcatacg  120
tttgacgcgc tcttggtgcg gagcgccacg aaggtaaccg aagagctgtt taaaaagatg  180
acttcgctga aaatcgtcgc cagagcaggt gtcggcgtcg acaatatcga tattgacgag  240
gcgacaaaac acggtgttat cgtcgtaaac gcgccaaacg ggaatacaat ttcaaccgct  300
gaacatacct ttgcaatgtt ttcagcgtta atgagacata ttccgcaggc aaacatctcc  360
gtgaaatcaa gggagtggaa tcgttcggct tacgtcggtt cagagcttta cggaaaaacg  420
ctcggcatca tcggaatggg ccgcatcgga agcgaaatcg cgagccgcgc aaaagcattc  480
ggtatgaccg ttcatgtatt tgacccgttc ctgacccaag aaagggcaag caagctcggc  540
gttaacgcga acagctttga agaagttctg gcatgcgccg acatcattac ggttcatacc  600
ccgctcacga aagaaacgaa gggacttttg aacaaagaaa ccatcgcaaa aacgaaaaaa  660
ggcgttcgtc tcgttaactg tgcaagaggc ggcatcatcg atgaagcagc gcttttggaa  720
```

```
gctctggaaa gcggacatgt cgctggcgct gccttggatg tattcgaagt cgagcctccg  780
gtcgattcaa aactgatcga tcatccgctt gtagtcgcga ctcctcactt gggcgcctca  840
acaaaagaag cccagctgaa tgtcgctgca caagtgtccg aagaagtcct tcagtatgcg  900
caaggaaacc ctgtgatgtc cgcgatcaac cttccggcca tgacaaagga ttcattcgaa  960
aaaatccagc cttatcatca gtttgccaat acgatcggaa accttgtgtc tcagtgcatg  1020
aatgagcctg ttcaagatgt agccatccaa tatgaaggct ccatcgccaa acttgaaacg  1080
tcatttatta cgaaaagcct tttggccgga tttctgaagc cgagggtcgc ggctaccgtt  1140
aacgaagtga atgccggcac cgttgcgaaa gagcgcggca tcagcttcag cgaaaaaatt  1200
tcttccaatg agtcaggcta tgaaaactgc atctctgtga ctgtcacggg agatgtaaca  1260
acattctctt taagagcgac gtacattccg cacttcggcg gacgcatcgt tgccttaaac  1320
ggctttgata ttgattttta tccggctgga caccttgtct acattcacca ccaggataaa  1380
ccaggggcta tcggccatgt cggacgaatt ttaggagacc atgacatcaa tatcgccact  1440
atgcaggtag gccgaaaaga aaaaggcgga gaagcgatca tgatgctttc ctttgaccgc  1500
caccttgagg acgatatttt agctgagctg aaaaacatcc cggatatcgt gtctgttaaa  1560
gccatcgacc ttccttaa                                                1578

SEQ ID NO: 31           moltype = DNA  length = 23
FEATURE                 Location/Qualifiers
source                  1..23
                        mol_type = unassigned DNA
                        organism = Bacillus licheniformis
SEQUENCE: 31
ctcgacttcg aatacatcca agg                                          23

SEQ ID NO: 32           moltype = DNA  length = 20
FEATURE                 Location/Qualifiers
misc_feature            1..20
                        note = synthesized DNA encoding variable targeting domain
source                  1..20
                        mol_type = other DNA
                        organism = synthetic construct
SEQUENCE: 32
ctcgacttcg aatacatcca                                              20

SEQ ID NO: 33           moltype = DNA  length = 76
FEATURE                 Location/Qualifiers
misc_feature            1..76
                        note = synthesized DNA encoding CER domain
source                  1..76
                        mol_type = other DNA
                        organism = synthetic construct
SEQUENCE: 33
gttttagagc tagaaatagc aagttaaaat aaggctagtc cgttatcaac ttgaaaaagt  60
ggcaccgagt cggtgc                                                  76

SEQ ID NO: 34           moltype = RNA  length = 96
FEATURE                 Location/Qualifiers
misc_feature            1..96
                        note = synthesized gRNA targeting target site 1
source                  1..96
                        mol_type = other RNA
                        organism = synthetic construct
SEQUENCE: 34
ctcgacttcg aatacatcca gttttagagc tagaaatagc aagttaaaat aaggctagtc  60
cgttatcaac ttgaaaaagt ggcaccgagt cggtgc                            96

SEQ ID NO: 35           moltype = DNA  length = 224
FEATURE                 Location/Qualifiers
misc_feature            1..224
                        note = synthesized spac promoter
source                  1..224
                        mol_type = other DNA
                        organism = synthetic construct
SEQUENCE: 35
gggtgaagtg gtcaagacct cactaggcac cttaaaaata gcgcaccctg aagaagattt  60
atttgaggta gcccttgcct acctagcttc caagaaagat atcctaacag cacaagagcg  120
gaaagatgtt ttgttctaca tccagaacaa cctctgctaa aattcctgaa aaattttgca  180
aaaagttgtt gactttatct acaaggtgtg gcataatgtg tgga                   224

SEQ ID NO: 36           moltype = DNA  length = 95
FEATURE                 Location/Qualifiers
misc_feature            1..95
                        note = synthesized t0 terminator
source                  1..95
                        mol_type = other DNA
                        organism = synthetic construct
SEQUENCE: 36
gactcctgtt gatagatcca gtaatgacct cagaactcca tctggatttg ttcagaacgc  60
tcggttgccg ccgggcgttt tttattggtg agaat                             95
```

```
SEQ ID NO: 37          moltype = DNA  length = 500
FEATURE                Location/Qualifiers
source                 1..500
                       mol_type = unassigned DNA
                       organism = Bacillus licheniformis
SEQUENCE: 37
aatggttctt tcccctgtcc taaacaaaaa acccgcttta ttgaaaaagc ggggctgttt  60
tacagacagg tcaaataaac gtttgaaaat gttcatttca aaacgcgcgg aacctccatc  120
ttctcccatc cagactatac tgtcggcttc ggaatcgcac cgaatcctgc ccataaaaag  180
gctcgcgggc ttagagcgct tgctcatcac cgccggtagg gaatttcacc ctgccccgaa  240
gattgatctt atttattttt aatactgata ttattataaa ttaattgtga aaaaatgtac  300
aggtgcaaag cttattgcgc tgttttggga catcctgcac gatatttcgg taaactcact  360
ttttccgcat actaaaaacc gcacattcac agttatttca tttttaattt tcgtctttcc  420
gcgtgaaact cattgacact ctttatggaa tatggtaaat tatcagatat ttatgacgct  480
tatttaggag gaaatcttac                                              500

SEQ ID NO: 38          moltype = DNA  length = 40
FEATURE                Location/Qualifiers
misc_feature           1..40
                       note = serA1 homology arm 1 forward primer
source                 1..40
                       mol_type = other DNA
                       organism = synthetic construct
SEQUENCE: 38
tgagtaaact tggtctgaca aatggttctt tcccctgtcc                        40

SEQ ID NO: 39          moltype = DNA  length = 46
FEATURE                Location/Qualifiers
misc_feature           1..46
                       note = serA1 homology arm 1 forward primer
source                 1..46
                       mol_type = other DNA
                       organism = synthetic construct
SEQUENCE: 39
aggttccgca gcttctgtgt aagatttcct cctaaataag cgtcat                 46

SEQ ID NO: 40          moltype = DNA  length = 500
FEATURE                Location/Qualifiers
source                 1..500
                       mol_type = unassigned DNA
                       organism = Streptococcus pyogenes
SEQUENCE: 40
acagaagctg cggaacctga aaagaattcc tttcaggttc cgtttttttt aggaattctc  60
cctgatctca agcatctggc ggggataaat ccgctctcct ttcaaatcgt tccattcttt  120
gaggcgctgt acagttacgc ccatttttttc ggcgatatga tgaagcgtat cccctttccg  180
cactacatat gtaccggtct tcgattcatc gtcatgaagg cggagtgttt ggccggcctt  240
gagatttgaa tgtttcaacc cgtttattct catgatctcc tcgatggata taccgctatc  300
cttgctgatt ctccagagcg tgtccccttt ttgaacggtc accgcaccgc tcattgtccc  360
ggcgttttga taaacgtgga tagaattttg ccggaacgcc tcctcacgaa gcaccgtcag  420
cggattgatt gcatatcttt tatcttcagt ccatgaaccg tgatgcattt caaaatgcag  480
gtgggttccg gtcgatattc                                              500

SEQ ID NO: 41          moltype = DNA  length = 46
FEATURE                Location/Qualifiers
misc_feature           1..46
                       note = serA1 homology arm 2 forward primer
source                 1..46
                       mol_type = other DNA
                       organism = synthetic construct
SEQUENCE: 41
atgacgctta tttaggagga aatcttacac agaagctgcg gaacct                 46

SEQ ID NO: 42          moltype = DNA  length = 41
FEATURE                Location/Qualifiers
misc_feature           1..41
                       note = serA1 homology arm 2 reverse primer
source                 1..41
                       mol_type = other DNA
                       organism = synthetic construct
SEQUENCE: 42
cagaagaaaa tggaggaatt cgaatatcga ccggaaccca c                      41

SEQ ID NO: 43          moltype = DNA  length = 415
FEATURE                Location/Qualifiers
misc_feature           1..415
                       note = DNA encoding ts1 gRNA expression cassette
source                 1..415
                       mol_type = other DNA
```

```
                         organism = synthetic construct
SEQUENCE: 43
gggtgaagtg gtcaagacct cactaggcac cttaaaaata gcgcaccctg aagaagattt  60
atttgaggta gcccttgcct acctagcttc caagaaagat atcctaacag cacaagagcg  120
gaaagatgtt ttgttctaca tccagaacaa cctctgctaa aattcctgaa aaattttgca  180
aaaagttgtt gactttatct acaaggtgtg gcataatgtg tggactcgac ttcgaataca  240
tccagtttta gagctagaaa tagcaagtta aaataaggct agtccgttat caacttgaaa  300
aagtggcacc gagtcggtgc gactcctgtt gatagatcca gtaatgacct cagaactcca  360
tctggatttg ttcagaacgc tcggttgccg ccgggcgttt tttattggtg agaat       415

SEQ ID NO: 44            moltype = DNA  length = 1000
FEATURE                  Location/Qualifiers
misc_feature             1..1000
                         note = serA1 deletion editing template
source                   1..1000
                         mol_type = other DNA
                         organism = synthetic construct
SEQUENCE: 44
aatggttctt tcccctgtcc taaacaaaaa acccgcttta ttgaaaaagc ggggctgttt  60
tacagacagg tcaaataaac gtttgaaaat gttcatttca aaacgcgcgg aacctccatc  120
ttctcccatc cagactatac tgtcggcttc ggaatcgcac cgaatcctgc ccataaaaag  180
gctcgcgggc ttagagcgct tgctcatcac cgccggtagg gaatttcacc ctgccccgaa  240
gattgatctt atttattttt aatactgata ttattataaa ttaattgtga aaaaatgtac  300
aggtgcaaag cttattgcgc tgttttggga catcctgcac gatatttcgg taaactcact  360
ttttccgcat actaaaaacc gcacattcac agttatttca tttttaattt tcgtctttcc  420
gcgtgaaact cattgacact ctttatggaa tatggtaaat tatcagatat ttatgacgct  480
tatttaggag gaaatcttac acagaagctg cggaacctga aaagaattcc tttcaggttc  540
cgtttttttt aggaattctc cctgatctca agcatctggc ggggataaat ccgctctcct  600
ttcaaatcgt tccattcttt gaggcgctgt acagttacgc ccattttttc ggcgatatga  660
tgaagcgtat ccccttttccg cactacatat gtaccggtct tcgattcatc gtcatgaagg  720
cggagtgttt ggccggcctt gagatttgaa tgtttcaacc cgtttattct catgatctcc  780
tcgatggata taccgctatc cttgctgatt ctccagagcg tgtccccttt ttgaacggtc  840
accgcaccgc tcattgtccc ggcgttttga taaacgtgga tagaattttg ccggaacgcc  900
tcctcacgaa gcaccgtcag cggattgatt gcatatcttt tatcttcagt ccatgaaccg  960
tgatgcattt caaaatgcag gtgggttccg gtcgatattc                       1000

SEQ ID NO: 45            moltype = DNA  length = 402
FEATURE                  Location/Qualifiers
source                   1..402
                         mol_type = unassigned DNA
                         organism = Streptococcus pyogenes
SEQUENCE: 45
atgacgaact ttggacacca tttacgacaa ttaagggaac ggaaaaaact gaccgtcaat  60
caactggcga tgtattccgg cgtcagttcg gcaggcattt cgcgaatcga aaacggaaag  120
cgcggcgtgc cgaagccggc gacgatcaga aaactggcgg acgctttgaa agtcccgtat  180
gaggaactga tggcatctgc aggctatatc agcgcgtcta cagtccagga agcaagaagc  240
agctatgatt ccatttacga catcgtgtca cagtacgatt tagaggacct ttctctgttt  300
gacagcgaaa agtggaaggt gctttcaaaa aaagacatcg aaaacctgga caaatatttc  360
gactttctcg tgcaggaagc aagcagccga aacaaaaact ga                     402

SEQ ID NO: 46            moltype = DNA  length = 20
FEATURE                  Location/Qualifiers
source                   1..20
                         mol_type = unassigned DNA
                         organism = Streptococcus pyogenes
SEQUENCE: 46
gatgccatca gttcctcata                                              20

SEQ ID NO: 47            moltype = DNA  length = 23
FEATURE                  Location/Qualifiers
source                   1..23
                         mol_type = unassigned DNA
                         organism = Streptococcus pyogenes
SEQUENCE: 47
gatgccatca gttcctcata cgg                                          23

SEQ ID NO: 48            moltype = DNA  length = 20
FEATURE                  Location/Qualifiers
misc_feature             1..20
                         note = synthesized DNA encoding variable targeting domain 2
source                   1..20
                         mol_type = other DNA
                         organism = synthetic construct
SEQUENCE: 48
gatgccatca gttcctcata                                              20

SEQ ID NO: 49            moltype = RNA  length = 96
FEATURE                  Location/Qualifiers
misc_feature             1..96
```

```
                       note = synthesized gRNA targeting target site 2
source                 1..96
                       mol_type = other RNA
                       organism = synthetic construct
SEQUENCE: 49
gatgccatca gttcctcata gttttagagc tagaaatagc aagttaaaat aaggctagtc  60
cgttatcaac ttgaaaaagt ggcaccgagt cggtgc                            96

SEQ ID NO: 50          moltype = DNA  length = 500
FEATURE                Location/Qualifiers
source                 1..500
                       mol_type = unassigned DNA
                       organism = Bacillus licheniformis
SEQUENCE: 50
ttgatattca gcaccctgcg catttcgacc gggagaacga ctctgccgag ctcatcgatt  60
ctccggacaa tcccggtatt tttcacgttt gaaaagcctc cttttctcct ttctttattg  120
acttttgtca acatctttat aataaaagag atcttcaaat tttttgttga aatactgaat  180
catctttccg atcacaagtt gtccgggcct cctttcgcca tttaaaactc tgctgagtgt  240
cgccggggat acgccgattt caatggcaag ctgatttaag gagagattgt gttcaatcat  300
gtactggaga acaaaatctc ttttgatatg aatctttttt accatgatta ctcccctttc  360
taatctctta tgtttctttt tatctacatt gaacatatac gatttgttaa cttttgtcaa  420
tacttttacc atccatatgt ttcctatagg caatattcgt actaaaatat tttataataa  480
gagattgcga ggttttggcc                                              500

SEQ ID NO: 51          moltype = DNA  length = 40
FEATURE                Location/Qualifiers
misc_feature           1..40
                       note = rghR1 homology arm 1 forward primer
source                 1..40
                       mol_type = other DNA
                       organism = synthetic construct
SEQUENCE: 51
tgagtaaact tggtctgaca ttgatattca gcaccctgcg                        40

SEQ ID NO: 52          moltype = DNA  length = 38
FEATURE                Location/Qualifiers
misc_feature           1..38
                       note = rghR1 homology arm 1 reverse primer
source                 1..38
                       mol_type = other DNA
                       organism = synthetic construct
SEQUENCE: 52
tgtgccgcgg agaagtatgg ccaaaacctc gcaatctc                          38

SEQ ID NO: 53          moltype = DNA  length = 500
FEATURE                Location/Qualifiers
source                 1..500
                       mol_type = unassigned DNA
                       organism = Streptococcus pyogenes
SEQUENCE: 53
atacttctcc gcggcacact ctcctctcta tcattttcgt ctgtttacga tcctgctgtt  60
attttatccc ttatgttaac ttttgtcaat atttttcctg tctaagtatt tcctatagtc  120
aacatttgta ttaaaatgtt catatcatga atttgcgggg gggatggcga tgacaaggtt  180
cggcgagcgg ctcaaagagc tgagggaaca aagaagcctg tcggttaatc agcttgccat  240
gtatgccggt gtgagcgccg cagccatttc cagagccgca gccatttcca gaatcgaaaa  300
cggccaccgc ggcgttccca agcccgcgac gatcagaaaa ttggccgagg ctctgaaaat  360
gccgtacgag cagctcatgg atattgccgg ttatatgaga gctgacgaga ttcgcgaaca  420
gccgcgcggc tatgtcacga tgcaggagat cgcggccaag cacggcgtcg aagacctgtg  480
gctgtttaaa cccgagaaat                                              500

SEQ ID NO: 54          moltype = DNA  length = 38
FEATURE                Location/Qualifiers
misc_feature           1..38
                       note = rghR1 homology arm 2 forward primer
source                 1..38
                       mol_type = other DNA
                       organism = synthetic construct
SEQUENCE: 54
gagattgcga ggttttggcc atacttctcc gcggcaca                          38

SEQ ID NO: 55          moltype = DNA  length = 44
FEATURE                Location/Qualifiers
misc_feature           1..44
                       note = rghR1 homology arm 2 reverse primer
source                 1..44
                       mol_type = other DNA
                       organism = synthetic construct
SEQUENCE: 55
cagaagaaaa tggaggaatt catttctcgg gtttaaacag ccac                   44
```

```
SEQ ID NO: 56          moltype = DNA  length = 415
FEATURE                Location/Qualifiers
misc_feature           1..415
                       note = DNA encoding ts2 expression cassette
source                 1..415
                       mol_type = other DNA
                       organism = synthetic construct
SEQUENCE: 56
gggtgaagtg gtcaagacct cactaggcac cttaaaaata gcgcaccctg aagaagattt  60
atttgaggta gcccttgcct acctagcttc caagaaagat atcctaacag cacaagagcg  120
gaaagatgtt ttgttctaca tccagaacaa cctctgctaa aattcctgaa aaattttgca  180
aaaagttgtt gactttatct acaaggtgtg gcataatgtg tggagatgcc atcagttcct  240
catagtttta gagctagaaa tagcaagtta aaataaggct agtccgttat caacttgaaa  300
aagtggcacc gagtcggtgc gactcctgtt gatagatcca gtaatgacct cagaactcca  360
tctggatttg ttcagaacgc tcggttgccg ccgggcgttt tttattggtg agaat       415

SEQ ID NO: 57          moltype = DNA  length = 1000
FEATURE                Location/Qualifiers
misc_feature           1..1000
                       note = synthesized rghR1 deletion editing template
source                 1..1000
                       mol_type = other DNA
                       organism = synthetic construct
SEQUENCE: 57
ttgatattca gcaccctgcg catttcgacc gggagaacga ctctgccgag ctcatcgatt  60
ctccggacaa tcccggtatt tttcacgttt gaaaagcctc cttttctcct ttctttattg  120
acttttgtca acatctttat aataaaagag atcttcaaat tttttgttga aatactgaat  180
catctttccg atcacaagtt gtccgggcct cctttcgcca tttaaaactc tgctgagtgt  240
cgccggggat acgccgattt caatggcaag ctgatttaag gagagattgt gttcaatcat  300
gtactggaga acaaaatctc ttttgatatg aatctttttt accatgatta ctccccttc  360
taatctctta tgtttctttt tatctacatt gaacatatac gatttgttaa cttttgtcaa  420
tacttttacc atccatatgt ttcctatagg caatattcgt actaaaatat tttataataa  480
gagattgcga ggttttggcc atacttctcc gcggcacact ctcctctcta tcattttcgt  540
ctgtttacga tcctgctgtt attttatccc ttatgttaac ttttgtcaat atttttcctg  600
tctaagtatt tcctatagtc aacatttgta ttaaaatgtt catatcatga atttgcgggg  660
gggatggcga tgacaaggtt cggcgagcgg ctcaaagagc tgagggaaca aagaagcctg  720
tcggttaatc agcttgccat gtatgccggt gtgagcgccg cagccatttc cagagccgca  780
gccatttcca gaatcgaaaa cggccaccgc ggcgttccca agcccgcgac gatcagaaaa  840
ttggccgagg ctctgaaaat gccgtacgag cagctcatgg atattgccgg ttatatgaga  900
gctgacgaga ttcgcgaaca gccgcgcggc tatgtcacga tgcaggagat cgcggccaag  960
cacggcgtcg aagacctgtg gctgtttaaa cccgagaaat                        1000

SEQ ID NO: 58          moltype = AA  length = 1368
FEATURE                Location/Qualifiers
REGION                 1..1368
                       note = synthesized Cas9 Y155H variant
source                 1..1368
                       mol_type = protein
                       organism = synthetic construct
SEQUENCE: 58
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIHLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 59          moltype = DNA  length = 33
FEATURE                Location/Qualifiers
misc_feature           1..33
                       note = Y155H forward primer
```

```
source                  1..33
                        mol_type = other DNA
                        organism = synthetic construct
SEQUENCE: 59
gatctgcgtt taatccatct tgcgttagcg cac                              33

SEQ ID NO: 60           moltype = DNA  length = 33
FEATURE                 Location/Qualifiers
misc_feature            1..33
                        note = Y155H reverse primer
source                  1..33
                        mol_type = other DNA
                        organism = synthetic construct
SEQUENCE: 60
gtgcgctaac gcaagatgga ttaaacgcag atc                              33

SEQ ID NO: 61           moltype = DNA  length = 9724
FEATURE                 Location/Qualifiers
misc_feature            1..9724
                        note = plasmid pRF827
source                  1..9724
                        mol_type = other DNA
                        organism = synthetic construct
SEQUENCE: 61
gggtgaagtg gtcaagacct cactaggcac cttaaaaata gcgcaccctg aagaagattt  60
atttgaggta gcccttgcct acctagcttc caagaaagat atcctaacag cacaagagcg  120
gaaagatgtt ttgttctaca tccagaacaa cctctgctaa aattcctgaa aaattttgca  180
aaaagttgtt gactttatct acaaggtgtg gcataatgtg tggactcgac ttcgaataca  240
tccagtttta gagctagaaa tagcaagtta aaataaggct agtccgttat caacttgaaa  300
aagtggcacc gagtcggtgc gactcctgtt gatagatcca gtaatgacct cagaactcca  360
tctggatttg ttcagaacgc tcggttgccg ccgggcgttt tttattggtg agaatgtcga  420
cctcgagagt tacgctaggg ataacagggt aatataggag ctccagtcgg cttaaaccag  480
ttttcgctgg tgcgaaaaaa gagtgtcttg tgacacctaa attcaaaatc tatcggtcag  540
atttataccg atttgatttt atatattctt gaataacata cgccgagtta tcacataaaa  600
gcgggaacca atcataaaat ttaaacttca ttgcataatc cattaaactc ttaaattcta  660
cgattccttg ttcatcaata aactcaatca tttctttaat taatttatat ctatctgttg  720
ttgttttctt taataattca ttaacatcta caccgccata aactatcata tcttcttttt  780
gatatttaaa tttattagga tcgtccatgt gaagcatata tctcacaaga cctttcacac  840
ttcctgcaat ctgcggaata gtcgcattca attcttctgt taattatttt tatctgttca  900
taagatttat taccctcata catcactaga atatgataat gctctttttt catcctacct  960
tctgtatcag tatccctatc atgtaatgga gacactacaa attgaatgtg taactctttt  1020
aaatactcta accactcggc ttttgctgat tctggatata aaacaaatgt ccaattacgt  1080
cctcttgaat tttcttgtt ttcagtttct tttattacat tttcgctcat gatataataa  1140
cggtgctaat acacttaaca aaatttagtc atagataggc agcatgccag tgctgtctat  1200
cttttttgt ttaaaatgca ccgtattcct cctttgcata ttttttattt agaataccgg  1260
ttgcatctga tttgctaata ttatattttt ctttgattct atttaatatc tcattttctt  1320
ctgttgtaag tcttaaagta acagcaactt ttttctcttc ttttctatct acaactatca  1380
ctgtacctcc caacatctgt ttttttcact ttaacataaa aaacaacctt ttaacattaa  1440
aaacccaata tttatttatt tgtttggaca atggacactg gacacctagg ggggaggtcg  1500
tagtaccccc ctatgtttc tcccctaaat aaccccaaaa atctaagaaa aaaagacctc  1560
aaaaaggtct ttaattaaca tctcaaattt cgcatttatt ccaatttcct ttttgcgtgt  1620
gatgcgagct catcggctcc gtcgatacta tgttatacgc caactttcaa aacaactttg  1680
aaaaagctgt tttctggtat ttaaggtttt agaatgcaag gaacagtgaa ttggagttcg  1740
tcttgttata attagcttct tggggtatct ttaaatactg tagaaaagag gaaggaaata  1800
ataaatggct aaaatgagaa tatcaccgga attgaaaaaa ctgatcgaaa aataccgctg  1860
cgtaaaagat acggaaggaa tgtctcctgc taaggtatat aagctggtgg gagaaaatga  1920
aaacctatat ttaaaaatga cggacagccg gtataaaggg accacctatg atgtggaacg  1980
ggaaaaggac atgatgctat ggctggaagg aaagctgcct gttccaaagg tcctgcactt  2040
tgaacggcat gatggctgga gcaatctgct catgagtgag gccgatggcg tcctttgctc  2100
ggaagagtat gaagatgaac aaagccctga aaagattatc gagctgtatg cggagtgcat  2160
caggctcttt cactccatcg acatatcgga ttgtccctat acgaatagct tagacagccg  2220
cttagccgaa ttggattact tactgaataa cgatctggcc gatgtggatt gcgaaaactg  2280
ggaagaagac actccattta aagatccgcg cgagctgtat gatttttaa agacggaaaa  2340
gcccgaagag gaacttgtct tttcccacgg cgacctggga gacagcaaca tctttgtgaa  2400
agatggcaaa gtaagtggct ttattgatct tgggagaagc ggcagggcgg acaagtggta  2460
tgacattgcc ttctgcgtcc ggtcgatcag ggaggatatc ggggaagaac agtatgtcga  2520
gctatttttt gacttactgg ggatcaagcc tgattgggag aaaataaaat attatatttt  2580
actggatgaa ttgttttagt gactgcagtg agatctggta atgactctct agcttgaggc  2640
atcaaataaa acgaaaggct cagtcgaaag actgggcctt tcgttttatc tgttgtttgt  2700
cggtgaacgc tctcctgagt aggacaaatc cgccgctcta gctaagcaga aggccatcct  2760
gacggatggc ctttttgcgt ttctacaaac tcttgttaac tctagagctg cctgccgcgt  2820
ttcggtgatg aagatcttcc cgatgattaa ttaattcaga acgctcggtt gccgccgggc  2880
gttttttatg aagcttcgtt gctggcgttt ttccataggc tccgcccccc tgacgagcat  2940
cacaaaaatc gacgctcaag tcagaggtgg cgaaacccga caggactata aagataccag  3000
gcgtttcccc ctggaagctc cctcgtgcgc tctcctgttc cgaccctgcc gcttaccgga  3060
tacctgtccg cctttctccc ttcgggaagc gtggcgcttt ctcatagctc acgctgtagg  3120
tatctcagtt cggtgtaggt cgttcgctcc aagctgggct gtgtgcacga accccccgtt  3180
cagcccgacc gctgcgcctt atccggtaac tatcgtcttg agtccaaccc ggtaagacac  3240
gacttatcgc cactggcagc agccactggt aacaggatta gcagagcgag gtatgtaggc  3300
```

```
ggtgctacag agttcttgaa gtggtggcct aactacggct acactagaag gacagtattt  3360
ggtatctgcg ctctgctgaa gccagttacc ttcggaaaaa gagttggtag ctcttgatcc  3420
ggcaaacaaa ccaccgctgg tagcggtggt ttttttgttt gcaagcagca gattacgcgc  3480
agaaaaaaag gatctcaaga agatcctttg atcttttcta cggggtctga cgctcagtgg  3540
aacgaaaact cacgttaagg gattttggtc atgagattat caaaaaggat cttcacctag  3600
atccttttaa attaaaaatg aagttttaaa tcaatctaaa gtatatatga gtaaacttgg  3660
tctgacaaat ggttctttcc cctgtcctaa acaaaaaacc cgctttattg aaaaagcggg  3720
gctgttttac agacaggtca aataaacgtt tgaaaatgtt catttcaaaa cgcgcggaac  3780
ctccatcttc tcccatccag actatactgt cggcttcgga atcgcaccga atcctgccca  3840
taaaaaggct cgcgggctta gagcgcttgc tcatcaccgc cggtagggaa tttcaccctg  3900
ccccgaagat tgatcttatt tatttttaat actgatatta ttataaatta attgtgaaaa  3960
aatgtacagg tgcaaagctt attgcgctgt tttgggacat cctgcacgat atttcggtaa  4020
actcactttt tccgcatact aaaaaccgca cattcacagt tatttcattt ttaattttcg  4080
tctttccgcg tgaaactcat tgacactctt tatggaatat ggtaaattat cagatattta  4140
tgacgcttat ttaggaggaa atcttacaca gaagctgcgg aacctgaaaa gaattccttt  4200
caggttccgt tttttttagg aattctccct gatctcaagc atctggcggg gataaatccg  4260
ctctcctttc aaatcgttcc attctttgag gcgctgtaca gttacgccca ttttttcggc  4320
gatatgatga agcgtatccc ctttccgcac tacatatgta ccggtcttcg attcatcgtc  4380
atgaaggcgg agtgtttggc cggccttgag atttgaatgt ttcaacccgt ttattctcat  4440
gatctcctcg atggatatac cgctatcctt gctgattctc cagagcgtgt ccccttttg  4500
aacggtcacc gcaccgctca ttgtcccggc gttttgataa acgtggatag aattttgccg  4560
gaacgcctcc tcacgaagca ccgtcagcgg attgattgca tatcttttat cttcagtcca  4620
tgaaccgtga tgcatttcaa aatgcaggtg ggttccggtc gatattcgaa ttcctccatt  4680
ttcttctgct atcaaaataa cagactcgtg attttccaaa cgagctttca aaaaagcctc  4740
tgccccttgc aaatcggatg cctgtctata aaattcccga tattggttaa acagcggcgc  4800
aatggcggcc gcatctgatg tctttgcttg gcgaatgttc atcttatttc ttcctccctc  4860
tcaataattt tttcattcta tcccttttct gtaaagttta tttttcagaa tacttttatc  4920
atcatgcttt gaaaaaatat cacgataata tccattgttc tcacggaagc acacgcaggt  4980
catttgaacg aattttttcg acaggaattt gccgggactc aggagcattt aacctaaaaa  5040
agcatgacat ttcagcataa tgaacattta ctcatgtcta ttttcgttct tttctgtatg  5100
aaaatagtta tttcgagtct ctacggaaat agcgagagat gatataccta aatagagata  5160
aaatcatctc aaaaaaatgg gtctactaaa atattattcc atctattaca ataaattcac  5220
agaatagtct tttaagtaag tctactctga atttttttaa aaggagaggg taactagtgg  5280
ccccaaaaaa gaaacgcaag gttatggata aaaaatacag cattggtctg gatatcggaa  5340
ccaacagcgt tgggtgggca gtaataacag atgaatacaa agtgccgtca aaaaaattta  5400
aggttctggg gaatacagat cgccacagca taaaaaagaa tctgattggg gcattgctgt  5460
ttgattcggg tgagacagct gaggccacgc gtctgaaacg tacagcaaga agacgttaca  5520
cacgtcgtaa aaatcgtatt tgctacttac aggaaatttt ttctaacgaa atggccaagg  5580
tagatgatag tttcttccat cgtctcgaag aatcttttct ggttgaggaa gataaaaaac  5640
acgaacgtca ccctatcttt ggcaatatcg tggatgaagt ggcctatcat gaaaaatacc  5700
ctacgattta tcatcttcgc aagaagttgg ttgatagtac ggacaaagcg gatctgcgtt  5760
taatccatct tgcgttagcg cacatgatca aatttcgtgg tcatttctta attgaaggtg  5820
atctgaatcc tgataactct gatgtggaca aattgtttat acaattagtg caaacctata  5880
atcagctgtt cgaggaaaac cccattaatg cctctggagt tgatgccaaa gcgattttaa  5940
gcgcgagact ttctaagtcc cggcgtctgg agaatctgat cgcccagtta ccaggggaaa  6000
agaaaaatgg tctgtttggt aatctgattg ccctcagtct ggggcttacc ccgaacttca  6060
aatccaattt tgacctggct gaggacgcaa agctgcagct gagcaaagat acttatgatg  6120
atgacctcga caatctgctc gcccagattg gtgaccaata tgcggatctg tttctggcag  6180
cgaagaatct ttcggatgct atcttgctgt cggatattct gcgtgttaat accgaaatca  6240
ccaaagcgcc tctgtctgca agtatgatca agagatacga cgagcaccac caggacctga  6300
ctcttcttaa ggcactggta cgccaacagc ttccggagaa atacaaagaa atattcttcg  6360
accagtccaa gaatggttac gcgggctaca tcgatggtgg tgcatcacag gaagagttct  6420
ataaatttat taaaccaatc cttgagaaaa tggatggcac ggaagagtta cttgttaaac  6480
ttaaccgcga agacttgctt agaaagcaac gtacattcga caacggctcc atcccacacc  6540
agattcattt aggtgaactt cacgccatct tgcgcagaca agaagatttc tatcccttct  6600
taaaagacaa tcgggagaaa atcgagaaga tcctgacgtt ccgcattccc tattatgtcg  6660
gtcccctggc acgtggtaat tctcggtttg cctggatgac gcgcaaaagt gaggaaacca  6720
tcaccccttg gaactttgaa gaagtcgtgg ataaaggtgc tagcgcgcag tcttttatag  6780
aaagaatgac gaacttcgat aaaaacttgc ccaacgaaaa agtcctgccc aagcactctc  6840
ttttatatga gtactttact gtgtacaacg aactgactaa agtgaaatac gttacggaag  6900
gtatgcgcaa acctgccttt cttagtggcg agcagaaaaa agcaattgtc gatcttctct  6960
ttaaaacgaa tcgcaaggta actgtaaaac agctgaagga agattatttc aaaaagatcg  7020
aatgctttga ttctgtcgag atctcgggtg tcgaagatcg tttcaacgct tccttaggga  7080
cctatcatga tttgctgaag ataataaaag acaaagactt tctcgacaat gaagaaaatg  7140
aagatattct ggaggatatt gttttgacct tgaccttatt cgaagataga gagatgatcg  7200
aggagcgctt aaaaacctat gcccacctgt ttgatgacaa agtcatgaag caattaaagc  7260
gccgcagata tacggggtgg ggccgcttga gccgcaagtt gattaacggt attagagaca  7320
agcagagcgg aaaaactatc ctggatttcc tcaaatctga cggatttgcg aaccgcaatt  7380
ttatgcagct tatacatgat gattcgctta cattcaaaga ggatattcag aaggctcagg  7440
tgtctgggca aggtgattca ctccacgaac atatagcaaa tttggccggc tctcctgcga  7500
ttaagaaggg gatcctgcaa acagttaaag ttgtggatga acttgtaaaa gtaatgggcc  7560
gccacaagcc ggagaatatc gtgatagaaa tggcgcgcga gaatcaaacg acacaaaaag  7620
gtcaaaagaa ctcaagagag agaatgaagc gcattgagga ggggataaag gaacttggat  7680
ctcaaattct gaaagaacat ccagttgaaa acactcagct gcaaaatgaa aaattgtacc  7740
tgtactacct gcagaatgga agagacatgt acgtggatca ggaattggat atcaatagac  7800
tctcggacta tgacgtagat cacattgtcc ctcagagctt cctcaaggat gattctatag  7860
ataataaagt acttacgaga tcggacaaaa atcgcggtaa atcggataac gtcccatcgg  7920
aggaagtcgt taaaaagatg aaaaactatt ggcgtcaact gctgaacgcc aagctgatca  7980
cacagcgtaa gtttgataat ctgactaaag ccgaacgcgg tggtcttagt gaactcgata  8040
```

```
aagcaggatt tataaaacgg cagttagtag aaacgcgcca aattacgaaa cacgtggctc  8100
agatcctcga ttctagaatg aatacaaagt acgatgaaaa cgataaactg atccgtgaag  8160
taaaagtcat taccttaaaa tctaaacttg tgtccgattt ccgcaaagat tttcagtttt  8220
acaaggtccg ggaaatcaat aactatcacc atgcacatga tgcatattta aatgcggttg  8280
taggcacggc ccttattaag aaatacccta aactcgaaag tgagtttgtt tatggggatt  8340
ataaagtgta tgacgttcgc aaaatgatcg cgaaatcaga acaggaaatc ggtaaggcta  8400
ccgctaaata ctttttttat tccaacatta tgaatttttt taagaccgaa ataactctcg  8460
cgaatggtga aatccgtaaa cggcctctta tagaaaccaa tggtgaaacg ggagaaatcg  8520
tttgggataa aggtcgtgac tttgccaccg ttcgtaaagt cctctcaatg ccgcaagtta  8580
acattgtcaa gaagacggaa gttcaaacag gggattctc caaagaatct atcctgccga  8640
agcgtaacag tgataaactt attgccagaa aaaaagattg ggatccaaaa aaatacggag  8700
gctttgattc ccctaccgtc gcgtatagtg tgctggtggt tgctaaagtc gagaaaggga  8760
aaagcaagaa attgaaatca gttaaagaac tgctgggtat tacaattatg gaaagatcgt  8820
cctttgagaa aaatccgatc gactttttag aggccaaggg gtataaggaa gtgaaaaaag  8880
atctcatcat caaattaccg aagtatagtc tttttgagct ggaaaacggc agaaaaagaa  8940
tgctggcctc cgcgggcgag ttacagaagg gaaatgagct ggcgctgcct tccaaatatg  9000
ttaattttct gtaccttgcc agtcattatg agaaactgaa gggcagcccc gaagataacg  9060
aacagaaaca attattcgtg gaacagcata agcactattt agatgaaatt atagagcaaa  9120
ttagtgaatt ttctaagcgc gttatcctcg cggatgctaa tttagacaaa gtactgtcag  9180
cttataataa acatcgggat aagccgatta gagaacaggc cgaaaatatc attcatttgt  9240
ttaccttaac caaccttgga gcaccagctg ccttcaaata tttcgatacc acaattgatc  9300
gtaaacggta tacaagtaca aaagaagtct tggacgcaac cctcattcat caatctatta  9360
ctggattata tgagacacgc attgatcttt cacagctggg cggagacaag aagaaaaaac  9420
tgaaactgca ccatcatcac catcatcatc accatcattg ataactcgag aaagcttaca  9480
taaaaaaccg gccttggccc cgccggtttt ttattatttt tcttcctccg catgttcaat  9540
ccgctccata atcgacggat ggctccctct gaaaatttta acgagaaacg gcgggttgac  9600
ccggctcagt cccgtaacgg ccaagtcctg aaacgtctca atcgccgctt cccggtttcc  9660
ggtcagctca atgccgtaac ggtcggcggc gttttcctga taccgggaga cggcattcgt  9720
aatc                                                                9724
```

```
SEQ ID NO: 62          moltype = DNA  length = 5042
FEATURE                Location/Qualifiers
misc_feature           1..5042
                       note = synthesized Y155H variant expression cassette
source                 1..5042
                       mol_type = other DNA
                       organism = synthetic construct
SEQUENCE: 62
attcctccat tttcttctgc tatcaaaata acagactcgt gattttccaa acgagctttc  60
aaaaaagcct ctgccccttg caaatcggat gcctgtctat aaaattcccg atattggtta  120
aacagcggcg caatggcggc cgcatctgat gtctttgctt ggcgaatgtt catcttattt  180
cttcctccct ctcaataatt ttttcattct atccctttc tgtaaagttt atttttcaga  240
atacttttat catcatgctt tgaaaaaata tcacgataat atccattgtt ctcacggaag  300
cacacgcagg tcatttgaac gaattttttc gacaggaatt tgccgggact caggagcatt  360
taacctaaaa aagcatgaca tttcagcata atgaacattt actcatgtct attttcgttc  420
ttttctgtat gaaaatagtt atttcgagtc tctacggaaa tagcgagaga tgatatacct  480
aaatagagat aaaatcatct caaaaaaatg ggtctactaa aatattattc catctattac  540
aataaattca cagaatagtc ttttaagtaa gtctactctg aatttttta aaaggagagg  600
gtaactagtg gccccaaaaa agaaacgcaa ggttatggat aaaaaataca gcattggtct  660
ggatatcgga accaacagcg ttgggtgggc agtaataaca gatgaataca aagtgccgtc  720
aaaaaaattt aaggttctgg ggaatacaga tcgccacagc ataaaaaaga atctgattgg  780
ggcattgctg tttgattcgg gtgagacagc tgaggccacg cgtctgaaac gtacagcaag  840
aagacgttac acacgtcgta aaaatcgtat ttgctactta caggaaattt tttctaacga  900
aatggccaag gtagatgata gtttcttcca tcgtctcgaa gaatcttttc tggttgagga  960
agataaaaaa cacgaacgtc accctatctt tggcaatatc gtggatgaag tggcctatca  1020
tgaaaaatac cctacgattt atcatcttcg caagaagttg gttgatagta cggacaaagc  1080
ggatctgcgt ttaatccatc ttgcgttagc gcacatgatc aaatttcgtg gtcatttctt  1140
aattgaaggt gatctgaatc ctgataactc tgatgtggac aaattgttta tacaattagt  1200
gcaaacctat aatcagctgt tcgaggaaaa ccccattaat gcctctggag ttgatgccaa  1260
agcgatttta agcgcgagac tttctaagtc ccggcgtctg gagaatctga tcgcccagtt  1320
accaggggaa aagaaaaatg gtctgtttgg taatctgatt gccctcagtc tggggcttac  1380
cccgaacttc aaatccaatt ttgacctggc tgaggacgca aagctgcagc tgagcaaaga  1440
tacttatgat gatgacctcg acaatctgct cgcccagatt ggtgaccaat atgcggatct  1500
gtttctggca gcgaagaatc tttcggatgc tatcttgctg tcggatattc tgcgtgttaa  1560
taccgaaatc accaaagcgc ctctgtctgc aagtatgatc aagagatacg acgagcacca  1620
ccaggacctg actcttctta aggcactggt acgccaacag cttccggaga aatacaaaga  1680
aatattcttc gaccagtcca agaatggtta cgcgggctac atcgatggtg gtgcatcaca  1740
ggaagagttc tataaattta ttaaaccaat ccttgagaaa atggatggca cggaagagtt  1800
acttgttaaa cttaaccgcg aagacttgct tagaaagcaa cgtacattcg acaacggctc  1860
catcccacac cagattcatt taggtgaact tcacgccatc ttgcgcagac aagaagattt  1920
ctatcccttc ttaaaagaca atcgggagaa aatcgagaag atcctgacgt tccgcattcc  1980
ctattatgtc ggtcccctgg cacgtggtaa ttctcggttt gcctggatga cgcgcaaaag  2040
tgaggaaacc atcacccctt ggaactttga agaagtcgtg gataaaggtg ctagcgcgca  2100
gtcttttata gaaagaatga cgaacttcga taaaaacttg cccaacgaaa aagtcctgcc  2160
caagcactct cttttatatg agtactttac tgtgtacaac gaactgacta aagtgaaata  2220
cgttacggaa ggtatgcgca aacctgcctt tcttagtggc gagcagaaaa aagcaattgt  2280
cgatcttctc tttaaaacga atcgcaaggt aactgtaaaa cagctgaagg aagattattt  2340
caaaaagatc gaatgctttg attctgtcga gatctcgggt gtcgaagatc gtttcaacgc  2400
ttccttaggg acctatcatg atttgctgaa gataataaaa gacaaagact ttctcgacaa  2460
```

-continued

```
tgaagaaaat gaagatattc tggaggatat tgttttgacc ttgaccttat tcgaagatag  2520
agagatgatc gaggagcgct taaaaaccta tgcccacctg tttgatgaca aagtcatgaa  2580
gcaattaaag cgccgcagat atacggggtg gggccgcttg agccgcaagt tgattaacgg  2640
tattagagac aagcagagcg gaaaaactat cctggatttc ctcaaatctg acggatttgc  2700
gaaccgcaat tttatgcagc ttatacatga tgattcgctt acattcaaag aggatattca  2760
gaaggctcag gtgtctgggc aaggtgattc actccacgaa catatagcaa atttggccgg  2820
ctctcctgcg attaagaagg ggatcctgca aacagttaaa gttgtggatg aacttgtaaa  2880
agtaatgggc cgccacaagc cggagaatat cgtgatagaa atggcgcgcg agaatcaaac  2940
gacacaaaaa ggtcaaaaga actcaagaga gagaatgaag cgcattgagg aggggataaa  3000
ggaacttgga tctcaaattc tgaaagaaca tccagttgaa aacactcagc tgcaaaatga  3060
aaaattgtac ctgtactacc tgcagaatgg aagagacatg tacgtggatc aggaattgga  3120
tatcaataga ctctcggact atgacgtaga tcacattgtc cctcagagct tcctcaagga  3180
tgattctata gataataaag tacttacgag atcggacaaa aatcgcggta aatcggataa  3240
cgtcccatcg gaggaagtcg ttaaaaagat gaaaaactat tggcgtcaac tgctgaacgc  3300
caagctgatc acacagcgta agtttgataa tctgactaaa gccgaacgcg gtggtcttag  3360
tgaactcgat aaagcaggat ttataaaacg gcagttagta gaaacgcgcc aaattacgaa  3420
acacgtggct cagatcctcg attctagaat gaatacaaag tacgatgaaa acgataaact  3480
gatccgtgaa gtaaaagtca ttaccttaaa atctaaactt gtgtccgatt tccgcaaaga  3540
ttttcagttt tacaaggtcc gggaaatcaa taactatcac catgcacatg atgcatattt  3600
aaatgcggtt gtaggcacgg cccttattaa gaaataccct aaactcgaaa gtgagtttgt  3660
ttatggggat tataaagtgt atgacgttcg caaaatgatc gcgaaatcag aacaggaaat  3720
cggtaaggct accgctaaat actttttta ttccaacatt atgaattttt ttaagaccga  3780
aataactctc gcgaatggtg aaatccgtaa acggcctctt atagaaacca atggtgaaac  3840
gggagaaatc gtttgggata aaggtcgtga ctttgccacc gttcgtaaag tcctctcaat  3900
gccgcaagtt aacattgtca agaagacgga agttcaaaca ggggggattct ccaaagaatc  3960
tatcctgccg aagcgtaaca gtgataaact tattgccaga aaaaaagatt gggatccaaa  4020
aaaatacgga ggctttgatt cccctaccgt cgcgtatagt gtgctggtgg ttgctaaagt  4080
cgagaaaggg aaaagcaaga aattgaaatc agttaaagaa ctgctgggta ttacaattat  4140
ggaaagatcg tcctttgaga aaaatccgat cgactttta gaggccaagg ggtataagga  4200
agtgaaaaaa gatctcatca tcaaattacc gaagtatagt ctttttgagc tggaaaacgg  4260
cagaaaaaga atgctggcct ccgcgggcga gttacagaag ggaaatgagc tggcgctgcc  4320
ttccaaatat gttaattttc tgtaccttgc cagtcattat gagaaactga agggcagccc  4380
cgaagataac gaacagaaac aattattcgt ggaacagcat aagcactatt tagatgaaat  4440
tatagagcaa attagtgaat ttctaagcg cgttatcctc gcggatgcta atttagacaa  4500
agtactgtca gcttataata aacatcggga taagccgatt agagaacagg ccgaaaatat  4560
cattcatttg tttaccttaa ccaaccttgg agcaccagct gccttcaaat atttcgatac  4620
cacaattgat cgtaaacggt atacaagtac aaaagaagtc ttggacgcaa ccctcattca  4680
tcaatctatt actggattat atgagacacg cattgatctt tcacagctgg gcggagacaa  4740
gaagaaaaaa ctgaaactgc accatcatca ccatcatcat caccatcatt gataaacata  4800
aaaaaccggc cttggccccg ccggtttttt attatttttc ttcctccgca tgttcaatcc  4860
gctccataat cgacggatgg ctccctctga aaattttaac gagaaacggc gggttgaccc  4920
ggctcagtcc cgtaacggcc aagtcctgaa acgtctcaat cgccgcttcc cggtttccgg  4980
tcagctcaat gccgtaacgg tcggcggcgt tttcctgata ccgggagacg gcattcgtaa  5040
tc                                                                5042

SEQ ID NO: 63          moltype = DNA  length = 9724
FEATURE                Location/Qualifiers
misc_feature           1..9724
                       note = plasmid pRF856
source                 1..9724
                       mol_type = other DNA
                       organism = synthetic construct
SEQUENCE: 63
gggtgaagtg gtcaagacct cactaggcac cttaaaaata gcgcaccctg aagaagattt  60
atttgaggta gcccttgcct acctagcttc caagaaagat atcctaacag cacaagagcg  120
gaaagatgtt ttgttctaca tccagaacaa cctctgctaa aattcctgaa aaattttgca  180
aaaagttgtt gactttatct acaaggtgtg gcataatgtg tggagatgcc atcagttcct  240
catagtttta gagctagaaa tagcaagtta aaataaggct agtccgttat caacttgaaa  300
aagtggcacc gagtcggtgc gactcctgtt gatagatcca gtaatgacct cagaactcca  360
tctggatttg ttcagaacgc tcggttgccg ccgggcgttt tttattggtg agaatgtcga  420
cctcgagagt tacgctaggg ataacagggt aatataggag ctccagtcgg cttaaaccag  480
ttttcgctgg tgcgaaaaaa gagtgtcttg tgacacctaa attcaaaatc tatcggtcag  540
atttataccg atttgatttt atatattctt gaataacata cgccgagtta tcacataaaa  600
gcgggaacca atcataaaat ttaaacttca ttgcataatc cattaaactc ttaaattcta  660
cgattccttg ttcatcaata aactcaatca tttctttaat taatttatat ctatctgttg  720
ttgttttctt taataattca ttaacatcta caccgccata aactatcata tcttcttttt  780
gatatttaaa tttattagga tcgtccatgt gaagcatata tctcacaaga cctttcacac  840
ttcctgcaat ctgcggaata gtcgcattca attcttctgt taattatttt tatctgttca  900
taagatttat taccctcata catcactaga atatgataat gctctttttt catcctacct  960
tctgtatcag tatccctatc atgtaatgga gacactacaa attgaatgtg taactctttt  1020
aaatactcta accactcggc ttttgctgat tctggatata aaacaaatgt ccaattacgt  1080
cctcttgaat ttttcttgtt ttcagtttct tttattacat tttcgctcat gatataataa  1140
cggtgctaat acacttaaca aaatttagtc atagataggc agcatgccag tgctgtctat  1200
cttttttttgt ttaaaatgca ccgtattcct cctttgcata tttttttatt agaataccgg  1260
ttgcatctga tttgctaata ttatattttt ctttgattct atttaatatc tcattttctt  1320
ctgttgtaag tcttaaagta acagcaactt ttttctcttc ttttctatct acaactatca  1380
ctgtacctcc caacatctgt ttttttcact ttaacataaa aaacaacctt ttaacattaa  1440
aaacccaata tttatttatt tgtttggaca atggacactg gacacctagg ggggaggtcg  1500
tagtaccccc ctatgttttc tcccctaaat aaccccaaaa atctaagaaa aaaagacctc  1560
```

-continued

```
aaaaaggtct ttaattaaca tctcaaattt cgcatttatt ccaatttcct ttttgcgtgt  1620
gatgcgagct catcggctcc gtcgatacta tgttatacgc caactttcaa aacaactttg  1680
aaaaagctgt tttctggtat ttaaggtttt agaatgcaag gaacagtgaa ttggagttcg  1740
tcttgttata attagcttct tggggtatct ttaaatactg tagaaaagag gaaggaaata  1800
ataaatggct aaaatgagaa tatcaccgga attgaaaaaa ctgatcgaaa aataccgctg  1860
cgtaaaagat acggaaggaa tgtctcctgc taaggtatat aagctggtgg gagaaaatga  1920
aaacctatat ttaaaaatga cggacagccg gtataaaggg accacctatg atgtggaacg  1980
ggaaaaggac atgatgctat ggctggaagg aaagctgcct gttccaaagg tcctgcactt  2040
tgaacggcat gatggctgga gcaatctgct catgagtgag gccgatggcg tcctttgctc  2100
ggaagagtat gaagatgaac aaagccctga aaagattatc gagctgtatg cggagtgcat  2160
caggctcttt cactccatcg acatatcgga ttgtccctat acgaatagct tagacagccg  2220
cttagccgaa ttggattact tactgaataa cgatctggcc gatgtggatt gcgaaaactg  2280
ggaagaagac actccattta aagatccgcg cgagctgtat gatttttttaa agacggaaaa  2340
gcccgaagag gaacttgtct tttcccacgg cgacctggga gacagcaaca tctttgtgaa  2400
agatggcaaa gtaagtggct ttattgatct tgggagaagc ggcagggcgg acaagtggta  2460
tgacattgcc ttctgcgtcc ggtcgatcag ggaggatatc ggggaagaac agtatgtcga  2520
gctatttttt gacttactgg ggatcaagcc tgattgggag aaaataaaat attatatttt  2580
actggatgaa ttgttttagt gactgcagtg agatctggta atgactctct agcttgaggc  2640
atcaaataaa acgaaaggct cagtcgaaag actgggcctt tcgttttatc tgttgtttgt  2700
cggtgaacgc tctcctgagt aggacaaatc cgccgctcta gctaagcaga aggccatcct  2760
gacggatggc ctttttgcgt ttctacaaac tcttgttaac tctagagctg cctgccgcgt  2820
ttcggtgatg aagatcttcc cgatgattaa ttaattcaga acgctcggtt gccgccgggc  2880
gttttttatg aagcttcgtt gctggcgttt ttccataggc tccgcccccc tgacgagcat  2940
cacaaaaatc gacgctcaag tcagaggtgg cgaaacccga caggactata aagataccag  3000
gcgtttcccc ctggaagctc cctcgtgcgc tctcctgttc cgaccctgcc gcttaccgga  3060
tacctgtccg cctttctccc ttcgggaagc gtggcgcttt ctcatagctc acgctgtagg  3120
tatctcagtt cggtgtaggt cgttcgctcc aagctgggct gtgtgcacga accccccgtt  3180
cagcccgacc gctgcgcctt atccggtaac tatcgtcttg agtccaaccc ggtaagacac  3240
gacttatcgc cactggcagc agccactggt aacaggatta gcagagcgag gtatgtaggc  3300
ggtgctacag agttcttgaa gtggtggcct aactacggct acactagaag gacagtattt  3360
ggtatctgcg ctctgctgaa gccagttacc ttcggaaaaa gagttggtag ctcttgatcc  3420
ggcaaacaaa ccaccgctgg tagcggtggt ttttttgttt gcaagcagca gattacgcgc  3480
agaaaaaaag gatctcaaga agatcctttg atcttttcta cggggtctga cgctcagtgg  3540
aacgaaaact cacgttaagg gattttggtc atgagattat caaaaaggat cttcacctag  3600
atccttttaa attaaaaatg aagttttaaa tcaatctaaa gtatatatga gtaaacttgg  3660
tctgacattg atattcagca ccctgcgcat ttcgaccggg agaacgactc tgccgagctc  3720
atcgattctc cggacaatcc cggtattttt cacgtttgaa aagcctcctt ttctcctttc  3780
tttattgact tttgtcaaca tctttataat aaaagagatc ttcaaatttt ttgttgaaat  3840
actgaatcat ctttccgatc acaagttgtc cgggcctcct ttcgccattt aaaactctgc  3900
tgagtgtcgc cggggatacg ccgatttcaa tggcaagctg atttaaggag agattgtgtt  3960
caatcatgta ctggagaaca aaatctcttt tgatatgaat ctttttttacc atgattactc  4020
ccctttctaa tctcttatgt ttctttttat ctacattgaa catatacgat ttgttaactt  4080
ttgtcaatac ttttaccatc catatgtttc ctataggcaa tattcgtact aaaatatttt  4140
ataataagag attgcgaggt tttggccata cttctccgcg gcacactctc ctctctatca  4200
ttttcgtctg tttacgatcc tgctgttatt ttatccctta tgttaacttt tgtcaatatt  4260
tttcctgtct aagtatttcc tatagtcaac atttgtatta aaatgttcat atcatgaatt  4320
tgcggggggg atggcgatga caaggttcgg cgagcggctc aaagagctga gggaacaaag  4380
aagcctgtcg gttaatcagc ttgccatgta tgccggtgtg agcgccgcag ccatttccag  4440
agccgcagcc atttccagaa tcgaaaacgg ccaccgcggc gttcccaagc ccgcgacgat  4500
cagaaaattg gccgaggctc tgaaaatgcc gtacgagcag ctcatggata ttgccggtta  4560
tatgagagct gacgagattc gcgaacagcc gcgcggctat gtcacgatgc aggagatcgc  4620
ggccaagcac ggcgtcgaag acctgtggct gtttaaaccc gagaaatgaa ttcctccatt  4680
ttcttctgct atcaaaataa cagactcgtg attttccaaa cgagctttca aaaaagcctc  4740
tgccccttgc aaatcggatg cctgtctata aaattcccga tattggttaa acagcggcgc  4800
aatggcggcc gcatctgatg tctttgcttg gcgaatgttc atcttatttc ttcctccctc  4860
tcaataattt tttcattcta tcccttttct gtaaagttta tttttcagaa tacttttatc  4920
atcatgcttt gaaaaaatat cacgataata tccattgttc tcacggaagc acacgcaggt  4980
catttgaacg aattttttcg acaggaattt gccgggactc aggagcattt aacctaaaaa  5040
agcatgacat ttcagcataa tgaacattta ctcatgtcta ttttcgttct tttctgtatg  5100
aaaatagtta tttcgagtct ctacggaaat agcgagagat gatataccta aatagagata  5160
aaatcatctc aaaaaaatgg gtctactaaa atattattcc atctattaca ataaattcac  5220
agaatagtct tttaagtaag tctactctga attttttttaa aaggagaggg taactagtgg  5280
ccccaaaaaa gaaacgcaag gttatggata aaaaatacag cattggtctg gatatcggaa  5340
ccaacagcgt tgggtgggca gtaataacag atgaatacaa agtgccgtca aaaaaattta  5400
aggttctggg gaatacagat cgccacagca taaaaaagaa tctgattggg gcattgctgt  5460
ttgattcggg tgagacagct gaggccacgc gtctgaaacg tacagcaaga agacgttaca  5520
cacgtcgtaa aaatcgtatt tgctacttac aggaaatttt ttctaacgaa atggccaagg  5580
tagatgatag tttcttccat cgtctcgaag aatcttttct ggttgaggaa gataaaaaac  5640
acgaacgtca ccctatcttt ggcaatatcg tggatgaagt ggcctatcat gaaaaatacc  5700
ctacgattta tcatcttcgc aagaagttgg ttgatagtac ggacaaagcg gatctgcgtt  5760
taatccatct tgcgttagcg cacatgatca aatttcgtgg tcatttctta attgaaggtg  5820
atctgaatcc tgataactct gatgtggaca aattgtttat acaattagtg caaacctata  5880
atcagctgtt cgaggaaaac cccattaatg cctctggagt tgatgccaaa gcgattttaa  5940
gcgcgagact ttctaagtcc cggcgtctgg agaatctgat cgcccagtta ccaggggaaa  6000
agaaaaatgg tctgtttggt aatctgattg ccctcagtct ggggcttacc ccgaacttca  6060
aatccaattt tgacctggct gaggacgcaa agctgcagct gagcaaagat acttatgatg  6120
atgacctcga caatctgctc gcccagattg gtgaccaata tgcggatctg tttctggcag  6180
cgaagaatct ttcggatgct atcttgctgt cggatattct gcgtgttaat accgaaatca  6240
ccaaagcgcc tctgtctgca agtatgatca agagatacga cgagcaccac caggacctga  6300
```

```
ctcttcttaa ggcactggta cgccaacagc ttccggagaa atacaaagaa atattcttcg  6360
accagtccaa gaatggttac gcgggctaca tcgatggtgg tgcatcacag gaagagttct  6420
ataaatttat taaaccaatc cttgagaaaa tggatggcac ggaagagtta cttgttaaac  6480
ttaaccgcga agacttgctt agaaagcaac gtacattcga caacggctcc atcccacacc  6540
agattcattt aggtgaactt cacgccatct tgcgcagaca agaagatttc tatcccttct  6600
taaaagacaa tcgggagaaa atcgagaaga tcctgacgtt ccgcattccc tattatgtcg  6660
gtcccctggc acgtggtaat tctcggtttg cctggatgac gcgcaaaagt gaggaaacca  6720
tcacccccttg gaactttgaa gaagtcgtgg ataaaggtgc tagcgcgcag tcttttatag  6780
aaagaatgac gaacttcgat aaaaacttgc ccaacgaaaa agtcctgccc aagcactctc  6840
ttttatatga gtactttact gtgtacaacg aactgactaa agtgaaatac gttacggaag  6900
gtatgcgcaa acctgccttt cttagtggcg agcagaaaaa agcaattgtc gatcttctct  6960
ttaaaacgaa tcgcaaggta actgtaaaac agctgaagga agattatttc aaaaagatcg  7020
aatgctttga ttctgtcgag atctcgggtg tcgaagatcg tttcaacgct tccttaggga  7080
cctatcatga tttgctgaag ataataaaag acaaagactt tctcgacaat gaagaaaatg  7140
aagatattct ggaggatatt gttttgacct tgaccttatt cgaagataga gagatgatcg  7200
aggagcgctt aaaaacctat gcccacctgt ttgatgacaa agtcatgaag caattaaagc  7260
gccgcagata tacggggtgg ggccgcttga gccgcaagtt gattaacggt attagagaca  7320
agcagagcgg aaaaactatc ctggatttcc tcaaatctga cggatttgcg aaccgcaatt  7380
ttatgcagct tatacatgat gattcgctta cattcaaaga ggatattcag aaggctcagg  7440
tgtctgggca aggtgattca ctccacgaac atatagcaaa tttggccggc tctcctgcga  7500
ttaagaaggg gatcctgcaa acagttaaag ttgtggatga acttgtaaaa gtaatgggcc  7560
gccacaagcc ggagaatatc gtgatagaaa tggcgcgcga gaatcaaacg acacaaaaag  7620
gtcaaaagaa ctcaagagag agaatgaagc gcattgagga ggggataaag gaacttggat  7680
ctcaaattct gaaagaacat ccagttgaaa acactcagct gcaaaatgaa aaattgtacc  7740
tgtactacct gcagaatgga agagacatgt acgtggatca ggaattggat atcaatagac  7800
tctcggacta tgacgtagat cacattgtcc ctcagagctt cctcaaggat gattctatag  7860
ataataaagt acttacgaga tcggacaaaa atcgcggtaa atcggataac gtcccatcgg  7920
aggaagtcgt taaaaagatg aaaaactatt ggcgtcaact gctgaacgcc aagctgatca  7980
cacagcgtaa gtttgataat ctgactaaag ccgaacgcgg tggtcttagt gaactcgata  8040
aagcaggatt tataaaacgg cagttagtag aaacgcgcca aattacgaaa cacgtggctc  8100
agatcctcga ttctagaatg aatacaaagt acgatgaaaa cgataaactg atccgtgaag  8160
taaaagtcat taccttaaaa tctaaacttg tgtccgattt ccgcaaagat tttcagtttt  8220
acaaggtccg ggaaatcaat aactatcacc atgcacatga tgcatattta aatgcggttg  8280
taggcacggc ccttattaag aaataccta aactcgaaag tgagtttgtt tatggggatt  8340
ataaagtgta tgacgttcgc aaaatgatcg cgaaatcaga acaggaaatc ggtaaggcta  8400
ccgctaaata cttttttat tccaacatta tgaatttttt taagaccgaa ataactctcg  8460
cgaatggtga aatccgtaaa cggcctctta tagaaaccaa tggtgaaacg ggagaaatcg  8520
tttgggataa aggtcgtgac tttgccaccg ttcgtaaagt cctctcaatg ccgcaagtta  8580
acattgtcaa gaagacggaa gttcaaacag gggattctc caaagaatct atcctgccga  8640
agcgtaacag tgataaactt attgccagaa aaaaagattg ggatccaaaa aaatacggag  8700
gctttgattc ccctaccgtc gcgtatagtg tgctggtggt tgctaaagtc gagaaaggga  8760
aaagcaagaa attgaaatca gttaaagaac tgctgggtat tacaattatg gaaagatcgt  8820
cctttgagaa aaatccgatc gactttttag aggccaaggg gtataaggaa gtgaaaaaag  8880
atctcatcat caaattaccg aagtatagtc tttttgagct ggaaaacggc agaaaaagaa  8940
tgctggcctc cgcgggcgag ttacagaagg gaaatgagct ggcgctgcct tccaaatatg  9000
ttaattttct gtaccttgcc agtcattatg agaaactgaa gggcagcccc gaagataacg  9060
aacagaaaca attattcgtg gaacagcata agcactattt agatgaaatt atagagcaaa  9120
ttagtgaatt ttctaagcgc gttatcctcg cggatgctaa tttagacaaa gtactgtcag  9180
cttataataa acatcgggat aagccgatta gagaacaggc cgaaaatatc attcatttgt  9240
ttaccttaac caaccttgga gcaccagctg ccttcaaata tttcgatacc acaattgatc  9300
gtaaacggta tacaagtaca aaagaagtct tggacgcaac cctcattcat caatctatta  9360
ctggattata tgagacacgc attgatcttt cacagctggg cggagacaag aagaaaaaac  9420
tgaaactgca ccatcatcac catcatcatc accatcattg ataactcgag aaagcttaca  9480
taaaaaaccg gccttggccc cgccggtttt ttattatttt tcttcctccg catgttcaat  9540
ccgctccata atcgacggat ggctccctct gaaaatttta acgagaaacg gcgggttgac  9600
ccggctcagt cccgtaacgg ccaagtcctg aaacgtctca atcgccgctt cccggtttcc  9660
ggtcagctca atgccgtaac ggtcggcggc gttttcctga taccgggaga cggcattcgt  9720
aatc                                                               9724
```

```
SEQ ID NO: 64         moltype = DNA  length = 6393
FEATURE               Location/Qualifiers
misc_feature          1..6393
                      note = synthesized pBL.comK-syn
source                1..6393
                      mol_type = other DNA
                      organism = synthetic construct
SEQUENCE: 64
aagcttcata tgcaagggtt tattgttttc taaaatctga ttaccaatta gaatgaatat  60
ttcccaaata ttaaataata aaacaaaaaa attgaaaaaa gtgtttccac catttttttca  120
atttttttat aattttttta atctgttatt taaatagttt atagttaaat ttacattttc  180
attagtccat tcaatattct ctccaagata actacgaact gctaacaaaa ttctctccct  240
atgttctaat ggagaagatt cagccactgc atttcccgca atatcttttg gtatgatttt  300
acccgtgtcc atagttaaaa tcatacggca taaagttaat atagagttgg tttcatcatc  360
ctgataatta tctattaatt cctctgacga atccataatg gctcttctca catcagaaaa  420
tggaatatca ggtagtaatt cctctaagtc ataatttccg tatattcttt tattttttcg  480
ttttgcttgg taaagcatta tggttaaatc tgaatttaat tccttctgag gaatgtatcc  540
ttgttcataa agctcttgta accattctcc ataaataaat tcttgtttgg gaggatgatt  600
ccacggtacc atttcttgct gaataataat tgttaattca atatatcgta agttgctttt  660
atctcctatt tttttgaaa taggtctaat tttttgtata agtatttctt tactttgatc  720
```

```
tgtcaatggt tcagatacga cgactaaaaa gtcaagatca ctatttggtt ttagtccact  780
ctcaactcct gatccaaaca tgtaagtacc aataaggtta ttttttaaat gtttccgaag  840
tattttttttc actttattaa tttgttcgta tgtattcaaa tatatcctcc tcactatttt  900
gattagtacc tattttatat ccatagttgt taattaaata aacttaattt agtttattta  960
tggatttcat tggcttctaa atttttttatc tagataataa ttattttagt taattttatt  1020
ctagattata tatgatatga tctttcattt ccataaaact aaagtaagtg taaacctatt  1080
cattgtttta aaaatatctc ttgccagtca cgttacgtta ttagttatag ttattataac  1140
atgtattcac gaacgggcgc gccggtatcc gcgcttcttg agcactattt attcaaagcc  1200
gctccagatc aatagcgctt tttcagctcc ctgaggatga attcgtatat cagctgattc  1260
cggtcttctt tcggatagag cataaattcc tgtttcttct gcatggggtt tccttcaatc  1320
ctgtcgataa attttgttct cagccatgcc gttcggtaaa cctggttttc gaaagatgag  1380
atggatacgg gcagctccag cgtttccccg ttgacaaacg tgacaaacgt gttgtcatac  1440
tttgccgcgc aaaactcgtg aacatgcgca tgggaaagcc acccgcactg aggacgagtt  1500
gaggaaaatg tggggaaaag aaaaatgttg tttgagtgat ccaccatgat cggcggttta  1560
tgggaaactt taatgacttc atatgtgccc gcttttcttc ccgcatagct cgatccgaaa  1620
tagcggcagc ttctttcgat aatttgaaac ggcttcatat tgacgcggaa agtcctgtcg  1680
gtctcaagta tttttgaggc ggatttctcc ccctcaccca gaggcaggac agccattgtc  1740
gaactgttta cttcatacgt atcctttgtc atatcctctg tgctcatgtg atttccccct  1800
taaaaataaa ttcattcaaa tacagatgca ttttatttca tatagtaagt acatcaccta  1860
ttagtttgtt gtttaaacaa actaacttat tttcatctta tataacctcg tcagtatttt  1920
caatattttt tttagttttt tatgaacaca ttagatttaa taaagggaag attcgctatg  1980
tactatgttg atacttaatt taaagattaa acaaatggag tggatgaagt ggatatcgct  2040
gatcaaacct ttgtcaaaaa agtaaatcaa aagttattat taaaagaaat ccttaaaaat  2100
tcacctattt caagagcaaa attatctgaa atgactggat taaataaatc aactgtctca  2160
tcacaggtaa acacgttaat gaaagaaagt atggtatttg aaataggtca aggacaatca  2220
agtggcggaa gaagacctgt catgcttgtt tttaataaaa aggcaggata ctccgttgga  2280
atagatgttg gtgtggatta tattaatggc attttaacag accttgaagg aacaatcgtt  2340
cttgatcaat accgccattt ggaatccaat tctccagaaa taacgaaaga cattttgatt  2400
gatatgattc atcactttat tacgcaaatg ccccaatctc cgtacgggtt tattggtata  2460
ggtacttgcg tgcctggact cattgataaa gatcaaaaaa ttgttttcac tccgaactcc  2520
aactggagag atattgactt aaaatcttcg atacaagaga agtacaatgt gtctgttttt  2580
attgaaaatg aggcaaatgc tggcgcatat ggagaaaaac tatttggagc tgcaaaaaat  2640
cacgataaca ttatttacgt aagtatcagc acaggaatag ggatcggtgt tattatcaac  2700
aatcatttat atagaggagt aagcggcttc tctggagaaa tgggacatat gacaatagac  2760
tttaatggtc ctaaatgcag ttgcggaaac cgaggatgct gggaattgta tgcttcagag  2820
aaggctttat ttaaatctct tcagaccaaa gagaaaaaac tgtcctatca agatatcata  2880
aacctcgccc atctgaatga tatcggaacc ttaaatgcat tacaaaattt tggattctat  2940
ttaggaatag gccttaccaa tattctaaat actctcaacc cacaagccgt aattttaaga  3000
aatagcataa ttgaatcgca tcctatggtt ttaaattcaa tgagaagtga agtatcatca  3060
agggtttatt cccaattagg caatagctat gaattattgc catcttcctt aggacagaat  3120
gcaccggcat taggaatgtc ctccattgtg attgatcatt ttctggacat gattacaatg  3180
taatttttta tggaatggac agctcatctt taaagatgag tttttttatt ctaggagtat  3240
ttctgaagca atagtgacat ggcaccttct catatgaaaa aggagttcta aaataaaaat  3300
ctccttttttc atgtgcaaat tatttttctt tataacgaaa atatctaaat gacaatgcat  3360
atgcaagagg ggatcacata aatatatatt ttaaaaatat cccactttat ccaattttcg  3420
tttgttgaac taatgggtgc tttagttgaa gaataaaaga ccacattaaa aaatgtggtc  3480
ttttgtgttt ttttaaagga tttgagcgta gcgaaaaatc cttttcttttc ttatcttgat  3540
actatataga aacaacatca tttttcaaaa ttaggtcaaa gccttgtgta tcaagggttt  3600
gatggttctt tgacaggtaa aaactccttc tgctattatt aaatactata tagaaacaac  3660
atcattttttc aaaattaggt caaagccttg tgtatcaagg gtttgatggt tctttgacag  3720
gtaaaaactc cttctgctat tattaaggtg tcgaatcaaa ataatagaat gctagagaac  3780
tagctcagaa ggagtttttt tgttgattta ttcatctgaa aatgattata gcatcctcga  3840
agataaaacc gcaacaggta aaaagcggga ttggaagggg aaaaagagac ggacgaacct  3900
catggcggag cattacgaag cgttagagag taagattggg gcaccttact atggcaaaaa  3960
ggctgaaaaa ctaattagtt gtgcagagta tctttcgttt aagagagacc cggagacggg  4020
caagttaaaa ctgtatcaag cccatttttg taaagtgagg ttatgtccga tgtgtgcgtg  4080
gcgcaggtcg ttaaaaattg cttatcacaa taagttgatc gtagaggaag ccaatagaca  4140
gtacggctgc ggatggattt ttctcacgct gacgattcga aatgtaaagg gagaacggct  4200
gaagccacaa atttctgcga tgatggaagg ctttaggaaa ctgttccagt acaaaaaagt  4260
aaaaacttcg gttcttggat ttttcagagc tttagagatt accaaaaatc atgaagaaga  4320
tacatatcat cctcatttttc atgtgttgat accagtaagg aaaaattatt ttgggaaaaa  4380
ctatattaag caggcggagt ggacgagcct ttggaaaaag gcgatgaaat tggattacac  4440
tccaattgtc gatattcgtc gagtgaaagg taaagctaag attgacgctg aacagattga  4500
aaacgatgtg cggaacgcaa tgatggagca aaaagctgtt ctcgaaatct ctaaatatcc  4560
ggttaaggat acggatgttg tgcgcggtaa taaggtgact gaagacaatc tgaacacggt  4620
gctttacttg gatgatgcgt tggcagctcg aaggttaatt ggatacggtg gcattttgaa  4680
ggagatacat aaagagctga atcttggtga tgcggaggac ggcgatctgg tcaagattga  4740
ggaagaagat gacgaggttg caaatggtgc atttgaggtt atggcttatt ggcatcctgg  4800
cattaaaaaat tacataatca aataaaaaaa gcagaccttt agaaggcctg ctttttttaac  4860
taacccattt gtattgtgtt gaaatatgtt ttgtatggtg cactctcagt acaatctgct  4920
ctgatgccgc atagttaagc cagccccgac acccgccaac acccgctgac gcgccctgac  4980
gggcttgtct gctcccggca tccgcttaca gacaagctgt gaccgtctcc gggagctgca  5040
tgtgtcagag gttttcaccg tcatcaccga aacgcgcgag acgaaagggc ctcgtgatac  5100
gcctattttt ataggttaat gtcatgataa taatggtttc ttagcgattc acaaaaaata  5160
ggcacacgaa aaacaagtta agggatgcag tttatgcatc ccttaactta aaatactaaa  5220
aatgcccata ttttttcctc cttataaaat tagtataatt atagcacgag atctaaaagg  5280
atctaggtga agatcctttt tgataatctc atgaccaaaa tcccttaacg tgagttttcg  5340
ttccactgag cgtcagaccc cgtagaaaag atcaaaggat cttcttgaga tccttttttt  5400
ctgcgcgtaa tctgctgctt gcaaacaaaa aaaccaccgc taccagcggt ggtttgtttg  5460
```

```
ccggatcaag agctaccaac tctttttccg aaggtaactg gcttcagcag agcgcagata  5520
ccaaatactg ttcttctagt gtagccgtag ttaggccacc acttcaagaa ctctgtagca  5580
ccgcctacat acctcgctct gctaatcctg ttaccagtgg ctgctgccag tggcgataag  5640
tcgtgtctta ccgggttgga ctcaagacga tagttaccgg ataaggcgca gcggtcgggc  5700
tgaacggggg gttcgtgcac acagcccagc ttggagcgaa cgacctacac cgaactgaga  5760
tacctacagc gtgagctatg agaaagcgcc acgcttcccg aagggagaaa ggcggacagg  5820
tatccggtaa gcggcagggt cggaacagga gagcgcacga gggagcttcc agggggaaac  5880
gcctggtatc tttatagtcc tgtcgggttt cgccacctct gacttgagcg tcgatttttg  5940
tgatgctcgt caggggggcg gagcctatgg aaaaacgcca gcaacgcggc ctttttacgg  6000
ttcctggcct tttgctggcc ttttgctcac atgttctttc ctgcgttatc ccctgattct  6060
gtggataacc gtattaccgc ctttgagtga gctgataccg ctcgccgcag ccgaacgacc  6120
gagcgcagcg agtcagtgag cgaggaagcg gaagagcgcc caatacgcaa accgcctctc  6180
cccgcgcgtt ggccgattca ttaatgcagc tggcacgaca ggtttcccga ctggaaagcg  6240
ggcagtgagc gcaacgcaat taatgtgagt tagctcactc attaggcacc ccaggcttta  6300
cactttatgc ttccggctcg tatgttgtgt ggaattgtga gcggataaca atttcacaca  6360
ggaaacagct atgaccatga ttacgccgga tcc                              6393
```

```
SEQ ID NO: 65          moltype = DNA  length = 2800
FEATURE                Location/Qualifiers
source                 1..2800
                       mol_type = unassigned DNA
                       organism = Bacillus licheniformis
SEQUENCE: 65
tagagacgag acgtctcacc ttgttgtgtt tcattttgtc actctctcct tttcgatcac  60
atctcacgaa aagaggaatg gttctttccc ctgtcctaaa caaaaaaccc gctttattga  120
aaaagcgggg ctgttttaca gacaggtcaa ataaacgttt gaaaatgttc atttcaaaac  180
gcgcggaacc tccatcttct cccatccaga ctatactgtc ggcttcggaa tcgcaccgaa  240
tcctgcccat aaaaaggctc gcgggcttag agcgcttgct catcaccgcc ggtagggaat  300
ttcaccctgc cccgaagatt gatcttattt atttttaata ctgatattat tataaattaa  360
ttgtgaaaaa atgtacaggt gcaaagctta ttgcgctgtt ttgggacatc ctgcacgata  420
tttcggtaaa ctcacttttt ccgcatacta aaaaccgcac attcacagtt atttcatttt  480
taattttcgt ctttccgcgt gaaactcatt gacactcttt atggaatatg gtaaattatc  540
agatatttat gacgcttatt taggaggaaa tcttacatgt ttcgagtatt ggtctcagat  600
aaaatgtcca gcgacggcct caaaccatta atggaagcag attttattga aattgtagaa  660
aagaatgttg cggaagcgga agacgagctt catacgtttg acgcgctctt ggtgcggagc  720
gccacgaagg taaccgaaga gctgtttaaa aagatgactt cgctgaaaat cgtcgccaga  780
gcaggtgtcg gcgtcgacaa tatcgatatt gacgaggcga caaaacacgg tgttatcgtc  840
gtaaacgcgc caaacgggaa tacaatttca accgctgaac atacctttgc aatgtttttca  900
gcgttaatga gacatattcc gcaggcaaac atctccgtga aatcaaggga gtggaatcgt  960
tcggcttacg tcggttcaga gctttacgga aaaacgctcg gcatcatcgg aatgggccgc  1020
atcggaagcg aaatcgcgag ccgcgcaaaa gcattcggta tgaccgttca tgtatttgac  1080
ccgttcctga cccaagaaag ggcaagcaag ctcggcgtta acgcgaacag ctttgaagaa  1140
gttctggcat gcgccgacat cattacggtt catacccccgc tcacgaaaga aacgaaggga  1200
cttttgaaca aagaaaccat cgcaaaaacg aaaaaaggcg ttcgtctcgt taactgtgca  1260
agaggcggca tcatcgatga agcagcgctt ttggaagctc tggaaagcgg acatgtcgct  1320
ggcgctgcct tggatgtatt cgaagtcgag cctccggtcg attcaaaact gatcgatcat  1380
ccgcttgtag tcgcgactcc tcacttgggc gcctcaacaa aagaagccca gctgaatgtc  1440
gctgcacaag tgtccgaaga agtccttcag tatgcgcaag gaaaccctgt gatgtccgcg  1500
atcaaccttc cggccatgac aaaggattca ttcgaaaaaa tccagcctta tcatcagttt  1560
gccaatacga tcggaaacct tgtgtctcag tgcatgaatg agcctgttca agatgtagcc  1620
atccaatatg aaggctccat cgccaaactt gaaacgtcat ttattacgaa aagccttttg  1680
gccggatttc tgaagccgag ggtcgcggct accgttaacg aagtgaatgc cggcaccgtt  1740
gcgaaagagc gcggcatcag cttcagcgaa aaaatttctt ccaatgagtc aggctatgaa  1800
aactgcatct ctgtgactgt cacgggagat gtaacaacat tctctttaag agcgacgtac  1860
attccgcact tcggcggacg catcgttgcc ttaaacggct ttgatattga tttttatccg  1920
gctggacacc ttgtctacat tcaccaccag gataaaccag gggctatcgg ccatgtcgga  1980
cgaattttag gagaccatga catcaatatc gccactatgc aggtaggccg aaaagaaaaa  2040
ggcggagaag cgatcatgat gctttccttt gaccgccacc ttgaggacga tattttagct  2100
gagctgaaaa acatcccgga tatcgtgtct gttaaagcca tcgaccttcc ttaaacagaa  2160
gctgcggaac ctgaaaagaa ttcctttcag gttccgtttt ttttaggaat tctccctgat  2220
ctcaagcatc tggcggggat aaatccgctc tcctttcaaa tcgttccatt ctttgaggcg  2280
ctgtacagtt acgcccattt tttcggcgat atgatgaagc gtatcccctt tccgcactac  2340
atatgtaccg gtcttcgatt catcgtcatg aaggcggagt gtttggccgg ccttgagatt  2400
tgaatgtttc aacccgttta ttctcatgat ctcctcgatg gatataccgc tatccttgct  2460
gattctccag agcgtgtccc ctttttgaac ggtcaccgca ccgctcattg tcccggcgtt  2520
ttgataaacg tggatagaat tttgccggaa cgcctcctca cgaagcaccg tcagcggatt  2580
gattgcatat cttttatctt cagtccatga accgtgatgc atttcaaaat gcaggtgggt  2640
tccggtcgat attcccgtat tgccgatgat tccgatttgc tcgccttttt tcacccgctc  2700
cttttccttt ttcaggcgtt tgcttaagtg ggcataaacg gtttcatatc cgttgtcatg  2760
tttaataaat atcacttggc cgtaggagtc ggattgatac                        2800
```

```
SEQ ID NO: 66          moltype = DNA  length = 1222
FEATURE                Location/Qualifiers
misc_feature           1..1222
                       note = target site 1 edited locus
source                 1..1222
                       mol_type = other DNA
                       organism = synthetic construct
SEQUENCE: 66
```

```
tagagacgag acgtctcacc ttgttgtgtt tcattttgtc actctctcct tttcgatcac  60
atctcacgaa aagaggaatg gttctttccc ctgtcctaaa caaaaaaccc gctttattga  120
aaaagcgggg ctgttttaca gacaggtcaa ataaacgttt gaaaatgttc atttcaaaac  180
gcgcggaacc tccatcttct cccatccaga ctatactgtc ggcttcggaa tcgcaccgaa  240
tcctgcccat aaaaaggctc gcgggcttag agcgcttgct catcaccgcc ggtagggaat  300
ttcaccctgc cccgaagatt gatcttattt atttttaata ctgatattat tataaattaa  360
ttgtgaaaaa atgtacaggt gcaaagctta ttgcgctgtt ttgggacatc ctgcacgata  420
tttcggtaaa ctcacttttt ccgcatacta aaaaccgcac attcacagtt atttcatttt  480
taattttcgt ctttccgcgt gaaactcatt gacactcttt atggaatatg gtaaattatc  540
agatatttat gacgcttatt taggaggaaa tcttacacag aagctgcgga acctgaaaag  600
aattcctttc aggttccgtt ttttttagga attctccctg atctcaagca tctggcgggg  660
ataaatccgc tctcctttca aatcgttcca ttctttgagg cgctgtacag ttacgcccat  720
tttttcggcg atatgatgaa gcgtatcccc tttccgcact acatatgtac cggtcttcga  780
ttcatcgtca tgaaggcgga gtgtttggcc ggccttgaga tttgaatgtt tcaacccgtt  840
tattctcatg atctcctcga tggatatacc gctatccttg ctgattctcc agagcgtgtc  900
cccttttga acggtcaccg caccgctcat tgtcccggcg ttttgataaa cgtggataga  960
attttgccgg aacgcctcct cacgaagcac cgtcagcgga ttgattgcat atcttttatc  1020
ttcagtccat gaaccgtgat gcatttcaaa atgcaggtgg gttccggtcg atattccccgt  1080
attgccgatg attccgattt gctcgccttt tttcacccgc tcctttttcct ttttcaggcg  1140
tttgcttaag tgggcataaa cggtttcata tccgttgtca tgtttaataa atatcacttg  1200
gccgtaggag tcggattgat ac                                          1222

SEQ ID NO: 67          moltype = DNA  length = 20
FEATURE                Location/Qualifiers
misc_feature           1..20
                       note = primer
source                 1..20
                       mol_type = other DNA
                       organism = synthetic construct
SEQUENCE: 67
tagagacgag acgtctcacc                                             20

SEQ ID NO: 68          moltype = DNA  length = 21
FEATURE                Location/Qualifiers
misc_feature           1..21
                       note = primer
source                 1..21
                       mol_type = other DNA
                       organism = synthetic construct
SEQUENCE: 68
gtatcaatcc gactcctacg g                                           21

SEQ ID NO: 69          moltype = DNA  length = 1517
FEATURE                Location/Qualifiers
source                 1..1517
                       mol_type = unassigned DNA
                       organism = Bacillus licheniformis
SEQUENCE: 69
atcaaacatg ccatgtttgc ggcgtatttt gtcaaaatga tattttcgcc gtcggtatat  60
atttcgagcg ggtccttttc attgatattc agcaccctgc gcatttcgac cgggagaacg  120
actctgccga gctcatcgat tctccggaca atcccggtat ttttcacgtt tgaaaagcct  180
ccttttctcc tttctttatt gacttttgtc aacatcttta taataaaaga gatcttcaaa  240
ttttttgttg aaatactgaa tcatctttcc gatcacaagt tgtccgggcc tcctttcgcc  300
atttaaaact ctgctgagtg tcgccgggga tacgccgatt tcaatggcaa gctgatttaa  360
ggagagattg tgttcaatca tgtactggag aacaaaatct cttttgatat gaatcttttt  420
taccatgatt actccccttt ctaatctctt atgtttcttt ttatctacat tgaacatata  480
cgatttgtta actttttgtca atacttttac catccatatg tttcctatag gcaatattcg  540
tactaaaata ttttataata agagattgcg aggttttggc catgacgaac tttggacacc  600
atttacgaca attaagggaa cggaaaaaac tgaccgtcaa tcaactggcg atgtattccg  660
gcgtcagttc ggcaggcatt tcgcgaatcg aaaacggaaa gcgcggcgtg ccgaagccgg  720
cgacgatcag aaaactggcg gacgctttga aagtcccgta tgaggaactg atggcatctg  780
caggctatat cagcgcgtct acagtccagg aagcaagaag cagctatgat tccatttacg  840
acatcgtgtc acagtacgat ttagaggacc tttctctgtt tgacagcgaa aagtggaagg  900
tgctttcaaa aaaagacatc gaaaacctgg acaaatattt cgactttctc gtgcaggaag  960
caagcagccg aaacaaaaac tgaatacttc tccgcggcac actctcctct ctatcatttt  1020
cgtctgttta cgatcctgct gttattttat cccttatgtt aacttttgtc aatattttttc  1080
ctgtctaagt atttcctata gtcaacattt gtattaaaat gttcatatca tgaatttgcg  1140
ggggggatgg cgatgacaag gttcggcgag cggctcaaag agctgaggga acaaagaagc  1200
ctgtcggtta atcagcttgc catgtatgcc ggtgtgagcg ccgcagccat ttccagagcc  1260
gcagccattt ccagaatcga aaacggccac cgcggcgttc ccaagcccgc gacgatcaga  1320
aaattggccg aggctctgaa aatgccgtac gagcagctca tggatattgc cggttatatg  1380
agagctgacg agattcgcga acagccgcgc ggctatgtca cgatgcagga gatcgcggcc  1440
aagcacggcg tcgaagacct gtggctgttt aaacccgaga aatgggactg tttgtcccgc  1500
gaagacctgc tcaacct                                                1517

SEQ ID NO: 70          moltype = DNA  length = 1115
FEATURE                Location/Qualifiers
misc_feature           1..1115
                       note = target site 2 edited locus
```

```
source                1..1115
                      mol_type = other DNA
                      organism = synthetic construct
SEQUENCE: 70
atcaaacatg ccatgtttgc ggcgtatttt gtcaaaatga tattttcgcc gtcggtatat  60
atttcgagcg ggtccttttc attgatattc agcaccctgc gcatttcgac cgggagaacg  120
actctgccga gctcatcgat tctccggaca atcccggtat tttcacgtt tgaaaagcct  180
ccttttctcc tttctttatt gacttttgtc aacatcttta taataaaaga gatcttcaaa  240
ttttttgttg aaatactgaa tcatctttcc gatcacaagt tgtccgggcc tcctttcgcc  300
atttaaaact ctgctgagtg tcgccgggga tacgccgatt tcaatggcaa gctgatttaa  360
ggagagattg tgttcaatca tgtactggag aacaaaatct cttttgatat gaatcttttt  420
taccatgatt actccccttt ctaatctctt atgtttcttt ttatctacat tgaacatata  480
cgatttgtta acttttgtca atacttttac catccatatg tttcctatag gcaatattcg  540
tactaaaata ttttataata agagattgcg aggttttggc catacttctc cgcggcacac  600
tctcctctct atcattttcg tctgtttacg atcctgctgt tattttatcc cttatgttaa  660
cttttgtcaa tatttttcct gtctaagtat ttcctatagt caacatttgt attaaaatgt  720
tcatatcatg aatttgcggg ggggatggcg atgacaaggt tcggcgagcg gctcaaagag  780
ctgagggaac aaagaagcct gtcggttaat cagcttgcca tgtatgccgg tgtgagcgcc  840
gcagccattt ccagagccgc agccatttcc agaatcgaaa acggccaccg cggcgttccc  900
aagcccgcga cgatcagaaa attggccgag gctctgaaaa tgccgtacga gcagctcatg  960
gatattgccg gttatatgag agctgacgag attcgcgaac agccgcgcgg ctatgtcacg  1020
atgcaggaga tcgcggccaa gcacggcgtc gaagacctgt ggctgtttaa acccgagaaa  1080
tgggactgtt tgtcccgcga agacctgctc aacct                            1115

SEQ ID NO: 71         moltype = DNA  length = 20
FEATURE               Location/Qualifiers
misc_feature          1..20
                      note = primer
source                1..20
                      mol_type = other DNA
                      organism = synthetic construct
SEQUENCE: 71
atcaaacatg ccatgtttgc                                              20

SEQ ID NO: 72         moltype = DNA  length = 18
FEATURE               Location/Qualifiers
misc_feature          1..18
                      note = primer
source                1..18
                      mol_type = other DNA
                      organism = synthetic construct
SEQUENCE: 72
aggttgagca ggtcttcg                                                18

SEQ ID NO: 73         moltype = DNA  length = 4272
FEATURE               Location/Qualifiers
misc_feature          1..4272
                      note = Yarrowia codon optimized Cas9
source                1..4272
                      mol_type = other DNA
                      organism = synthetic construct
SEQUENCE: 73
atggggggtt ctcatcatca tcatcatcat ggtatggcta gcatgactgg tggacagcaa  60
atgggtcggg atctgtacga cgatgacgat aaggatccga gctcgagatc tgcagctggt  120
accatatggg aattcgacaa gaaatactcc atcggcctgg acattggaac caactctgtc  180
ggctgggctg tcatcaccga cgagtacaag gtgccctcca agaaattcaa ggtcctcgga  240
aacaccgatc gacactccat caagaaaaac ctcattggtg ccctgttgtt cgattctggc  300
gagactgccg aagctaccag actcaagcga actgctcggc gacgttacac ccgacggaag  360
aaccgaatct gctacctgca ggagatcttt tccaacgaga tggccaaggt ggacgattcg  420
ttctttcatc gactggagga atccttcctc gtcgaggaag acaagaaaca cgagcgtcat  480
cccatctttg gcaacattgt ggacgaggtt gcttaccacg agaagtatcc taccatctac  540
cacctgcgaa agaaactcgt cgattccacc gacaaggcgg atctcagact tatctacctc  600
gctctggcac acatgatcaa gtttcgaggt catttcctca tcgagggcga tctcaatccc  660
gacaacagcg atgtggacaa gctgttcatt cagctcgttc agacctacaa ccagctgttc  720
gaggaaaacc ccatcaatgc ctccggagtc gatgcaaagg ccatcttgtc tgctcgactc  780
tcgaagagca gacgactgga gaacctcatt gcccaacttc ctggcgagaa aaagaacgga  840
ctgtttggca acctcattgc cctttctctt ggtctcacac ccaacttcaa gtccaacttc  900
gatctggcgg aggacgccaa gctccagctg tccaaggaca cctacgacga tgacctcgac  960
aacctgcttg cacagattgg cgatcagtac gccgacctgt ttctcgctgc caagaacctt  1020
tcggatgcta ttctcttgtc tgacattctg cgagtcaaca ccgagatcac aaaggctccc  1080
ctttctgcct ccatgatcaa gcgatacgac gagcaccatc aggatctcac actgctcaag  1140
gctcttgtcc gacagcaact gcccgagaag tacaaggaga tcttttttcga tcagtcgaag  1200
aacggctacg ctggatacat cgacggcgga gcctctcagg aagagttcta caagttcatc  1260
aagccaattc tcgagaagat ggacggaacc gaggaactgc ttgtcaagct caatcgagag  1320
gatctgcttc ggaagcaacg aaccttcgac aacggcagca ttcctcatca gatccacctc  1380
ggtgagctgc acgccattct tcgacgtcag gaagacttct accccttct caaggacaac  1440
cgagagaaga tcgagaagat tcttaccttt cgaatcccct actatgttgg tcctcttgcc  1500
agaggaaact ctcgatttgc ttggatgact cgaaagtccg aggaaaccat cactccctgg  1560
aacttcgagg aagtcgtgga caagggtgcc tctgcacagt ccttcatcga gcgaatgacc  1620
```

```
aacttcgaca agaatctgcc caacgagaag gttcttccca agcattcgct gctctacgag  1680
tactttacag tctacaacga actcaccaaa gtcaagtacg ttaccgaggg aatgcgaaag  1740
cctgccttct tgtctggcga acagaagaaa gccattgtcg atctcctgtt caagaccaac  1800
cgaaaggtca ctgttaagca gctcaaggag gactacttca agaaaatcga gtgtttcgac  1860
agcgtcgaga tttccggagt tgaggaccga ttcaacgcct ctttgggcac ctatcacgat  1920
ctgctcaaga ttatcaagga caaggatttt ctcgacaacg aggaaaacga ggacattctg  1980
gaggacatcg tgctcactct taccctgttc gaagatcggg agatgatcga ggaacgactc  2040
aagacatacg ctcacctgtt cgacgacaag gtcatgaaac aactcaagcg acgtagatac  2100
accggctggg gaagactttc gcgaaagctc atcaacggca tcagagacaa gcagtccgga  2160
aagaccattc tggactttct caagtccgat ggctttgcca accgaaactt catgcagctc  2220
attcacgacg attctcttac cttcaaggag gacatccaga aggcacaagt gtccggtcag  2280
ggcgacagct tgcacgaaca tattgccaac ctggctggtt cgccagccat caagaaaggc  2340
attctccaga ctgtcaaggt tgtcgacgag ctggtgaagg tcatgggacg tcacaagccc  2400
gagaacattg tgatcgagat ggccagagag aaccagacaa ctcaaaaggg tcagaaaaac  2460
tcgcgagagc ggatgaagcg aatcgaggaa ggcatcaagg agctgggatc ccagattctc  2520
aaggagcatc ccgtcgagaa cactcaactg cagaacgaga agctgtatct ctactatctg  2580
cagaatggtc gagacatgta cgtggatcag gaactggaca tcaatcgtct cagcgactac  2640
gatgtggacc acattgtccc tcaatccttt ctcaaggacg attctatcga caacaaggtc  2700
cttacacgat ccgacaagaa cagaggcaag tcggacaacg ttcccagcga agaggtggtc  2760
aaaaagatga agaactactg gcgacagctg ctcaacgcca agctcattac ccagcgaaag  2820
ttcgacaatc ttaccaaggc cgagcgaggc ggtctgtccg agctcgacaa ggctggcttc  2880
atcaagcgtc aactcgtcga gaccagacag atcacaaagc acgtcgcaca gattctcgat  2940
tctcggatga acaccaagta cgacgagaac gacaagctca tccgagaggt caaggtgatt  3000
actctcaagt ccaaactggt ctccgatttc cgaaaggact ttcagttcta caaggtgcga  3060
gagatcaaca attaccacca tgcccacgat gcttacctca acgccgtcgt tggcactgcg  3120
ctcatcaaga aataccccaa gctcgaaagc gagttcgttt acggcgatta caaggtctac  3180
gacgttcgaa agatgattgc caagtccgaa caggagattg gcaaggctac tgccaagtac  3240
ttcttttact ccaacatcat gaactttttc aagaccgaga tcaccttggc caacggagag  3300
attcgaaaga gaccacttat cgagaccaac ggcgaaactg gagagatcgt gtgggacaag  3360
ggtcgagact ttgcaaccgt gcgaaaggtt ctgtcgatgc ctcaggtcaa catcgtcaag  3420
aaaaccgagg ttcagactgg cggattctcc aaggagtcga ttctgcccaa gcgaaactcc  3480
gacaagctca tcgctcgaaa gaaagactgg gatcccaaga aatacggtgg cttcgattct  3540
cctaccgtcg cctattccgt gcttgtcgtt gcgaaggtcg agaagggcaa gtccaaaaag  3600
ctcaagtccg tcaaggagct gctcggaatt accatcatgg agcgatcgag cttcgagaag  3660
aatcccatcg acttcttgga agccaagggt tacaaggagg tcaagaaaga cctcattatc  3720
aagctgccca agtactctct gttcgaactg gagaacggtc gaaagcgtat gctcgcctcc  3780
gctggcgagc tgcagaaggg aaacgagctt gccttgcctt cgaagtacgt caactttctc  3840
tatctggctt ctcactacga gaagctcaag ggttctcccg aggacaacga acagaagcaa  3900
ctcttcgttg agcagcacaa acattacctc gacgagatta tcgagcagat ttccgagttt  3960
tcgaagcgag tcatcctggc tgatgccaac ttggacaagg tgctctctgc ctacaacaag  4020
catcgggaca aacccattcg agaacaggcg gagaacatca ttcacctgtt tactcttacc  4080
aacctgggtg ctcctgcagc tttcaagtac ttcgatacca ctatcgaccg aaagcggtac  4140
acatccacca aggaggttct cgatgccacc ctgattcacc agtccatcac tggcctgtac  4200
gagacccgaa tcgacctgtc tcagcttggt ggcgactcca gagccgatcc caagaaaaag  4260
cgaaaggtct aa                                                      4272
```

```
SEQ ID NO: 74          moltype = AA  length = 9
FEATURE                Location/Qualifiers
source                 1..9
                       mol_type = protein
                       organism = Streptococcus pyogenes
SEQUENCE: 74
MAPKKKRKV                                                          9
```

```
SEQ ID NO: 75          moltype = DNA  length = 546
FEATURE                Location/Qualifiers
source                 1..546
                       mol_type = unassigned DNA
                       organism = Streptococcus pyogenes
SEQUENCE: 75
tcgacgttta aaccatcatc taagggcctc aaaactacct cggaactgct gcgctgatct  60
ggacaccaca gaggttccga gcactttagg ttgcaccaaa tgtcccacca ggtgcaggca  120
gaaaacgctg gaacagcgtg tacagtttgt cttaacaaaa agtgagggcg ctgaggtcga  180
gcagggtggt gtgacttgtt atagccttta gagctgcgaa agcgcgtatg gatttggctc  240
atcaggccag attgagggtc tgtggacaca tgtcatgtta gtgtacttca atcgccccct  300
ggatatagcc ccgacaatag gccgtggcct catttttttg ccttccgcac atttccattg  360
ctcggtaccc acaccttgct tctcctgcac ttgccaacct taatactggt ttacattgac  420
caacatctta caagcggggg gcttgtctag ggtatatata aacagtggct ctcccaatcg  480
gttgccagtc tctttttttcc tttctttccc cacagattcg aaatctaaac tacacatcac  540
accatg                                                             546
```

```
SEQ ID NO: 76          moltype = DNA  length = 4683
FEATURE                Location/Qualifiers
misc_feature           1..4683
                       note = Yarrowia Cas9 expression cassette
source                 1..4683
                       mol_type = other DNA
                       organism = synthetic construct
SEQUENCE: 76
```

-continued

```
tcgacgttta aaccatcatc taagggcctc aaaactacct cggaactgct gcgctgatct  60
ggacaccaca gaggttccga gcactttagg ttgcaccaaa tgtcccacca ggtgcaggca  120
gaaaacgctg gaacagcgtg tacagtttgt cttaacaaaa agtgagggcg ctgaggtcga  180
gcagggtggt gtgacttgtt atagccttta gagctgcgaa agcgcgtatg gatttggctc  240
atcaggccag attgagggtc tgtggacaca tgtcatgtta gtgtacttca atcgcccccct  300
ggatatagcc ccgacaatag gccgtggcct catttttttg ccttccgcac atttccattg  360
ctcggtaccc acaccttgct tctcctgcac ttgccaacct taatactggt ttacattgac  420
caacatctta caagcggggg gcttgtctag ggtatatata aacagtggct ctcccaatcg  480
gttgccagtc tcttttttcc tttctttccc cacagattcg aaatctaaac tacacatcac  540
accatggaca agaaatactc catcggcctg gacattggaa ccaactctgt cggctgggct  600
gtcatcaccg acgagtacaa ggtgccctcc aagaaattca aggtcctcgg aaacaccgat  660
cgacactcca tcaagaaaaa cctcattggt gccctgttgt tcgattctgg cgagactgcc  720
gaagctacca gactcaagcg aactgctcgg cgacgttaca cccgacggaa gaaccgaatc  780
tgctacctgc aggagatctt ttccaacgag atggccaagg tggacgattc gttctttcat  840
cgactggagg aatccttcct cgtcgaggaa gacaagaaac acgagcgtca tcccatcttt  900
ggcaacattg tggacgaggt tgcttaccac gagaagtatc ctaccatcta ccacctgcga  960
aagaaactcg tcgattccac cgacaaggcg gatctcagac ttatctacct cgctctggca  1020
cacatgatca agtttcgagg tcatttcctc atcgagggcg atctcaatcc cgacaacagc  1080
gatgtggaca agctgttcat tcagctcgtt cagacctaca accagctgtt cgaggaaaac  1140
cccatcaatg cctccggagt cgatgcaaag gccatcttgt ctgctcgact ctcgaagagc  1200
agacgactgg agaacctcat tgcccaactt cctggcgaga aaaagaacgg actgtttggc  1260
aacctcattg ccctttctct tggtctcaca cccaacttca agtccaactt cgatctggcg  1320
gaggacgcca agctccagct gtccaaggac acctacgacg atgacctcga caacctgctt  1380
gcacagattg gcgatcagta cgccgacctg tttctcgctg ccaagaacct ttcggatgct  1440
attctcttgt ctgacattct gcgagtcaac accgagatca caaaggctcc cctttctgcc  1500
tccatgatca agcgatacga cgagcaccat caggatctca cactgctcaa ggctcttgtc  1560
cgacagcaac tgcccgagaa gtacaaggag atcttttttcg atcagtcgaa gaacggctac  1620
gctggataca tcgacggcgg agcctctcag gaagagttct acaagttcat caagccaatt  1680
ctcgagaaga tggacggaac cgaggaactg cttgtcaagc tcaatcgaga ggatctgctt  1740
cggaagcaac gaaccttcga caacggcagc attcctcatc agatccacct cggtgagctg  1800
cacgccattc ttcgacgtca ggaagacttc taccccttc tcaaggacaa ccgagagaag  1860
atcgagaaga ttcttacctt tcgaatcccc tactatgttg gtcctcttgc cagaggaaac  1920
tctcgatttg cttggatgac tcgaaagtcc gaggaaacca tcactccctg gaacttcgag  1980
gaagtcgtgg acaagggtgc ctctgcacag tccttcatcg agcgaatgac caacttcgac  2040
aagaatctgc ccaacgagaa ggttcttccc aagcattcgc tgctctacga gtactttaca  2100
gtctacaacg aactcaccaa agtcaagtac gttaccgagg gaatgcgaaa gcctgccttc  2160
ttgtctggcg aacagaagaa agccattgtc gatctcctgt tcaagaccaa ccgaaaggtc  2220
actgttaagc agctcaagga ggactacttc aagaaaatcg agtgtttcga cagcgtcgag  2280
atttccggag ttgaggaccg attcaacgcc tctttgggca cctatcacga tctgctcaag  2340
attatcaagg acaaggattt tctcgacaac gaggaaaacg aggacattct ggaggacatc  2400
gtgctcactc ttaccctgtt cgaagatcgg gagatgatcg aggaacgact caagacatac  2460
gctcacctgt tcgacgacaa ggtcatgaaa caactcaagc gacgtagata caccggctgg  2520
ggaagacttt cgcgaaagct catcaacggc atcagagaca agcagtccgg aaagaccatt  2580
ctggactttc tcaagtccga tggctttgcc aaccgaaact tcatgcagct cattcacgac  2640
gattctctta ccttcaagga ggacatccag aaggcacaag tgtccggtca gggcgacagc  2700
ttgcacgaac atattgccaa cctggctggt tcgccagcca tcaagaaagg cattctccag  2760
actgtcaagg ttgtcgacga gctggtgaag gtcatgggac gtcacaagcc cgagaacatt  2820
gtgatcgaga tggccagaga gaaccagaca actcaaaagg gtcagaaaaa ctcgcgagag  2880
cggatgaagc gaatcgagga aggcatcaag gagctgggat cccagattct caaggagcat  2940
cccgtcgaga acactcaact gcagaacgag aagctgtatc tctactatct gcagaatggt  3000
cgagacatgt acgtggatca ggaactggac atcaatcgtc tcagcgacta cgatgtggac  3060
cacattgtcc ctcaatcctt tctcaaggac gattctatcg acaacaaggt ccttacacga  3120
tccgacaaga acagaggcaa gtcggacaac gttcccagcg aagaggtggt caaaaagatg  3180
aagaactact ggcgacagct gctcaacgcc aagctcatta cccagcgaaa gttcgacaat  3240
cttaccaagg ccgagcgagg cggtctgtcc gagctcgaca aggctggctt catcaagcgt  3300
caactcgtcg agaccagaca gatcacaaag cacgtcgcac agattctcga ttctcggatg  3360
aacaccaagt acgacgagaa cgacaagctc atccgagagg tcaaggtgat tactctcaag  3420
tccaaactgg tctccgattt ccgaaaggac tttcagttct acaaggtgcg agagatcaac  3480
aattaccacc atgcccacga tgcttacctc aacgccgtcg ttggcactgc gctcatcaag  3540
aaataccccca agctcgaaag cgagttcgtt tacggcgatt acaaggtcta cgacgttcga  3600
aagatgattg ccaagtccga acaggagatt ggcaaggcta ctgccaagta cttcttttac  3660
tccaacatca tgaacttttt caagaccgag atcaccttgg ccaacggaga gattcgaaag  3720
agaccactta tcgagaccaa cggcgaaact ggagagatcg tgtgggacaa gggtcgagac  3780
tttgcaaccg tgcgaaaggt tctgtcgatg cctcaggtca acatcgtcaa gaaaaccgag  3840
gttcagactg gcggattctc caaggagtcg attctgccca agcgaaactc cgacaagctc  3900
atcgctcgaa agaaagactg ggatcccaag aaatacggtg gcttcgattc tcctaccgtc  3960
gcctattccg tgcttgtcgt tgcgaaggtc gagaagggca agtccaaaaa gctcaagtcc  4020
gtcaaggagc tgctcggaat taccatcatg gagcgatcga gcttcgagaa gaatcccatc  4080
gacttcttgg aagccaaggg ttacaaggag gtcaagaaag acctcattat caagctgccc  4140
aagtactctc tgttcgaact ggagaacggt cgaaagcgta tgctcgcctc cgctggcgag  4200
ctgcagaagg gaaacgagct tgccttgcct tcgaagtacg tcaactttct ctatctggct  4260
tctcactacg agaagctcaa gggttctccc gaggacaacg aacagaagca actcttcgtt  4320
gagcagcaca aacattacct cgacgagatt atcgagcaga tttccgagtt ttcgaagcga  4380
gtcatcctgg ctgatgccaa cttggacaag gtgctctctg cctacaacaa gcatcgggac  4440
aaacccattc gagaacaggc ggagaacatc attcacctgt ttactcttac caacctgggt  4500
gctcctgcag ctttcaagta cttcgatacc actatcgacc gaaagcggta cacatccacc  4560
aaggaggttc tcgatgccac cctgattcac cagtccatca ctggcctgta cgagacccga  4620
atcgacctgt ctcagcttgg tggcgactcc agagccgatc ccaagaaaaa gcgaaaggtc  4680
taa                                                                4683
```

```
SEQ ID NO: 77          moltype = DNA  length = 10706
FEATURE                Location/Qualifiers
misc_feature           1..10706
                       note = plasmid pZufCas9
source                 1..10706
                       mol_type = other DNA
                       organism = synthetic construct
SEQUENCE: 77
catggacaag aaatactcca tcggcctgga cattggaacc aactctgtcg gctgggctgt  60
catcaccgac gagtacaagg tgccctccaa gaaattcaag gtcctcggaa acaccgatcg  120
acactccatc aagaaaaacc tcattggtgc cctgttgttc gattctggcg agactgccga  180
agctaccaga ctcaagcgaa ctgctcggcg acgttacacc cgacggaaga accgaatctg  240
ctacctgcag gagatctttt ccaacgagat ggccaaggtg gacgattcgt tctttcatcg  300
actggaggaa tccttcctcg tcgaggaaga caagaaacac gagcgtcatc ccatctttgg  360
caacattgtg gacgaggttg cttaccacga gaagtatcct accatctacc acctgcgaaa  420
gaaactcgtc gattccaccg acaaggcgga tctcagactt atctacctcg ctctggcaca  480
catgatcaag tttcgaggtc atttcctcat cgagggcgat ctcaatcccg acaacagcga  540
tgtggacaag ctgttcattc agctcgttca gacctacaac cagctgttcg aggaaaaccc  600
catcaatgcc tccggagtcg atgcaaaggc catcttgtct gctcgactct cgaagagcag  660
acgactggag aacctcattg cccaacttcc tggcgagaaa aagaacggac tgtttggcaa  720
cctcattgcc ctttctcttg gtctcacacc caacttcaag tccaacttcg atctggcgga  780
ggacgccaag ctccagctgt ccaaggacac ctacgacgat gacctcgaca acctgcttgc  840
acagattggc gatcagtacg ccgacctgtt tctcgctgcc aagaaccttt cggatgctat  900
tctcttgtct gacattctgc gagtcaacac cgagatcaca aaggctcccc tttctgcctc  960
catgatcaag cgatacgacg agcaccatca ggatctcaca ctgctcaagg ctcttgtccg  1020
acagcaactg cccgagaagt acaaggagat cttttttcgat cagtcgaaga acggctacgc  1080
tggatacatc gacggcggag cctctcagga agagttctac aagttcatca agccaattct  1140
cgagaagatg gacggaaccg aggaactgct tgtcaagctc aatcgagagg atctgcttcg  1200
gaagcaacga accttcgaca acggcagcat tcctcatcag atccacctcg gtgagctgca  1260
cgccattctt cgacgtcagg aagacttcta ccccttttctc aaggacaacc gagagaagat  1320
cgagaagatt cttacctttc gaatccccta ctatgttggt cctcttgcca gaggaaactc  1380
tcgatttgct tggatgactc gaaagtccga ggaaaccatc actccctgga acttcgagga  1440
agtcgtggac aagggtgcct ctgcacagtc cttcatcgag cgaatgacca acttcgacaa  1500
gaatctgccc aacgagaagg ttcttcccaa gcattcgctg ctctacgagt actttacagt  1560
ctacaacgaa ctcaccaaag tcaagtacgt taccgaggga atgcgaaagc ctgccttctt  1620
gtctggcgaa cagaagaaag ccattgtcga tctcctgttc aagaccaacc gaaaggtcac  1680
tgttaagcag ctcaaggagg actacttcaa gaaaatcgag tgtttcgaca gcgtcgagat  1740
ttccggagtt gaggaccgat tcaacgcctc tttgggcacc tatcacgatc tgctcaagat  1800
tatcaaggac aaggatttc tcgacaacga ggaaaacgag gacattctgg aggacatcgt  1860
gctcactctt accctgttcg aagatcggga gatgatcgag gaacgactca agacatacgc  1920
tcacctgttc gacgacaagg tcatgaaaca actcaagcga cgtagataca ccggctgggg  1980
aagactttcg cgaaagctca tcaacggcat cagagacaag cagtccggaa agaccattct  2040
ggactttctc aagtccgatg gctttgccaa ccgaaacttc atgcagctca ttcacgacga  2100
ttctcttacc ttcaaggagg acatccagaa ggcacaagtg tccggtcagg gcgacagctt  2160
gcacgaacat attgccaacc tggctggttc gccagccatc aagaaaggca ttctccagac  2220
tgtcaaggtt gtcgacgagc tggtgaaggt catgggacgt cacaagcccg agaacattgt  2280
gatcgagatg gccagagaga accagacaac tcaaaagggt cagaaaaact cgcgagagcg  2340
gatgaagcga atcgaggaag gcatcaagga gctgggatcc cagattctca aggagcatcc  2400
cgtcgagaac actcaactgc agaacgagaa gctgtatctc tactatctgc agaatggtcg  2460
agacatgtac gtggatcagg aactggacat caatcgtctc agcgactacg atgtggacca  2520
cattgtccct caatcctttc tcaaggacga ttctatcgac aacaaggtcc ttacacgatc  2580
cgacaagaac agaggcaagt cggacaacgt tcccagcgaa gaggtggtca aaaagatgaa  2640
gaactactgg cgacagctgc tcaacgccaa gctcattacc cagcgaaagt tcgacaatct  2700
taccaaggcc gagcgaggcg gtctgtccga gctcgacaag gctggcttca tcaagcgtca  2760
actcgtcgag accagacaga tcacaaagca cgtcgcacag attctcgatt ctcggatgaa  2820
caccaagtac gacgagaacg acaagctcat ccgagaggtc aaggtgatta ctctcaagtc  2880
caaactggtc tccgatttcc gaaaggactt tcagttctac aaggtgcgag agatcaacaa  2940
ttaccaccat gcccacgatg cttacctcaa cgccgtcgtt ggcactgcgc tcatcaagaa  3000
ataccccaag ctcgaaagcg agttcgttta cggcgattac aaggtctacg acgttcgaaa  3060
gatgattgcc aagtccgaac aggagattgg caaggctact gccaagtact tcttttactc  3120
caacatcatg aactttttca agaccgagat caccttggcc aacggagaga ttcgaaagag  3180
accacttatc gagaccaacg gcgaaactgg agagatcgtg tgggacaagg gtcgagactt  3240
tgcaaccgtg cgaaaggttc tgtcgatgcc tcaggtcaac atcgtcaaga aaaccgaggt  3300
tcagactggc ggattctcca aggagtcgat tctgcccaag cgaaactccg acaagctcat  3360
cgctcgaaag aaagactggg atcccaagaa atacggtggc ttcgattctc ctaccgtcgc  3420
ctattccgtg cttgtcgttg cgaaggtcga gaagggcaag tccaaaaagc tcaagtccgt  3480
caaggagctg ctcggaatta ccatcatgga gcgatcgagc ttcgagaaga atcccatcga  3540
cttcttggaa gccaagggtt acaaggaggt caagaaagac ctcattatca agctgcccaa  3600
gtactctctg ttcgaactgg agaacggtcg aaagcgtatg ctcgcctccg ctggcgagct  3660
gcagaaggga aacgagcttg ccttgccttc gaagtacgtc aactttctct atctggcttc  3720
tcactacgag aagctcaagg gttctcccga ggacaacgaa cagaagcaac tcttcgttga  3780
gcagcacaaa cattacctcg acgagattat cgagcagatt tccgagtttt cgaagcgagt  3840
catcctggct gatgccaact tggacaaggt gctctctgcc tacaacaagc atcgggacaa  3900
acccattcga gaacaggcgg agaacatcat tcacctgttt actcttacca acctgggtgc  3960
tcctgcagct ttcaagtact tcgataccac tatcgaccga aagcggtaca catccaccaa  4020
ggaggttctc gatgccaccc tgattcacca gtccatcact ggcctgtacg agacccgaat  4080
cgacctgtct cagcttggtg gcgactccag agccgatccc aagaaaaagc gaaaggtcta  4140
agcggccgca agtgtggatg gggaagtgag tgcccggttc tgtgtgcaca attggcaatc  4200
```

```
caagatggat ggattcaaca cagggatata gcgagctacg tggtggtgcg aggatatagc  4260
aacggatatt tatgtttgac acttgagaat gtacgataca agcactgtcc aagtacaata  4320
ctaaacatac tgtacatact catactcgta cccgggcaac ggtttcactt gagtgcagtg  4380
gctagtgctc ttactcgtac agtgtgcaat actgcgtatc atagtctttg atgtatatcg  4440
tattcattca tgttagttgc gtacgagccg gaagcataaa gtgtaaagcc tggggtgcct  4500
aatgagtgag ctaactcaca ttaattgcgt tgcgctcact gcccgctttc cagtcgggaa  4560
acctgtcgtg ccagctgcat taatgaatcg gccaacgcgc ggggagaggc ggtttgcgta  4620
ttgggcgctc ttccgcttcc tcgctcactg actcgctgcg ctcggtcgtt cggctgcggc  4680
gagcggtatc agctcactca aaggcggtaa tacggttatc cacagaatca ggggataacg  4740
caggaaagaa catgtgagca aaaggccagc aaaaggccag gaaccgtaaa aaggccgcgt  4800
tgctggcgtt tttccatagg ctccgccccc ctgacgagca tcacaaaaat cgacgctcaa  4860
gtcagaggtg gcgaaacccg acaggactat aaagatacca ggcgtttccc cctggaagct  4920
ccctcgtgcg ctctcctgtt ccgaccctgc cgcttaccgg atacctgtcc gcctttctcc  4980
cttcgggaag cgtggcgctt tctcatagct cacgctgtag gtatctcagt tcggtgtagg  5040
tcgttcgctc caagctgggc tgtgtgcacg aaccccccgt tcagcccgac cgctgcgcct  5100
tatccggtaa ctatcgtctt gagtccaacc cggtaagaca cgacttatcg ccactggcag  5160
cagccactgg taacaggatt agcagagcga ggtatgtagg cggtgctaca gagttcttga  5220
agtggtggcc taactacggc tacactagaa ggacagtatt tggtatctgc gctctgctga  5280
agccagttac cttcggaaaa agagttggta gctcttgatc cggcaaacaa accaccgctg  5340
gtagcggtgg tttttttgtt tgcaagcagc agattacgcg cagaaaaaaa ggatctcaag  5400
aagatccttt gatcttttct acggggtctg acgctcagtg gaacgaaaac tcacgttaag  5460
ggattttggt catgagatta tcaaaaagga tcttcaccta gatcctttta aattaaaaat  5520
gaagttttaa atcaatctaa agtatatatg agtaaacttg gtctgacagt taccaatgct  5580
taatcagtga ggcacctatc tcagcgatct gtctatttcg ttcatccata gttgcctgac  5640
tccccgtcgt gtagataact acgatacggg agggcttacc atctggcccc agtgctgcaa  5700
tgataccgcg agacccacgc tcaccggctc cagatttatc agcaataaac cagccagccg  5760
gaagggccga gcgcagaagt ggtcctgcaa ctttatccgc ctccatccag tctattaatt  5820
gttgccggga agctagagta agtagttcgc cagttaatag tttgcgcaac gttgttgcca  5880
ttgctacagg catcgtggtg tcacgctcgt cgtttggtat ggcttcattc agctccggtt  5940
cccaacgatc aaggcgagtt acatgatccc ccatgttgtg caaaaaagcg gttagctcct  6000
tcggtcctcc gatcgttgtc agaagtaagt tggccgcagt gttatcactc atggttatgg  6060
cagcactgca taattctctt actgtcatgc catccgtaag atgcttttct gtgactggtg  6120
agtactcaac caagtcattc tgagaatagt gtatgcggcg accgagttgc tcttgcccgg  6180
cgtcaatacg ggataatacc gcgccacata gcagaacttt aaaagtgctc atcattggaa  6240
aacgttcttc ggggcgaaaa ctctcaagga tcttaccgct gttgagatcc agttcgatgt  6300
aacccactcg tgcacccaac tgatcttcag catcttttac tttcaccagc gtttctgggt  6360
gagcaaaaac aggaaggcaa aatgccgcaa aaaagggaat aagggcgaca cggaaatgtt  6420
gaatactcat actcttcctt tttcaatatt attgaagcat ttatcagggt tattgtctca  6480
tgagcggata catatttgaa tgtatttaga aaaataaaca aataggggtt ccgcgcacat  6540
ttccccgaaa agtgccacct gacgcgccct gtagcggcgc attaagcgcg gcgggtgtgg  6600
tggttacgcg cagcgtgacc gctacacttg ccagcgccct agcgcccgct cctttcgctt  6660
tcttcccttc ctttctcgcc acgttcgccg gctttccccg tcaagctcta aatcgggggc  6720
tccctttagg gttccgattt agtgctttac ggcacctcga ccccaaaaaa cttgattagg  6780
gtgatggttc acgtagtggg ccatcgccct gatagacggt ttttcgccct ttgacgttgg  6840
agtccacgtt ctttaatagt ggactcttgt tccaaactgg aacaacactc aaccctatct  6900
cggtctattc ttttgattta taagggattt tgccgatttc ggcctattgg ttaaaaaatg  6960
agctgattta acaaaaattt aacgcgaatt ttaacaaaat attaacgctt acaatttcca  7020
ttcgccattc aggctgcgca actgttggga agggcgatcg gtgcgggcct cttcgctatt  7080
acgccagctg gcgaaagggg gatgtgctgc aaggcgatta agttgggtaa cgccagggtt  7140
ttcccagtca cgacgttgta aaacgacggc cagtgaattg taatacgact cactataggg  7200
cgaattgggt accgggcccc ccctcgaggt cgatggtgtc gataagcttg atatcgaatt  7260
catgtcacac aaaccgatct tcgcctcaag gaaacctaat tctacatccg agagactgcc  7320
gagatccagt ctacactgat taattttcgg gccaataatt taaaaaaatc gtgttatata  7380
atattatatg tattatatat atacatcatg atgatactga cagtcatgtc ccattgctaa  7440
atagacagac tccatctgcc gcctccaact gatgttctca atatttaagg ggtcatctcg  7500
cattgtttaa taataaacag actccatcta ccgcctccaa atgatgttct caaaatatat  7560
tgtatgaact tatttttatt acttagtatt attagacaac ttacttgctt tatgaaaaac  7620
acttcctatt taggaaacaa tttataatgg cagttcgttc atttaacaat ttatgtagaa  7680
taaatgttat aaatgcgtat gggaaatctt aaatatggat agcataaatg atatctgcat  7740
tgcctaattc gaaatcaaca gcaacgaaaa aaatcccttg tacaacataa atagtcatcg  7800
agaaatatca actatcaaag aacagctatt cacacgttac tattgagatt attattggac  7860
gagaatcaca cactcaactg tctttctctc ttctagaaat acaggtacaa gtatgtacta  7920
ttctcattgt tcatacttct agtcatttca tcccacatat tccttggatt tctctccaat  7980
gaatgacatt ctatcttgca aattcaacaa ttataataag atataccaaa gtagcggtat  8040
agtggcaatc aaaaagcttc tctggtgtgc ttctcgtatt tatttttatt ctaatgatcc  8100
attaaaggta tatatttatt tcttgttata taatcctttt gtttattaca tgggctggat  8160
acataaaggt attttgattt aatttttttgc ttaaattcaa tccccccctcg ttcagtgtca  8220
actgtaatgg taggaaatta ccatactttt gaagaagcaa aaaaaatgaa agaaaaaaaa  8280
aatcgtattt ccaggttaga cgttccgcag aatctagaat gcggtatgcg gtacattgtt  8340
cttcgaacgt aaaagttgcg ctccctgaga tattgtacat ttttgctttt acaagtacaa  8400
gtacatcgta caactatgta ctactgttga tgcatccaca acagtttgtt ttgttttttt  8460
ttgttttttt tttttctaat gattcattac cgctatgtat acctacttgt acttgtagta  8520
agccgggtta ttggcgttca attaatcata gacttatgaa tctgcacggt gtgcgctgcg  8580
agttactttt agcttatgca tgctacttgg gtgtaatatt gggatctgtt cggaaatcaa  8640
cggatgctca atcgatttcg acagtaatta attaagtcat acacaagtca gctttcttcg  8700
agcctcatat aagtataagt agttcaacgt attagcactg tacccagcat ctccgtatcg  8760
agaaacacaa caacatgccc cattggacag atcatgcgga tacacaggtt gtgcagtatc  8820
atacatactc gatcagacag gtcgtctgac catcatacaa gctgaacaag cgctccatac  8880
ttgcacgctc tctatataca cagttaaatt acatatccat agtctaacct ctaacagtta  8940
```

```
atcttctggt aagcctccca gccagccttc tggtatcgct tggcctcctc aataggatct  9000
cggttctggc cgtacagacc tcggccgaca attatgatat ccgttccggt agacatgaca  9060
tcctcaacag ttcggtactg ctgtccgaga gcgtctccct tgtcgtcaag acccaccccg  9120
ggggtcagaa taagccagtc ctcagagtcg cccttaggtc ggttctgggc aatgaagcca  9180
accacaaact cggggtcgga tcgggcaagc tcaatggtct gcttggagta ctcgccagtg  9240
gccagagagc ccttgcaaga cagctcggcc agcatgagca gacctctggc cagcttctcg  9300
ttgggagagg ggactaggaa ctccttgtac tgggagttct cgtagtcaga gacgtcctcc  9360
ttcttctgtt cagagacagt ttcctcggca ccagctcgca ggccagcaat gattccggtt  9420
ccgggtacac cgtgggcgtt ggtgatatcg gaccactcgg cgattcggtg acaccggtac  9480
tggtgcttga cagtgttgcc aatatctgcg aactttctgt cctcgaacag gaagaaaccg  9540
tgcttaagag caagttcctt gagggggagc acagtgccgg cgtaggtgaa gtcgtcaatg  9600
atgtcgatat gggttttgat catgcacaca taaggtccga ccttatcggc aagctcaatg  9660
agctccttgg tggtggtaac atccagagaa gcacacaggt tggttttctt ggctgccacg  9720
agcttgagca ctcgagcggc aaaggcggac ttgtggacgt tagctcgagc ttcgtaggag  9780
ggcattttgg tggtgaagag gagactgaaa taaatttagt ctgcagaact ttttatcgga  9840
accttatctg gggcagtgaa gtatatgtta tggtaatagt tacgagttag ttgaacttat  9900
agatagactg gactatacgg ctatcggtcc aaattagaaa gaacgtcaat ggctctctgg  9960
gcgtcgcctt tgccgacaaa aatgtgatca tgatgaaagc cagcaatgac gttgcagctg  10020
atattgttgt cggccaaccg cgccgaaaac gcagctgtca gacccacagc ctccaacgaa  10080
gaatgtatcg tcaaagtgat ccaagcacac tcatagttgg agtcgtactc caaaggcggc  10140
aatgacgagt cagacagata ctcgtcgacg tttaaaccat catctaaggg cctcaaaact  10200
acctcggaac tgctgcgctg atctggacac cacagaggtt ccgagcactt taggttgcac  10260
caaatgtccc accaggtgca ggcagaaaac gctggaacag cgtgtacagt ttgtcttaac  10320
aaaaagtgag ggcgctgagg tcgagcaggg tggtgtgact tgttatagcc tttagagctg  10380
cgaaagcgcg tatggatttg gctcatcagg ccagattgag ggtctgtgga cacatgtcat  10440
gttagtgtac ttcaatcgcc ccctggatat agccccgaca ataggccgtg gcctcatttt  10500
tttgccttcc gcacatttcc attgctcggt acccacacct tgcttctcct gcacttgcca  10560
accttaatac tggtttacat tgaccaacat cttacaagcg gggggcttgt ctagggtata  10620
tataaacagt ggctctccca atcggttgcc agtctctttt ttcctttctt tccccacaga  10680
ttcgaaatct aaactacaca tcacac                                       10706

SEQ ID NO: 78          moltype = DNA  length = 4144
FEATURE                Location/Qualifiers
misc_feature           1..4144
                       note = Cas9-SV40 fusion
source                 1..4144
                       mol_type = other DNA
                       organism = synthetic construct
SEQUENCE: 78
acaagaaata ctccatcggc ctggacattg gaaccaactc tgtcggctgg gctgtcatca  60
ccgacgagta caaggtgccc tccaagaaat tcaaggtcct cggaaacacc gatcgacact  120
ccatcaagaa aaacctcatt ggtgccctgt tgttcgattc tggcgagact gccgaagcta  180
ccagactcaa gcgaactgct cggcgacgtt acacccgacg gaagaaccga atctgctacc  240
tgcaggagat cttttccaac gagatggcca aggtggacga ttcgttcttt catcgactgg  300
aggaatcctt cctcgtcgag gaagacaaga aacacgagcg tcatcccatc tttggcaaca  360
ttgtggacga ggttgcttac cacgagaagt atcctaccat ctaccacctg cgaaagaaac  420
tcgtcgattc caccgacaag gcggatctca gacttatcta cctcgctctg gcacacatga  480
tcaagtttcg aggtcatttc ctcatcgagg gcgatctcaa tcccgacaac agcgatgtgg  540
acaagctgtt cattcagctc gttcagacct acaaccagct gttcgaggaa aaccccatca  600
atgcctccgg agtcgatgca aaggccatct tgtctgctcg actctcgaag agcagacgac  660
tggagaacct cattgcccaa cttcctggcg agaaaaagaa cggactgttt ggcaacctca  720
ttgccctttc tcttggtctc acacccaact tcaagtccaa cttcgatctg gcggaggacg  780
ccaagctcca gctgtccaag gacacctacg acgatgacct cgacaacctg cttgcacaga  840
ttggcgatca gtacgccgac ctgtttctcg ctgccaagaa cctttcggat gctattctct  900
tgtctgacat tctgcgagtc aacaccgaga tcacaaaggc tccccttttct gcctccatga  960
tcaagcgata cgacgagcac catcaggatc tcacactgct caaggctctt gtccgacagc  1020
aactgcccga gaagtacaag gagatctttt tcgatcagtc gaagaacggc tacgctggat  1080
acatcgacgg cggagcctct caggaagagt tctacaagtt catcaagcca attctcgaga  1140
agatggacgg aaccgaggaa ctgcttgtca agctcaatcg agaggatctg cttcggaagc  1200
aacgaacctt cgacaacggc agcattcctc atcagatcca cctcggtgag ctgcacgcca  1260
ttcttcgacg tcaggaagac ttctacccct ttctcaagga caaccgagag aagatcgaga  1320
agattcttac ctttcgaatc ccctactatg ttggtcctct tgccagagga aactctcgat  1380
ttgcttggat gactcgaaag tccgaggaaa ccatcactcc ctggaacttc gaggaagtcg  1440
tggacaaggg tgcctctgca cagtccttca tcgagcgaat gaccaacttc gacaagaatc  1500
tgcccaacga gaaggttctt cccaagcatt cgctgctcta cgagtacttt acagtctaca  1560
acgaactcac caaagtcaag tacgttaccg agggaatgcg aaagcctgcc ttcttgtctg  1620
gcgaacagaa gaaagccatt gtcgatctcc tgttcaagac caaccgaaag gtcactgtta  1680
agcagctcaa ggaggactac ttcaagaaaa tcgagtgttt cgacagcgtc gagatttccg  1740
gagttgagga ccgattcaac gcctctttgg gcacctatca cgatctgctc aagattatca  1800
aggacaagga ttttctcgac aacgaggaaa acgaggacat tctggaggac atcgtgctca  1860
ctcttaccct gttcgaagat cgggagatga tcgaggaacg actcaagaca tacgctcacc  1920
tgttcgacga caaggtcatg aaacaactca agcgacgtag atacaccggc tggggaagac  1980
tttcgcgaaa gctcatcaac ggcatcagag acaagcagtc cggaaagacc attctggact  2040
ttctcaagtc cgatggcttt gccaaccgaa acttcatgca gctcattcac gacgattctc  2100
ttaccttcaa ggaggacatc cagaaggcac aagtgtccgg tcagggcgac agcttgcacg  2160
aacatattgc caacctggct ggttcgccag ccatcaagaa aggcattctc cagactgtca  2220
aggttgtcga cgagctggtg aaggtcatgg gacgtcacaa gcccgagaac attgtgatcg  2280
agatggccag agagaaccag acaactcaaa agggtcagaa aaactcgcga gagcggatga  2340
agcgaatcga ggaaggcatc aaggagctgg gatcccagat tctcaaggag catcccgtcg  2400
```

```
agaacactca actgcagaac gagaagctgt atctctacta tctgcagaat ggtcgagaca  2460
tgtacgtgga tcaggaactg gacatcaatc gtctcagcga ctacgatgtg gaccacattg  2520
tccctcaatc ctttctcaag gacgattcta tcgacaacaa ggtccttaca cgatccgaca  2580
agaacagagg caagtcggac aacgttccca gcgaagaggt ggtcaaaaag atgaagaact  2640
actggcgaca gctgctcaac gccaagctca ttacccagcg aaagttcgac aatcttacca  2700
aggccgagcg aggcggtctg tccgagctcg acaaggctgg cttcatcaag cgtcaactcg  2760
tcgagaccag acagatcaca aagcacgtcg cacagattct cgattctcgg atgaacacca  2820
agtacgacga gaacgacaag ctcatccgag aggtcaaggt gattactctc aagtccaaac  2880
tggtctccga tttccgaaag gactttcagt tctacaaggt gcgagagatc aacaattacc  2940
accatgccca cgatgcttac ctcaacgccg tcgttggcac tgcgctcatc aagaaatacc  3000
ccaagctcga aagcgagttc gtttacggcg attacaaggt ctacgacgtt cgaaagatga  3060
ttgccaagtc cgaacaggag attggcaagg ctactgccaa gtacttcttt tactccaaca  3120
tcatgaactt tttcaagacc gagatcacct tggccaacgg agagattcga aagagaccac  3180
ttatcgagac caacggcgaa actggagaga tcgtgtggga caagggtcga gactttgcaa  3240
ccgtgcgaaa ggttctgtcg atgcctcagg tcaacatcgt caagaaaacc gaggttcaga  3300
ctggcggatt ctccaaggag tcgattctgc ccaagcgaaa ctccgacaag ctcatcgctc  3360
gaaagaaaga ctgggatccc aagaaatacg gtggcttcga ttctcctacc gtcgcctatt  3420
ccgtgcttgt cgttgcgaag gtcgagaagg gcaagtccaa aaagctcaag tccgtcaagg  3480
agctgctcgg aattaccatc atggagcgat cgagcttcga gaagaatccc atcgacttct  3540
tggaagccaa gggttacaag gaggtcaaga aagacctcat tatcaagctg cccaagtact  3600
ctctgttcga actggagaac ggtcgaaagc gtatgctcgc ctccgctggc gagctgcaga  3660
agggaaacga gcttgccttg ccttcgaagt acgtcaactt tctctatctg gcttctcact  3720
acgagaagct caagggttct cccgaggaca acgaacagaa gcaactcttc gttgagcagc  3780
acaaacatta cctcgacgag attatcgagc agatttccga gttttcgaag cgagtcatcc  3840
tggctgatgc caacttggac aaggtgctct ctgcctacaa caagcatcgg gacaaaccca  3900
ttcgagaaca ggcggagaac atcattcacc tgtttactct taccaacctg ggtgctcctg  3960
cagctttcaa gtacttcgat accactatcg accgaaagcg gtacacatcc accaaggagg  4020
ttctcgatgc caccctgatt caccagtcca tcactggcct gtacgagacc cgaatcgacc  4080
tgtctcagct tggtggcgac tccagagccg atcccaagaa aaagcgaaag gtctaagcgg  4140
ccgc                                                                4144

SEQ ID NO: 79           moltype = DNA  length = 35
FEATURE                 Location/Qualifiers
misc_feature            1..35
                        note = Cas9-SV40 forward primer
source                  1..35
                        mol_type = other DNA
                        organism = synthetic construct
SEQUENCE: 79
gggggaattc gacaagaaat actccatcgg cctgg                              35

SEQ ID NO: 80           moltype = DNA  length = 31
FEATURE                 Location/Qualifiers
misc_feature            1..31
                        note = Cas9-SV40 reverse primer
source                  1..31
                        mol_type = other DNA
                        organism = synthetic construct
SEQUENCE: 80
ccccaagctt agcggccgct tagacctttc g                                  31

SEQ ID NO: 81           moltype = DNA  length = 4166
FEATURE                 Location/Qualifiers
misc_feature            1..4166
                        note = Cas9-SV40 PCR product
source                  1..4166
                        mol_type = other DNA
                        organism = synthetic construct
SEQUENCE: 81
gggggaattc gacaagaaat actccatcgg cctggacatt ggaaccaact ctgtcggctg  60
ggctgtcatc accgacgagt acaaggtgcc ctccaagaaa ttcaaggtcc tcggaaacac  120
cgatcgacac tccatcaaga aaaacctcat tggtgccctg ttgttcgatt ctggcgagac  180
tgccgaagct accagactca agcgaactgc tcggcgacgt tacacccgac ggaagaaccg  240
aatctgctac ctgcaggaga tcttttccaa cgagatggcc aaggtggacg attcgttctt  300
tcatcgactg gaggaatcct tcctcgtcga ggaagacaag aaacacgagc gtcatcccat  360
ctttggcaac attgtggacg aggttgctta ccacgagaag tatcctacca tctaccacct  420
gcgaaagaaa ctcgtcgatt ccaccgacaa ggcggatctc agacttatct acctcgctct  480
ggcacacatg atcaagtttc gaggtcattt cctcatcgag ggcgatctca atcccgacaa  540
cagcgatgtg gacaagctgt tcattcagct cgttcagacc tacaaccagc tgttcgagga  600
aaaccccatc aatgcctccg gagtcgatgc aaaggccatc ttgtctgctc gactctcgaa  660
gagcagacga ctggagaacc tcattgccca acttcctggc gagaaaaaga acggactgtt  720
tggcaacctc attgcccttt ctcttggtct cacacccaac ttcaagtcca acttcgatct  780
ggcggaggac gccaagctcc agctgtccaa ggacacctac gacgatgacc tcgacaacct  840
gcttgcacag attggcgatc agtacgccga cctgtttctc gctgccaaga acctttcgga  900
tgctattctc ttgtctgaca ttctgcgagt caacaccgag atcacaaagg ctcccctttc  960
tgcctccatg atcaagcgat acgacgagca ccatcaggat ctcacactgc tcaaggctct  1020
tgtccgacag caactgcccg agaagtacaa ggagatcttt ttcgatcagt cgaagaacgg  1080
ctacgctgga tacatcgacg gcggagcctc tcaggaagag ttctacaagt tcatcaagcc  1140
aattctcgag aagatggacg gaaccgagga actgcttgtc aagctcaatc gagaggatct  1200
```

```
gcttcggaag caacgaacct tcgacaacgg cagcattcct catcagatcc acctcggtga  1260
gctgcacgcc attcttcgac gtcaggaaga cttctacccc tttctcaagg acaaccgaga  1320
gaagatcgag aagattctta cctttcgaat cccctactat gttggtcctc ttgccagagg  1380
aaactctcga tttgcttgga tgactcgaaa gtccgaggaa accatcactc cctggaactt  1440
cgaggaagtc gtggacaagg gtgcctctgc acagtccttc atcgagcgaa tgaccaactt  1500
cgacaagaat ctgcccaacg agaaggttct tcccaagcat tcgctgctct acgagtactt  1560
tacagtctac aacgaactca ccaaagtcaa gtacgttacc gagggaatgc gaaagcctgc  1620
cttcttgtct ggcgaacaga agaaagccat tgtcgatctc ctgttcaaga ccaaccgaaa  1680
ggtcactgtt aagcagctca aggaggacta cttcaagaaa atcgagtgtt tcgacagcgt  1740
cgagatttcc ggagttgagg accgattcaa cgcctctttg ggcacctatc acgatctgct  1800
caagattatc aaggacaagg attttctcga caacgaggaa aacgaggaca ttctggagga  1860
catcgtgctc actcttaccc tgttcgaaga tcgggagatg atcgaggaac gactcaagac  1920
atacgctcac ctgttcgacg acaaggtcat gaaacaactc aagcgacgta gatacaccgg  1980
ctggggaaga ctttcgcgaa agctcatcaa cggcatcaga gacaagcagt ccggaaagac  2040
cattctggac tttctcaagt ccgatggctt tgccaaccga aacttcatgc agctcattca  2100
cgacgattct cttaccttca aggaggacat ccagaaggca caagtgtccg gtcagggcga  2160
cagcttgcac gaacatattg ccaacctggc tggttcgcca gccatcaaga aaggcattct  2220
ccagactgtc aaggttgtcg acgagctggt gaaggtcatg ggacgtcaca agcccgagaa  2280
cattgtgatc gagatggcca gagagaacca gacaactcaa aagggtcaga aaaactcgcg  2340
agagcggatg aagcgaatcg aggaaggcat caaggagctg ggatcccaga ttctcaagga  2400
gcatcccgtc gagaacactc aactgcagaa cgagaagctg tatctctact atctgcagaa  2460
tggtcgagac atgtacgtgg atcaggaact ggacatcaat cgtctcagcg actacgatgt  2520
ggaccacatt gtccctcaat cctttctcaa ggacgattct atcgacaaca aggtccttac  2580
acgatccgac aagaacagag gcaagtcgga caacgttccc agcgaagagg tggtcaaaaa  2640
gatgaagaac tactggcgac agctgctcaa cgccaagctc attacccagc gaaagttcga  2700
caatcttacc aaggccgagc gaggcggtct gtccgagctc gacaaggctg gcttcatcaa  2760
gcgtcaactc gtcgagacca gacagatcac aaagcacgtc gcacagattc tcgattctcg  2820
gatgaacacc aagtacgacg agaacgacaa gctcatccga gaggtcaagg tgattactct  2880
caagtccaaa ctggtctccg atttccgaaa ggactttcag ttctacaagg tgcgagagat  2940
caacaattac caccatgccc acgatgctta cctcaacgcc gtcgttggca ctgcgctcat  3000
caagaaatac cccaagctcg aaagcgagtt cgtttacggc gattacaagg tctacgacgt  3060
tcgaaagatg attgccaagt ccgaacagga gattggcaag gctactgcca agtacttctt  3120
ttactccaac atcatgaact ttttcaagac cgagatcacc ttggccaacg gagagattcg  3180
aaagagacca cttatcgaga ccaacggcga aactggagag atcgtgtggg acaagggtcg  3240
agactttgca accgtgcgaa aggttctgtc gatgcctcag gtcaacatcg tcaagaaaac  3300
cgaggttcag actggcggat tctccaagga gtcgattctg cccaagcgaa actccgacaa  3360
gctcatcgct cgaaagaaag actgggatcc caagaaatac ggtggcttcg attctcctac  3420
cgtcgcctat tccgtgcttg tcgttgcgaa ggtcgagaag ggcaagtcca aaaagctcaa  3480
gtccgtcaag gagctgctcg gaattaccat catggagcga tcgagcttcg agaagaatcc  3540
catcgacttc ttggaagcca agggttacaa ggaggtcaag aaagacctca ttatcaagct  3600
gcccaagtac tctctgttcg aactggagaa cggtcgaaag cgtatgctcg cctccgctgg  3660
cgagctgcag aagggaaacg agcttgcctt gccttcgaag tacgtcaact ttctctatct  3720
ggcttctcac tacgagaagc tcaagggttc tcccgaggac aacgaacaga agcaactctt  3780
cgttgagcag cacaaacatt acctcgacga gattatcgag cagatttccg agttttcgaa  3840
gcgagtcatc ctggctgatg ccaacttgga caaggtgctc tctgcctaca acaagcatcg  3900
ggacaaaccc attcgagaac aggcggagaa catcattcac ctgtttactc ttaccaacct  3960
gggtgctcct gcagctttca agtacttcga taccactatc gaccgaaagc ggtacacatc  4020
caccaaggag gttctcgatg ccaccctgat tcaccagtcc atcactggcc tgtacgagac  4080
ccgaatcgac ctgtctcagc ttggtggcga ctccagagcc gatcccaaga aaaagcgaaa  4140
ggtctaagcg gccgctaagc ttgggg                                    4166
```

```
SEQ ID NO: 82          moltype = DNA  length = 4092
FEATURE                Location/Qualifiers
misc_feature           1..4092
                       note = plasmid pBAD/HisB
source                 1..4092
                       mol_type = other DNA
                       organism = synthetic construct
SEQUENCE: 82
aagaaaccaa ttgtccatat tgcatcagac attgccgtca ctgcgtcttt tactggctct  60
tctcgctaac caaaccggta accccgctta ttaaaagcat tctgtaacaa agcgggacca  120
aagccatgac aaaaacgcgt aacaaaagtg tctataatca cggcagaaaa gtccacattg  180
attatttgca cggcgtcaca ctttgctatg ccatagcatt tttatccata agattagcgg  240
atcctacctg acgcttttta tcgcaactct ctactgtttc tccatacccg tttttgggc  300
taacaggagg aattaaccat gggggggttct catcatcatc atcatcatgg tatggctagc  360
atgactggtg gacagcaaat gggtcgggat ctgtacgacg atgacgataa ggatccgagc  420
tcgagatctg cagctggtac catatgggaa ttcgaagctt ggctgttttg gcggatgaga  480
gaagattttc agcctgatac agattaaatc agaacgcaga agcggtctga taaaacagaa  540
tttgcctggc ggcagtagcg cggtggtccc acctgacccc atgccgaact cagaagtgaa  600
acgccgtagc gccgatggta gtgtggggtc tccccatgcg agagtaggga actgccaggc  660
atcaaataaa acgaaaggct cagtcgaaag actgggcctt tcgttttatc tgttgtttgt  720
cggtgaacgc tctcctgagt aggacaaatc cgccgggagc ggatttgaac gttgcgaagc  780
aacggcccgg agggtggcgg gcaggacgcc cgccataaac tgccaggcat caaattaagc  840
agaaggccat cctgacggat ggcctttttg cgtttctaca aactcttttg tttatttttc  900
taaatacatt caaatatgta tccgctcatg agacaataac cctgataaat gcttcaataa  960
tattgaaaaa ggaagagtat gagtattcaa catttccgtg tcgcccttat tccctttttt  1020
gcggcatttt gccttcctgt ttttgctcac ccagaaacgc tggtgaaagt aaaagatgct  1080
gaagatcagt tgggtgcacg agtgggttac atcgaactgg atctcaacag cggtaagatc  1140
cttgagagtt ttcgccccga agaacgtttt ccaatgatga gcacttttaa agttctgcta  1200
```

```
tgtggcgcgg tattatcccg tgttgacgcc gggcaagagc aactcggtcg ccgcatacac  1260
tattctcaga atgacttggt tgagtactca ccagtcacag aaaagcatct tacggatggc  1320
atgacagtaa gagaattatg cagtgctgcc ataaccatga gtgataacac tgcggccaac  1380
ttacttctga caacgatcgg aggaccgaag gagctaaccg cttttttgca caacatgggg  1440
gatcatgtaa ctcgccttga tcgttgggaa ccggagctga atgaagccat accaaacgac  1500
gagcgtgaca ccacgatgcc tgtagcaatg gcaacaacgt tgcgcaaact attaactggc  1560
gaactactta ctctagcttc ccggcaacaa ttaatagact ggatggaggc ggataaagtt  1620
gcaggaccac ttctgcgctc ggcccttccg gctggctggt ttattgctga taaatctgga  1680
gccggtgagc gtgggtctcg cggtatcatt gcagcactgg ggccagatgg taagccctcc  1740
cgtatcgtag ttatctacac gacggggagt caggcaacta tggatgaacg aaatagacag  1800
atcgctgaga taggtgcctc actgattaag cattggtaac tgtcagacca agtttactca  1860
tatatacttt agattgattt aaaacttcat ttttaattta aaaggatcta ggtgaagatc  1920
ctttttgata atctcatgac caaaatccct taacgtgagt tttcgttcca ctgagcgtca  1980
gaccccgtag aaaagatcaa aggatcttct tgagatcctt tttttctgcg cgtaatctgc  2040
tgcttgcaaa caaaaaaacc accgctacca gcggtggttt gtttgccgga tcaagagcta  2100
ccaactcttt ttccgaaggt aactggcttc agcagagcgc agataccaaa tactgtcctt  2160
ctagtgtagc cgtagttagg ccaccacttc aagaactctg tagcaccgcc tacatacctc  2220
gctctgctaa tcctgttacc agtggctgct gccagtggcg ataagtcgtg tcttaccggg  2280
ttggactcaa gacgatagtt accggataag gcgcagcggt cgggctgaac ggggggttcg  2340
tgcacacagc ccagcttgga gcgaacgacc tacaccgaac tgagatacct acagcgtgag  2400
ctatgagaaa gcgccacgct tcccgaaggg agaaaggcgg acaggtatcc ggtaagcggc  2460
agggtcggaa caggagagcg cacgagggag cttccagggg gaaacgcctg gtatctttat  2520
agtcctgtcg ggtttcgcca cctctgactt gagcgtcgat ttttgtgatg ctcgtcaggg  2580
gggcggagcc tatggaaaaa cgccagcaac gcggcctttt tacggttcct ggccttttgc  2640
tggccttttg ctcacatgtt ctttcctgcg ttatcccctg attctgtgga taaccgtatt  2700
accgcctttg agtgagctga taccgctcgc cgcagccgaa cgaccgagcg cagcgagtca  2760
gtgagcgagg aagcggaaga gcgcctgatg cggtattttc tccttacgca tctgtgcggt  2820
atttcacacc gcatatggtg cactctcagt acaatctgct ctgatgccgc atagttaagc  2880
cagtatacac tccgctatcg ctacgtgact gggtcatggc tgcgccccga cacccgccaa  2940
cacccgctga cgcgccctga cgggcttgtc tgctcccggc atccgcttac agacaagctg  3000
tgaccgtctc cgggagctgc atgtgtcaga ggttttcacc gtcatcaccg aaacgcgcga  3060
ggcagcagat caattcgcgc gcgaaggcga agcggcatgc ataatgtgcc tgtcaaatgg  3120
acgaagcagg gattctgcaa accctatgct actccgtcaa gccgtcaatt gtctgattcg  3180
ttaccaatta tgacaacttg acggctacat cattcacttt ttcttcacaa ccggcacgga  3240
actcgctcgg gctggccccg gtgcattttt taaatacccg cgagaaatag agttgatcgt  3300
caaaaccaac attgcgaccg acggtggcga taggcatccg ggtggtgctc aaaagcagct  3360
tcgcctggct gatacgttgg tcctcgcgcc agcttaagac gctaatccct aactgctggc  3420
ggaaaagatg tgacagacgc gacggcgaca agcaaacatg ctgtgcgacg ctggcgatat  3480
caaaattgct gtctgccagg tgatcgctga tgtactgaca agcctcgcgt acccgattat  3540
ccatcggtgg atggagcgac tcgttaatcg cttccatgcg ccgcagtaac aattgctcaa  3600
gcagatttat cgccagcagc tccgaatagc gcccttcccc ttgcccggcg ttaatgattt  3660
gcccaaacag gtcgctgaaa tgcggctggt gcgcttcatc cgggcgaaag aaccccgtat  3720
tggcaaatat tgacggccag ttaagccatt catgccagta ggcgcgcgga cgaaagtaaa  3780
cccactggtg ataccattcg cgagcctccg gatgacgacc gtagtgatga atctctcctg  3840
gcgggaacag caaaatatca cccggtcggc aaacaaattc tcgtccctga tttttcacca  3900
ccccctgacc gcgaatggtg agattgagaa tataaccttt cattcccagc ggtcggtcga  3960
taaaaaaatc gagataaccg ttggcctcaa tcggcgttaa acccgccacc agatgggcat  4020
taaacgagta tcccggcagc aggggatcat tttgcgcttc agccatactt ttcatactcc  4080
cgccattcag ag                                                      4092
```

```
SEQ ID NO: 83           moltype = DNA  length = 8237
FEATURE                 Location/Qualifiers
misc_feature            1..8237
                        note = plamsid pRF48
source                  1..8237
                        mol_type = other DNA
                        organism = synthetic construct
SEQUENCE: 83
aattcgacaa gaaatactcc atcggcctgg acattggaac caactctgtc ggctgggctg  60
tcatcaccga cgagtacaag gtgccctcca agaaattcaa ggtcctcgga aacaccgatc  120
gacactccat caagaaaaac ctcattggtg ccctgttgtt cgattctggc gagactgccg  180
aagctaccag actcaagcga actgctcggc gacgttacac ccgacggaag aaccgaatct  240
gctacctgca ggagatcttt tccaacgaga tggccaaggt ggacgattcg ttctttcatc  300
gactggagga atccttcctc gtcgaggaag acaagaaaca cgagcgtcat cccatctttg  360
gcaacattgt ggacgaggtt gcttaccacg agaagtatcc taccatctac cacctgcgaa  420
agaaactcgt cgattccacc gacaaggcgg atctcagact tatctacctc gctctggcac  480
acatgatcaa gtttcgaggt catttcctca tcgagggcga tctcaatccc gacaacagcg  540
atgtggacaa gctgttcatt cagctcgttc agacctacaa ccagctgttc gaggaaaacc  600
ccatcaatgc ctccggagtc gatgcaaagg ccatcttgtc tgctcgactc tcgaagagca  660
gacgactgga gaacctcatt gcccaacttc ctggcgagaa aaagaacgga ctgtttggca  720
acctcattgc cctttctctt ggtctcacac ccaacttcaa gtccaacttc gatctggcgg  780
aggacgccaa gctccagctg tccaaggaca cctacgacga tgacctcgac aacctgcttg  840
cacagattgg cgatcagtac gccgacctgt ttctcgctgc caagaacctt tcggatgcta  900
ttctcttgtc tgacattctg cgagtcaaca ccgagatcac aaaggctccc ctttctgcct  960
ccatgatcaa gcgatacgac gagcaccatc aggatctcac actgctcaag gctcttgtcc  1020
gacagcaact gcccgagaag tacaaggaga tctttttcga tcagtcgaag aacggctacg  1080
ctggatacat cgacggcgga gcctctcagg aagagttcta caagttcatc aagccaattc  1140
tcgagaagat ggacggaacc gaggaactgc ttgtcaagct caatcgagag gatctgcttc  1200
ggaagcaacg aaccttcgac aacggcagca ttcctcatca gatccacctc ggtgagctgc  1260
```

-continued

```
acgccattct tcgacgtcag gaagacttct accccctttct caaggacaac cgagagaaga  1320
tcgagaagat tcttaccttt cgaatcccct actatgttgg tcctcttgcc agaggaaact  1380
ctcgatttgc ttggatgact cgaaagtccg aggaaaccat cactccctgg aacttcgagg  1440
aagtcgtgga caagggtgcc tctgcacagt ccttcatcga gcgaatgacc aacttcgaca  1500
agaatctgcc caacgagaag gttcttccca agcattcgct gctctacgag tactttacag  1560
tctacaacga actcaccaaa gtcaagtacg ttaccgaggg aatgcgaaag cctgccttct  1620
tgtctggcga acagaagaaa gccattgtcg atctcctgtt caagaccaac cgaaaggtca  1680
ctgttaagca gctcaaggag gactacttca agaaaatcga gtgtttcgac agcgtcgaga  1740
tttccggagt tgaggaccga ttcaacgcct ctttgggcac ctatcacgat ctgctcaaga  1800
ttatcaagga caaggatttt ctcgacaacg aggaaaacga ggacattctg gaggacatcg  1860
tgctcactct taccctgttc gaagatcggg agatgatcga ggaacgactc aagacatacg  1920
ctcacctgtt cgacgacaag gtcatgaaac aactcaagcg acgtagatac accggctggg  1980
gaagactttc gcgaaagctc atcaacggca tcagagacaa gcagtccgga aagaccattc  2040
tggactttct caagtccgat ggctttgcca accgaaactt catgcagctc attcacgacg  2100
attctcttac cttcaaggag gacatccaga aggcacaagt gtccggtcag ggcgacagct  2160
tgcacgaaca tattgccaac ctggctggtt cgccagccat caagaaaggc attctccaga  2220
ctgtcaaggt tgtcgacgag ctggtgaagg tcatgggacg tcacaagccc gagaacattg  2280
tgatcgagat ggccagagag aaccagacaa ctcaaaaggg tcagaaaaac tcgcgagagc  2340
ggatgaagcg aatcgaggaa ggcatcaagg agctgggatc ccagattctc aaggagcatc  2400
ccgtcgagaa cactcaactg cagaacgaga agctgtatct ctactatctg cagaatggtc  2460
gagacatgta cgtggatcag gaactggaca tcaatcgtct cagcgactac gatgtggacc  2520
acattgtccc tcaatccttt ctcaaggacg attctatcga caacaaggtc cttacacgat  2580
ccgacaagaa cagaggcaag tcggacaacg ttcccagcga agaggtggtc aaaaagatga  2640
agaactactg gcgacagctg ctcaacgcca agctcattac ccagcgaaag ttcgacaatc  2700
ttaccaaggc cgagcgaggc ggtctgtccg agctcgacaa ggctggcttc atcaagcgtc  2760
aactcgtcga gaccagacag atcacaaagc acgtcgcaca gattctcgat tctcggatga  2820
acaccaagta cgacgagaac gacaagctca tccgagaggt caaggtgatt actctcaagt  2880
ccaaactggt ctccgatttc cgaaaggact ttcagttcta caaggtgcga gagatcaaca  2940
attaccacca tgcccacgat gcttacctca acgccgtcgt tggcactgcg ctcatcaaga  3000
aataccccaa gctcgaaagc gagttcgttt acggcgatta caaggtctac gacgttcgaa  3060
agatgattgc caagtccgaa caggagattg gcaaggctac tgccaagtac ttcttttact  3120
ccaacatcat gaactttttc aagaccgaga tcaccttggc caacggagag attcgaaaga  3180
gaccacttat cgagaccaac ggcgaaactg gagagatcgt gtgggacaag ggtcgagact  3240
ttgcaaccgt gcgaaaggtt ctgtcgatgc ctcaggtcaa catcgtcaag aaaaccgagg  3300
ttcagactgg cggattctcc aaggagtcga ttctgcccaa gcgaaactcc gacaagctca  3360
tcgctcgaaa gaaagactgg gatcccaaga aatacggtgg cttcgattct cctaccgtcg  3420
cctattccgt gcttgtcgtt gcgaaggtcg agaagggcaa gtccaaaaag ctcaagtccg  3480
tcaaggagct gctcggaatt accatcatgg agcgatcgag cttcgagaag aatcccatcg  3540
acttcttgga agccaagggt tacaaggagg tcaagaaaga cctcattatc aagctgccca  3600
agtactctct gttcgaactg gagaacggtc gaaagcgtat gctcgcctcc gctggcgagc  3660
tgcagaaggg aaacgagctt gccttgcctt cgaagtacgt caactttctc tatctggctt  3720
ctcactacga gaagctcaag ggttctcccg aggacaacga acagaagcaa ctcttcgttg  3780
agcagcacaa acattacctc gacgagatta tcgagcagat ttccgagttt tcgaagcgag  3840
tcatcctggc tgatgccaac ttggacaagg tgctctctgc ctacaacaag catcgggaca  3900
aacccattcg agaacaggcg gagaacatca ttcacctgtt tactcttacc aacctgggtg  3960
ctcctgcagc tttcaagtac ttcgatacca ctatcgaccg aaagcggtac acatccacca  4020
aggaggttct cgatgccacc ctgattcacc agtccatcac tggcctgtac gagacccgaa  4080
tcgacctgtc tcagcttggt ggcgactcca gagccgatcc caagaaaaag cgaaaggtct  4140
aagcggccgc taagcttggc tgttttggcg gatgagagaa gattttcagc ctgatacaga  4200
ttaaatcaga acgcagaagc ggtctgataa aacagaattt gcctggcggc agtagcgcgg  4260
tggtcccacc tgaccccatg ccgaactcag aagtgaaacg ccgtagcgcc gatggtagtg  4320
tggggtctcc ccatgcgaga gtagggaact gccaggcatc aaataaaacg aaaggctcag  4380
tcgaaagact gggcctttcg ttttatctgt tgtttgtcgg tgaacgctct cctgagtagg  4440
acaaatccgc cgggagcgga tttgaacgtt gcgaagcaac ggcccggagg gtggcgggca  4500
ggacgcccgc cataaactgc caggcatcaa attaagcaga aggccatcct gacggatggc  4560
ctttttgcgt ttctacaaac tcttttgttt atttttctaa atacattcaa atatgtatcc  4620
gctcatgaga caataaccct gataaatgct tcaataatat tgaaaaagga agagtatgag  4680
tattcaacat ttccgtgtcg cccttattcc cttttttgcg gcattttgcc ttcctgtttt  4740
tgctcaccca gaaacgctgg tgaaagtaaa agatgctgaa gatcagttgg gtgcacgagt  4800
gggttacatc gaactggatc tcaacagcgg taagatcctt gagagttttc gccccgaaga  4860
acgttttcca atgatgagca cttttaaagt tctgctatgt ggcgcggtat tatcccgtgt  4920
tgacgccggg caagagcaac tcggtcgccg catacactat tctcagaatg acttggttga  4980
gtactcacca gtcacagaaa agcatcttac ggatggcatg acagtaagag aattatgcag  5040
tgctgccata accatgagtg ataacactgc ggccaactta cttctgacaa cgatcggagg  5100
accgaaggag ctaaccgctt ttttgcacaa catgggggat catgtaactc gccttgatcg  5160
ttgggaaccg gagctgaatg aagccatacc aaacgacgag cgtgacacca cgatgcctgt  5220
agcaatggca acaacgttgc gcaaactatt aactggcgaa ctacttactc tagcttcccg  5280
gcaacaatta atagactgga tggaggcgga taaagttgca ggaccacttc tgcgctcggc  5340
ccttccggct ggctggttta ttgctgataa atctggagcc ggtgagcgtg ggtctcgcgg  5400
tatcattgca gcactggggc cagatggtaa gccctcccgt atcgtagtta tctacacgac  5460
ggggagtcag gcaactatgg atgaacgaaa tagacagatc gctgagatag gtgcctcact  5520
gattaagcat tggtaactgt cagaccaagt ttactcatat atactttaga ttgatttaaa  5580
acttcatttt taatttaaaa ggatctaggt gaagatcctt tttgataatc tcatgaccaa  5640
aatcccttaa cgtgagtttt cgttccactg agcgtcagac cccgtagaaa agatcaaagg  5700
atcttcttga gatccttttt ttctgcgcgt aatctgctgc ttgcaaacaa aaaaaccacc  5760
gctaccagcg gtggtttgtt tgccggatca agagctacca actctttttc cgaaggtaac  5820
tggcttcagc agagcgcaga taccaaatac tgtccttcta gtgtagccgt agttaggcca  5880
ccacttcaag aactctgtag caccgcctac atacctcgct ctgctaatcc tgttaccagt  5940
ggctgctgcc agtggcgata agtcgtgtct taccgggttg gactcaagac gatagttacc  6000
```

```
ggataaggcg cagcggtcgg gctgaacggg gggttcgtgc acacagccca gcttggagcg  6060
aacgacctac accgaactga gatacctaca gcgtgagcta tgagaaagcg ccacgcttcc  6120
cgaagggaga aaggcggaca ggtatccggt aagcggcagg gtcggaacag gagagcgcac  6180
gagggagctt ccagggggaa acgcctggta tctttatagt cctgtcgggt ttcgccacct  6240
ctgacttgag cgtcgatttt tgtgatgctc gtcagggggg cggagcctat ggaaaaacgc  6300
cagcaacgcg gcctttttac ggttcctggc cttttgctgg ccttttgctc acatgttctt  6360
tcctgcgtta tcccctgatt ctgtggataa ccgtattacc gcctttgagt gagctgatac  6420
cgctcgccgc agccgaacga ccgagcgcag cgagtcagtg agcgaggaag cggaagagcg  6480
cctgatgcgg tattttctcc ttacgcatct gtgcggtatt tcacaccgca tatggtgcac  6540
tctcagtaca atctgctctg atgccgcata gttaagccag tatacactcc gctatcgcta  6600
cgtgactggg tcatggctgc gccccgacac ccgccaacac ccgctgacgc gccctgacgg  6660
gcttgtctgc tcccggcatc cgcttacaga caagctgtga ccgtctccgg gagctgcatg  6720
tgtcagaggt tttcaccgtc atcaccgaaa cgcgcgaggc agcagatcaa ttcgcgcgcg  6780
aaggcgaagc ggcatgcata atgtgcctgt caaatggacg aagcagggat tctgcaaacc  6840
ctatgctact ccgtcaagcc gtcaattgtc tgattcgtta ccaattatga caacttgacg  6900
gctacatcat tcacttttc ttcacaaccg gcacggaact cgctcgggct ggccccggtg  6960
cattttttaa atacccgcga gaaatagagt tgatcgtcaa aaccaacatt gcgaccgacg  7020
gtggcgatag gcatccgggt ggtgctcaaa agcagcttcg cctggctgat acgttggtcc  7080
tcgcgccagc ttaagacgct aatccctaac tgctggcgga aaagatgtga cagacgcgac  7140
ggcgacaagc aaacatgctg tgcgacgctg gcgatatcaa aattgctgtc tgccaggtga  7200
tcgctgatgt actgacaagc ctcgcgtacc cgattatcca tcggtggatg gagcgactcg  7260
ttaatcgctt ccatgcgccg cagtaacaat tgctcaagca gatttatcgc cagcagctcc  7320
gaatagcgcc cttccccttg cccggcgtta atgatttgcc caaacaggtc gctgaaatgc  7380
ggctggtgcg cttcatccgg gcgaaagaac cccgtattgg caaatattga cggccagtta  7440
agccattcat gccagtaggc gcgcggacga aagtaaaccc actggtgata ccattcgcga  7500
gcctccggat gacgaccgta gtgatgaatc tctcctggcg ggaacagcaa aatatcaccc  7560
ggtcggcaaa caaattctcg tccctgattt ttcaccaccc cctgaccgcg aatggtgaga  7620
ttgagaatat aacctttcat tcccagcggt cggtcgataa aaaaatcgag ataaccgttg  7680
gcctcaatcg gcgttaaacc cgccaccaga tgggcattaa acgagtatcc cggcagcagg  7740
ggatcatttt gcgcttcagc catacttttc atactcccgc cattcagaga agaaaccaat  7800
tgtccatatt gcatcagaca ttgccgtcac tgcgtctttt actggctctt ctcgctaacc  7860
aaaccggtaa ccccgcttat taaaagcatt ctgtaacaaa gcgggaccaa agccatgaca  7920
aaaacgcgta acaaaagtgt ctataatcac ggcagaaaag tccacattga ttatttgcac  7980
ggcgtcacac tttgctatgc catagcattt ttatccataa gattagcgga tcctacctga  8040
cgctttttat cgcaactctc tactgtttct ccatacccgt ttttgggct aacaggagga  8100
attaaccatg gggggttctc atcatcatca tcatcatggt atggctagca tgactggtgg  8160
acagcaaatg ggtcgggatc tgtacgacga tgacgataag gatccgagct cgagatctgc  8220
agctggtacc atatggg                                                8237
```

```
SEQ ID NO: 84           moltype = DNA  length = 6493
FEATURE                 Location/Qualifiers
misc_feature            1..6493
                        note = E.Coli Cas9 expression cassette
source                  1..6493
                        mol_type = other DNA
                        organism = synthetic construct
SEQUENCE: 84
tgcactctca gtacaatctg ctctgatgcc gcatagttaa gccagtatac actccgctat  60
cgctacgtga ctgggtcatg gctgcgcccc gacacccgcc aacacccgct gacgcgccct  120
gacgggcttg tctgctcccg gcatccgctt acagacaagc tgtgaccgtc tccgggagct  180
gcatgtgtca gaggttttca ccgtcatcac cgaaacgcgc gaggcagcag atcaattcgc  240
gcgcgaaggc gaagcggcat gcataatgtg cctgtcaaat ggacgaagca gggattctgc  300
aaaccctatg ctactccgtc aagccgtcaa ttgtctgatt cgttaccaat tatgacaact  360
tgacggctac atcattcact tttcttcac aaccggcacg gaactcgctc gggctggccc  420
cggtgcattt tttaaatacc cgcgagaaat agagttgatc gtcaaaacca acattgcgac  480
cgacggtggc gataggcatc cgggtggtgc tcaaaagcag cttcgcctgg ctgatacgtt  540
ggtcctcgcg ccagcttaag acgctaatcc ctaactgctg gcggaaaaga tgtgacagac  600
gcgacggcga caagcaaaca tgctgtgcga cgctggcgat atcaaaattg ctgtctgcca  660
ggtgatcgct gatgtactga caagcctcgc gtacccgatt atccatcggt ggatggagcg  720
actcgttaat cgcttccatg cgccgcagta acaattgctc aagcagattt atcgccagca  780
gctccgaata gcgcccttcc ccttgcccgg cgttaatgat ttgcccaaac aggtcgctga  840
aatgcggctg gtgcgcttca tccgggcgaa agaaccccgt attggcaaat attgacggcc  900
agttaagcca ttcatgccag taggcgcgcg gacgaaagta aacccactgg tgataccatt  960
cgcgagcctc cggatgacga ccgtagtgat gaatctctcc tggcgggaac agcaaaatat  1020
cacccggtcg gcaaacaaat tctcgtccct gatttttcac cacccctga ccgcgaatgg  1080
tgagattgag aatataacct ttcattccca gcggtcggtc gataaaaaaa tcgagataac  1140
cgttggcctc aatcggcgtt aaacccgcca ccagatgggc attaaacgag tatcccggca  1200
gcaggggatc attttgcgct tcagccatac ttttcatact cccgccattc agagaagaaa  1260
ccaattgtcc atattgcatc agacattgcc gtcactgcgt cttttactgg ctcttctcgc  1320
taaccaaacc ggtaaccccg cttattaaaa gcattctgta acaaagcggg accaaagcca  1380
tgacaaaaac gcgtaacaaa agtgtctata atcacggcag aaaagtccac attgattatt  1440
tgcacggcgt cacactttgc tatgccatag catttttatc cataagatta gcggatccta  1500
cctgacgctt tttatcgcaa ctctctactg tttctccata cccgtttttt gggctaacag  1560
gaggaattaa ccatgggggg ttctcatcat catcatcatc atggtatggc tagcatgact  1620
ggtggacagc aaatgggtcg ggatctgtac gacgatgacg ataaggatcc gagctcgaga  1680
tctgcagctg gtaccatatg ggaattcgac aagaaatact ccatcggcct ggacattgga  1740
accaactctg tcggctgggc tgtcatcacc gacgagtaca aggtgccctc caagaaattc  1800
aaggtcctcg gaaacaccga tcgacactcc atcaagaaaa acctcattgg tgccctgttg  1860
ttcgattctg gcgagactgc cgaagctacc agactcaagc gaactgctcg gcgacgttac  1920
```

```
acccgacgga agaaccgaat ctgctacctg caggagatct tttccaacga gatggccaag  1980
gtggacgatt cgttctttca tcgactggag gaatccttcc tcgtcgagga agacaagaaa  2040
cacgagcgtc atcccatctt tggcaacatt gtggacgagg ttgcttacca cgagaagtat  2100
cctaccatct accacctgcg aaagaaactc gtcgattcca ccgacaaggc ggatctcaga  2160
cttatctacc tcgctctggc acacatgatc aagtttcgag gtcatttcct catcgagggc  2220
gatctcaatc ccgacaacag cgatgtggac aagctgttca ttcagctcgt tcagacctac  2280
aaccagctgt tcgaggaaaa ccccatcaat gcctccggag tcgatgcaaa ggccatcttg  2340
tctgctcgac tctcgaagag cagacgactg gagaacctca ttgcccaact tcctggcgag  2400
aaaaagaacg gactgtttgg caacctcatt gccctttctc ttggtctcac acccaacttc  2460
aagtccaact tcgatctggc ggaggacgcc aagctccagc tgtccaagga cacctacgac  2520
gatgacctcg acaacctgct tgcacagatt ggcgatcagt acgccgacct gtttctcgct  2580
gccaagaacc tttcggatgc tattctcttg tctgacattc tgcgagtcaa caccgagatc  2640
acaaaggctc ccctttctgc ctccatgatc aagcgatacg acgagcacca tcaggatctc  2700
acactgctca aggctcttgt ccgacagcaa ctgcccgaga agtacaagga gatctttttc  2760
gatcagtcga agaacggcta cgctggatac atcgacggcg gagcctctca ggaagagttc  2820
tacaagttca tcaagccaat tctcgagaag atggacggaa ccgaggaact gcttgtcaag  2880
ctcaatcgag aggatctgct tcggaagcaa cgaaccttcg acaacggcag cattcctcat  2940
cagatccacc tcggtgagct gcacgccatt cttcgacgtc aggaagactt ctaccccttt  3000
ctcaaggaca accgagagaa gatcgagaag attcttacct ttcgaatccc ctactatgtt  3060
ggtcctcttg ccagaggaaa ctctcgattt gcttggatga ctcgaaagtc cgaggaaacc  3120
atcactccct ggaacttcga ggaagtcgtg gacaagggtg cctctgcaca gtccttcatc  3180
gagcgaatga ccaacttcga caagaatctg cccaacgaga aggttcttcc caagcattcg  3240
ctgctctacg agtactttac agtctacaac gaactcacca aagtcaagta cgttaccgag  3300
ggaatgcgaa agcctgcctt cttgtctggc gaacagaaga aagccattgt cgatctcctg  3360
ttcaagacca accgaaaggt cactgttaag cagctcaagg aggactactt caagaaaatc  3420
gagtgtttcg acagcgtcga gatttccgga gttgaggacc gattcaacgc ctctttgggc  3480
acctatcacg atctgctcaa gattatcaag gacaaggatt ttctcgacaa cgaggaaaac  3540
gaggacattc tggaggacat cgtgctcact cttaccctgt tcgaagatcg ggagatgatc  3600
gaggaacgac tcaagacata cgctcacctg ttcgacgaca aggtcatgaa acaactcaag  3660
cgacgtagat acaccggctg ggggaagactt tcgcgaaagc tcatcaacgg catcagagac  3720
aagcagtccg gaaagaccat tctggacttt ctcaagtccg atggctttgc caaccgaaac  3780
ttcatgcagc tcattcacga cgattctctt accttcaagg aggacatcca gaaggcacaa  3840
gtgtccggtc agggcgacag cttgcacgaa catattgcca acctggctgg ttcgccagcc  3900
atcaagaaag gcattctcca gactgtcaag gttgtcgacg agctggtgaa ggtcatggga  3960
cgtcacaagc ccgagaacat tgtgatcgag atggccagag agaaccagac aactcaaaag  4020
ggtcagaaaa actcgcgaga gcggatgaag cgaatcgagg aaggcatcaa ggagctggga  4080
tcccagattc tcaaggagca tcccgtcgag aacactcaac tgcagaacga gaagctgtat  4140
ctctactatc tgcagaatgg tcgagacatg tacgtggatc aggaactgga catcaatcgt  4200
ctcagcgact acgatgtgga ccacattgtc cctcaatcct ttctcaagga cgattctatc  4260
gacaacaagg tccttacacg atccgacaag aacagaggca agtcggacaa cgttcccagc  4320
gaagaggtgg tcaaaaagat gaagaactac tggcgacagc tgctcaacgc caagctcatt  4380
acccagcgaa agttcgacaa tcttaccaag gccgagcgag gcggtctgtc cgagctcgac  4440
aaggctggct tcatcaagcg tcaactcgtc gagaccagac agatcacaaa gcacgtcgca  4500
cagattctcg attctcggat gaacaccaag tacgacgaga acgacaagct catccgagag  4560
gtcaaggtga ttactctcaa gtccaaactg gtctccgatt tccgaaagga ctttcagttc  4620
tacaaggtgc gagagatcaa caattaccac catgcccacg atgcttacct caacgccgtc  4680
gttggcactg cgctcatcaa gaaatacccc aagctcgaaa gcgagttcgt ttacggcgat  4740
tacaaggtct acgacgttcg aaagatgatt gccaagtccg aacaggagat tggcaaggct  4800
actgccaagt acttctttta ctccaacatc atgaactttt tcaagaccga gatcaccttg  4860
gccaacggag agattcgaaa gagaccactt atcgagacca acggcgaaac tggagagatc  4920
gtgtgggaca agggtcgaga ctttgcaacc gtgcgaaagg ttctgtcgat gcctcaggtc  4980
aacatcgtca agaaaaccga ggttcagact ggcggattct ccaaggagtc gattctgccc  5040
aagcgaaact ccgacaagct catcgctcga aagaaagact gggatcccaa gaaatacggt  5100
ggcttcgatt ctcctaccgt cgcctattcc gtgcttgtcg ttgcgaaggt cgagaagggc  5160
aagtccaaaa agctcaagtc cgtcaaggag ctgctcggaa ttaccatcat ggagcgatcg  5220
agcttcgaga agaatcccat cgacttcttg gaagccaagg gttacaagga ggtcaagaaa  5280
gacctcatta tcaagctgcc caagtactct ctgttcgaac tggagaacgg tcgaaagcgt  5340
atgctcgcct ccgctggcga gctgcagaag ggaaacgagc ttgccttgcc ttcgaagtac  5400
gtcaactttc tctatctggc ttctcactac gagaagctca agggttctcc cgaggacaac  5460
gaacagaagc aactcttcgt tgagcagcac aaacattacc tcgacgagat tatcgagcag  5520
atttccgagt tttcgaagcg agtcatcctg gctgatgcca acttggacaa ggtgctctct  5580
gcctacaaca agcatcggga caaacccatt cgagaacagg cggagaacat cattcacctg  5640
tttactctta ccaacctggg tgctcctgca gctttcaagt acttcgatac cactatcgac  5700
cgaaagcggt acacatccac caaggaggtt ctcgatgcca ccctgattca ccagtccatc  5760
actggcctgt acgagacccg aatcgacctg tctcagcttg gtggcgactc cagagccgat  5820
cccaagaaaa agcgaaaggt ctaagcggcc gctaagcttg gctgttttgg cggatgagag  5880
aagattttca gcctgataca gattaaatca gaacgcagaa gcggtctgat aaaacagaat  5940
ttgcctggcg gcagtagcgc ggtggtccca cctgacccca tgccgaactc agaagtgaaa  6000
cgccgtagcg ccgatggtag tgtggggtct ccccatgcga gagtagggaa ctgccaggca  6060
tcaaataaaa cgaaaggctc agtcgaaaga ctgggccttt cgttttatct gttgtttgtc  6120
ggtgaacgct ctcctgagta ggacaaatcc gccgggagcg gatttgaacg ttgcgaagca  6180
acggcccgga gggtggcggg caggacgccc gccataaact gccaggcatc aaattaagca  6240
gaaggccatc ctgacggatg gcctttttgc gtttctacaa actcttttgt ttatttttct  6300
aaatacattc aaatatgtat ccgctcatga gacaataacc ctgataaatg cttcaataat  6360
attgaaaaag gaagagtatg agtattcaac atttccgtgt cgcccttatt cccttttttg  6420
cggcattttg ccttcctgtt tttgctcacc cagaaacgct ggtgaaagta aaagatgctg  6480
aagatcagtt ggg                                                    6493
```

SEQ ID NO: 85          moltype = DNA  length = 5681

```
FEATURE                 Location/Qualifiers
misc_feature            1..5681
                        note = plasmid pKO3
misc_feature            1039
                        note = n is a, c, g, or t
misc_feature            1109
                        note = n is a, c, g, or t
misc_feature            1661..1662
                        note = n is a, c, g, or t
misc_feature            1665
                        note = n is a, c, g, or t
misc_feature            3573..3574
                        note = n is a, c, g, or t
misc_feature            5648
                        note = n is a, c, g, or t
source                  1..5681
                        mol_type = other DNA
                        organism = synthetic construct
SEQUENCE: 85
ccctttcgtc ttcgaataaa tacctgtgac ggaagatcac ttcgcagaat aaataaatcc  60
tggtgtccct gttgataccg ggaagccctg ggccaacttt tggcgaaaat gagacgttga  120
tcggcacgta agaggttcca actttcacca taatgaaata agatcactac cgggcgtatt  180
ttttgagtta tcgagatttt caggagctaa ggaagctaaa atggagaaaa aaatcactgg  240
atataccacc gttgatatat cccaatggca tcgtaaagaa cattttgagg catttcagtc  300
agttgctcaa tgtacctata accagaccgt tcagctggat attacggcct ttttaaagac  360
cgtaaagaaa aataagcaca agttttatcc ggcctttatt cacattcttg cccgcctgat  420
gaatgctcat ccggaattcc gtatggcaat gaaagacggt gagctggtga tatgggatag  480
tgttcaccct tgttacaccg ttttccatga gcaaactgaa acgttttcat cgctctggag  540
tgaataccac gacgatttcc ggcagtttct acacatatat tcgcaagatg tggcgtgtta  600
cggtgaaaac ctggcctatt tccctaaagg gtttattgag aatatgtttt tcgtctcagc  660
caatccctgg gtgagtttca ccagttttga tttaaacgtg gccaatatgg acaacttctt  720
cgcccccgtt ttcaccatgg gcaaatatta tacgcaaggc gacaaggtgc tgatgccgct  780
ggcgattcag gttcatcatg ccgtttgtga tggcttccat gtcggcagaa tgcttaatga  840
attacaacag tactgcgatg agtggcaggg cggggcgtaa tttttttaag gcagttattg  900
gtgcccttaa acgcctggtg ctacgcctga ataagtgata ataagcggat gaatggcaga  960
aattcgaaag caaattcgac ccggtcgtcg gttcagggca gggtcgttaa atagccgctt  1020
atgtctattg ctggtttant cggtacccgg ggatcgcggc cgcggaccgg atcctctaga  1080
gcggccgcga tcctctagag tcgaccggng aatggcgaat gggacgcgcc ctgtagcggc  1140
gcattaagcg cggcgggtgt ggtggttacg cgcagcgtga ccgctacact tgccagcgcc  1200
ctagcgcccg ctcctttcgc tttcttccct tcctttctcg ccacgttcgc cggctttccc  1260
cgtcaagctc taaatcgggg gctcccttta gggttccgat ttagtgcttt acggcacctc  1320
gaccccaaaa aacttgatta gggtgatggt tcacgtagtg ggccatcgcc ctgatagacg  1380
gtttttcgcc ctttgacgtt ggagtccacg ttctttaata gtggactctt gttccaaact  1440
ggaacaacac tcaaccctat ctcggtctat tcttttgatt tataagggat tttgccgatt  1500
tcggcctatt ggttaaaaaa tgagctgatt taacaaaaat ttaacgcgaa ttttaacaaa  1560
atattaacgc ttacaattta ggtggcactt ttcggggaaa tgtgcgcgga acccctattt  1620
gtttattttt ctaaatacat tcaaatatgt atccgctcat nncangatcc tttttaaccc  1680
atcacatata cctgccgttc actattattt agtgaaatga gatattatga tattttctga  1740
attgtgatta aaaaggcaac tttatgccca tgcaacagaa actataaaaa atacagagaa  1800
tgaaaagaaa cagatagatt ttttagttct ttaggcccgt agtctgcaaa tccttttatg  1860
attttctatc aaacaaaaga ggaaaataga ccagttgcaa tccaaacgag agtctaatag  1920
aatgaggtcg aaaagtaaat cgcgcgggtt tgttactgat aaagcaggca agacctaaaa  1980
tgtgtaaagg gcaaagtgta tactttggcg tcacccctta catattttag gtcttttttt  2040
attgtgcgta actaacttgc catcttcaaa caggagggct ggaagaagca gaccgctaac  2100
acagtacata aaaaaggaga catgaacgat gaacatcaaa aagtttgcaa aacaagcaac  2160
agtattaacc tttactaccg cactgctggc aggaggcgca actcaagcgt ttgcgaaaga  2220
aacgaaccaa aagccatata aggaaacata cggcatttcc catattacac gccatgatat  2280
gctgcaaatc cctgaacagc aaaaaaatga aaaatatcaa gttcctgaat tcgattcgtc  2340
cacaattaaa aatatctctt ctgcaaaagg cctggacgtt tgggacagct ggccattaca  2400
aaacgctgac ggcactgtcg caaactatca cggctaccac atcgtctttg cattagccgg  2460
agatcctaaa aatgcggatg acacatcgat ttacatgttc tatcaaaaag tcggcgaaac  2520
ttctattgac agctggaaaa acgctggccg cgtctttaaa gacagcgaca aattcgatgc  2580
aaatgattct atcctaaaag accaaacaca agaatggtca ggttcagcca catttacatc  2640
tgacggaaaa atccgtttat tctacactga tttctccggt aaacattacg gcaaacaaac  2700
actgacaact gcacaagtta acgtatcagc atcagacagc tctttgaaca tcaacggtgt  2760
agaggattat aaatcaatct ttgacggtga cggaaaaacg tatcaaaatg tacagcagtt  2820
catcgatgaa ggcaactaca gctcaggcga caaccatacg ctgagagatc ctcactacgt  2880
agaagataaa ggccacaaat acttagtatt tgaagcaaac actggaactg aagatggcta  2940
ccaaggcgaa gaatctttat ttaacaaagc atactatggc aaaagcacat cattcttccg  3000
tcaagaaagt caaaaacttc tgcaaagcga taaaaaacgc acggctgagt tagcaaacgg  3060
cgctctcggt atgattgagc taaacgatga ttacacactg aaaaaagtga tgaaaccgct  3120
gattgcatct aacacagtaa cagatgaaat tgaacgcgcg aacgtcttta aaatgaacgg  3180
caaatggtac ctgttcactg actcccgcgg atcaaaaatg acgattgacg gcattacgtc  3240
taacgatatt tacatgcttg gttatgtttc taattcttta actggcccat acaagccgct  3300
gaacaaaact ggccttgtgt taaaaatgga tcttgatcct aacgatgtaa cctttactta  3360
ctcacacttc gctgtacctc aagcgaaagg aaacaatgtc gtgattacaa gctatatgac  3420
aaacagagga ttctacgcag acaaacaatc aacgtttgcg ccaagcttcc tgctgaacat  3480
caaaggcaag aaaacatctg ttgtcaaaga cagcatcctt gaacaaggac aattaacagt  3540
taacaaataa aaacgcaaaa gaaaatgccg atnnccggtt tattgactac cggaagcagt  3600
```

```
gtgaccgtgt gcttctcaaa tgcctcaggc tgtctatgtg tgactgttga gctgtaacaa  3660
gttgtctcag gtgttcaatt tcatgttcta gttgctttgt tttactggtt tcacctgttc  3720
tattaggtgt tacatgctgt tcatctgtta cattgtcgat ctgttcatgg tgaacagctt  3780
taaatgcacc aaaaactcgt aaaagctctg atgtatctat cttttttaca ccgttttcat  3840
ctgtgcatat ggacagtttt ccctttgata tctaacggtg aacagttgtt ctacttttgt  3900
ttgttagtct tgatgcttca ctgatagata caagagccat aagaacctca gatccttccg  3960
tatttagcca gtatgttctc tagtgtggtt cgttgttttt gcgtgagcca tgagaacgaa  4020
ccattgagat catgcttact ttgcatgtca ctcaaaaatt ttgcctcaaa actggtgagc  4080
tgaatttttg cagttaaagc atcgtgtagt gtttttctta gtccgttacg taggtaggaa  4140
tctgatgtaa tggttgttgg tattttgtca ccattcattt ttatctggtt gttctcaagt  4200
tcggttacga gatccatttg tctatctagt tcaacttgga aaatcaacgt atcagtcggg  4260
cggcctcgct tatcaaccac caatttcata ttgctgtaag tgtttaaatc tttacttatt  4320
ggtttcaaaa cccattggtt aagcctttta aactcatggt agttattttc aagcattaac  4380
atgaacttaa attcatcaag gctaatctct atatttgcct tgtgagtttt cttttgtgtt  4440
agttctttta ataaccactc ataaatcctc atagagtatt tgttttcaaa agacttaaca  4500
tgttccagat tatattttat gaattttttt aactggaaaa gataaggcaa tatctcttca  4560
ctaaaaacta attctaattt ttcgcttgag aacttggcat agtttgtcca ctggaaaatc  4620
tcaaagcctt taaccaaagg attcctgatt tccacagttc tcgtcatcag ctctctggtt  4680
gctttagcta atacacccata agcattttcc ctactgatgt tcatcatctg agcgtattgg  4740
ttataagtga acgataccgt ccgttctttc cttgtagggt tttcaatcgt ggggttgagt  4800
agtgccacac agcataaaat tagcttggtt tcatgctccg ttaagtcata gcgactaatc  4860
gctagttcat ttgctttgaa aacaactaat tcagacatac atctcaattg gtctaggtga  4920
ttttaatcac tataccaatt gagatgggct agtcaatgat aattactagt ccttttcctt  4980
tgagttgtgg gtatctgtaa attctgctag acctttgctg gaaaacttgt aaattctgct  5040
agaccctctg taaattccgc tagacctttg tgtgtttttt ttgtttatat tcaagtggtt  5100
ataatttata gaataaagaa agaataaaaa aagataaaaa gaatagatcc cagccctgtg  5160
tataactcac tactttagtc agttccgcag tattacaaaa ggatgtcgca aacgctgttt  5220
gctcctctac aaaacagacc ttaaaaccct aaaggcttaa gtagcaccct cgcaagctcg  5280
ggcaaatcgc tgaatattcc ttttgtctcc gaccatcagg cacctgagtc gctgtctttt  5340
tcgtgacatt cagttcgctg cgctcacggc tctggcagtg aatgggggta aatggcacta  5400
caggcgcctt ttatggattc atgcaaggaa actacccata atacaagaaa agcccgtcac  5460
gggcttctca gggcgtttta tggcgggtct gctatgtggt gctatctgac tttttgctgt  5520
tcagcagttc ctgccctctg attttccagt ctgaccactt cggattatcc cgtgacaggt  5580
cattcagact ggctaatgca cccagtaagg cagcggtatc atcaacaggc ttacccgtct  5640
tactgtcngg atcgacgctc tcccttatgc gactcctgca t                     5681
```

```
SEQ ID NO: 86           moltype = DNA  length = 12166
FEATURE                 Location/Qualifiers
misc_feature            1..12166
                        note = plasmid pRF97
source                  1..12166
                        mol_type = other DNA
                        organism = synthetic construct
SEQUENCE: 86
ccctttcgtc ttcgaataaa tacctgtgac ggaagatcac ttcgcagaat aaataaatcc  60
tggtgtccct gttgataccg ggaagccctg ggccaacttt tggcgaaaat gagacgttga  120
tcggcacgta agaggttcca actttcacca taatgaaata agatcactac cgggcgtatt  180
ttttgagtta tcgagatttt caggagctaa ggaagctaaa atggagaaaa aaatcactgg  240
atataccacc gttgatatat cccaatggca tcgtaaagaa cattttgagg catttcagtc  300
agttgctcaa tgtacctata accagaccgt tcagctggat attacggcct ttttaaagac  360
cgtaaagaaa aataagcaca agttttatcc ggcctttatt cacattcttg cccgcctgat  420
gaatgctcat ccggaattcc gtatggcaat gaaagacggt gagctggtga tatgggatag  480
tgttcaccct tgttacaccg ttttccatga gcaaactgaa acgttttcat cgctctggag  540
tgaataccac gacgatttcc ggcagtttct acacatatat tcgcaagatg tggcgtgtta  600
cggtgaaaac ctggcctatt tccctaaagg gtttattgag aatatgtttt tcgtctcagc  660
caatccctgg gtgagtttca ccagttttga tttaaacgtg gccaatatgg acaacttctt  720
cgcccccgtt ttcaccatgg gcaaatatta tacgcaaggc gacaaggtgc tgatgccgct  780
ggcgattcag gttcatcatg ccgtttgtga tggcttccat gtcggcagaa tgcttaatga  840
attacaacag tactgcgatg agtggcaggg cggggcgtaa tttttttaag gcagttattg  900
gtgcccttaa acgcctggtg ctacgcctga ataagtgata ataagcggat gaatggcaga  960
aattcgaaag caaattcgac ccggtcgtcg gttcagggca gggtcgttaa atagccgctt  1020
atgtctattg ctggtttatc ggtacccccc aactgatctt cagcatcttt tactttcacc  1080
agcgtttctg ggtgagcaaa aacaggaagg caaaatgccg caaaaaaggg aataagggcg  1140
acacggaaat gttgaatact catactcttc ctttttcaat attattgaag catttatcag  1200
ggttattgtc tcatgagcgg atacatattt gaatgtattt agaaaaataa acaaaagagt  1260
ttgtagaaac gcaaaaaggc catccgtcag gatggccttc tgcttaattt gatgcctggc  1320
agtttatggc gggcgtcctg cccgccaccc tccgggccgt tgcttcgcaa cgttcaaatc  1380
cgctcccggc ggatttgtcc tactcaggag agcgttcacc gacaaacaac agataaaacg  1440
aaaggcccag tctttcgact gagcctttcg ttttatttga tgcctggcag ttccctactc  1500
tcgcatgggg agaccccaca ctaccatcgg cgctacggcg tttcacttct gagttcggca  1560
tggggtcagg tgggaccacc gcgctactgc cgccaggcaa attctgtttt atcagaccgc  1620
ttctgcgttc tgatttaatc tgtatcaggc tgaaaatctt ctctcatccg ccaaaacagc  1680
caagcttagc ggccgcttag acctttcgct tttcttggg atcggctctg gagtcgccac  1740
caagctgaga caggtcgatt cgggtctcgt acaggccagt gatggactgg tgaatcaggg  1800
tggcatcgag aacctccttg gtggatgtgt accgctttcg gtcgatagtg gtatcgaagt  1860
acttgaaagc tgcaggagca cccaggttgg taagagtaaa caggtgaatg atgttctccg  1920
cctgttctcg aatgggtttg tcccgatgct tgttgtaggc agagagcacc ttgtccaagt  1980
tggcatcagc caggatgact cgcttcgaaa actcggaaat ctgctcgata atctcgtcga  2040
ggtaatgttt gtgctgctca acgaagagtt gcttctgttc gttgtcctcg ggagaaccct  2100
```

-continued

```
tgagcttctc gtagtgagaa gccagataga gaaagttgac gtacttcgaa ggcaaggcaa  2160
gctcgtttcc cttctgcagc tcgccagcgg aggcgagcat acgctttcga ccgttctcca  2220
gttcgaacag agagtacttg ggcagcttga taatgaggtc tttcttgacc tccttgtaac  2280
ccttggcttc caagaagtcg atgggattct tctcgaagct cgatcgctcc atgatggtaa  2340
ttccgagcag ctccttgacg gacttgagct ttttggactt gcccttctcg accttcgcaa  2400
cgacaagcac ggaataggcg acggtaggag aatcgaagcc accgtatttc ttgggatccc  2460
agtctttctt tcgagcgatg agcttgtcgg agtttcgctt gggcagaatc gactccttgg  2520
agaatccgcc agtctgaacc tcggttttct tgacgatgtt gacctgaggc atcgacagaa  2580
cctttcgcac ggttgcaaag tctcgaccct tgtcccacac gatctctcca gtttcgccgt  2640
tggtctcgat aagtggtctc tttcgaatct ctccgttggc caaggtgatc tcggtcttga  2700
aaaagttcat gatgttggag taaaagaagt acttggcagt agccttgcca atctcctgtt  2760
cggacttggc aatcatcttt cgaacgtcgt agaccttgta atcgccgtaa acgaactcgc  2820
tttcgagctt ggggtatttc ttgatgagcg cagtgccaac gacggcgttg aggtaagcat  2880
cgtgggcatg gtggtaattg ttgatctctc gcaccttgta gaactgaaag tcctttcgga  2940
aatcggagac cagtttggac ttgagagtaa tcaccttgac ctctcggatg agcttgtcgt  3000
tctcgtcgta cttggtgttc atccgagaat cgagaatctg tgcgacgtgc tttgtgatct  3060
gtctggtctc gacgagttga cgcttgatga agccagcctt gtcgagctcg gacagaccgc  3120
ctcgctcggc cttggtaaga ttgtcgaact ttcgctgggt aatgagcttg gcgttgagca  3180
gctgtcgcca gtagttcttc atctttttga ccacctcttc gctgggaacg ttgtccgact  3240
tgcctctgtt cttgtcggat cgtgtaagga ccttgttgtc gatagaatcg tccttgagaa  3300
aggattgagg gacaatgtgg tccacatcgt agtcgctgag acgattgatg tccagttcct  3360
gatccacgta catgtctcga ccattctgca gatagtagag atacagcttc tcgttctgca  3420
gttgagtgtt ctcgacggga tgctccttga gaatctggga tcccagctcc ttgatgcctt  3480
cctcgattcg cttcatccgc tctcgcgagt tttctgacc cttttgagtt gtctggttct  3540
ctctggccat ctcgatcaca atgttctcgg gcttgtgacg tcccatgacc ttcaccagct  3600
cgtcgacaac cttgacagtc tggagaatgc ctttcttgat ggctggcgaa ccagccaggt  3660
tggcaatatg ttcgtgcaag ctgtcgccct gaccggacac ttgtgccttc tggatgtcct  3720
ccttgaaggt aagagaatcg tcgtgaatga gctgcatgaa gtttcggttg gcaaagccat  3780
cggacttgag aaagtccaga atggtctttc cggactgctt gtctctgatg ccgttgatga  3840
gctttcgcga aagtcttccc cagccggtgt atctacgtcg cttgagttgt ttcatgacct  3900
tgtcgtcgaa caggtgagcg tatgtcttga gtcgttcctc gatcatctcc cgatcttcga  3960
acagggtaag agtgagcacg atgtcctcca gaatgtcctc gttttcctcg ttgtcgagaa  4020
aatccttgtc cttgataatc ttgagcagat cgtgataggt gcccaaagag gcgttgaatc  4080
ggtcctcaac tccggaaatc tcgacgctgt cgaaacactc gattttcttg aagtagtcct  4140
ccttgagctg cttaacagtg acctttcggt tggtcttgaa caggagatcg acaatggctt  4200
tcttctgttc gccagacaag aaggcaggct ttcgcattcc ctcggtaacg tacttgactt  4260
tggtgagttc gttgtagact gtaaagtact cgtagagcag cgaatgcttg ggaagaacct  4320
tctcgttggg cagattcttg tcgaagttgg tcattcgctc gatgaaggac tgtgcagagg  4380
caccccttgtc cacgacttcc tcgaagttcc agggagtgat ggtttcctcg gactttcgag  4440
tcatccaagc aaatcgagag tttcctctgg caagaggacc aacatagtag gggattcgaa  4500
aggtaagaat cttctcgatc ttctctcggt tgtccttgag aaaggggtag aagtcttcct  4560
gacgtcgaag aatggcgtgc agctcaccga ggtggatctg atgaggaatg ctgccgttgt  4620
cgaaggttcg ttgcttccga agcagatcct ctcgattgag cttgacaagc agttcctcgg  4680
ttccgtccat cttctcgaga attggcttga tgaacttgta gaactcttcc tgagaggctc  4740
cgccgtcgat gtatccagcg tagccgttct tcgactgatc gaaaaagatc tccttgtact  4800
tctcgggcag ttgctgtcgg acaagagcct tgagcagtgt gagatcctga tggtgctcgt  4860
cgtatcgctt gatcatggag gcagaaaggg gagcctttgt gatctcggtg ttgactcgca  4920
gaatgtcaga caagagaata gcatccgaaa ggttcttggc agcgagaaac aggtcggcgt  4980
actgatcgcc aatctgtgca agcaggttgt cgaggtcatc gtcgtaggtg tccttggaca  5040
gctggagctt ggcgtcctcc gccagatcga agttggactt gaagttgggt gtgagaccaa  5100
gagaaagggc aatgaggttg ccaaacagtc cgttcttttt ctcgccagga agttgggcaa  5160
tgaggttctc cagtcgtctg ctcttcgaga gtcgagcaga caagatggcc tttgcatcga  5220
ctccggaggc attgatgggg ttttcctcga acagctggtt gtaggtctga acgagctgaa  5280
tgaacagctt gtccacatcg ctgttgtcgg gattgagatc gccctcgatg aggaaatgac  5340
ctcgaaactt gatcatgtgt gccagagcga ggtagataag tctgagatcc gccttgtcgg  5400
tggaatcgac gagtttcttt cgcaggtggt agatggtagg atacttctcg tggtaagcaa  5460
cctcgtccac aatgttgcca aagatgggat gacgctcgtg tttcttgtct tcctcgacga  5520
ggaaggattc ctccagtcga tgaaagaacg aatcgtccac cttggccatc tcgttggaaa  5580
agatctcctg caggtagcag attcggttct tccgtcgggt gtaacgtcgc cgagcagttc  5640
gcttgagtct ggtagcttcg gcagtctcgc cagaatcgaa caacagggca ccaatgaggt  5700
ttttcttgat ggagtgtcga tcggtgtttc cgaggacctt gaatttcttg gagggcacct  5760
tgtactcgtc ggtgatgaca gcccagccga cagagttggt tccaatgtcc aggccgatgg  5820
agtatttctt gtcgaattcc catatggtac cagctgcaga tctcgagctc ggatccttat  5880
cgtcatcgtc gtacagatcc cgacccattt gctgtccacc agtcatgcta gccataccat  5940
gatgatgatg atgatgagaa ccccccatgg ttaattcctc ctgttagccc aaaaaacggg  6000
tatggagaaa cagtagagag ttgcgataaa aagcgtcagg taggatccgc taatcttatg  6060
gataaaaatg ctatggcata gcaaagtgtg acgccgtgca aataatcaat gtggactttt  6120
ctgccgtgat tatagacact tttgttacgc gtttttgtca tggctttggt cccgctttgt  6180
tacagaatgc ttttaataag cggggttacc ggtttggtta gcgagaagag ccagtaaaag  6240
acgcagtgac ggcaatgtct gatgcaatat ggacaattgg tttcttctct gaatggcggg  6300
agtatgaaaa gtatggctga agcgcaaaat gatcccctgc tgccgggata ctcgtttaat  6360
gcccatctgg tggcgggttt aacgccgatt gaggccaacg gttatctcga tttttttatc  6420
gaccgaccgc tgggaatgaa aggttatatt ctcaatctca ccattcgcgg tcagggggtg  6480
gtgaaaaatc agggacgaga atttgtttgc cgaccgggtg atattttgct gttcccgcca  6540
ggagagattc atcactacgg tcgtcatccg gaggctcgcg aatggtatca ccagtgggtt  6600
tactttcgtc cgcgcgccta ctggcatgaa tggcttaact ggccgtcaat atttgccaat  6660
acggggttct ttcgcccgga tgaagcgcac cagccgcatt tcagcgacct gtttgggcaa  6720
atcattaacg ccgggcaagg ggaagggcgc tattcggagc tgctggcgat aaatctgctt  6780
gagcaattgt tactgcggcg catggaagcg attaacgagt cgctccatcc accgatggat  6840
```

```
aatcgggtac gcgaggcttg tcagtacatc agcgatcacc tggcagacag caattttgat  6900
atcgccagcg tcgcacagca tgtttgcttg tcgccgtcgc gtctgtcaca tcttttccgc  6960
cagcagttag ggattagcgt cttaagctgg cgcgaggacc aacgtatcag ccaggcgaag  7020
ctgcttttga gcaccacccg gatgcctatc gccaccgtcg gtcgcaatgt tggttttgac  7080
gatcaactct atttctcgcg ggtatttaaa aaatgcaccg gggccagccc gagcgagttc  7140
cgtgccggtt gtgaagaaaa agtgaatgat gtagccgtca agttgtcata attggtaacg  7200
aatcagacaa ttgacggctt gacggagtag catagggttt gcagaatccc tgcttcgtcc  7260
atttgacagg cacattatgc atgccgcttc gccttcgcgc gcgaattgat ctgctgcctc  7320
gcgcgtttcg gtgatgacgg tgaaaacctc tgacacatgc agctcccgga gacggtcaca  7380
gcttgtctgt aagcggatgc cgggagcaga caagcccgtc agggcgcgtc agcgggtgtt  7440
ggcgggtgtc ggggcgcagc catgacccag tcacgtagcg atagcggagt gtatactggc  7500
ttaactatgc ggcatcagag cagattgtac tgagagtgca ggggatcgcg gccgcggacc  7560
ggatcctcta gagcggccgc gatcctctag agtcgaccgg gaatggcgaa tgggacgcgc  7620
cctgtagcgg cgcattaagc gcggcgggtg tggtggttac gcgcagcgtg accgctacac  7680
ttgccagcgc cctagcgccc gctcctttcg ctttcttccc ttcctttctc gccacgttcg  7740
ccggctttcc ccgtcaagct ctaaatcggg ggctcccttt agggttccga tttagtgctt  7800
tacggcacct cgaccccaaa aaacttgatt agggtgatgg ttcacgtagt gggccatcgc  7860
cctgatagac ggtttttcgc cctttgacgt tggagtccac gttctttaat agtggactct  7920
tgttccaaac tggaacaaca ctcaacccta tctcggtcta ttcttttgat ttataaggga  7980
ttttgccgat ttcggcctat tggttaaaaa atgagctgat ttaacaaaaa tttaacgcga  8040
attttaacaa aatattaacg cttacaattt aggtggcact tttcggggaa atgtgcgcgg  8100
aacccctatt tgtttatttt tctaaataca ttcaaatatg tatccgctca tcagatcctt  8160
tttaacccat cacatatacc tgccgttcac tattatttag tgaaatgaga tattatgata  8220
ttttctgaat tgtgattaaa aaggcaactt tatgcccatg caacagaaac tataaaaaat  8280
acagagaatg aaaagaaaca gatagatttt ttagttcttt aggcccgtag tctgcaaatc  8340
cttttatgat ttctatcaa acaaaagagg aaaatagacc agttgcaatc caaacgagag  8400
tctaatagaa tgaggtcgaa aagtaaatcg cgcgggtttg ttactgataa agcaggcaag  8460
acctaaaatg tgtaaagggc aaagtgtata ctttggcgtc accccttaca tattttaggt  8520
cttttttat tgtgcgtaac taacttgcca tcttcaaaca ggagggctgg aagaagcaga  8580
ccgctaacac agtacataaa aaaggagaca tgaacgatga acatcaaaaa gtttgcaaaa  8640
caagcaacag tattaacctt tactaccgca ctgctggcag gaggcgcaac tcaagcgttt  8700
gcgaaagaaa cgaaccaaaa gccatataag gaaacatacg gcatttccca tattacacgc  8760
catgatatgc tgcaaatccc tgaacagcaa aaaaatgaaa aatatcaagt tcctgaattc  8820
gattcgtcca caattaaaaa tatctcttct gcaaaaggcc tggacgtttg ggacagctgg  8880
ccattacaaa acgctgacgg cactgtcgca aactatcacg gctaccacat cgtctttgca  8940
ttagccggag atcctaaaaa tgcggatgac acatcgattt acatgttcta tcaaaaagtc  9000
ggcgaaactt ctattgacag ctggaaaaac gctggccgcg tctttaaaga cagcgacaaa  9060
ttcgatgcaa atgattctat cctaaaagac caaacacaag aatggtcagg ttcagccaca  9120
tttacatctg acggaaaaat ccgtttattc tacactgatt tctccggtaa acattacggc  9180
aaacaaacac tgacaactgc acaagttaac gtatcagcat cagacagctc tttgaacatc  9240
aacggtgtag aggattataa atcaatcttt gacggtgacg gaaaaacgta tcaaaatgta  9300
cagcagttca tcgatgaagg caactacagc tcaggcgaca accatacgct gagagatcct  9360
cactacgtag aagataaagg ccacaaatac ttagtatttg aagcaaacac tggaactgaa  9420
gatggctacc aaggcgaaga atctttattt aacaaagcat actatggcaa aagcacatca  9480
ttcttccgtc aagaaagtca aaaacttctg caaagcgata aaaaacgcac ggctgagtta  9540
gcaaacggcg ctctcggtat gattgagcta aacgatgatt acacactgaa aaaagtgatg  9600
aaaccgctga ttgcatctaa cacagtaaca gatgaaattg aacgcgcgaa cgtctttaaa  9660
atgaacggca aatggtacct gttcactgac tcccgcggat caaaaatgac gattgacggc  9720
attacgtcta acgatattta catgcttggt tatgtttcta attctttaac tggcccatac  9780
aagccgctga acaaaactgg ccttgtgtta aaaatggatc ttgatcctaa cgatgtaacc  9840
tttacttact cacacttcgc tgtacctcaa gcgaaaggaa acaatgtcgt gattacaagc  9900
tatatgacaa acagaggatt ctacgcagac aaacaatcaa cgtttgcgcc aagcttcctg  9960
ctgaacatca aaggcaagaa aacatctgtt gtcaaagaca gcatccttga acaaggacaa  10020
ttaacagtta acaaataaaa acgcaaaaga aaatgccgat ccggtttatt gactaccgga  10080
agcagtgtga ccgtgtgctt ctcaaatgcc tcaggctgtc tatgtgtgac tgttgagctg  10140
taacaagttg tctcaggtgt tcaatttcat gttctagttg ctttgtttta ctggtttcac  10200
ctgttctatt aggtgttaca tgctgttcat ctgttacatt gtcgatctgt tcatggtgaa  10260
cagctttaaa tgcaccaaaa actcgtaaaa gctctgatgt atctatcttt tttacaccgt  10320
tttcatctgt gcatatggac agttttccct ttgatatcta acggtgaaca gttgttctac  10380
ttttgtttgt tagtcttgat gcttcactga tagatacaag agccataaga acctcagatc  10440
cttccgtatt tagccagtat gttctctagt gtggttcgtt gtttttgcgt gagccatgag  10500
aacgaaccat tgagatcatg cttactttgc atgtcactca aaaattttgc ctcaaaactg  10560
gtgagctgaa tttttgcagt taaagcatcg tgtagtgttt ttcttagtcc gttacgtagg  10620
taggaatctg atgtaatggt tgttggtatt ttgtcaccat tcatttttat ctggttgttc  10680
tcaagttcgg ttacgagatc catttgtcta tctagttcaa cttggaaaat caacgtatca  10740
gtcgggcggc ctcgcttatc aaccaccaat ttcatattgc tgtaagtgtt taaatcttta  10800
cttattggtt tcaaaaccca ttggttaagc cttttaaact catggtagtt attttcaagc  10860
attaacatga acttaaattc atcaaggcta atctctatat ttgccttgtg agttttcttt  10920
tgtgttagtt cttttaataa ccactcataa atcctcatag agtatttgtt ttcaaaagac  10980
ttaacatgtt ccagattata ttttatgaat ttttttaact ggaaaagata aggcaatatc  11040
tcttcactaa aaactaattc taatttttcg cttgagaact tggcatagtt tgtccactgg  11100
aaaatctcaa agcctttaac caaaggattc ctgatttcca cagttctcgt catcagctct  11160
ctggttgctt tagctaatac accataagca ttttccctac tgatgttcat catctgagcg  11220
tattggttat aagtgaacga taccgtccgt tctttccttg tagggttttc aatcgtgggg  11280
ttgagtagtg ccacacagca taaaattagc ttggtttcat gctccgttaa gtcatagcga  11340
ctaatcgcta gttcatttgc tttgaaaaca actaattcag acatacatct caattggtct  11400
aggtgatttt aatcactata ccaattgaga tgggctagtc aatgataatt actagtcctt  11460
ttcctttgag ttgtgggtat ctgtaaattc tgctagacct ttgctggaaa acttgtaaat  11520
tctgctagac cctctgtaaa ttccgctaga cctttgtgtg ttttttttgt ttatattcaa  11580
```

```
gtggttataa tttatagaat aaagaaagaa taaaaaaaga taaaaagaat agatcccagc  11640
cctgtgtata actcactact ttagtcagtt ccgcagtatt acaaaaggat gtcgcaaacg  11700
ctgtttgctc ctctacaaaa cagaccttaa aaccctaaag gcttaagtag caccctcgca  11760
agctcgggca aatcgctgaa tattcctttt gtctccgacc atcaggcacc tgagtcgctg  11820
tctttttcgt gacattcagt tcgctgcgct cacggctctg gcagtgaatg ggggtaaatg  11880
gcactacagg cgccttttat ggattcatgc aaggaaacta cccataatac aagaaaagcc  11940
cgtcacgggc ttctcagggc gttttatggc gggtctgcta tgtggtgcta tctgactttt  12000
tgctgttcag cagttcctgc cctctgattt tccagtctga ccacttcgga ttatcccgtg  12060
acaggtcatt cagactggct aatgcaccca gtaaggcagc ggtatcatca acaggcttac  12120
ccgtcttact gtcggatcga cgctctccct tatgcgactc ctgcat                 12166
```

```
SEQ ID NO: 87          moltype = DNA  length = 410
FEATURE                Location/Qualifiers
misc_feature           1..410
                       note = Y155H encoding synthetic fragment
source                 1..410
                       mol_type = other DNA
                       organism = synthetic construct
SEQUENCE: 87
ctccagtcgt ctgctcttcg agagtcgagc agacaagatg gcctttgcat cgactccgga  60
ggcattgatg gggttttcct cgaacagctg gttgtaggtc tgaacgagct gaatgaacag  120
cttgtccaca tcgctgttgt cgggattgag atcgccctcg atgaggaaat gacctcgaaa  180
cttgatcatg tgtgccagag cgagatggat aagtctgaga tccgccttgt cggtggaatc  240
gacgagtttc tttcgcaggt ggtagatggt aggatacttc tcgtggtaag caacctcgtc  300
cacaatgttg ccaaagatgg gatgacgctc gtgtttcttg tcttcctcga cgaggaagga  360
ttcctccagt cgatgaaaga acgaatcgtc caccttggcc atctcgttgg             410
```

```
SEQ ID NO: 88          moltype = DNA  length = 20
FEATURE                Location/Qualifiers
misc_feature           1..20
                       note = Y155H synthetic fragment forward primer
source                 1..20
                       mol_type = other DNA
                       organism = synthetic construct
SEQUENCE: 88
ccaacgagat ggccaaggtg                                              20
```

```
SEQ ID NO: 89          moltype = DNA  length = 20
FEATURE                Location/Qualifiers
misc_feature           1..20
                       note = Y155H synthetic fragment reverse primer
source                 1..20
                       mol_type = other DNA
                       organism = synthetic construct
SEQUENCE: 89
ccaacgagat ggccaaggtg                                              20
```

```
SEQ ID NO: 90          moltype = DNA  length = 11794
FEATURE                Location/Qualifiers
misc_feature           1..11794
                       note = pRF97-Y155H fragment of plasmid
source                 1..11794
                       mol_type = other DNA
                       organism = synthetic construct
SEQUENCE: 90
caccttggcc atctcgttgg aaaagatctc ctgcaggtag cagattcggt tcttccgtcg  60
ggtgtaacgt cgccgagcag ttcgcttgag tctggtagct tcggcagtct cgccagaatc  120
gaacaacagg gcaccaatga ggtttttctt gatggagtgt cgatcggtgt ttccgaggac  180
cttgaatttc ttggagggca ccttgtactc gtcggtgatg acagcccagc cgacagagtt  240
ggttccaatg tccaggccga tggagtattt cttgtcgaat tcccatatgg taccagctgc  300
agatctcgag ctcggatcct tatcgtcatc gtcgtacaga tcccgaccca tttgctgtcc  360
accagtcatg ctagccatac catgatgatg atgatgatga gaacccccca tggttaattc  420
ctcctgttag cccaaaaaac gggtatggag aaacagtaga gagttgcgat aaaaagcgtc  480
aggtaggatc cgctaatctt atggataaaa atgctatggc atagcaaagt gtgacgccgt  540
gcaaataatc aatgtggact ttctgccgt gattatagac acttttgtta cgcgtttttg  600
tcatggcttt ggtcccgctt tgttacagaa tgcttttaat aagcggggtt accggtttgg  660
ttagcgagaa gagccagtaa aagacgcagt gacggcaatg tctgatgcaa tatggacaat  720
tggtttcttc tctgaatggc gggagtatga aaagtatggc tgaagcgcaa aatgatcccc  780
tgctgccggg atactcgttt aatgcccatc tggtggcggg tttaacgccg attgaggcca  840
acggttatct cgattttttt atcgaccgac cgctgggaat gaaaggttat attctcaatc  900
tcaccattcg cggtcagggg gtggtgaaaa atcagggacg agaatttgtt tgccgaccgg  960
gtgatatttt gctgttcccg ccaggagaga ttcatcacta cggtcgtcat ccggaggctc  1020
gcgaatggta tcaccagtgg gtttactttc gtccgcgcgc ctactggcat gaatggctta  1080
actggccgtc aatatttgcc aatacggggt tctttcgccc ggatgaagcg caccagccgc  1140
atttcagcga cctgtttggg caaatcatta acgccgggca aggggaaggg cgctattcgg  1200
agctgctggc gataaatctg cttgagcaat tgttactgcg gcgcatggaa gcgattaacg  1260
agtcgctcca tccaccgatg gataatcggg tacgcgaggc ttgtcagtac atcagcgatc  1320
acctggcaga cagcaatttt gatatcgcca gcgtcgcaca gcatgtttgc ttgtcgccgt  1380
cgcgtctgtc acatcttttc cgccagcagt tagggattag cgtcttaagc tggcgcgagg  1440
```

-continued

```
accaacgtat cagccaggcg aagctgcttt tgagcaccac ccggatgcct atcgccaccg  1500
tcggtcgcaa tgttggtttt gacgatcaac tctatttctc gcgggtattt aaaaaatgca  1560
ccggggccag cccgagcgag ttccgtgccg gttgtgaaga aaaagtgaat gatgtagccg  1620
tcaagttgtc ataattggta acgaatcaga caattgacgg cttgacggag tagcataggg  1680
tttgcagaat ccctgcttcg tccatttgac aggcacatta tgcatgccgc ttcgccttcg  1740
cgcgcgaatt gatctgctgc ctcgcgcgtt tcggtgatga cggtgaaaac ctctgacaca  1800
tgcagctccc ggagacggtc acagcttgtc tgtaagcgga tgccgggagc agacaagccc  1860
gtcagggcgc gtcagcgggt gttggcgggt gtcggggcgc agccatgacc cagtcacgta  1920
gcgatagcgg agtgtatact ggcttaacta tgcggcatca gagcagattg tactgagagt  1980
gcaggggatc gcggccgcgg accggatcct ctagagcggc cgcgatcctc tagagtcgac  2040
cggtggcgaa tgggacgcgc cctgtagcgg cgcattaagc gcggcgggtg tggtggttac  2100
gcgcagcgtg accgctacac ttgccagcgc cctagcgccc gctcctttcg ctttcttccc  2160
ttcctttctc gccacgttcg ccggctttcc ccgtcaagct ctaaatcggg ggctcccttt  2220
agggttccga tttagtgctt tacggcacct cgaccccaaa aaacttgatt agggtgatgg  2280
ttcacgtagt gggccatcgc cctgatagac ggtttttcgc cctttgacgt tggagtccac  2340
gttctttaat agtggactct tgttccaaac tggaacaaca ctcaacccta tctcggtcta  2400
ttcttttgat ttataaggga ttttgccgat ttcggcctat tggttaaaaa atgagctgat  2460
ttaacaaaaa tttaacgcga attttaacaa aatattaacg cttacaattt aggtggcact  2520
tttcggggaa atgtgcgcgg aacccctatt tgtttatttt tctaaataca ttcaaatatg  2580
tatccgctca ccgcgatcct ttttaaccca tcacatatac ctgccgttca ctattattta  2640
gtgaaatgag atattatgat attttctgaa ttgtgattaa aaaggcaact ttatgcccat  2700
gcaacagaaa ctataaaaaa tacagagaat gaaaagaaac agatagattt tttagttctt  2760
taggcccgta gtctgcaaat ccttttatga ttttctatca aacaaaagag gaaaatagac  2820
cagttgcaat ccaaacgaga gtctaataga atgaggtcga aaagtaaatc gcgcgggttt  2880
gttactgata aagcaggcaa gacctaaaat gtgtaaaggg caaagtgtat actttggcgt  2940
cacccctac atattttagg tcttttttta ttgtgcgtaa ctaacttgcc atcttcaaac  3000
aggagggctg gaagaagcag accgctaaca cagtacataa aaaaggagac atgaacgatg  3060
aacatcaaaa agtttgcaaa acaagcaaca gtattaacct ttactaccgc actgctggca  3120
ggaggcgcaa ctcaagcgtt tgcgaaagaa acgaaccaaa agccatataa ggaaacatac  3180
ggcatttccc atattacacg ccatgatatg ctgcaaatcc ctgaacagca aaaaaatgaa  3240
aaatatcaag ttcctgagtt cgattcgtcc acaattaaaa atatctcttc tgcaaaaggc  3300
ctggacgttt gggacagctg gccattacaa aacgctgacg gcactgtcgc aaactatcac  3360
ggctaccaca tcgtctttgc attagccgga gatcctaaaa atgcggatga cacatcgatt  3420
tacatgttct atcaaaaagt cggcgaaact tctattgaca gctggaaaaa cgctggccgc  3480
gtctttaaag acagcgacaa attcgatgca aatgattcta tcctaaaaga ccaaacacaa  3540
gaatggtcag gttcagccac atttacatct gacggaaaaa tccgtttatt ctacactgat  3600
ttctccggta aacattacgg caaacaaaca ctgacaactg cacaagttaa cgtatcagca  3660
tcagacagct ctttgaacat caacggtgta gaggattata aatcaatctt tgacggtgac  3720
ggaaaaacgt atcaaaatgt acagcagttc atcgatgaag gcaactacag ctcaggcgac  3780
aaccatacgc tgagagatcc tcactacgta gaagataaag gccacaaata cttagtattt  3840
gaagcaaaca ctggaactga agatggctac caaggcgaag aatctttatt taacaaagca  3900
tactatggca aaagcacatc attcttccgt caagaaagtc aaaaacttct gcaaagcgat  3960
aaaaaacgca cggctgagtt agcaaacggc gctctcggta tgattgagct aaacgatgat  4020
tacacactga aaaaagtgat gaaaccgctg attgcatcta acacagtaac agatgaaatt  4080
gaacgcgcga acgtctttaa aatgaacggc aaatggtacc tgttcactga ctcccgcgga  4140
tcaaaaatga cgattgacgg cattacgtct aacgatattt acatgcttgg ttatgtttct  4200
aattctttaa ctggcccata caagccgctg aacaaaactg gccttgtgtt aaaaatggat  4260
cttgatccta acgatgtaac ctttacttac tcacacttcg ctgtacctca agcgaaagga  4320
aacaatgtcg tgattacaag ctatatgaca aacagaggat tctacgcaga caaacaatca  4380
acgtttgcgc caagcttcct gctgaacatc aaaggcaaga aaacatctgt tgtcaaagac  4440
agcatccttg aacaaggaca attaacagtt aacaaataaa aacgcaaaag aaaatgccga  4500
tattgactac cggaagcagt gtgaccgtgt gcttctcaaa tgcctgattc aggctgtcta  4560
tgtgtgactg ttgagctgta acaagttgtc tcaggtgttc aatttcatgt tctagttgct  4620
ttgttttact ggtttcacct gttctattag gtgttacatg ctgttcatct gttacattgt  4680
cgatctgttc atggtgaaca gctttaaatg caccaaaaac tcgtaaaagc tctgatgtat  4740
ctatcttttt tacaccgttt tcatctgtgc atatggacag ttttcccttt gatatgtaac  4800
ggtgaacagt tgttctactt ttgtttgtta gtcttgatgc ttcactgata gatacaagag  4860
ccataagaac ctcagatcct tccgtattta gccagtatgt tctctagtgt ggttcgttgt  4920
ttttgcgtga gccatgagaa cgaaccattg agatcatact tactttgcat gtcactcaaa  4980
aattttgcct caaaactggt gagctgaatt tttgcagtta aagcatcgtg tagtgttttt  5040
cttagtccgt tatgtaggta ggaatctgat gtaatggttg ttggtatttt gtcaccattc  5100
atttttatct ggttgttctc aagttcggtt acgagatcca tttgtctatc tagttcaact  5160
tggaaaatca acgtatcagt cgggcggcct cgcttatcaa ccaccaattt catattgctg  5220
taagtgttta aatctttact tattggtttc aaaacccatt ggttaagcct tttaaactca  5280
tggtagttat tttcaagcat taacatgaac ttaaattcat caaggctaat ctctatattt  5340
gccttgtgag ttttcttttg tgttagttct tttaataacc actcataaat cctcatagag  5400
tatttgtttt caaaagactt aacatgttcc agattatatt ttatgaattt ttttaactgg  5460
aaaagataag gcaatatctc ttcactaaaa actaattcta atttttcgct tgagaacttg  5520
gcatagtttg tccactggaa aatctcaaag cctttaacca aaggattcct gatttccaca  5580
gttctcgtca tcagctctct ggttgcttta gctaatacac cataagcatt ttccctactg  5640
atgttcatca tctgaacgta ttggttataa gtgaacgata ccgtccgttc tttccttgta  5700
gggttttcaa tcgtggggtt gagtagtgcc acacagcata aaattagctt ggtttcatgc  5760
tccgttaagt catagcgact aatcgctagt tcatttgctt tgaaaacaac taattcagac  5820
atacatctca attggtctag gtgattttaa tcactatacc aattgagatg ggctagtcaa  5880
tgataattac tagtcctttt cctttgagtt gtgggtatct gtaaattctg ctagaccttt  5940
gctggaaaac ttgtaaattc tgctagaccc tctgtaaatt ccgctagacc tttgtgtgtt  6000
ttttttgttt atattcaagt ggttataatt tatagaataa agaaagaata aaaaaagata  6060
aaaagaatag atcccagccc tgtgtataac tcactacttt agtcagttcc gcagtattac  6120
aaaaggatgt cgcaaacgct gtttgctcct ctacaaaaca gaccttaaaa ccctaaaggc  6180
```

-continued

```
ttaagtagca ccctcgcaag ctcgggcaaa tcgctgaata ttccttttgt ctccgaccat  6240
caggcacctg agtcgctgtc tttttcgtga cattcagttc gctgcgctca cggctctggc  6300
agtgaatggg ggtaaatggc actacaggcg ccttttatgg attcatgcaa ggaaactacc  6360
cataatacaa gaaaagcccg tcacgggctt ctcagggcgt tttatggcgg gtctgctatg  6420
tggtgctatc tgactttttg ctgttcagca gttcctgccc tctgattttc cagtctgacc  6480
acttcggatt atcccgtgac aggtcattca gactggctaa tgcacccagt aaggcagcgg  6540
tatcatcaac aggcttaccc gtcttactgt cggggatcga cgctctccct tatgcgactc  6600
ctgcaccttt cgtcttcgaa taaatacctg tgacggaaga tcacttcgca gaataaataa  6660
atcctggtgt ccctgttgat accgggaagc cctgggccaa cttttggcga aaatgagacg  6720
ttgatcggca cgtaagaggt tccaactttc accataatga aataagatca ctaccgggcg  6780
tatttttga gttatcgaga ttttcaggag ctaaggaagc taaaatggag aaaaaaatca  6840
ctggatatac caccgttgat atatcccaat ggcatcgtaa agaacatttt gaggcatttc  6900
agtcagttgc tcaatgtacc tataaccaga ccgttcagct ggatattacg gcctttttaa  6960
agaccgtaaa gaaaaataag cacaagtttt atccggcctt tattcacatt cttgcccgcc  7020
tgatgaatgc tcatccggaa ttccgtatgg caatgaaaga cggtgagctg gtgatatggg  7080
atagtgttca cccttgttac accgttttcc atgagcaaac tgaaacgttt tcatcgctct  7140
ggagtgaata ccacgacgat ttccggcagt ttctacacat atattcgcaa gatgtggcgt  7200
gttacggtga aaacctggcc tatttcccta aagggtttat tgagaatatg tttttcgtct  7260
cagccaatcc ctgggtgagt ttcaccagtt ttgatttaaa cgtggccaat atggacaact  7320
tcttcgcccc cgttttcacc atgggcaaat attatacgca aggcgacaag gtgctgatgc  7380
cgctggcgat tcaggttcat catgccgttt gtgatggctt ccatgtcggc agaatgctta  7440
atgaattaca acagtactgc gatgagtggc agggcggggc gtaatttttt taaggcagtt  7500
attggtgccc ttaaacgcct ggttgctacg cctgaataag tgataataag cggatgaatg  7560
gcagaaattc gaaagcaaat tcgacccggt cgtcggttca gggcagggtc gttaaatagc  7620
cgcttatgtc tattgctggt ctcggtaccc tgcacccaac tgatcttcag catcttttac  7680
tttcaccagc gtttctgggt gagcaaaaac aggaaggcaa aatgccgcaa aaaagggaat  7740
aagggcgaca cggaaatgtt gaatactcat actcttcctt tttcaatatt attgaagcat  7800
ttatcagggt tattgtctca tgagcggata catatttgaa tgtatttaga aaaataaaca  7860
aaagagtttg tagaaacgca aaaaggccat ccgtcaggat ggccttctgc ttaatttgat  7920
gcctggcagt ttatggcggg cgtcctgccc gccaccctcc gggccgttgc ttcgcaacgt  7980
tcaaatccgc tcccggcgga tttgtcctac tcaggagagc gttcaccgac aaacaacaga  8040
taaaacgaaa ggcccagtct ttcgactgag cctttcgttt tatttgatgc ctggcagttc  8100
cctactctcg catggggaga ccccacacta ccatcggcgc tacggcgttt cacttctgag  8160
ttcggcatgg ggtcaggtgg gaccaccgcg ctactgccgc caggcaaatt ctgttttatc  8220
agaccgcttc tgcgttctga tttaatctgt atcaggctga aaatcttctc tcatccgcca  8280
aaacagccaa gcttagcggc cgcttagacc tttcgctttt tcttgggatc ggctctggag  8340
tcgccaccaa gctgagacag gtcgattcgg gtctcgtaca ggccagtgat ggactggtga  8400
atcagggtgg catcgagaac ctccttggtg gatgtgtacc gctttcggtc gatagtggta  8460
tcgaagtact tgaaagctgc aggagcaccc aggttggtaa gagtaaacag gtgaatgatg  8520
ttctccgcct gttctcgaat gggtttgtcc cgatgcttgt tgtaggcaga gagcaccttg  8580
tccaagttgg catcagccag gatgactcgc ttcgaaaact cggaaatctg ctcgataatc  8640
tcgtcgaggt aatgtttgtg ctgctcaacg aagagttgct tctgttcgtt gtcctcggga  8700
gaacccttga gcttctcgta gtgagaagcc agatagagaa agttgacgta cttcgaaggc  8760
aaggcaagct cgtttccctt ctgcagctcg ccagcggagg cgagcatacg ctttcgaccg  8820
ttctccagtt cgaacagaga gtacttgggc agcttgataa tgaggtcttt cttgacctcc  8880
ttgtaaccct tggcttccaa gaagtcgatg ggattcttct cgaagctcga tcgctccatg  8940
atggtaattc cgagcagctc cttgacggac ttgagctttt tggacttgcc cttctcgacc  9000
ttcgcaacga caagcacgga ataggcgacg gtaggagaat cgaagccacc gtatttcttg  9060
ggatcccagt ctttctttcg agcgatgagc ttgtcggagt ttcgcttggg cagaatcgac  9120
tccttggaga atccgccagt ctgaacctcg gttttcttga cgatgttgac ctgaggcatc  9180
gacagaacct ttcgcacggt tgcaaagtct cgacccttgt cccacacgat ctctccagtt  9240
tcgccgttgg tctcgataag tggtctcttt cgaatctctc cgttggccaa ggtgatctcg  9300
gtcttgaaaa agttcatgat gttggagtaa aagaagtact tggcagtagc cttgccaatc  9360
tcctgttcgg acttggcaat catctttcga acgtcgtaga ccttgtaatc gccgtaaacg  9420
aactcgcttt cgagcttggg gtatttcttg atgagcgcag tgccaacgac ggcgttgagg  9480
taagcatcgt gggcatggtg gtaattgttg atctctcgca ccttgtagaa ctgaaagtcc  9540
tttcggaaat cggagaccag tttggacttg agagtaatca ccttgacctc tcggatgagc  9600
ttgtcgttct cgtcgtactt ggtgttcatc cgagaatcga gaatctgtgc gacgtgcttt  9660
gtgatctgtc tggtctcgac gagttgacgc ttgatgaagc cagccttgtc gagctcggac  9720
agaccgcctc gctcggcctt ggtaagattg tcgaactttc gctgggtaat gagcttggcg  9780
ttgagcagct gtcgccagta gttcttcatc tttttgacca cctcttcgct gggaacgttg  9840
tccgacttgc ctctgttctt gtcggatcgt gtaaggacct tgttgtcgat agaatcgtcc  9900
ttgagaaagg attgagggac aatgtggtcc acatcgtagt cgctgagacg attgatgtcc  9960
agttcctgat ccacgtacat gtctcgacca ttctgcagat agtagagata cagcttctcg  10020
ttctgcagtt gagtgttctc gacgggatgc tccttgagaa tctgggatcc cagctccttg  10080
atgccttcct cgattcgctt catccgctct cgcgagtttt tctgaccctt ttgagttgtc  10140
tggttctctc tggccatctc gatcacaatg ttctcgggct tgtgacgtcc catgaccttc  10200
accagctcgt cgacaacctt gacagtctgg agaatgcctt tcttgatggc tggcgaacca  10260
gccaggttgg caatatgttc gtgcaagctg tcgccctgac cggacacttg tgccttctgg  10320
atgtcctcct tgaaggtaag agaatcgtcg tgaatgagct gcatgaagtt tcggttggca  10380
aagccatcgg acttgagaaa gtccagaatg gtctttccgg actgcttgtc tctgatgccg  10440
ttgatgagct ttcgcgaaag tcttccccag ccggtgtatc tacgtcgctt gagttgtttc  10500
atgaccttgt cgtcgaacag gtgagcgtat gtcttgagtc gttcctcgat catctcccga  10560
tcttcgaaca gggtaagagt gagcacgatg tcctccagaa tgtcctcgtt ttcctcgttg  10620
tcgagaaaat ccttgtcctt gataatcttg agcagatcgt gataggtgcc caaagaggcg  10680
ttgaatcggt cctcaactcc ggaaatctcg acgctgtcga aacactcgat tttcttgaag  10740
tagtcctcct tgagctgctt aacagtgacc tttcggttgg tcttgaacag gagatcgaca  10800
atggctttct tctgttcgcc agacaagaag gcaggctttc gcattccctc ggtaacgtac  10860
ttgactttgg tgagttcgtt gtagactgta aagtactcgt agagcagcga atgcttggga  10920
```

```
agaaccttct cgttgggcag attcttgtcg aagttggtca ttcgctcgat gaaggactgt  10980
gcagaggcac ccttgtccac gacttcctcg aagttccagg gagtgatggt ttcctcggac  11040
tttcgagtca tccaagcaaa tcgagagttt cctctggcaa gaggaccaac atagtagggg  11100
attcgaaagg taagaatctt ctcgatcttc tctcggttgt ccttgagaaa ggggtagaag  11160
tcttcctgac gtcgaagaat ggcgtgcagc tcaccgaggt ggatctgatg aggaatgctg  11220
ccgttgtcga aggttcgttg cttccgaagc agatcctctc gattgagctt gacaagcagt  11280
tcctcggttc cgtccatctt ctcgagaatt ggcttgatga acttgtagaa ctcttcctga  11340
gaggctccgc cgtcgatgta tccagcgtag ccgttcttcg actgatcgaa aaagatctcc  11400
ttgtacttct cgggcagttg ctgtcggaca agagccttga gcagtgtgag atcctgatgg  11460
tgctcgtcgt atcgcttgat catggaggca gaaaggggag cctttgtgat ctcggtgttg  11520
actcgcagaa tgtcagacaa gagaatagca tccgaaaggt tcttggcagc gagaaacagg  11580
tcggcgtact gatcgccaat ctgtgcaagc aggttgtcga ggtcatcgtc gtaggtgtcc  11640
ttggacagct ggagcttggc gtcctccgcc agatcgaagt tggacttgaa gttgggtgtg  11700
agaccaagag aaagggcaat gaggttgcca aacagtccgt tctttttctc gccaggaagt  11760
tgggcaatga ggttctccag tcgtctgctc ttcg                              11794

SEQ ID NO: 91          moltype = DNA  length = 20
FEATURE                Location/Qualifiers
misc_feature           1..20
                       note = pRF97-Y155H fragment forward primer
source                 1..20
                       mol_type = other DNA
                       organism = synthetic construct
SEQUENCE: 91
caccttggcc atctcgttgg                                              20

SEQ ID NO: 92          moltype = DNA  length = 20
FEATURE                Location/Qualifiers
misc_feature           1..20
                       note = pRF97-Y155H fragment reverse primer
source                 1..20
                       mol_type = other DNA
                       organism = synthetic construct
SEQUENCE: 92
cgaagagcag acgactggag                                              20

SEQ ID NO: 93          moltype = DNA  length = 12164
FEATURE                Location/Qualifiers
misc_feature           1..12164
                       note = plasmid pRF861
source                 1..12164
                       mol_type = other DNA
                       organism = synthetic construct
SEQUENCE: 93
cctttcgtct tcgaataaat acctgtgacg gaagatcact tcgcagaata aataaatcct  60
ggtgtccctg ttgataccgg gaagccctgg gccaactttt ggcgaaaatg agacgttgat  120
cggcacgtaa gaggttccaa ctttcaccat aatgaaataa gatcactacc gggcgtattt  180
tttgagttat cgagattttc aggagctaag gaagctaaaa tggagaaaaa aatcactgga  240
tataccaccg ttgatatatc ccaatggcat cgtaaagaac attttgaggc atttcagtca  300
gttgctcaat gtacctataa ccagaccgtt cagctggata ttacggcctt tttaaagacc  360
gtaaagaaaa ataagcacaa gttttatccg gcctttattc acattcttgc ccgcctgatg  420
aatgctcatc cggaattccg tatggcaatg aaagacggtg agctggtgat atgggatagt  480
gttcaccctt gttacaccgt tttccatgag caaactgaaa cgttttcatc gctctggagt  540
gaataccacg acgatttccg gcagtttcta cacatatatt cgcaagatgt ggcgtgttac  600
ggtgaaaacc tggcctattt ccctaaaggg tttattgaga atatgttttt cgtctcagcc  660
aatccctggg tgagtttcac cagttttgat ttaaacgtgg ccaatatgga caacttcttc  720
gcccccgttt tcaccatggg caaatattat acgcaaggcg acaaggtgct gatgccgctg  780
gcgattcagg ttcatcatgc cgtttgtgat ggcttccatg tcggcagaat gcttaatgaa  840
ttacaacagt actgcgatga gtggcagggc ggggcgtaat ttttttaagg cagttattgg  900
tgcccttaaa cgcctggttg ctacgcctga ataagtgata ataagcggat gaatggcaga  960
aattcgaaag caaattcgac ccggtcgtcg gttcagggca gggtcgttaa atagccgctt  1020
atgtctattg ctggtctcgg taccctgcac ccaactgatc ttcagcatct tttactttca  1080
ccagcgtttc tgggtgagca aaaacaggaa ggcaaaatgc cgcaaaaaag ggaataaggg  1140
cgacacggaa atgttgaata ctcatactct tcctttttca atattattga agcatttatc  1200
agggttattg tctcatgagc ggatacatat ttgaatgtat ttagaaaaat aaacaaaaga  1260
gtttgtagaa acgcaaaaag gccatccgtc aggatggcct tctgcttaat ttgatgcctg  1320
gcagtttatg gcgggcgtcc tgcccgccac cctccgggcc gttgcttcgc aacgttcaaa  1380
tccgctcccg gcggatttgt cctactcagg agagcgttca ccgacaaaca acagataaaa  1440
cgaaaggccc agtctttcga ctgagccttt cgttttattt gatgcctggc agttccctac  1500
tctcgcatgg ggagacccca cactaccatc ggcgctacgg cgtttcactt ctgagttcgg  1560
catggggtca ggtgggacca ccgcgctact gccgccaggc aaattctgtt ttatcagacc  1620
gcttctgcgt tctgatttaa tctgtatcag gctgaaaatc ttctctcatc cgccaaaaca  1680
gccaagctta gcggccgctt agacctttcg ctttttcttg ggatcggctc tggagtcgcc  1740
accaagctga gacaggtcga ttcgggtctc gtacaggcca gtgatggact ggtgaatcag  1800
ggtggcatcg agaacctcct tggtggatgt gtaccgcttt cggtcgatag tggtatcgaa  1860
gtacttgaaa gctgcaggag cacccaggtt ggtaagagta aacaggtgaa tgatgttctc  1920
cgcctgttct cgaatgggtt tgtcccgatg cttgttgtag gcagagagca ccttgtccaa  1980
gttggcatca gccaggatga ctcgcttcga aaactcggaa atctgctcga taatctcgtc  2040
gaggtaatgt ttgtgctgct caacgaagag ttgcttctgt tcgttgtcct cgggagaacc  2100
```

```
cttgagcttc tcgtagtgag aagccagata gagaaagttg acgtacttcg aaggcaaggc  2160
aagctcgttt cccttctgca gctcgccagc ggaggcgagc atacgctttc gaccgttctc  2220
cagttcgaac agagagtact tgggcagctt gataatgagg tctttcttga cctccttgta  2280
acccttggct tccaagaagt cgatgggatt cttctcgaag ctcgatcgct ccatgatggt  2340
aattccgagc agctccttga cggacttgag ctttttggac ttgcccttct cgaccttcgc  2400
aacgacaagc acggaatagg cgacggtagg agaatcgaag ccaccgtatt tcttgggatc  2460
ccagtctttc tttcgagcga tgagcttgtc ggagtttcgc ttgggcagaa tcgactcctt  2520
ggagaatccg ccagtctgaa cctcggtttt cttgacgatg ttgacctgag gcatcgacag  2580
aacctttcgc acggttgcaa agtctcgacc cttgtcccac acgatctctc cagtttcgcc  2640
gttggtctcg ataagtggtc tctttcgaat ctctccgttg gccaaggtga tctcggtctt  2700
gaaaaagttc atgatgttgg agtaaaagaa gtacttggca gtagccttgc caatctcctg  2760
ttcggacttg gcaatcatct ttcgaacgtc gtagaccttg taatcgccgt aaacgaactc  2820
gctttcgagc ttggggtatt tcttgatgag cgcagtgcca acgacggcgt tgaggtaagc  2880
atcgtgggca tggtggtaat tgttgatctc tcgcaccttg tagaactgaa agtcctttcg  2940
gaaatcggag accagtttgg acttgagagt aatcaccttg acctctcgga tgagcttgtc  3000
gttctcgtcg tacttggtgt tcatccgaga atcgagaatc tgtgcgacgt gctttgtgat  3060
ctgtctggtc tcgacgagtt gacgcttgat gaagccagcc ttgtcgagct cggacagacc  3120
gcctcgctcg gccttggtaa gattgtcgaa ctttcgctgg gtaatgagct tggcgttgag  3180
cagctgtcgc cagtagttct tcatcttttt gaccacctct tcgctgggaa cgttgtccga  3240
cttgcctctg ttcttgtcgg atcgtgtaag gaccttgttg tcgatagaat cgtccttgag  3300
aaaggattga gggacaatgt ggtccacatc gtagtcgctg agacgattga tgtccagttc  3360
ctgatccacg tacatgtctc gaccattctg cagatagtag agatacagct tctcgttctg  3420
cagttgagtg ttctcgacgg gatgctcctt gagaatctgg gatcccagct ccttgatgcc  3480
ttcctcgatt cgcttcatcc gctctcgcga gtttttctga ccctttttgag ttgtctggtt  3540
ctctctggcc atctcgatca caatgttctc gggcttgtga cgtcccatga ccttcaccag  3600
ctcgtcgaca accttgacag tctggagaat gcctttcttg atggctggcg aaccagccag  3660
gttggcaata tgttcgtgca agctgtcgcc ctgaccggac acttgtgcct tctggatgtc  3720
ctccttgaag gtaagagaat cgtcgtgaat gagctgcatg aagtttcggt tggcaaagcc  3780
atcggacttg agaaagtcca gaatggtctt tccggactgc ttgtctctga tgccgttgat  3840
gagctttcgc gaaagtcttc cccagccggt gtatctacgt cgcttgagtt gtttcatgac  3900
cttgtcgtcg aacaggtgag cgtatgtctt gagtcgttcc tcgatcatct cccgatcttc  3960
gaacagggta agagtgagca cgatgtcctc cagaatgtcc tcgttttcct cgttgtcgag  4020
aaaatccttg tccttgataa tcttgagcag atcgtgatag gtgcccaaag aggcgttgaa  4080
tcggtcctca actccggaaa tctcgacgct gtcgaaacac tcgattttct tgaagtagtc  4140
ctccttgagc tgcttaacag tgacctttcg gttggtcttg aacaggagat cgacaatggc  4200
tttcttctgt tcgccagaca agaaggcagg ctttcgcatt ccctcggtaa cgtacttgac  4260
tttggtgagt tcgttgtaga ctgtaaagta ctcgtagagc agcgaatgct tgggaagaac  4320
cttctcgttg ggcagattct tgtcgaagtt ggtcattcgc tcgatgaagg actgtgcaga  4380
ggcacccttg tccacgactt cctcgaagtt ccagggagtg atggtttcct cggactttcg  4440
agtcatccaa gcaaatcgag agtttcctct ggcaagagga ccaacatagt aggggattcg  4500
aaaggtaaga atcttctcga tcttctctcg gttgtccttg agaaaggggt agaagtcttc  4560
ctgacgtcga agaatggcgt gcagctcacc gaggtggatc tgatgaggaa tgctgccgtt  4620
gtcgaaggtt cgttgcttcc gaagcagatc ctctcgattg agcttgacaa gcagttcctc  4680
ggttccgtcc atcttctcga gaattggctt gatgaacttg tagaactctt cctgagaggc  4740
tccgccgtcg atgtatccag cgtagccgtt cttcgactga tcgaaaaaga tctccttgta  4800
cttctcgggc agttgctgtc ggacaagagc cttgagcagt gtgagatcct gatggtgctc  4860
gtcgtatcgc ttgatcatgg aggcagaaag gggagccttt gtgatctcgg tgttgactcg  4920
cagaatgtca gacaagagaa tagcatccga aaggttcttg gcagcgagaa acaggtcggc  4980
gtactgatcg ccaatctgtg caagcaggtt gtcgaggtca tcgtcgtagg tgtccttgga  5040
cagctggagc ttggcgtcct ccgccagatc gaagttggac ttgaagttgg gtgtgagacc  5100
aagagaaagg gcaatgaggt tgccaaacag tccgttcttt ttctcgccag gaagttgggc  5160
aatgaggttc tccagtcgtc tgctcttcga gagtcgagca gacaagatgg cctttgcatc  5220
gactccggag gcattgatgg ggttttcctc gaacagctgg ttgtaggtct gaacgagctg  5280
aatgaacagc ttgtccacat cgctgttgtc gggattgaga tcgccctcga tgaggaaatg  5340
acctcgaaac ttgatcatgt gtgccagagc gagatggata agtctgagat ccgccttgtc  5400
ggtggaatcg acgagtttct ttcgcaggtg gtagatggta ggatacttct cgtggtaagc  5460
aacctcgtcc acaatgttgc caaagatggg atgacgctcg tgtttcttgt cttcctcgac  5520
gaggaaggat tcctccagtc gatgaaagaa cgaatcgtcc accttggcca tctcgttgga  5580
aaagatctcc tgcaggtagc agattcggtt cttccgtcgg gtgtaacgtc gccgagcagt  5640
tcgcttgagt ctggtagctt cggcagtctc gccagaatcg aacaacaggg caccaatgag  5700
gtttttcttg atggagtgtc gatcggtgtt tccgaggacc ttgaatttct tggagggcac  5760
cttgtactcg tcggtgatga cagcccagcc gacagagttg gttccaatgt ccaggccgat  5820
ggagtatttc ttgtcgaatt cccatatggt accagctgca gatctcgagc tcggatcctt  5880
atcgtcatcg tcgtacagat cccgacccat ttgctgtcca ccagtcatgc tagccatacc  5940
atgatgatga tgatgatgag aaccccccat ggttaattcc tcctgttagc ccaaaaaacg  6000
ggtatggaga aacagtagag agttgcgata aaaagcgtca ggtaggatcc gctaatctta  6060
tggataaaaa tgctatggca tagcaaagtg tgacgccgtg caaataatca atgtggactt  6120
ttctgccgtg attatagaca cttttgttac gcgtttttgt catggctttg gtcccgcttt  6180
gttacagaat gcttttaata agcggggtta ccggtttggt tagcgagaag agccagtaaa  6240
agacgcagtg acggcaatgt ctgatgcaat atggacaatt ggtttcttct ctgaatggcg  6300
ggagtatgaa aagtatggct gaagcgcaaa atgatcccct gctgccggga tactcgttta  6360
atgcccatct ggtggcgggt ttaacgccga ttgaggccaa cggttatctc gattttttta  6420
tcgaccgacc gctgggaatg aaaggttata ttctcaatct caccattcgc ggtcaggggg  6480
tggtgaaaaa tcagggacga gaatttgttt gccgaccggg tgatattttg ctgttcccgc  6540
caggagagat tcatcactac ggtcgtcatc cggaggctcg cgaatggtat caccagtggg  6600
tttactttcg tccgcgcgcc tactggcatg aatggcttaa ctggccgtca atatttgcca  6660
atacggggtt ctttcgcccg gatgaagcgc accagccgca tttcagcgac ctgtttgggc  6720
aaatcattaa cgccgggcaa ggggaagggc gctattcgga gctgctggcg ataaatctgc  6780
ttgagcaatt gttactgcgg cgcatggaag cgattaacga gtcgctccat ccaccgatgg  6840
```

```
ataatcgggt acgcgaggct tgtcagtaca tcagcgatca cctggcagac agcaattttg  6900
atatcgccag cgtcgcacag catgtttgct tgtcgccgtc gcgtctgtca catcttttcc  6960
gccagcagtt agggattagc gtcttaagct ggcgcgagga ccaacgtatc agccaggcga  7020
agctgctttt gagcaccacc cggatgccta tcgccaccgt cggtcgcaat gttggttttg  7080
acgatcaact ctatttctcg cgggtattta aaaaatgcac cggggccagc ccgagcgagt  7140
tccgtgccgg ttgtgaagaa aaagtgaatg atgtagccgt caagttgtca taattggtaa  7200
cgaatcagac aattgacggc ttgacggagt agcatagggt ttgcagaatc cctgcttcgt  7260
ccatttgaca ggcacattat gcatgccgct tcgccttcgc gcgcgaattg atctgctgcc  7320
tcgcgcgttt cggtgatgac ggtgaaaacc tctgacacat gcagctcccg gagacggtca  7380
cagcttgtct gtaagcggat gccgggagca gacaagcccg tcagggcgcg tcagcgggtg  7440
ttggcgggtg tcggggcgca gccatgaccc agtcacgtag cgatagcgga gtgtatactg  7500
gcttaactat gcggcatcag agcagattgt actgagagtg caggggatcg cggccgcgga  7560
ccggatcctc tagagcggcc gcgatcctct agagtcgacc ggtggcgaat gggacgcgcc  7620
ctgtagcggc gcattaagcg cggcgggtgt ggtggttacg cgcagcgtga ccgctacact  7680
tgccagcgcc ctagcgcccg ctcctttcgc tttcttccct tcctttctcg ccacgttcgc  7740
cggctttccc cgtcaagctc taaatcgggg gctcccttta gggttccgat ttagtgcttt  7800
acggcacctc gaccccaaaa aacttgatta gggtgatggt tcacgtagtg ggccatcgcc  7860
ctgatagacg gtttttcgcc ctttgacgtt ggagtccacg ttctttaata gtggactctt  7920
gttccaaact ggaacaacac tcaaccctat ctcggtctat tcttttgatt tataagggat  7980
tttgccgatt tcggcctatt ggttaaaaaa tgagctgatt taacaaaaat ttaacgcgaa  8040
ttttaacaaa atattaacgc ttacaattta ggtggcactt ttcggggaaa tgtgcgcgga  8100
acccctattt gtttattttt ctaaatacat tcaaatatgt atccgctcac cgcgatcctt  8160
tttaacccat cacatatacc tgccgttcac tattatttag tgaaatgaga tattatgata  8220
ttttctgaat tgtgattaaa aaggcaactt tatgcccatg caacagaaac tataaaaaat  8280
acagagaatg aaaagaaaca gatagatttt ttagttcttt aggcccgtag tctgcaaatc  8340
cttttatgat tttctatcaa acaaaagagg aaaatagacc agttgcaatc caaacgagag  8400
tctaatagaa tgaggtcgaa aagtaaatcg cgcgggtttg ttactgataa agcaggcaag  8460
acctaaaatg tgtaaagggc aaagtgtata ctttggcgtc accccttaca tattttaggt  8520
ctttttttat tgtgcgtaac taacttgcca tcttcaaaca ggagggctgg aagaagcaga  8580
ccgctaacac agtacataaa aaaggagaca tgaacgatga acatcaaaaa gtttgcaaaa  8640
caagcaacag tattaacctt tactaccgca ctgctggcag gaggcgcaac tcaagcgttt  8700
gcgaaagaaa cgaaccaaaa gccatataag gaaacatacg gcatttccca tattacacgc  8760
catgatatgc tgcaaatccc tgaacagcaa aaaaatgaaa aatatcaagt tcctgagttc  8820
gattcgtcca caattaaaaa tatctcttct gcaaaaggcc tggacgtttg ggacagctgg  8880
ccattacaaa acgctgacgg cactgtcgca aactatcacg gctaccacat cgtctttgca  8940
ttagccggag atcctaaaaa tgcggatgac acatcgattt acatgttcta tcaaaaagtc  9000
ggcgaaactt ctattgacag ctggaaaaac gctggccgcg tctttaaaga cagcgacaaa  9060
ttcgatgcaa atgattctat cctaaaagac caaacacaag aatggtcagg ttcagccaca  9120
tttacatctg acggaaaaat ccgtttattc tacactgatt tctccggtaa acattacggc  9180
aaacaaacac tgacaactgc acaagttaac gtatcagcat cagacagctc tttgaacatc  9240
aacggtgtag aggattataa atcaatcttt gacggtgacg gaaaaacgta tcaaaatgta  9300
cagcagttca tcgatgaagg caactacagc tcaggcgaca accatacgct gagagatcct  9360
cactacgtag aagataaagg ccacaaatac ttagtatttg aagcaaacac tggaactgaa  9420
gatggctacc aaggcgaaga atctttattt aacaaagcat actatggcaa aagcacatca  9480
ttcttccgtc aagaaagtca aaaacttctg caaagcgata aaaaacgcac ggctgagtta  9540
gcaaacggcg ctctcggtat gattgagcta aacgatgatt acacactgaa aaaagtgatg  9600
aaaccgctga ttgcatctaa cacagtaaca gatgaaattg aacgcgcgaa cgtctttaaa  9660
atgaacggca aatggtacct gttcactgac tcccgcggat caaaaatgac gattgacggc  9720
attacgtcta acgatattta catgcttggt tatgtttcta attctttaac tggcccatac  9780
aagccgctga acaaaactgg ccttgtgtta aaaatggatc ttgatcctaa cgatgtaacc  9840
tttacttact cacacttcgc tgtacctcaa gcgaaaggaa acaatgtcgt gattacaagc  9900
tatatgacaa acagaggatt ctacgcagac aaacaatcaa cgtttgcgcc aagcttcctg  9960
ctgaacatca aaggcaagaa aacatctgtt gtcaaagaca gcatccttga acaaggacaa  10020
ttaacagtta acaaataaaa acgcaaaaga aaatgccgat attgactacc ggaagcagtg  10080
tgaccgtgtg cttctcaaat gcctgattca ggctgtctat gtgtgactgt tgagctgtaa  10140
caagttgtct caggtgttca atttcatgtt ctagttgctt tgttttactg gtttcacctg  10200
ttctattagg tgttacatgc tgttcatctg ttacattgtc gatctgttca tggtgaacag  10260
ctttaaatgc accaaaaact cgtaaaagct ctgatgtatc tatctttttt acaccgtttt  10320
catctgtgca tatggacagt tttccctttg atatgtaacg gtgaacagtt gttctacttt  10380
tgtttgttag tcttgatgct tcactgatag atacaagagc cataagaacc tcagatcctt  10440
ccgtatttag ccagtatgtt ctctagtgtg gttcgttgtt tttgcgtgag ccatgagaac  10500
gaaccattga gatcatactt actttgcatg tcactcaaaa attttgcctc aaaactggtg  10560
agctgaattt ttgcagttaa agcatcgtgt agtgtttttc ttagtccgtt atgtaggtag  10620
gaatctgatg taatggttgt tggtattttg tcaccattca tttttatctg gttgttctca  10680
agttcggtta cgagatccat ttgtctatct agttcaactt ggaaaatcaa cgtatcagtc  10740
gggcggcctc gcttatcaac caccaatttc atattgctgt aagtgtttaa atctttactt  10800
attggtttca aaacccattg gttaagcctt ttaaactcat ggtagttatt ttcaagcatt  10860
aacatgaact taaattcatc aaggctaatc tctatatttg ccttgtgagt tttcttttgt  10920
gttagttctt ttaataacca ctcataaatc ctcatagagt atttgtttc aaaagactta  10980
acatgttcca gattatattt tatgaatttt tttaactgga aaagataagg caatatctct  11040
tcactaaaaa ctaattctaa tttttcgctt gagaacttgg catagtttgt ccactggaaa  11100
atctcaaagc ctttaaccaa aggattcctg atttccacag ttctcgtcat cagctctctg  11160
gttgctttag ctaatacacc ataagcattt tccctactga tgttcatcat ctgaacgtat  11220
tggttataag tgaacgatac cgtccgttct ttccttgtag ggttttcaat cgtggggttg  11280
agtagtgcca cacagcataa aattagcttg gtttcatgct ccgttaagtc atagcgacta  11340
atcgctagtt catttgcttt gaaaacaact aattcagaca tacatctcaa ttggtctagg  11400
tgattttaat cactatacca attgagatgg gctagtcaat gataattact agtccttttc  11460
ctttgagttg tgggtatctg taaattctgc tagacctttg ctggaaaact tgtaaattct  11520
gctagaccct ctgtaaattc cgctagacct ttgtgtgttt tttttgttta tattcaagtg  11580
```

```
gttataattt atagaataaa gaaagaataa aaaaagataa aaagaataga tcccagccct  11640
gtgtataact cactacttta gtcagttccg cagtattaca aaaggatgtc gcaaacgctg  11700
tttgctcctc tacaaaacag accttaaaac cctaaaggct taagtagcac cctcgcaagc  11760
tcgggcaaat cgctgaatat tccttttgtc tccgaccatc aggcacctga gtcgctgtct  11820
ttttcgtgac attcagttcg ctgcgctcac ggctctggca gtgaatgggg gtaaatggca  11880
ctacaggcgc cttttatgga ttcatgcaag gaaactaccc ataatacaag aaaagcccgt  11940
cacgggcttc tcagggcgtt ttatggcggg tctgctatgt ggtgctatct gactttttgc  12000
tgttcagcag ttcctgccct ctgattttcc agtctgacca cttcggatta tcccgtgaca  12060
ggtcattcag actggctaat gcacccagta aggcagcggt atcatcaaca ggcttacccg  12120
tcttactgtc ggggatcgac gctctccctt atgcgactcc tgca                    12164

SEQ ID NO: 94          moltype = DNA  length = 918
FEATURE                Location/Qualifiers
source                 1..918
                       mol_type = unassigned DNA
                       organism = Streptococcus pyogenes
SEQUENCE: 94
atgaacttca gacgcctgaa atacttcgta aaaattgtag atattggtag cctgacccag  60
gctgctgaag tattgcatat cgcacaacca gcgctcagcc agcaggttgc cacactggaa  120
ggtgagttaa atcaacaact tttgatccgt acaaagcggg gcgttacacc aacagacgcc  180
ggaaaaattc tctataccca tgcgcgggcc attttacgtc agtgtgaaca ggcccaactg  240
gcggtgcata acgttggtca ggcattatcg gggcaagtct cgattggctt tgcaccagga  300
accgctgcgt catccatcac catgccctta ttacaggcgg ttcgcgctga atttccggag  360
atcgttatct atcttcatga aaatagtggt gcagtgctta acgaaaaatt gataaatcac  420
caactcgata tggcggtgat ttatgagcat tcccctgtgg ctggtgtatc cagtcaggct  480
ttgctgaaag aagatctttt tctggtagga actcaagatt gcccggggca aagcgttgat  540
gtgaatgcta ttgcgcaaat gaacctcttt ctccccagtg attacagtgc tattagactt  600
cgtgttgatg aggctttttc cctacggcga ctcacggcaa aagttattgg tgaaattgag  660
tctattgcca cgcttaccgc agcgattgcc agcggcatgg gcgttgcagt attacccgaa  720
tcggccgcgc gttcgttatg tggcgcagta aatgggtgga tgtcacgcat taccactcct  780
tccatgagtc tctctttgtc attaaattta cccgccagag cgaacttatc gccacaggca  840
caggcagtga aagagttgtt aatgtcagtg attagttctc cagtgatgga aaaaaggcag  900
tggcaattgg tgagctaa                                                 918

SEQ ID NO: 95          moltype = DNA  length = 20
FEATURE                Location/Qualifiers
source                 1..20
                       mol_type = unassigned DNA
                       organism = Streptococcus pyogenes
SEQUENCE: 95
tatgcaatac ttcagcagcc                                               20

SEQ ID NO: 96          moltype = DNA  length = 23
FEATURE                Location/Qualifiers
source                 1..23
                       mol_type = unassigned DNA
                       organism = Streptococcus pyogenes
SEQUENCE: 96
tatgcaatac ttcagcagcc tgg                                           23

SEQ ID NO: 97          moltype = DNA  length = 20
FEATURE                Location/Qualifiers
source                 1..20
                       mol_type = unassigned DNA
                       organism = Streptococcus pyogenes
SEQUENCE: 97
acaaccagcg ctcagccagc                                               20

SEQ ID NO: 98          moltype = DNA  length = 23
FEATURE                Location/Qualifiers
source                 1..23
                       mol_type = unassigned DNA
                       organism = Streptococcus pyogenes
SEQUENCE: 98
acaaccagcg ctcagccagc agg                                           23

SEQ ID NO: 99          moltype = DNA  length = 56
FEATURE                Location/Qualifiers
source                 1..56
                       mol_type = unassigned DNA
                       organism = Streptococcus pyogenes
SEQUENCE: 99
aagaatcata aaaaatttat ttgctttcag gaaaattttt ctgtataata gattca      56

SEQ ID NO: 100         moltype = DNA  length = 247
FEATURE                Location/Qualifiers
misc_feature           1..247
                       note = synthesized nac target site 1 gRNA expression
                        cassette
```

```
source                  1..247
                        mol_type = other DNA
                        organism = synthetic construct
SEQUENCE: 100
aagaatcata aaaaatttat ttgctttcag gaaaattttt ctgtataata gattcatatg  60
caatacttca gcagccgttt tagagctaga aatagcaagt taaaataagg ctagtccgtt  120
atcaacttga aaaagtggca ccgagtcggt gcgactcctg ttgatagatc cagtaatgac  180
ctcagaactc catctggatt tgttcagaac gctcggttgc cgccgggcgt tttttattgg  240
tgagaat                                                            247

SEQ ID NO: 101          moltype = DNA  length = 247
FEATURE                 Location/Qualifiers
misc_feature            1..247
                        note = synthesized nac target site 2 gRNA expression
                         cassette
source                  1..247
                        mol_type = other DNA
                        organism = synthetic construct
SEQUENCE: 101
aagaatcata aaaaatttat ttgctttcag gaaaattttt ctgtataata gattcaacaa  60
ccagcgctca gccagcgttt tagagctaga aatagcaagt taaaataagg ctagtccgtt  120
atcaacttga aaaagtggca ccgagtcggt gcgactcctg ttgatagatc cagtaatgac  180
ctcagaactc catctggatt tgttcagaac gctcggttgc cgccgggcgt tttttattgg  240
tgagaat                                                            247

SEQ ID NO: 102          moltype = DNA  length = 500
FEATURE                 Location/Qualifiers
source                  1..500
                        mol_type = unassigned DNA
                        organism = Streptococcus pyogenes
SEQUENCE: 102
gaagttcatg ttgcctccgg tttttaagaa tcggcccaag tgccgccatt acttacaacc  60
agattgcaag atgcttgcca gttttatttt ggtgttgatg tacaagctaa ccaactgtca  120
aataagagat tatgatagat tcgtcatttg ctcctttaat cagctgtcgc gttcccctgc  180
cctataaaag gagggtatgc accacgatgg ttcattaccc aataagattg aaagctcacc  240
actttgttga aattgacagc aaacaaacaa aaaaatgcat ttcacccttt gacatcacca  300
tgcactgcca ttaatatgcg ccccgttcac acgattcctc tgtagttcag tcggtagaac  360
ggcggactgt taatccgtat gtcactggtt cgagtccagt cagaggagcc aaattcaaaa  420
aagcctgctt tctagcaggc tttttgcttt ctaattacca acgctcttaa aacatctgtc  480
ttgaaccaga actaatttgc                                              500

SEQ ID NO: 103          moltype = DNA  length = 500
FEATURE                 Location/Qualifiers
source                  1..500
                        mol_type = unassigned DNA
                        organism = Streptococcus pyogenes
SEQUENCE: 103
cgtcccctgg attagctcga gccgaacctc cgggaaaagt tcgcgaaaag ctttaatgac  60
ctctggcaag ctataacgtg cctgagtatg cgtcgttgca atagtgagaa cgccagacgt  120
atcgttggta aacaggtctg caagccgacg aacattactg gcttcattca gaatacgttc  180
tgcaatgacc agtaatgctt tgcccggttc agtcatgccc agcagtcgct tacctcgtcg  240
aacaaatatt tcgatgccaa gttcatcctc cagttcccga atatgacggc tgacgcctga  300
ctgtgaggta aaaagcatat tcgcaacctc tgtcaggttg taatcctgac gtgcagcctc  360
gcggattatc tttagttgtt ggaaattcac ggtaaactcc gggcagttca gatttcccgt  420
tattgttaaa gtctaatgcc cggcataaca aataataaaa acccgcatct tattccatcc  480
cgatataaca cttagctcac                                              500

SEQ ID NO: 104          moltype = DNA  length = 1000
FEATURE                 Location/Qualifiers
misc_feature            1..1000
                        note = synthesized nac deletion editing template
source                  1..1000
                        mol_type = other DNA
                        organism = synthetic construct
SEQUENCE: 104
cgtcccctgg attagctcga gccgaacctc cgggaaaagt tcgcgaaaag ctttaatgac  60
ctctggcaag ctataacgtg cctgagtatg cgtcgttgca atagtgagaa cgccagacgt  120
atcgttggta aacaggtctg caagccgacg aacattactg gcttcattca gaatacgttc  180
tgcaatgacc agtaatgctt tgcccggttc agtcatgccc agcagtcgct tacctcgtcg  240
aacaaatatt tcgatgccaa gttcatcctc cagttcccga atatgacggc tgacgcctga  300
ctgtgaggta aaaagcatat tcgcaacctc tgtcaggttg taatcctgac gtgcagcctc  360
gcggattatc tttagttgtt ggaaattcac ggtaaactcc gggcagttca gatttcccgt  420
tattgttaaa gtctaatgcc cggcataaca aataataaaa acccgcatct tattccatcc  480
cgatataaca cttagctcac gaagttcatg ttgcctccgg tttttaagaa tcggcccaag  540
tgccgccatt acttacaacc agattgcaag atgcttgcca gttttatttt ggtgttgatg  600
tacaagctaa ccaactgtca aataagagat tatgatagat tcgtcatttg ctcctttaat  660
cagctgtcgc gttcccctgc cctataaaag gagggtatgc accacgatgg ttcattaccc  720
aataagattg aaagctcacc actttgttga aattgacagc aaacaaacaa aaaaatgcat  780
ttcacccttt gacatcacca tgcactgcca ttaatatgcg ccccgttcac acgattcctc  840
```

```
tgtagttcag tcggtagaac ggcggactgt taatccgtat gtcactggtt cgagtccagt  900
cagaggagcc aaattcaaaa aagcctgctt tctagcaggc tttttgcttt ctaattacca  960
acgctcttaa aacatctgtc ttgaaccaga actaatttgc                        1000

SEQ ID NO: 105         moltype = DNA  length = 20
FEATURE                Location/Qualifiers
misc_feature           1..20
                       note = 5' pRF97 or pRF861 identity fragment
source                 1..20
                       mol_type = other DNA
                       organism = synthetic construct
SEQUENCE: 105
cgaatcagac aattgacggc                                              20

SEQ ID NO: 106         moltype = DNA  length = 21
FEATURE                Location/Qualifiers
misc_feature           1..21
                       note = 3' pRF97 or pRF861 identity fragment
source                 1..21
                       mol_type = other DNA
                       organism = synthetic construct
SEQUENCE: 106
gcttccggta gtcaataaac c                                            21

SEQ ID NO: 107         moltype = DNA  length = 1288
FEATURE                Location/Qualifiers
misc_feature           1..1288
                       note = nacETsite1
source                 1..1288
                       mol_type = other DNA
                       organism = synthetic construct
SEQUENCE: 107
cgaatcagac aattgacggc cgtcccctgg attagctcga gccgaacctc cgggaaaagt  60
tcgcgaaaag ctttaatgac ctctggcaag ctataacgtg cctgagtatg cgtcgttgca  120
atagtgagaa cgccagacgt atcgttggta aacaggtctg caagccgacg aacattactg  180
gcttcattca gaatacgttc tgcaatgacc agtaatgctt tgcccggttc agtcatgccc  240
agcagtcgct tacctcgtcg aacaaatatt tcgatgccaa gttcatcctc cagttcccga  300
atatgacggc tgacgcctga ctgtgaggta aaaagcatat tcgcaacctc tgtcaggttg  360
taatcctgac gtgcagcctc gcggattatc tttagttgtt ggaaattcac ggtaaactcc  420
gggcagttca gatttcccgt tattgttaaa gtctaatgcc cggcataaca aataataaaa  480
acccgcatct tattccatcc cgatataaca cttagctcac gaagttcatg ttgcctccgg  540
tttttaagaa tcggcccaag tgccgccatt acttacaacc agattgcaag atgcttgcca  600
gttttatttt ggtgttgatg tacaagctaa ccaactgtca aataagagat tatgatagat  660
tcgtcatttg ctcctttaat cagctgtcgc gttcccctgc cctataaaag gagggtatgc  720
accacgatgg ttcattaccc aataagattg aaagctcacc actttgttga aattgacagc  780
aaacaaacaa aaaaatgcat ttcacccttt gacatcacca tgcactgcca ttaatatgcg  840
ccccgttcac acgattcctc tgtagttcag tcggtagaac ggcggactgt taatccgtat  900
gtcactggtt cgagtccagt cagaggagcc aaattcaaaa aagcctgctt tctagcaggc  960
tttttgcttt ctaattacca acgctcttaa aacatctgtc ttgaaccaga actaatttgc  1020
aagaatcata aaaaatttat ttgctttcag gaaaattttt ctgtataata gattcatatg  1080
caatacttca gcagccgttt tagagctaga aatagcaagt taaaataagg ctagtccgtt  1140
atcaacttga aaaagtggca ccgagtcggt gcgactcctg ttgatagatc cagtaatgac  1200
ctcagaactc catctggatt tgttcagaac gctcggttgc cgccgggcgt tttttattgg  1260
tgagaatggt ttattgacta ccggaagc                                     1288

SEQ ID NO: 108         moltype = DNA  length = 1288
FEATURE                Location/Qualifiers
misc_feature           1..1288
                       note = nacETsite2
source                 1..1288
                       mol_type = other DNA
                       organism = synthetic construct
SEQUENCE: 108
cgaatcagac aattgacggc cgtcccctgg attagctcga gccgaacctc cgggaaaagt  60
tcgcgaaaag ctttaatgac ctctggcaag ctataacgtg cctgagtatg cgtcgttgca  120
atagtgagaa cgccagacgt atcgttggta aacaggtctg caagccgacg aacattactg  180
gcttcattca gaatacgttc tgcaatgacc agtaatgctt tgcccggttc agtcatgccc  240
agcagtcgct tacctcgtcg aacaaatatt tcgatgccaa gttcatcctc cagttcccga  300
atatgacggc tgacgcctga ctgtgaggta aaaagcatat tcgcaacctc tgtcaggttg  360
taatcctgac gtgcagcctc gcggattatc tttagttgtt ggaaattcac ggtaaactcc  420
gggcagttca gatttcccgt tattgttaaa gtctaatgcc cggcataaca aataataaaa  480
acccgcatct tattccatcc cgatataaca cttagctcac gaagttcatg ttgcctccgg  540
tttttaagaa tcggcccaag tgccgccatt acttacaacc agattgcaag atgcttgcca  600
gttttatttt ggtgttgatg tacaagctaa ccaactgtca aataagagat tatgatagat  660
tcgtcatttg ctcctttaat cagctgtcgc gttcccctgc cctataaaag gagggtatgc  720
accacgatgg ttcattaccc aataagattg aaagctcacc actttgttga aattgacagc  780
aaacaaacaa aaaaatgcat ttcacccttt gacatcacca tgcactgcca ttaatatgcg  840
ccccgttcac acgattcctc tgtagttcag tcggtagaac ggcggactgt taatccgtat  900
gtcactggtt cgagtccagt cagaggagcc aaattcaaaa aagcctgctt tctagcaggc  960
```

```
tttttgcttt ctaattacca acgctcttaa aacatctgtc ttgaaccaga actaatttgc  1020
aagaatcata aaaaatttat ttgctttcag gaaaattttt ctgtataata gattcaacaa  1080
ccagcgctca gccagcgttt tagagctaga aatagcaagt taaaataagg ctagtccgtt  1140
atcaacttga aaaagtggca ccgagtcggt gcgactcctg ttgatagatc cagtaatgac  1200
ctcagaactc catctggatt tgttcagaac gctcggttgc cgccgggcgt tttttattgg  1260
tgagaatggt ttattgacta ccggaagc                                    1288

SEQ ID NO: 109          moltype = DNA  length = 9322
FEATURE                 Location/Qualifiers
misc_feature            1..9322
                        note = pRF97-cassette
source                  1..9322
                        mol_type = other DNA
                        organism = synthetic construct
SEQUENCE: 109
ggtttattga ctaccggaag cagtgtgacc gtgtgcttct caaatgcctc aggctgtcta  60
tgtgtgactg ttgagctgta acaagttgtc tcaggtgttc aatttcatgt tctagttgct  120
ttgttttact ggtttcacct gttctattag gtgttacatg ctgttcatct gttacattgt  180
cgatctgttc atggtgaaca gctttaaatg caccaaaaac tcgtaaaagc tctgatgtat  240
ctatcttttt tacaccgttt tcatctgtgc atatggacag ttttcccttt gatatctaac  300
ggtgaacagt tgttctactt ttgtttgtta gtcttgatgc ttcactgata gatacaagag  360
ccataagaac ctcagatcct tccgtattta gccagtatgt tctctagtgt ggttcgttgt  420
ttttgcgtga gccatgagaa cgaaccattg agatcatgct tactttgcat gtcactcaaa  480
aattttgcct caaaactggt gagctgaatt tttgcagtta aagcatcgtg tagtgttttt  540
cttagtccgt tacgtaggta ggaatctgat gtaatggttg ttggtatttt gtcaccattc  600
atttttatct ggttgttctc aagttcggtt acgagatcca tttgtctatc tagttcaact  660
tggaaaatca acgtatcagt cgggcggcct cgcttatcaa ccaccaattt catattgctg  720
taagtgttta aatctttact tattggtttc aaaacccatt ggttaagcct tttaaactca  780
tggtagttat tttcaagcat taacatgaac ttaaattcat caaggctaat ctctatattt  840
gccttgtgag ttttcttttg tgttagttct tttaataacc actcataaat cctcatagag  900
tatttgtttt caaaagactt aacatgttcc agattatatt ttatgaattt ttttaactgg  960
aaaagataag gcaatatctc ttcactaaaa actaattcta atttttcgct tgagaacttg  1020
gcatagtttg tccactggaa aatctcaaag cctttaacca aaggattcct gatttccaca  1080
gttctcgtca tcagctctct ggttgcttta gctaatacac cataagcatt ttccctactg  1140
atgttcatca tctgagcgta ttggttataa gtgaacgata ccgtccgttc tttccttgta  1200
gggttttcaa tcgtggggtt gagtagtgcc acacagcata aaattagctt ggtttcatgc  1260
tccgttaagt catagcgact aatcgctagt tcatttgctt tgaaaacaac taattcagac  1320
atacatctca attggtctag gtgattttaa tcactatacc aattgagatg ggctagtcaa  1380
tgataattac tagtcctttt cctttgagtt gtgggtatct gtaaattctg ctagaccttt  1440
gctggaaaac ttgtaaattc tgctagaccc tctgtaaatt ccgctagacc tttgtgtgtt  1500
tttttgttt atattcaagt ggttataatt tatagaataa agaaagaata aaaaaagata  1560
aaaagaatag atcccagccc tgtgtataac tcactacttt agtcagttcc gcagtattac  1620
aaaaggatgt cgcaaacgct gtttgctcct ctacaaaaca gaccttaaaa ccctaaaggc  1680
ttaagtagca ccctcgcaag ctcgggcaaa tcgctgaata ttccttttgt ctccgaccat  1740
caggcacctg agtcgctgtc tttttcgtga cattcagttc gctgcgctca cggctctggc  1800
agtgaatggg ggtaaatggc actacaggcg ccttttatgg attcatgcaa ggaaactacc  1860
cataatacaa gaaaagcccg tcacgggctt ctcagggcgt tttatggcgg gtctgctatg  1920
tggtgctatc tgacttttg ctgttcagca gttcctgccc tctgattttc cagtctgacc  1980
acttcggatt atcccgtgac aggtcattca gactggctaa tgcacccagt aaggcagcgg  2040
tatcatcaac aggcttaccc gtcttactgt cggatcgacg ctctccctta tgcgactcct  2100
gcatcccttt cgtcttcgaa taaatacctg tgacggaaga tcacttcgca gaataaataa  2160
atcctggtgt ccctgttgat accgggaagc cctgggccaa cttttggcga aaatgagacg  2220
ttgatcggca cgtaagaggt tccaactttc accataatga aataagatca ctaccgggcg  2280
tattttttga gttatcgaga ttttcaggag ctaaggaagc taaaatggag aaaaaaatca  2340
ctggatatac caccgttgat atatcccaat ggcatcgtaa agaacatttt gaggcatttc  2400
agtcagttgc tcaatgtacc tataaccaga ccgttcagct ggatattacg gcctttttaa  2460
agaccgtaaa gaaaaataag cacaagtttt atccggcctt tattcacatt cttgcccgcc  2520
tgatgaatgc tcatccggaa ttccgtatgg caatgaaaga cggtgagctg gtgatatggg  2580
atagtgttca cccttgttac accgttttcc atgagcaaac tgaaacgttt tcatcgctct  2640
ggagtgaata ccacgacgat ttccggcagt ttctacacat atattcgcaa gatgtggcgt  2700
gttacggtga aaacctggcc tatttcccta aagggtttat tgagaatatg tttttcgtct  2760
cagccaatcc ctgggtgagt ttcaccagtt ttgatttaaa cgtggccaat atggacaact  2820
tcttcgcccc cgttttcacc atgggcaaat attatacgca aggcgacaag gtgctgatgc  2880
cgctggcgat tcaggttcat catgccgttt gtgatggctt ccatgtcggc agaatgctta  2940
atgaattaca acagtactgc gatgagtggc agggcggggc gtaatttttt taaggcagtt  3000
attggtgccc ttaaacgcct ggtgctacgc ctgaataagt gataataagc ggatgaatgg  3060
cagaaattcg aaagcaaatt cgacccggtc gtcggttcag ggcagggtcg ttaaatagcc  3120
gcttatgtct attgctggtt tatcggtacc ccccaactga tcttcagcat cttttacttt  3180
caccagcgtt tctgggtgag caaaaacagg aaggcaaaat gccgcaaaaa agggaataag  3240
ggcgacacgg aaatgttgaa tactcatact cttccttttt caatattatt gaagcattta  3300
tcagggttat tgtctcatga gcggatacat atttgaatgt atttagaaaa ataaacaaaa  3360
gagtttgtag aaacgcaaaa aggccatccg tcaggatggc cttctgctta atttgatgcc  3420
tggcagttta tggcgggcgt cctgcccgcc accctccggg ccgttgcttc gcaacgttca  3480
aatccgctcc cggcggattt gtcctactca ggagagcgtt caccgacaaa caacagataa  3540
aacgaaaggc ccagtctttc gactgagcct ttcgttttat ttgatgcctg gcagttccct  3600
actctcgcat ggggagaccc cacactacca tcggcgctac ggcgtttcac ttctgagttc  3660
ggcatggggt caggtgggac caccgcgcta ctgccgccag gcaaattctg ttttatcaga  3720
ccgcttctgc gttctgattt aatctgtatc aggctgaaaa tcttctctca tccgccaaaa  3780
cagccaagct tagcggccgc ttagaccttt cgctttttct tgggatcggc tctggagtcg  3840
```

-continued

```
ccaccaagct gagacaggtc gattcgggtc tcgtacaggc cagtgatgga ctggtgaatc  3900
agggtggcat cgagaacctc cttggtggat gtgtaccgct ttcggtcgat agtggtatcg  3960
aagtacttga aagctgcagg agcacccagg ttggtaagag taaacaggtg aatgatgttc  4020
tccgcctgtt ctcgaatggg tttgtcccga tgcttgttgt aggcagagag caccttgtcc  4080
aagttggcat cagccaggat gactcgcttc gaaaactcgg aaatctgctc gataatctcg  4140
tcgaggtaat gtttgtgctg ctcaacgaag agttgcttct gttcgttgtc ctcgggagaa  4200
cccttgagct tctcgtagtg agaagccaga tagagaaagt tgacgtactt cgaaggcaag  4260
gcaagctcgt ttcccttctg cagctcgcca gcggaggcga gcatacgctt tcgaccgttc  4320
tccagttcga acagagagta cttgggcagc ttgataatga ggtctttctt gacctccttg  4380
taacccttgg cttccaagaa gtcgatggga ttcttctcga agctcgatcg ctccatgatg  4440
gtaattccga gcagctcctt gacggacttg agctttttgg acttgccctt ctcgaccttc  4500
gcaacgacaa gcacggaata ggcgacggta ggagaatcga agccaccgta tttcttggga  4560
tcccagtctt tctttcgagc gatgagcttg tcggagtttc gcttgggcag aatcgactcc  4620
ttggagaatc cgccagtctg aacctcggtt ttcttgacga tgttgacctg aggcatcgac  4680
agaacctttc gcacggttgc aaagtctcga cccttgtccc acacgatctc tccagtttcg  4740
ccgttggtct cgataagtgg tctctttcga atctctccgt tggccaaggt gatctcggtc  4800
ttgaaaaagt tcatgatgtt ggagtaaaag aagtacttgg cagtagcctt gccaatctcc  4860
tgttcggact tggcaatcat ctttcgaacg tcgtagacct tgtaatcgcc gtaaacgaac  4920
tcgctttcga gcttggggta tttcttgatg agcgcagtgc caacgacggc gttgaggtaa  4980
gcatcgtggg catggtggta attgttgatc tctcgcacct tgtagaactg aaagtccttt  5040
cggaaatcgg agaccagttt ggacttgaga gtaatcacct tgacctctcg gatgagcttg  5100
tcgttctcgt cgtacttggt gttcatccga gaatcgagaa tctgtgcgac gtgctttgtg  5160
atctgtctgg tctcgacgag ttgacgcttg atgaagccag ccttgtcgag ctcggacaga  5220
ccgcctcgct cggccttggt aagattgtcg aactttcgct gggtaatgag cttggcgttg  5280
agcagctgtc gccagtagtt cttcatcttt ttgaccacct cttcgctggg aacgttgtcc  5340
gacttgcctc tgttcttgtc ggatcgtgta aggaccttgt tgtcgataga atcgtccttg  5400
agaaaggatt gagggacaat gtggtccaca tcgtagtcgc tgagacgatt gatgtccagt  5460
tcctgatcca cgtacatgtc tcgaccattc tgcagatagt agagatacag cttctcgttc  5520
tgcagttgag tgttctcgac gggatgctcc ttgagaatct gggatcccag ctccttgatg  5580
ccttcctcga ttcgcttcat ccgctctcgc gagtttttct gaccctttttg agttgtctgg  5640
ttctctctgg ccatctcgat cacaatgttc tcgggcttgt gacgtcccat gaccttcacc  5700
agctcgtcga caaccttgac agtctggaga atgcctttct tgatggctgg cgaaccagcc  5760
aggttggcaa tatgttcgtg caagctgtcg ccctgaccgg acacttgtgc cttctggatg  5820
tcctccttga aggtaagaga atcgtcgtga atgagctgca tgaagtttcg gttggcaaag  5880
ccatcggact tgagaaagtc cagaatggtc tttccggact gcttgtctct gatgccgttg  5940
atgagctttc gcgaaagtct tccccagccg gtgtatctac gtcgcttgag ttgtttcatg  6000
accttgtcgt cgaacaggtg agcgtatgtc ttgagtcgtt cctcgatcat ctcccgatct  6060
tcgaacaggg taagagtgag cacgatgtcc tccagaatgt cctcgtttc ctcgttgtcg  6120
agaaaatcct tgtccttgat aatcttgagc agatcgtgat aggtgcccaa agaggcgttg  6180
aatcggtcct caactccgga aatctcgacg ctgtcgaaac actcgatttt cttgaagtag  6240
tcctccttga gctgcttaac agtgaccttt cggttggtct tgaacaggag atcgacaatg  6300
gctttcttct gttcgccaga caagaaggca ggctttcgca ttccctcggt aacgtacttg  6360
actttggtga gttcgttgta gactgtaaag tactcgtaga gcagcgaatg cttgggaaga  6420
accttctcgt tgggcagatt cttgtcgaag ttggtcattc gctcgatgaa ggactgtgca  6480
gaggcaccct tgtccacgac ttcctcgaag ttccagggag tgatggtttc ctcggacttt  6540
cgagtcatcc aagcaaatcg agagtttcct ctggcaagag gaccaacata gtaggggatt  6600
cgaaaggtaa gaatcttctc gatcttctct cggttgtcct tgagaaaggg gtagaagtct  6660
tcctgacgtc gaagaatggc gtgcagctca ccgaggtgga tctgatgagg aatgctgccg  6720
ttgtcgaagg ttcgttgctt ccgaagcaga tcctctcgat tgagcttgac aagcagttcc  6780
tcggttccgt ccatcttctc gagaattggc ttgatgaact tgtagaactc ttcctgagag  6840
gctccgccgt cgatgtatcc agcgtagccg ttcttcgact gatcgaaaaa gatctccttg  6900
tacttctcgg gcagttgctg tcggacaaga gccttgagca gtgtgagatc ctgatggtgc  6960
tcgtcgtatc gcttgatcat ggaggcagaa aggggagcct ttgtgatctc ggtgttgact  7020
cgcagaatgt cagacaagag aatagcatcc gaaaggttct tggcagcgag aaacaggtcg  7080
gcgtactgat cgccaatctg tgcaagcagg ttgtcgaggt catcgtcgta ggtgtccttg  7140
gacagctgga gcttggcgtc ctccgccaga tcgaagttgg acttgaagtt gggtgtgaga  7200
ccaagagaaa gggcaatgag gttgccaaac agtccgttct ttttctcgcc aggaagttgg  7260
gcaatgaggt tctccagtcg tctgctcttc gagagtcgag cagacaagat ggcctttgca  7320
tcgactccgg aggcattgat ggggttttcc tcgaacagct ggttgtaggt ctgaacgagc  7380
tgaatgaaca gcttgtccac atcgctgttg tcgggattga gatcgccctc gatgaggaaa  7440
tgacctcgaa acttgatcat gtgtgccaga gcgaggtaga taagtctgag atccgccttg  7500
tcggtggaat cgacgagttt ctttcgcagg tggtagatgg taggatactt ctcgtggtaa  7560
gcaacctcgt ccacaatgtt gccaaagatg ggatgacgct cgtgtttctt gtcttcctcg  7620
acgaggaagg attcctccag tcgatgaaag aacgaatcgt ccaccttggc catctcgttg  7680
gaaaagatct cctgcaggta gcagattcgg ttcttccgtc gggtgtaacg tcgccgagca  7740
gttcgcttga gtctggtagc ttcggcagtc tcgccagaat cgaacaacag ggcaccaatg  7800
aggtttttct tgatggagtg tcgatcggtg tttccgagga ccttgaattt cttggagggc  7860
accttgtact cgtcggtgat gacagcccag ccgacagagt tggttccaat gtccaggccg  7920
atggagtatt tcttgtcgaa ttcccatatg gtaccagctg cagatctcga gctcggatcc  7980
ttatcgtcat cgtcgtacag atcccgaccc atttgctgtc caccagtcat gctagccata  8040
ccatgatgat gatgatgatg agaacccccc atggttaatt cctcctgtta gcccaaaaaa  8100
cgggtatgga gaaacagtag agagttgcga taaaaagcgt caggtaggat ccgctaatct  8160
tatggataaa aatgctatgg catagcaaag tgtgacgccg tgcaaataat caatgtggac  8220
ttttctgccg tgattataga cacttttgtt acgcgttttt gtcatggctt tggtcccgct  8280
ttgttacaga atgcttttaa taagcggggt taccggtttg gttagcgaga agagccagta  8340
aaagacgcag tgacggcaat gtctgatgca atatggacaa ttggtttctt ctctgaatgg  8400
cgggagtatg aaaagtatgg ctgaagcgca aaatgatccc ctgctgccgg gatactcgtt  8460
taatgcccat ctggtggcgg gtttaacgcc gattgaggcc aacggttatc tcgatttttt  8520
tatcgaccga ccgctgggaa tgaaaggtta tattctcaat ctcaccattc gcggtcaggg  8580
```

```
ggtggtgaaa aatcagggac gagaatttgt ttgccgaccg ggtgatattt tgctgttccc  8640
gccaggagag attcatcact acggtcgtca tccggaggct cgcgaatggt atcaccagtg  8700
ggtttacttt cgtccgcgcg cctactggca tgaatggctt aactggccgt caatatttgc  8760
caatacgggg ttctttcgcc cggatgaagc gcaccagccg catttcagcg acctgtttgg  8820
gcaaatcatt aacgccgggc aaggggaagg gcgctattcg gagctgctgg cgataaatct  8880
gcttgagcaa ttgttactgc ggcgcatgga agcgattaac gagtcgctcc atccaccgat  8940
ggataatcgg gtacgcgagg cttgtcagta catcagcgat cacctggcag acagcaattt  9000
tgatatcgcc agcgtcgcac agcatgtttg cttgtcgccg tcgcgtctgt cacatctttt  9060
ccgccagcag ttagggatta gcgtcttaag ctggcgcgag gaccaacgta tcagccaggc  9120
gaagctgctt ttgagcacca cccggatgcc tatcgccacc gtcggtcgca atgttggttt  9180
tgacgatcaa ctctatttct cgcgggtatt taaaaaatgc accggggcca gcccgagcga  9240
gttccgtgcc ggttgtgaag aaaaagtgaa tgatgtagcc gtcaagttgt cataattggt  9300
aacgaatcag acaattgacg gc                                           9322

SEQ ID NO: 110          moltype = DNA  length = 9322
FEATURE                 Location/Qualifiers
misc_feature            1..9322
                        note = pRF861-cassette
source                  1..9322
                        mol_type = other DNA
                        organism = synthetic construct
SEQUENCE: 110
ggtttattga ctaccggaag cagtgtgacc gtgtgcttct caaatgcctc aggctgtcta  60
tgtgtgactg ttgagctgta acaagttgtc tcaggtgttc aatttcatgt tctagttgct  120
ttgttttact ggtttcacct gttctattag gtgttacatg ctgttcatct gttacattgt  180
cgatctgttc atggtgaaca gctttaaatg caccaaaaac tcgtaaaagc tctgatgtat  240
ctatcttttt tacaccgttt tcatctgtgc atatggacag ttttcccttt gatatctaac  300
ggtgaacagt tgttctactt ttgtttgtta gtcttgatgc ttcactgata gatacaagag  360
ccataagaac ctcagatcct tccgtattta gccagtatgt tctctagtgt ggttcgttgt  420
ttttgcgtga gccatgagaa cgaaccattg agatcatgct tactttgcat gtcactcaaa  480
aattttgcct caaaactggt gagctgaatt tttgcagtta aagcatcgtg tagtgttttt  540
cttagtccgt tacgtaggta ggaatctgat gtaatggttg ttggtatttt gtcaccattc  600
atttttatct ggttgttctc aagttcggtt acgagatcca tttgtctatc tagttcaact  660
tggaaaatca acgtatcagt cgggcggcct cgcttatcaa ccaccaattt catattgctg  720
taagtgttta aatctttact tattggtttc aaaacccatt ggttaagcct tttaaactca  780
tggtagttat tttcaagcat taacatgaac ttaaattcat caaggctaat ctctatattt  840
gccttgtgag ttttcttttg tgttagttct tttaataacc actcataaat cctcatagag  900
tatttgtttt caaaagactt aacatgttcc agattatatt ttatgaattt ttttaactgg  960
aaaagataag gcaatatctc ttcactaaaa actaattcta atttttcgct tgagaacttg  1020
gcatagtttg tccactggaa aatctcaaag cctttaacca aaggattcct gatttccaca  1080
gttctcgtca tcagctctct ggttgcttta gctaatacac cataagcatt ttccctactg  1140
atgttcatca tctgagcgta ttggttataa gtgaacgata ccgtccgttc tttccttgta  1200
gggttttcaa tcgtggggtt gagtagtgcc acacagcata aaattagctt ggtttcatgc  1260
tccgttaagt catagcgact aatcgctagt tcatttgctt tgaaaacaac taattcagac  1320
atacatctca attggtctag gtgattttaa tcactatacc aattgagatg ggctagtcaa  1380
tgataattac tagtcctttt cctttgagtt gtgggtatct gtaaattctg ctagaccttt  1440
gctggaaaac ttgtaaattc tgctagaccc tctgtaaatt ccgctagacc tttgtgtgtt  1500
ttttttgttt atattcaagt ggttataatt tatagaataa agaaagaata aaaaaagata  1560
aaaagaatag atcccagccc tgtgtataac tcactacttt agtcagttcc gcagtattac  1620
aaaaggatgt cgcaaacgct gtttgctcct ctacaaaaca gaccttaaaa ccctaaaggc  1680
ttaagtagca ccctcgcaag ctcgggcaaa tcgctgaata ttccttttgt ctccgaccat  1740
caggcacctg agtcgctgtc tttttcgtga cattcagttc gctgcgctca cggctctggc  1800
agtgaatggg ggtaaatggc actacaggcg cctttttatgg attcatgcaa ggaaactacc  1860
cataatacaa gaaaagcccg tcacgggctt ctcagggcgt tttatggcgg gtctgctatg  1920
tggtgctatc tgacttttttg ctgttcagca gttcctgccc tctgattttc cagtctgacc  1980
acttcggatt atcccgtgac aggtcattca gactggctaa tgcacccagt aaggcagcgg  2040
tatcatcaac aggcttaccc gtcttactgt cggatcgacg ctctccctta tgcgactcct  2100
gcatcccttt cgtcttcgaa taaatacctg tgacggaaga tcacttcgca gaataaataa  2160
atcctggtgt ccctgttgat accgggaagc cctgggccaa cttttggcga aaatgagacg  2220
ttgatcggca cgtaagaggt tccaactttc accataatga aataagatca ctaccgggcg  2280
tatttttttga gttatcgaga ttttcaggag ctaaggaagc taaaatggag aaaaaaatca  2340
ctggatatac caccgttgat atatcccaat ggcatcgtaa agaacatttt gaggcatttc  2400
agtcagttgc tcaatgtacc tataaccaga ccgttcagct ggatattacg gcctttttaa  2460
agaccgtaaa gaaaaataag cacaagtttt atccggcctt tattcacatt cttgcccgcc  2520
tgatgaatgc tcatccggaa ttccgtatgg caatgaaaga cggtgagctg gtgatatggg  2580
atagtgttca cccttgttac accgttttcc atgagcaaac tgaaacgttt tcatcgctct  2640
ggagtgaata ccacgacgat ttccggcagt ttctacacat atattcgcaa gatgtggcgt  2700
gttacggtga aaacctggcc tatttcccta aagggtttat tgagaatatg tttttcgtct  2760
cagccaatcc ctgggtgagt ttcaccagtt ttgatttaaa cgtggccaat atggacaact  2820
tcttcgcccc cgttttcacc atgggcaaat attatacgca aggcgacaag gtgctgatgc  2880
cgctggcgat tcaggttcat catgccgttt gtgatggctt ccatgtcggc agaatgctta  2940
atgaattaca acagtactgc gatgagtggc agggcggggc gtaatttttt taaggcagtt  3000
attggtgccc ttaaacgcct ggtgctacgc ctgaataagt gataataagc ggatgaatgg  3060
cagaaattcg aaagcaaatt cgacccggtc gtcggttcag ggcagggtcg ttaaatagcc  3120
gcttatgtct attgctggtt tatcggtacc ccccaactga tcttcagcat cttttacttt  3180
caccagcgtt tctgggtgag caaaaacagg aaggcaaaat gccgcaaaaa agggaataag  3240
ggcgacacgg aaatgttgaa tactcatact cttccttttt caatattatt gaagcattta  3300
tcagggttat tgtctcatga gcggatacat atttgaatgt atttagaaaa ataaacaaaa  3360
gagtttgtag aaacgcaaaa aggccatccg tcaggatggc cttctgctta atttgatgcc  3420
```

-continued

```
tggcagttta tggcgggcgt cctgcccgcc accctccggg ccgttgcttc gcaacgttca  3480
aatccgctcc cggcggattt gtcctactca ggagagcgtt caccgacaaa caacagataa  3540
aacgaaaggc ccagtctttc gactgagcct ttcgttttat ttgatgcctg gcagttccct  3600
actctcgcat ggggagaccc cacactacca tcggcgctac ggcgtttcac ttctgagttc  3660
ggcatggggt caggtgggac caccgcgcta ctgccgccag gcaaattctg ttttatcaga  3720
ccgcttctgc gttctgattt aatctgtatc aggctgaaaa tcttctctca tccgccaaaa  3780
cagccaagct tagcggccgc ttagaccttt cgctttttct tgggatcggc tctggagtcg  3840
ccaccaagct gagacaggtc gattcgggtc tcgtacaggc cagtgatgga ctggtgaatc  3900
agggtggcat cgagaacctc cttggtggat gtgtaccgct ttcggtcgat agtggtatcg  3960
aagtacttga aagctgcagg agcacccagg ttggtaagag taaacaggtg aatgatgttc  4020
tccgcctgtt ctcgaatggg tttgtcccga tgcttgttgt aggcagagag caccttgtcc  4080
aagttggcat cagccaggat gactcgcttc gaaaactcgg aaatctgctc gataatctcg  4140
tcgaggtaat gtttgtgctg ctcaacgaag agttgcttct gttcgttgtc ctcgggagaa  4200
cccttgagct tctcgtagtg agaagccaga tagagaaagt tgacgtactt cgaaggcaag  4260
gcaagctcgt ttcccttctg cagctcgcca gcggaggcga gcatacgctt tcgaccgttc  4320
tccagttcga acagagagta cttgggcagc ttgataatga ggtctttctt gacctccttg  4380
taacccttgg cttccaagaa gtcgatggga ttcttctcga agctcgatcg ctccatgatg  4440
gtaattccga gcagctcctt gacggacttg agctttttgg acttgccctt ctcgaccttc  4500
gcaacgacaa gcacggaata ggcgacggta ggagaatcga agccaccgta tttcttggga  4560
tcccagtctt tctttcgagc gatgagcttg tcggagtttc gcttgggcag aatcgactcc  4620
ttggagaatc cgccagtctg aacctcggtt ttcttgacga tgttgacctg aggcatcgac  4680
agaacctttc gcacggttgc aaagtctcga cccttgtccc acacgatctc tccagtttcg  4740
ccgttggtct cgataagtgg tctctttcga atctctccgt tggccaaggt gatctcggtc  4800
ttgaaaaagt tcatgatgtt ggagtaaaag aagtacttgg cagtagcctt gccaatctcc  4860
tgttcggact tggcaatcat ctttcgaacg tcgtagacct tgtaatcgcc gtaaacgaac  4920
tcgctttcga gcttggggta tttcttgatg agcgcagtgc caacgacggc gttgaggtaa  4980
gcatcgtggg catggtggta attgttgatc tctcgcacct tgtagaactg aaagtccttt  5040
cggaaatcgg agaccagttt ggacttgaga gtaatcacct tgacctctcg gatgagcttg  5100
tcgttctcgt cgtacttggt gttcatccga gaatcgagaa tctgtgcgac gtgctttgtg  5160
atctgtctgg tctcgacgag ttgacgcttg atgaagccag ccttgtcgag ctcggacaga  5220
ccgcctcgct cggccttggt aagattgtcg aactttcgct gggtaatgag cttggcgttg  5280
agcagctgtc gccagtagtt cttcatcttt ttgaccacct cttcgctggg aacgttgtcc  5340
gacttgcctc tgttcttgtc ggatcgtgta aggaccttgt tgtcgataga atcgtccttg  5400
agaaaggatt gagggacaat gtggtccaca tcgtagtcgc tgagacgatt gatgtccagt  5460
tcctgatcca cgtacatgtc tcgaccattc tgcagatagt agagatacag cttctcgttc  5520
tgcagttgag tgttctcgac gggatgctcc ttgagaatct gggatcccag ctccttgatg  5580
ccttcctcga ttcgcttcat ccgctctcgc gagtttttct gacccttttg agttgtctgg  5640
ttctctctgg ccatctcgat cacaatgttc tcgggcttgt gacgtcccat gaccttcacc  5700
agctcgtcga caaccttgac agtctggaga atgcctttct tgatggctgg cgaaccagcc  5760
aggttggcaa tatgttcgtg caagctgtcg ccctgaccgg acacttgtgc cttctggatg  5820
tcctccttga aggtaagaga atcgtcgtga atgagctgca tgaagtttcg gttggcaaag  5880
ccatcggact tgagaaagtc cagaatggtc tttccggact gcttgtctct gatgccgttg  5940
atgagctttc gcgaaagtct tccccagccg gtgtatctac gtcgcttgag ttgtttcatg  6000
accttgtcgt cgaacaggtg agcgtatgtc ttgagtcgtt cctcgatcat ctcccgatct  6060
tcgaacaggg taagagtgag cacgatgtcc tccagaatgt cctcgttttc ctcgttgtcg  6120
agaaaatcct tgtccttgat aatcttgagc agatcgtgat aggtgcccaa agaggcgttg  6180
aatcggtcct caactccgga aatctcgacg ctgtcgaaac actcgatttt cttgaagtag  6240
tcctccttga gctgcttaac agtgaccttt cggttggtct tgaacaggag atcgacaatg  6300
gctttcttct gttcgccaga caagaaggca ggctttcgca ttccctcggt aacgtacttg  6360
actttggtga gttcgttgta gactgtaaag tactcgtaga gcagcgaatg cttgggaaga  6420
accttctcgt tgggcagatt cttgtcgaag ttggtcattc gctcgatgaa ggactgtgca  6480
gaggcaccct tgtccacgac ttcctcgaag ttccagggag tgatggtttc ctcggacttt  6540
cgagtcatcc aagcaaatcg agagtttcct ctggcaagag gaccaacata gtaggggatt  6600
cgaaaggtaa gaatcttctc gatcttctct cggttgtcct tgagaaaggg gtagaagtct  6660
tcctgacgtc gaagaatggc gtgcagctca ccgaggtgga tctgatgagg aatgctgccg  6720
ttgtcgaagg ttcgttgctt ccgaagcaga tcctctcgat tgagcttgac aagcagttcc  6780
tcggttccgt ccatcttctc gagaattggc ttgatgaact tgtagaactc ttcctgagag  6840
gctccgccgt cgatgtatcc agcgtagccg ttcttcgact gatcgaaaaa gatctccttg  6900
tacttctcgg gcagttgctg tcggacaaga gccttgagca gtgtgagatc ctgatggtgc  6960
tcgtcgtatc gcttgatcat ggaggcagaa aggggagcct ttgtgatctc ggtgttgact  7020
cgcagaatgt cagacaagag aatagcatcc gaaaggttct tggcagcgag aaacaggtcg  7080
gcgtactgat cgccaatctg tgcaagcagg ttgtcgaggt catcgtcgta ggtgtccttg  7140
gacagctgga gcttggcgtc ctccgccaga tcgaagttgg acttgaagtt gggtgtgaga  7200
ccaagagaaa gggcaatgag gttgccaaac agtccgttct ttttctcgcc aggaagttgg  7260
gcaatgaggt tctccagtcg tctgctcttc gagagtcgag cagacaagat ggcctttgca  7320
tcgactccgg aggcattgat ggggttttcc tcgaacagct ggttgtaggt ctgaacgagc  7380
tgaatgaaca gcttgtccac atcgctgttg tcgggattga gatcgccctc gatgaggaaa  7440
tgacctcgaa acttgatcat gtgtgccaga gcgagatgga taagtctgag atccgccttg  7500
tcggtggaat cgacgagttt ctttcgcagg tggtagatgg taggatactt ctcgtggtaa  7560
gcaacctcgt ccacaatgtt gccaaagatg ggatgacgct cgtgtttctt gtcttcctcg  7620
acgaggaagg attcctccag tcgatgaaag aacgaatcgt ccaccttggc catctcgttg  7680
gaaaagatct cctgcaggta gcagattcgg ttcttccgtc gggtgtaacg tcgccgagca  7740
gttcgcttga gtctggtagc ttcggcagtc tcgccagaat cgaacaacag ggcaccaatg  7800
aggtttttct tgatggagtg tcgatcggtg tttccgagga ccttgaattt cttggagggc  7860
accttgtact cgtcggtgat gacagcccag ccgacagagt tggttccaat gtccaggccg  7920
atggagtatt tcttgtcgaa ttcccatatg gtaccagctg cagatctcga gctcggatcc  7980
ttatcgtcat cgtcgtacag atcccgaccc atttgctgtc caccagtcat gctagccata  8040
ccatgatgat gatgatgatg agaacccccc atggttaatt cctcctgtta gcccaaaaaa  8100
cgggtatgga gaaacagtag agagttgcga taaaaagcgt caggtaggat ccgctaatct  8160
```

```
tatggataaa aatgctatgg catagcaaag tgtgacgccg tgcaaataat caatgtggac  8220
ttttctgccg tgattataga cacttttgtt acgcgttttt gtcatggctt tggtcccgct  8280
ttgttacaga atgcttttaa taagcggggt taccggtttg gttagcgaga agagccagta  8340
aaagacgcag tgacggcaat gtctgatgca atatggacaa ttggtttctt ctctgaatgg  8400
cgggagtatg aaaagtatgg ctgaagcgca aaatgatccc ctgctgccgg gatactcgtt  8460
taatgcccat ctggtggcgg gtttaacgcc gattgaggcc aacggttatc tcgatttttt  8520
tatcgaccga ccgctgggaa tgaaaggtta tattctcaat ctcaccattc gcggtcaggg  8580
ggtggtgaaa aatcagggac gagaatttgt ttgccgaccg ggtgatattt tgctgttccc  8640
gccaggagag attcatcact acggtcgtca tccggaggct cgcgaatggt atcaccagtg  8700
ggtttacttt cgtccgcgcg cctactggca tgaatggctt aactggccgt caatatttgc  8760
caatacgggg ttctttcgcc cggatgaagc gcaccagccg catttcagcg acctgtttgg  8820
gcaaatcatt aacgccgggc aaggggaagg gcgctattcg gagctgctgg cgataaatct  8880
gcttgagcaa ttgttactgc ggcgcatgga agcgattaac gagtcgctcc atccaccgat  8940
ggataatcgg gtacgcgagg cttgtcagta catcagcgat cacctggcag acagcaattt  9000
tgatatcgcc agcgtcgcac agcatgtttg cttgtcgccg tcgcgtctgt cacatctttt  9060
ccgccagcag ttagggatta gcgtcttaag ctggcgcgag gaccaacgta tcagccaggc  9120
gaagctgctt ttgagcacca cccggatgcc tatcgccacc gtcggtcgca atgttggttt  9180
tgacgatcaa ctctatttct cgcgggtatt taaaaaatgc accggggcca gcccgagcga  9240
gttccgtgcc ggttgtgaag aaaaagtgaa tgatgtagcc gtcaagttgt cataattggt  9300
aacgaatcag acaattgacg gc                                            9322

SEQ ID NO: 111          moltype = DNA  length = 21
FEATURE                 Location/Qualifiers
misc_feature            1..21
                        note = primer
source                  1..21
                        mol_type = other DNA
                        organism = synthetic construct
SEQUENCE: 111
ggtttattga ctaccggaag c                                             21

SEQ ID NO: 112          moltype = DNA  length = 20
FEATURE                 Location/Qualifiers
misc_feature            1..20
                        note = primer
source                  1..20
                        mol_type = other DNA
                        organism = synthetic construct
SEQUENCE: 112
gccgtcaatt gtctgattcg                                               20

SEQ ID NO: 113          moltype = DNA  length = 10569
FEATURE                 Location/Qualifiers
misc_feature            1..10569
                        note = pRF97-nacETsite1 plasmid
source                  1..10569
                        mol_type = other DNA
                        organism = synthetic construct
SEQUENCE: 113
ccctttcgtc ttcgaataaa tacctgtgac ggaagatcac ttcgcagaat aaataaatcc  60
tggtgtccct gttgataccg ggaagccctg ggccaacttt tggcgaaaat gagacgttga  120
tcggcacgta agaggttcca actttcacca taatgaaata agatcactac cgggcgtatt  180
ttttgagtta tcgagatttt caggagctaa ggaagctaaa atggagaaaa aaatcactgg  240
atataccacc gttgatatat cccaatggca tcgtaaagaa cattttgagg catttcagtc  300
agttgctcaa tgtacctata accagaccgt tcagctggat attacggcct ttttaaagac  360
cgtaaagaaa aataagcaca agttttatcc ggcctttatt cacattcttg cccgcctgat  420
gaatgctcat ccggaattcc gtatggcaat gaaagacggt gagctggtga tatgggatag  480
tgttcaccct tgttacaccg ttttccatga gcaaactgaa acgttttcat cgctctggag  540
tgaataccac gacgatttcc ggcagtttct acacatatat tcgcaagatg tggcgtgtta  600
cggtgaaaac ctggcctatt tccctaaagg gtttattgag aatatgtttt tcgtctcagc  660
caatccctgg gtgagtttca ccagttttga tttaaacgtg gccaatatgg acaacttctt  720
cgcccccgtt ttcaccatgg gcaaatatta tacgcaaggc gacaaggtgc tgatgccgct  780
ggcgattcag gttcatcatg ccgtttgtga tggcttccat gtcggcagaa tgcttaatga  840
attacaacag tactgcgatg agtggcaggg cggggcgtaa tttttttaag gcagttattg  900
gtgcccttaa acgcctggtg ctacgcctga ataagtgata ataagcggat gaatggcaga  960
aattcgaaag caaattcgac ccggtcgtcg gttcagggca gggtcgttaa atagccgctt  1020
atgtctattg ctggtttatc ggtacccccc aactgatctt cagcatcttt tactttcacc  1080
agcgtttctg ggtgagcaaa aacaggaagg caaaatgccg caaaaaaggg aataagggcg  1140
acacggaaat gttgaatact catactcttc ctttttcaat attattgaag catttatcag  1200
ggttattgtc tcatgagcgg atacatattt gaatgtattt agaaaaataa acaaaagagt  1260
ttgtagaaac gcaaaaaggc catccgtcag gatggccttc tgcttaattt gatgcctggc  1320
agtttatggc gggcgtcctg cccgccaccc tccgggccgt tgcttcgcaa cgttcaaatc  1380
cgctcccggc ggatttgtcc tactcaggag agcgttcacc gacaaacaac agataaaacg  1440
aaaggcccag tctttcgact gagcctttcg ttttatttga tgcctggcag ttccctactc  1500
tcgcatgggg agaccccaca ctaccatcgg cgctacggcg tttcacttct gagttcggca  1560
tggggtcagg tgggaccacc gcgctactgc cgccaggcaa attctgtttt atcagaccgc  1620
ttctgcgttc tgatttaatc tgtatcaggc tgaaaatctt ctctcatccg ccaaaacagc  1680
caagcttagc ggccgcttag acctttcgct tttcttggg atcggctctg gagtcgccac  1740
caagctgaga caggtcgatt cgggtctcgt acaggccagt gatggactgg tgaatcaggg  1800
```

-continued

```
tggcatcgag aacctccttg gtggatgtgt accgctttcg gtcgatagtg gtatcgaagt  1860
acttgaaagc tgcaggagca cccaggttgg taagagtaaa caggtgaatg atgttctccg  1920
cctgttctcg aatgggtttg tcccgatgct tgttgtaggc agagagcacc ttgtccaagt  1980
tggcatcagc caggatgact cgcttcgaaa actcggaaat ctgctcgata atctcgtcga  2040
ggtaatgttt gtgctgctca acgaagagtt gcttctgttc gttgtcctcg ggagaaccct  2100
tgagcttctc gtagtgagaa gccagataga gaaagttgac gtacttcgaa ggcaaggcaa  2160
gctcgtttcc cttctgcagc tcgccagcgg aggcgagcat acgctttcga ccgttctcca  2220
gttcgaacag agagtacttg ggcagcttga taatgaggtc tttcttgacc tccttgtaac  2280
ccttggcttc caagaagtcg atgggattct tctcgaagct cgatcgctcc atgatggtaa  2340
ttccgagcag ctccttgacg gacttgagct ttttggactt gcccttctcg accttcgcaa  2400
cgacaagcac ggaataggcg acggtaggag aatcgaagcc accgtatttc ttgggatccc  2460
agtctttctt tcgagcgatg agcttgtcgg agtttcgctt gggcagaatc gactccttgg  2520
agaatccgcc agtctgaacc tcggttttct tgacgatgtt gacctgaggc atcgacagaa  2580
cctttcgcac ggttgcaaag tctcgaccct tgtcccacac gatctctcca gtttcgccgt  2640
tggtctcgat aagtggtctc tttcgaatct ctccgttggc caaggtgatc tcggtcttga  2700
aaaagttcat gatgttggag taaaagaagt acttggcagt agccttgcca atctcctgtt  2760
cggacttggc aatcatcttt cgaacgtcgt agaccttgta atcgccgtaa acgaactcgc  2820
tttcgagctt ggggtatttc ttgatgagcg cagtgccaac gacggcgttg aggtaagcat  2880
cgtgggcatg gtggtaattg ttgatctctc gcaccttgta gaactgaaag tcctttcgga  2940
aatcggagac cagtttggac ttgagagtaa tcaccttgac ctctcggatg agcttgtcgt  3000
tctcgtcgta cttggtgttc atccgagaat cgagaatctg tgcgacgtgc tttgtgatct  3060
gtctggtctc gacgagttga cgcttgatga agccagcctt gtcgagctcg gacagaccgc  3120
ctcgctcggc cttggtaaga ttgtcgaact ttcgctgggt aatgagcttg gcgttgagca  3180
gctgtcgcca gtagttcttc atctttttga ccacctcttc gctgggaacg ttgtccgact  3240
tgcctctgtt cttgtcggat cgtgtaagga ccttgttgtc gatagaatcg tccttgagaa  3300
aggattgagg gacaatgtgg tccacatcgt agtcgctgag acgattgatg tccagttcct  3360
gatccacgta catgtctcga ccattctgca gatagtagag atacagcttc tcgttctgca  3420
gttgagtgtt ctcgacggga tgctccttga gaatctggga tcccagctcc ttgatgcctt  3480
cctcgattcg cttcatccgc tctcgcgagt tttctgacc cttttgagtt gtctggttct  3540
ctctggccat ctcgatcaca atgttctcgg gcttgtgacg tcccatgacc ttcaccagct  3600
cgtcgacaac cttgacagtc tggagaatgc ctttcttgat ggctggcgaa ccagccaggt  3660
tggcaatatg ttcgtgcaag ctgtcgccct gaccggacac ttgtgccttc tggatgtcct  3720
ccttgaaggt aagagaatcg tcgtgaatga gctgcatgaa gtttcggttg gcaaagccat  3780
cggacttgag aaagtccaga atggtctttc cggactgctt gtctctgatg ccgttgatga  3840
gctttcgcga aagtcttccc cagccggtgt atctacgtcg cttgagttgt ttcatgacct  3900
tgtcgtcgaa caggtgagcg tatgtcttga gtcgttcctc gatcatctcc cgatcttcga  3960
acagggtaag agtgagcacg atgtcctcca gaatgtcctc gttttcctcg ttgtcgagaa  4020
aatccttgtc cttgataatc ttgagcagat cgtgataggt gcccaaagag gcgttgaatc  4080
ggtcctcaac tccggaaatc tcgacgctgt cgaaacactc gattttcttg aagtagtcct  4140
ccttgagctg cttaacagtg acctttcggt tggtcttgaa caggagatcg acaatggctt  4200
tcttctgttc gccagacaag aaggcaggct ttcgcattcc ctcggtaacg tacttgactt  4260
tggtgagttc gttgtagact gtaaagtact cgtagagcag cgaatgcttg ggaagaacct  4320
tctcgttggg cagattcttg tcgaagttgg tcattcgctc gatgaaggac tgtgcagagg  4380
cacccttgtc cacgacttcc tcgaagttcc agggagtgat ggtttcctcg gactttcgag  4440
tcatccaagc aaatcgagag tttcctctgg caagaggacc aacatagtag gggattcgaa  4500
aggtaagaat cttctcgatc ttctctcggt tgtccttgag aaaggggtag aagtcttcct  4560
gacgtcgaag aatggcgtgc agctcaccga ggtggatctg atgaggaatg ctgccgttgt  4620
cgaaggttcg ttgcttccga agcagatcct ctcgattgag cttgacaagc agttcctcgg  4680
ttccgtccat cttctcgaga attggcttga tgaacttgta gaactcttcc tgagaggctc  4740
cgccgtcgat gtatccagcg tagccgttct tcgactgatc gaaaaagatc tccttgtact  4800
tctcgggcag ttgctgtcgg acaagagcct tgagcagtgt gagatcctga tggtgctcgt  4860
cgtatcgctt gatcatggag gcagaaaggg gagcctttgt gatctcggtg ttgactcgca  4920
gaatgtcaga caagagaata gcatccgaaa ggttcttggc agcgagaaac aggtcggcgt  4980
actgatcgcc aatctgtgca agcaggttgt cgaggtcatc gtcgtaggtg tccttggaca  5040
gctggagctt ggcgtcctcc gccagatcga agttggactt gaagttgggt gtgagaccaa  5100
gagaaagggc aatgaggttg ccaaacagtc cgttcttttt ctcgccagga agttgggcaa  5160
tgaggttctc cagtcgtctg ctcttcgaga gtcgagcaga caagatggcc tttgcatcga  5220
ctccggaggc attgatgggg ttttcctcga acagctggtt gtaggtctga acgagctgaa  5280
tgaacagctt gtccacatcg ctgttgtcgg gattgagatc gccctcgatg aggaaatgac  5340
ctcgaaactt gatcatgtgt gccagagcga ggtagataag tctgagatcc gccttgtcgg  5400
tggaatcgac gagtttcttt cgcaggtggt agatggtagg atacttctcg tggtaagcaa  5460
cctcgtccac aatgttgcca aagatgggat gacgctcgtg tttcttgtct tcctcgacga  5520
ggaaggattc ctccagtcga tgaaagaacg aatcgtccac cttggccatc tcgttggaaa  5580
agatctcctg caggtagcag attcggttct tccgtcgggt gtaacgtcgc cgagcagttc  5640
gcttgagtct ggtagcttcg gcagtctcgc cagaatcgaa caacagggca ccaatgaggt  5700
ttttcttgat ggagtgtcga tcggtgtttc cgaggacctt gaatttcttg gagggcacct  5760
tgtactcgtc ggtgatgaca gcccagccga cagagttggt tccaatgtcc aggccgatgg  5820
agtatttctt gtcgaattcc catatggtac cagctgcaga tctcgagctc ggatccttat  5880
cgtcatcgtc gtacagatcc cgacccattt gctgtccacc agtcatgcta gccataccat  5940
gatgatgatg atgatgagaa ccccccatgg ttaattcctc ctgttagccc aaaaaacggg  6000
tatggagaaa cagtagagag ttgcgataaa aagcgtcagg taggatccgc taatcttatg  6060
gataaaaatg ctatggcata gcaaagtgtg acgccgtgca aataatcaat gtggactttt  6120
ctgccgtgat tatagacact tttgttacgc gtttttgtca tggctttggt cccgctttgt  6180
tacagaatgc ttttaataag cggggttacc ggtttggtta gcgagaagag ccagtaaaag  6240
acgcagtgac ggcaatgtct gatgcaatat ggacaattgg tttcttctct gaatggcggg  6300
agtatgaaaa gtatggctga agcgcaaaat gatcccctgc tgccgggata ctcgtttaat  6360
gcccatctgg tggcgggttt aacgccgatt gaggccaacg gttatctcga ttttttttatc  6420
gaccgaccgc tgggaatgaa aggttatatt ctcaatctca ccattcgcgg tcagggggtg  6480
gtgaaaaatc agggacgaga atttgtttgc cgaccgggtg atattttgct gttcccgcca  6540
```

```
ggagagattc atcactacgg tcgtcatccg gaggctcgcg aatggtatca ccagtgggtt  6600
tactttcgtc cgcgcgccta ctggcatgaa tggcttaact ggccgtcaat atttgccaat  6660
acggggttct ttcgcccgga tgaagcgcac cagccgcatt tcagcgacct gtttgggcaa  6720
atcattaacg ccgggcaagg ggaagggcgc tattcggagc tgctggcgat aaatctgctt  6780
gagcaattgt tactgcggcg catggaagcg attaacgagt cgctccatcc accgatggat  6840
aatcgggtac gcgaggcttg tcagtacatc agcgatcacc tggcagacag caattttgat  6900
atcgccagcg tcgcacagca tgtttgcttg tcgccgtcgc gtctgtcaca tcttttccgc  6960
cagcagttag ggattagcgt cttaagctgg cgcgaggacc aacgtatcag ccaggcgaag  7020
ctgcttttga gcaccacccg gatgcctatc gccaccgtcg gtcgcaatgt tggttttgac  7080
gatcaactct atttctcgcg ggtatttaaa aaatgcaccg gggccagccc gagcgagttc  7140
cgtgccggtt gtgaagaaaa agtgaatgat gtagccgtca agttgtcata attggtaacg  7200
aatcagacaa ttgacggccg tcccctggat tagctcgagc cgaacctccg ggaaaagttc  7260
gcgaaaagct ttaatgacct ctggcaagct ataacgtgcc tgagtatgcg tcgttgcaat  7320
agtgagaacg ccagacgtat cgttggtaaa caggtctgca agccgacgaa cattactggc  7380
ttcattcaga atacgttctg caatgaccag taatgctttg cccggttcag tcatgcccag  7440
cagtcgctta cctcgtcgaa caaatatttc gatgccaagt tcatcctcca gttcccgaat  7500
atgacggctg acgcctgact gtgaggtaaa aagcatattc gcaacctctg tcaggttgta  7560
atcctgacgt gcagcctcgc ggattatctt tagttgttgg aaattcacgg taaactccgg  7620
gcagttcaga tttcccgtta ttgttaaagt ctaatgcccg gcataacaaa taataaaaac  7680
ccgcatctta ttccatcccg atataacact tagctcacga agttcatgtt gcctccggtt  7740
tttaagaatc ggcccaagtg ccgccattac ttacaaccag attgcaagat gcttgccagt  7800
tttattttgg tgttgatgta caagctaacc aactgtcaaa taagagatta tgatagattc  7860
gtcatttgct cctttaatca gctgtcgcgt tcccctgccc tataaaagga gggtatgcac  7920
cacgatggtt cattacccaa taagattgaa agctcaccac tttgttgaaa ttgacagcaa  7980
acaaacaaaa aaatgcattt caccctttga catcaccatg cactgccatt aatatgcgcc  8040
ccgttcacac gattcctctg tagttcagtc ggtagaacgg cggactgtta atccgtatgt  8100
cactggttcg agtccagtca gaggagccaa attcaaaaaa gcctgctttc tagcaggctt  8160
tttgctttct aattaccaac gctcttaaaa catctgtctt gaaccagaac taatttgcaa  8220
gaatcataaa aaatttattt gctttcagga aaatttttct gtataataga ttcatatgca  8280
atacttcagc agccgtttta gagctagaaa tagcaagtta aaataaggct agtccgttat  8340
caacttgaaa aagtggcacc gagtcggtgc gactcctgtt gatagatcca gtaatgacct  8400
cagaactcca tctggatttg ttcagaacgc tcggttgccg ccgggcgttt tttattggtg  8460
agaatggttt attgactacc ggaagcagtg tgaccgtgtg cttctcaaat gcctcaggct  8520
gtctatgtgt gactgttgag ctgtaacaag ttgtctcagg tgttcaattt catgttctag  8580
ttgctttgtt ttactggttt cacctgttct attaggtgtt acatgctgtt catctgttac  8640
attgtcgatc tgttcatggt gaacagcttt aaatgcacca aaaactcgta aaagctctga  8700
tgtatctatc ttttttacac cgttttcatc tgtgcatatg gacagttttc cctttgatat  8760
ctaacggtga acagttgttc tacttttgtt tgttagtctt gatgcttcac tgatagatac  8820
aagagccata agaacctcag atccttccgt atttagccag tatgttctct agtgtggttc  8880
gttgtttttg cgtgagccat gagaacgaac cattgagatc atgcttactt tgcatgtcac  8940
tcaaaaattt tgcctcaaaa ctggtgagct gaatttttgc agttaaagca tcgtgtagtg  9000
tttttcttag tccgttacgt aggtaggaat ctgatgtaat ggttgttggt attttgtcac  9060
cattcatttt tatctggttg ttctcaagtt cggttacgag atccatttgt ctatctagtt  9120
caacttggaa aatcaacgta tcagtcgggc ggcctcgctt atcaaccacc aatttcatat  9180
tgctgtaagt gtttaaatct ttacttattg gtttcaaaac ccattggtta agccttttaa  9240
actcatggta gttattttca agcattaaca tgaacttaaa ttcatcaagg ctaatctcta  9300
tatttgcctt gtgagttttc ttttgtgtta gttcttttaa taaccactca taaatcctca  9360
tagagtattt gttttcaaaa gacttaacat gttccagatt atattttatg aattttttta  9420
actggaaaag ataaggcaat atctcttcac taaaaactaa ttctaatttt tcgcttgaga  9480
acttggcata gtttgtccac tggaaaatct caaagccttt aaccaaagga ttcctgattt  9540
ccacagttct cgtcatcagc tctctggttg ctttagctaa tacaccataa gcattttccc  9600
tactgatgtt catcatctga gcgtattggt tataagtgaa cgataccgtc cgttctttcc  9660
ttgtagggtt ttcaatcgtg gggttgagta gtgccacaca gcataaaatt agcttggttt  9720
catgctccgt taagtcatag cgactaatcg ctagttcatt tgctttgaaa acaactaatt  9780
cagacataca tctcaattgg tctaggtgat tttaatcact ataccaattg agatgggcta  9840
gtcaatgata attactagtc cttttccttt gagttgtggg tatctgtaaa ttctgctaga  9900
cctttgctgg aaaacttgta aattctgcta gaccctctgt aaattccgct agacctttgt  9960
gtgttttttt tgtttatatt caagtggtta taatttatag aataaagaaa gaataaaaaa  10020
agataaaaag aatagatccc agccctgtgt ataactcact actttagtca gttccgcagt  10080
attacaaaag gatgtcgcaa acgctgtttg ctcctctaca aaacagacct taaaacccta  10140
aaggcttaag tagcaccctc gcaagctcgg gcaaatcgct gaatattcct tttgtctccg  10200
accatcaggc acctgagtcg ctgtcttttt cgtgacattc agttcgctgc gctcacggct  10260
ctggcagtga atgggggtaa atggcactac aggcgccttt tatggattca tgcaaggaaa  10320
ctacccataa tacaagaaaa gcccgtcacg ggcttctcag ggcgttttat ggcgggtctg  10380
ctatgtggtg ctatctgact ttttgctgtt cagcagttcc tgccctctga ttttccagtc  10440
tgaccacttc ggattatccc gtgacaggtc attcagactg gctaatgcac ccagtaaggc  10500
agcggtatca tcaacaggct tacccgtctt actgtcggat cgacgctctc ccttatgcga  10560
ctcctgcat                                                         10569
```

```
SEQ ID NO: 114          moltype = DNA  length = 10569
FEATURE                 Location/Qualifiers
misc_feature            1..10569
                        note = pRF97-nacETsite2 plasmid
source                  1..10569
                        mol_type = other DNA
                        organism = synthetic construct
SEQUENCE: 114
ccctttcgtc ttcgaataaa tacctgtgac ggaagatcac ttcgcagaat aaataaatcc  60
tggtgtccct gttgataccg ggaagccctg ggccaacttt tggcgaaaat gagacgttga  120
```

```
tcggcacgta agaggttcca actttcacca taatgaaata agatcactac cgggcgtatt  180
ttttgagtta tcgagatttt caggagctaa ggaagctaaa atggagaaaa aaatcactgg  240
atataccacc gttgatatat cccaatggca tcgtaaagaa cattttgagg catttcagtc  300
agttgctcaa tgtacctata accagaccgt tcagctggat attacggcct ttttaaagac  360
cgtaaagaaa aataagcaca agttttatcc ggcctttatt cacattcttg cccgcctgat  420
gaatgctcat ccggaattcc gtatggcaat gaaagacggt gagctggtga tatgggatag  480
tgttcaccct tgttacaccg ttttccatga gcaaactgaa acgttttcat cgctctggag  540
tgaataccac gacgatttcc ggcagtttct acacatatat tcgcaagatg tggcgtgtta  600
cggtgaaaac ctggcctatt tccctaaagg gtttattgag aatatgtttt tcgtctcagc  660
caatccctgg gtgagtttca ccagttttga tttaaacgtg gccaatatgg acaacttctt  720
cgcccccgtt ttcaccatgg gcaaatatta tacgcaaggc gacaaggtgc tgatgccgct  780
ggcgattcag gttcatcatg ccgtttgtga tggcttccat gtcggcagaa tgcttaatga  840
attacaacag tactgcgatg agtggcaggg cggggcgtaa tttttttaag gcagttattg  900
gtgcccttaa acgcctggtg ctacgcctga ataagtgata ataagcggat gaatggcaga  960
aattcgaaag caaattcgac ccggtcgtcg gttcagggca gggtcgttaa atagccgctt  1020
atgtctattg ctggtttatc ggtacccccc aactgatctt cagcatcttt tactttcacc  1080
agcgtttctg ggtgagcaaa aacaggaagg caaaatgccg caaaaaaggg aataagggcg  1140
acacggaaat gttgaatact catactcttc ctttttcaat attattgaag catttatcag  1200
ggttattgtc tcatgagcgg atacatattt gaatgtattt agaaaaataa acaaaagagt  1260
ttgtagaaac gcaaaaaggc catccgtcag gatggccttc tgcttaattt gatgcctggc  1320
agtttatggc gggcgtcctg cccgccaccc tccgggccgt tgcttcgcaa cgttcaaatc  1380
cgctcccggc ggatttgtcc tactcaggag agcgttcacc gacaaacaac agataaaacg  1440
aaaggcccag tctttcgact gagcctttcg ttttatttga tgcctggcag ttccctactc  1500
tcgcatgggg agaccccaca ctaccatcgg cgctacggcg tttcacttct gagttcggca  1560
tggggtcagg tgggaccacc gcgctactgc cgccaggcaa attctgtttt atcagaccgc  1620
ttctgcgttc tgatttaatc tgtatcaggc tgaaaatctt ctctcatccg ccaaaacagc  1680
caagcttagc ggccgcttag acctttcgct tttcttgggg atcggctctg gagtcgccac  1740
caagctgaga caggtcgatt cggtctcgt acaggccagt gatggactgg tgaatcaggg  1800
tggcatcgag aacctccttg gtggatgtgt accgctttcg gtcgatagtg gtatcgaagt  1860
acttgaaagc tgcaggagca cccaggttgg taagagtaaa caggtgaatg atgttctccg  1920
cctgttctcg aatgggtttg tcccgatgct tgttgtaggc agagagcacc ttgtccaagt  1980
tggcatcagc caggatgact cgcttcgaaa actcggaaat ctgctcgata atctcgtcga  2040
ggtaatgttt gtgctgctca acgaagagtt gcttctgttc gttgtcctcg ggagaaccct  2100
tgagcttctc gtagtgagaa gccagataga gaaagttgac gtacttcgaa ggcaaggcaa  2160
gctcgtttcc cttctgcagc tcgccagcgg aggcgagcat acgctttcga ccgttctcca  2220
gttcgaacag agagtacttg ggcagcttga taatgaggtc tttcttgacc tccttgtaac  2280
ccttggcttc caagaagtcg atgggattct tctcgaagct cgatcgctcc atgatggtaa  2340
ttccgagcag ctccttgacg gacttgagct ttttggactt gcccttctcg accttcgcaa  2400
cgacaagcac ggaataggcg acggtaggag aatcgaagcc accgtatttc ttgggatccc  2460
agtctttctt tcgagcgatg agcttgtcgg agtttcgctt gggcagaatc gactccttgg  2520
agaatccgcc agtctgaacc tcggttttct tgacgatgtt gacctgaggc atcgacagaa  2580
cctttcgcac ggttgcaaag tctcgaccct tgtcccacac gatctctcca gtttcgccgt  2640
tggtctcgat aagtggtctc tttcgaatct ctccgttggc caaggtgatc tcggtcttga  2700
aaaagttcat gatgttggag taaaagaagt acttggcagt agccttgcca atctcctgtt  2760
cggacttggc aatcatcttt cgaacgtcgt agaccttgta atcgccgtaa acgaactcgc  2820
tttcgagctt ggggtatttc ttgatgagcg cagtgccaac gacggcgttg aggtaagcat  2880
cgtgggcatg gtggtaattg ttgatctctc gcaccttgta gaactgaaag tcctttcgga  2940
aatcggagac cagtttggac ttgagagtaa tcaccttgac ctctcggatg agcttgtcgt  3000
tctcgtcgta cttggtgttc atccgagaat cgagaatctg tgcgacgtgc tttgtgatct  3060
gtctggtctc gacgagttga cgcttgatga agccagcctt gtcgagctcg gacagaccgc  3120
ctcgctcggc cttggtaaga ttgtcgaact ttcgctgggt aatgagcttg gcgttgagca  3180
gctgtcgcca gtagttcttc atctttttga ccacctcttc gctgggaacg ttgtccgact  3240
tgcctctgtt cttgtcggat cgtgtaagga ccttgttgtc gatagaatcg tccttgagaa  3300
aggattgagg gacaatgtgg tccacatcgt agtcgctgag acgattgatg tccagttcct  3360
gatccacgta catgtctcga ccattctgca gatagtagag atacagcttc tcgttctgca  3420
gttgagtgtt ctcgacggga tgctccttga gaatctggga tcccagctcc ttgatgcctt  3480
cctcgattcg cttcatccgc tctcgcgagt tttctgacc ctttgagtt gtctggttct  3540
ctctggccat ctcgatcaca atgttctcgg gcttgtgacg tcccatgacc ttcaccagct  3600
cgtcgacaac cttgacagtc tggagaatgc ctttcttgat ggctggcgaa ccagccaggt  3660
tggcaatatg ttcgtgcaag ctgtcgccct gaccggacac ttgtgccttc tggatgtcct  3720
ccttgaaggt aagagaatcg tcgtgaatga gctgcatgaa gtttcggttg gcaaagccat  3780
cggacttgag aaagtccaga atggtctttc cggactgctt gtctctgatg ccgttgatga  3840
gctttcgcga aagtcttccc cagccggtgt atctacgtcg cttgagttgt ttcatgacct  3900
tgtcgtcgaa caggtgagcg tatgtcttga gtcgttcctc gatcatctcc cgatcttcga  3960
acagggtaag agtgagcacg atgtcctcca gaatgtcctc gttttcctcg ttgtcgagaa  4020
aatccttgtc cttgataatc ttgagcagat cgtgataggt gcccaaagag gcgttgaatc  4080
ggtcctcaac tccggaaatc tcgacgctgt cgaaacactc gattttcttg aagtagtcct  4140
ccttgagctg cttaacagtg acctttcggt tggtcttgaa caggagatcg acaatggctt  4200
tcttctgttc gccagacaag aaggcaggct ttcgcattcc ctcggtaacg tacttgactt  4260
tggtgagttc gttgtagact gtaaagtact cgtagagcag cgaatgcttg ggaagaacct  4320
tctcgttggg cagattcttg tcgaagttgg tcattcgctc gatgaaggac tgtgcagagg  4380
cacccttgtc cacgacttcc tcgaagttcc agggagtgat ggtttcctcg gactttcgag  4440
tcatccaagc aaatcgagag tttcctctgg caagaggacc aacatagtag gggattcgaa  4500
aggtaagaat cttctcgatc ttctctcggt tgtccttgag aaaggggtag aagtcttcct  4560
gacgtcgaag aatggcgtgc agctcaccga ggtggatctg atgaggaatg ctgccgttgt  4620
cgaaggttcg ttgcttccga agcagatcct ctcgattgag cttgacaagc agttcctcgg  4680
ttccgtccat cttctcgaga attggcttga tgaacttgta gaactcttcc tgagaggctc  4740
cgccgtcgat gtatccagcg tagccgttct tcgactgatc gaaaaagatc tccttgtact  4800
tctcgggcag ttgctgtcgg acaagagcct tgagcagtgt gagatcctga tggtgctcgt  4860
```

```
cgtatcgctt gatcatggag gcagaaaggg gagcctttgt gatctcggtg ttgactcgca  4920
gaatgtcaga caagagaata gcatccgaaa ggttcttggc agcgagaaac aggtcggcgt  4980
actgatcgcc aatctgtgca agcaggttgt cgaggtcatc gtcgtaggtg tccttggaca  5040
gctggagctt ggcgtcctcc gccagatcga agttggactt gaagttgggt gtgagaccaa  5100
gagaaagggc aatgaggttg ccaaacagtc cgttcttttt ctcgccagga agttgggcaa  5160
tgaggttctc cagtcgtctg ctcttcgaga gtcgagcaga caagatggcc tttgcatcga  5220
ctccggaggc attgatgggg ttttcctcga acagctggtt gtaggtctga acgagctgaa  5280
tgaacagctt gtccacatcg ctgttgtcgg gattgagatc gccctcgatg aggaaatgac  5340
ctcgaaactt gatcatgtgt gccagagcga ggtagataag tctgagatcc gccttgtcgg  5400
tggaatcgac gagtttcttt cgcaggtggt agatggtagg atacttctcg tggtaagcaa  5460
cctcgtccac aatgttgcca aagatgggat gacgctcgtg tttcttgtct tcctcgacga  5520
ggaaggattc ctccagtcga tgaaagaacg aatcgtccac cttggccatc tcgttggaaa  5580
agatctcctg caggtagcag attcggttct tccgtcgggt gtaacgtcgc cgagcagttc  5640
gcttgagtct ggtagcttcg gcagtctcgc cagaatcgaa caacagggca ccaatgaggt  5700
ttttcttgat ggagtgtcga tcggtgtttc cgaggacctt gaatttcttg gagggcacct  5760
tgtactcgtc ggtgatgaca gcccagccga cagagttggt tccaatgtcc aggccgatgg  5820
agtatttctt gtcgaattcc catatggtac cagctgcaga tctcgagctc ggatccttat  5880
cgtcatcgtc gtacagatcc cgacccattt gctgtccacc agtcatgcta gccataccat  5940
gatgatgatg atgatgagaa ccccccatgg ttaattcctc ctgttagccc aaaaaacggg  6000
tatggagaaa cagtagagag ttgcgataaa aagcgtcagg taggatccgc taatcttatg  6060
gataaaaatg ctatggcata gcaaagtgtg acgccgtgca aataatcaat gtggactttt  6120
ctgccgtgat tatagacact tttgttacgc gtttttgtca tggctttggt cccgctttgt  6180
tacagaatgc ttttaataag cggggttacc ggtttggtta gcgagaagag ccagtaaaag  6240
acgcagtgac ggcaatgtct gatgcaatat ggacaattgg tttcttctct gaatggcggg  6300
agtatgaaaa gtatggctga agcgcaaaat gatcccctgc tgccgggata ctcgtttaat  6360
gcccatctgg tggcgggttt aacgccgatt gaggccaacg gttatctcga tttttttatc  6420
gaccgaccgc tgggaatgaa aggttatatt ctcaatctca ccattcgcgg tcaggggtg  6480
gtgaaaaatc agggacgaga atttgtttgc cgaccgggtg atattttgct gttcccgcca  6540
ggagagattc atcactacgg tcgtcatccg gaggctcgcg aatggtatca ccagtgggtt  6600
tactttcgtc cgcgcgccta ctggcatgaa tggcttaact ggccgtcaat atttgccaat  6660
acggggttct ttcgcccgga tgaagcgcac cagccgcatt tcagcgacct gtttgggcaa  6720
atcattaacg ccgggcaagg ggaagggcgc tattcggagc tgctggcgat aaatctgctt  6780
gagcaattgt tactgcggcg catggaagcg attaacgagt cgctccatcc accgatggat  6840
aatcgggtac gcgaggcttg tcagtacatc agcgatcacc tggcagacag caattttgat  6900
atcgccagcg tcgcacagca tgtttgcttg tcgccgtcgc gtctgtcaca tcttttccgc  6960
cagcagttag ggattagcgt cttaagctgg cgcgaggacc aacgtatcag ccaggcgaag  7020
ctgcttttga gcaccacccg gatgcctatc gccaccgtcg gtcgcaatgt tggttttgac  7080
gatcaactct atttctcgcg ggtatttaaa aaatgcaccg gggccagccc gagcgagttc  7140
cgtgccggtt gtgaagaaaa agtgaatgat gtagccgtca agttgtcata attggtaacg  7200
aatcagacaa ttgacggccg tcccctggat tagctcgagc cgaacctccg ggaaaagttc  7260
gcgaaaagct ttaatgacct ctggcaagct ataacgtgcc tgagtatgcg tcgttgcaat  7320
agtgagaacg ccagacgtat cgttggtaaa caggtctgca agccgacgaa cattactggc  7380
ttcattcaga atacgttctg caatgaccag taatgctttg cccggttcag tcatgcccag  7440
cagtcgctta cctcgtcgaa caaatatttc gatgccaagt tcatcctcca gttcccgaat  7500
atgacggctg acgcctgact gtgaggtaaa aagcatattc gcaacctctg tcaggttgta  7560
atcctgacgt gcagcctcgc ggattatctt tagttgttgg aaattcacgg taaactccgg  7620
gcagttcaga tttcccgtta ttgttaaagt ctaatgcccg gcataacaaa taataaaaac  7680
ccgcatctta ttccatcccg atataacact tagctcacga agttcatgtt gcctccggtt  7740
tttaagaatc ggcccaagtg ccgccattac ttacaaccag attgcaagat gcttgccagt  7800
tttattttgg tgttgatgta caagctaacc aactgtcaaa taagagatta tgatagattc  7860
gtcatttgct cctttaatca gctgtcgcgt tcccctgccc tataaaagga gggtatgcac  7920
cacgatggtt cattacccaa taagattgaa agctcaccac tttgttgaaa ttgacagcaa  7980
acaaacaaaa aaatgcattt caccctttga catcaccatg cactgccatt aatatgcgcc  8040
ccgttcacac gattcctctg tagttcagtc ggtagaacgg cggactgtta atccgtatgt  8100
cactggttcg agtccagtca gaggagccaa attcaaaaaa gcctgctttc tagcaggctt  8160
tttgctttct aattaccaac gctcttaaaa catctgtctt gaaccagaac taatttgcaa  8220
gaatcataaa aaatttattt gctttcagga aaatttttct gtataataga ttcaacaacc  8280
agcgctcagc cagcgtttta gagctagaaa tagcaagtta aaataaggct agtccgttat  8340
caacttgaaa aagtggcacc gagtcggtgc gactcctgtt gatagatcca gtaatgacct  8400
cagaactcca tctggatttg ttcagaacgc tcggttgccg ccgggcgttt tttattggtg  8460
agaatggttt attgactacc ggaagcagtg tgaccgtgtg cttctcaaat gcctcaggct  8520
gtctatgtgt gactgttgag ctgtaacaag ttgtctcagg tgttcaattt catgttctag  8580
ttgctttgtt ttactggttt cacctgttct attaggtgtt acatgctgtt catctgttac  8640
attgtcgatc tgttcatggt gaacagcttt aaatgcacca aaaactcgta aaagctctga  8700
tgtatctatc ttttttacac cgttttcatc tgtgcatatg gacagttttc cctttgatat  8760
ctaacggtga acagttgttc tacttttgtt tgttagtctt gatgcttcac tgatagatac  8820
aagagccata agaacctcag atccttccgt atttagccag tatgttctct agtgtggttc  8880
gttgtttttg cgtgagccat gagaacgaac cattgagatc atgcttactt tgcatgtcac  8940
tcaaaaattt tgcctcaaaa ctggtgagct gaatttttgc agttaaagca tcgtgtagtg  9000
tttttcttag tccgttacgt aggtaggaat ctgatgtaat ggttgttggt attttgtcac  9060
cattcatttt tatctggttg ttctcaagtt cggttacgag atccatttgt ctatctagtt  9120
caacttggaa aatcaacgta tcagtcgggc ggcctcgctt atcaaccacc aatttcatat  9180
tgctgtaagt gtttaaatct ttacttattg gtttcaaaac ccattggtta agccttttaa  9240
actcatggta gttattttca agcattaaca tgaacttaaa ttcatcaagg ctaatctcta  9300
tatttgcctt gtgagttttc ttttgtgtta gttcttttaa taaccactca taaatcctca  9360
tagagtattt gttttcaaaa gacttaacat gttccagatt atattttatg aatttttta  9420
actggaaaag ataaggcaat atctcttcac taaaaactaa ttctaatttt tcgcttgaga  9480
acttggcata gtttgtccac tggaaaatct caaagccttt aaccaaagga ttcctgattt  9540
ccacagttct cgtcatcagc tctctggttg ctttagctaa tacaccataa gcattttccc  9600
```

```
tactgatgtt catcatctga gcgtattggt tataagtgaa cgataccgtc cgttctttcc  9660
ttgtagggtt ttcaatcgtg ggttgagta gtgccacaca gcataaaatt agcttggttt  9720
catgctccgt taagtcatag cgactaatcg ctagttcatt tgctttgaaa acaactaatt  9780
cagacataca tctcaattgg tctaggtgat tttaatcact ataccaattg agatgggcta  9840
gtcaatgata attactagtc cttttccttt gagttgtggg tatctgtaaa ttctgctaga  9900
cctttgctgg aaaacttgta aattctgcta gaccctctgt aaattccgct agacctttgt  9960
gtgttttttt tgtttatatt caagtggtta taatttatag aataaagaaa gaataaaaaa  10020
agataaaaag aatagatccc agccctgtgt ataactcact actttagtca gttccgcagt  10080
attacaaaag gatgtcgcaa acgctgtttg ctcctctaca aaacagacct taaaacccta  10140
aaggcttaag tagcaccctc gcaagctcgg gcaaatcgct gaatattcct tttgtctccg  10200
accatcaggc acctgagtcg ctgtcttttt cgtgacattc agttcgctgc gctcacggct  10260
ctggcagtga atgggggtaa atggcactac aggcgccttt tatggattca tgcaaggaaa  10320
ctacccataa tacaagaaaa gcccgtcacg ggcttctcag ggcgttttat ggcgggtctg  10380
ctatgtggtg ctatctgact ttttgctgtt cagcagttcc tgccctctga ttttccagtc  10440
tgaccacttc ggattatccc gtgacaggtc attcagactg gctaatgcac ccagtaaggc  10500
agcggtatca tcaacaggct tacccgtctt actgtcggat cgacgctctc ccttatgcga  10560
ctcctgcat                                                         10569

SEQ ID NO: 115          moltype = DNA  length = 10569
FEATURE                 Location/Qualifiers
misc_feature            1..10569
                        note = pRF861-nacETsite1 plasmid
source                  1..10569
                        mol_type = other DNA
                        organism = synthetic construct
SEQUENCE: 115
ccctttcgtc ttcgaataaa tacctgtgac ggaagatcac ttcgcagaat aaataaatcc  60
tggtgtccct gttgataccg ggaagccctg ggccaacttt tggcgaaaat gagacgttga  120
tcggcacgta agaggttcca actttcacca taatgaaata agatcactac cgggcgtatt  180
ttttgagtta tcgagatttt caggagctaa ggaagctaaa atggagaaaa aaatcactgg  240
atataccacc gttgatatat cccaatggca tcgtaaagaa cattttgagg catttcagtc  300
agttgctcaa tgtacctata accagaccgt tcagctggat attacggcct ttttaaagac  360
cgtaaagaaa aataagcaca agttttatcc ggcctttatt cacattcttg cccgcctgat  420
gaatgctcat ccggaattcc gtatggcaat gaaagacggt gagctggtga tatgggatag  480
tgttcaccct tgttacaccg ttttccatga gcaaactgaa acgttttcat cgctctggag  540
tgaataccac gacgatttcc ggcagtttct acacatatat tcgcaagatg tggcgtgtta  600
cggtgaaaac ctggcctatt tccctaaagg gtttattgag aatatgtttt tcgtctcagc  660
caatccctgg gtgagtttca ccagttttga tttaaacgtg gccaatatgg acaacttctt  720
cgcccccgtt ttcaccatgg gcaaatatta tacgcaaggc gacaaggtgc tgatgccgct  780
ggcgattcag gttcatcatg ccgtttgtga tggcttccat gtcggcagaa tgcttaatga  840
attacaacag tactgcgatg agtggcaggg cggggcgtaa tttttttaag gcagttattg  900
gtgcccttaa acgcctggtg ctacgcctga ataagtgata ataagcggat gaatggcaga  960
aattcgaaag caaattcgac ccggtcgtcg gttcagggca gggtcgttaa atagccgctt  1020
atgtctattg ctggtttatc ggtacccccc aactgatctt cagcatcttt tactttcacc  1080
agcgtttctg ggtgagcaaa aacaggaagg caaaatgccg caaaaaaggg aataagggcg  1140
acacggaaat gttgaatact catactcttc ctttttcaat attattgaag catttatcag  1200
ggttattgtc tcatgagcgg atacatattt gaatgtattt agaaaaataa acaaaagagt  1260
ttgtagaaac gcaaaaaggc catccgtcag gatggccttc tgcttaattt gatgcctggc  1320
agtttatggc gggcgtcctg cccgccaccc tccgggccgt tgcttcgcaa cgttcaaatc  1380
cgctcccggc ggatttgtcc tactcaggag agcgttcacc gacaaacaac agataaaacg  1440
aaaggcccag tctttcgact gagcctttcg ttttatttga tgcctggcag ttccctactc  1500
tcgcatgggg agaccccaca ctaccatcgg cgctacggcg tttcacttct gagttcggca  1560
tggggtcagg tgggaccacc gcgctactgc cgccaggcaa attctgtttt atcagaccgc  1620
ttctgcgttc tgatttaatc tgtatcaggc tgaaaatctt ctctcatccg ccaaaacagc  1680
caagcttagc ggccgcttag acctttcgct ttttcttggg atcggctctg gagtcgccac  1740
caagctgaga caggtcgatt cggtctcgt acaggccagt gatggactgg tgaatcaggg  1800
tggcatcgag aacctccttg gtggatgtgt accgctttcg gtcgatagtg gtatcgaagt  1860
acttgaaagc tgcaggagca cccaggttgg taagagtaaa caggtgaatg atgttctccg  1920
cctgttctcg aatgggtttg tcccgatgct tgttgtaggc agagagcacc ttgtccaagt  1980
tggcatcagc caggatgact cgcttcgaaa actcggaaat ctgctcgata atctcgtcga  2040
ggtaatgttt gtgctgctca acgaagagtt gcttctgttc gttgtcctcg ggagaaccct  2100
tgagcttctc gtagtgagaa gccagataga gaaagttgac gtacttcgaa ggcaaggcaa  2160
gctcgtttcc cttctgcagc tcgccagcgg aggcgagcat acgctttcga ccgttctcca  2220
gttcgaacag agagtacttg ggcagcttga taatgaggtc tttcttgacc tccttgtaac  2280
ccttggcttc caagaagtcg atgggattct tctcgaagct cgatcgctcc atgatggtaa  2340
ttccgagcag ctccttgacg gacttgagct tttggactt gcccttctcg accttcgcaa  2400
cgacaagcac ggaataggcg acggtaggag aatcgaagcc accgtatttc ttgggatccc  2460
agtctttctt tcgagcgatg agcttgtcgg agtttcgctt gggcagaatc gactccttgg  2520
agaatccgcc agtctgaacc tcggttttct tgacgatgtt gacctgaggc atcgacagaa  2580
cctttcgcac ggttgcaaag tctcgaccct tgtcccacac gatctctcca gtttcgccgt  2640
tggtctcgat aagtggtctc tttcgaatct ctccgttggc caaggtgatc tcggtcttga  2700
aaaagttcat gatgttggag taaaagaagt acttggcagt agccttgcca atctcctgtt  2760
cggacttggc aatcatcttt cgaacgtcgt agaccttgta atcgccgtaa acgaactcgc  2820
tttcgagctt ggggtatttc ttgatgagcg cagtgccaac gacggcgttg aggtaagcat  2880
cgtgggcatg gtggtaattg ttgatctctc gcaccttgta gaactgaaag tcctttcgga  2940
aatcggagac cagtttggac ttgagagtaa tcaccttgac ctctcggatg agcttgtcgt  3000
tctcgtcgta cttggtgttc atccgagaat cgagaatctg tgcgacgtgc tttgtgatct  3060
gtctggtctc gacgagttga cgcttgatga agccagcctt gtcgagctcg gacagaccgc  3120
ctcgctcggc cttggtaaga ttgtcgaact ttcgctgggt aatgagcttg gcgttgagca  3180
```

```
gctgtcgcca gtagttcttc atctttttga ccacctcttc gctgggaacg ttgtccgact  3240
tgcctctgtt cttgtcggat cgtgtaagga ccttgttgtc gatagaatcg tccttgagaa  3300
aggattgagg gacaatgtgg tccacatcgt agtcgctgag acgattgatg tccagttcct  3360
gatccacgta catgtctcga ccattctgca gatagtagag atacagcttc tcgttctgca  3420
gttgagtgtt ctcgacggga tgctccttga gaatctggga tcccagctcc ttgatgcctt  3480
cctcgattcg cttcatccgc tctcgcgagt tttctgacc  cttttgagtt gtctggttct  3540
ctctggccat ctcgatcaca atgttctcgg gcttgtgacg tcccatgacc ttcaccagct  3600
cgtcgacaac cttgacagtc tggagaatgc ctttcttgat ggctggcgaa ccagccaggt  3660
tggcaatatg ttcgtgcaag ctgtcgccct gaccggacac ttgtgccttc tggatgtcct  3720
ccttgaaggt aagagaatcg tcgtgaatga gctgcatgaa gtttcggttg gcaaagccat  3780
cggacttgag aaagtccaga atggtctttc cggactgctt gtctctgatg ccgttgatga  3840
gctttcgcga aagtcttccc cagccggtgt atctacgtcg cttgagttgt ttcatgacct  3900
tgtcgtcgaa caggtgagcg tatgtcttga gtcgttcctc gatcatctcc cgatcttcga  3960
acagggtaag agtgagcacg atgtcctcca gaatgtcctc gttttcctcg ttgtcgagaa  4020
aatccttgtc cttgataatc ttgagcagat cgtgataggt gcccaaagag gcgttgaatc  4080
ggtcctcaac tccggaaatc tcgacgctgt cgaaacactc gattttcttg aagtagtcct  4140
ccttgagctg cttaacagtg acctttcggt tggtcttgaa caggagatcg acaatggctt  4200
tcttctgttc gccagacaag aaggcaggct ttcgcattcc ctcggtaacg tacttgactt  4260
tggtgagttc gttgtagact gtaaagtact cgtagagcag cgaatgcttg ggaagaacct  4320
tctcgttggg cagattcttg tcgaagttgg tcattcgctc gatgaaggac tgtgcagagg  4380
caccccttgtc cacgacttcc tcgaagttcc agggagtgat ggtttcctcg gactttcgag  4440
tcatccaagc aaatcgagag tttcctctgg caagaggacc aacatagtag gggattcgaa  4500
aggtaagaat cttctcgatc ttctctcggt tgtccttgag aaaggggtag aagtcttcct  4560
gacgtcgaag aatggcgtgc agctcaccga ggtggatctg atgaggaatg ctgccgttgt  4620
cgaaggttcg ttgcttccga agcagatcct ctcgattgag cttgacaagc agttcctcgg  4680
ttccgtccat cttctcgaga attggcttga tgaacttgta gaactcttcc tgagaggctc  4740
cgccgtcgat gtatccagcg tagccgttct tcgactgatc gaaaaagatc tccttgtact  4800
tctcgggcag ttgctgtcgg acaagagcct tgagcagtgt gagatcctga tggtgctcgt  4860
cgtatcgctt gatcatggag gcagaaaggg gagcctttgt gatctcggtg ttgactcgca  4920
gaatgtcaga caagagaata gcatccgaaa ggttcttggc agcgagaaac aggtcggcgt  4980
actgatcgcc aatctgtgca agcaggttgt cgaggtcatc gtcgtaggtg tccttggaca  5040
gctggagctt ggcgtcctcc gccagatcga agttggactt gaagttgggt gtgagaccaa  5100
gagaaagggc aatgaggttg ccaaacagtc cgttcttttt ctcgccagga agttgggcaa  5160
tgaggttctc cagtcgtctg ctcttcgaga gtcgagcaga caagatggcc tttgcatcga  5220
ctccggaggc attgatgggg ttttcctcga acagctggtt gtaggtctga acgagctgaa  5280
tgaacagctt gtccacatcg ctgttgtcgg gattgagatc gccctcgatg aggaaatgac  5340
ctcgaaactt gatcatgtgt gccagagcga gatggataag tctgagatcc gccttgtcgg  5400
tggaatcgac gagtttcttt cgcaggtggt agatggtagg atacttctcg tggtaagcaa  5460
cctcgtccac aatgttgcca aagatgggat gacgctcgtg tttcttgtct tcctcgacga  5520
ggaaggattc ctccagtcga tgaaagaacg aatcgtccac cttggccatc tcgttggaaa  5580
agatctcctg caggtagcag attcggttct tccgtcgggt gtaacgtcgc cgagcagttc  5640
gcttgagtct ggtagcttcg gcagtctcgc cagaatcgaa caacagggca ccaatgaggt  5700
ttttcttgat ggagtgtcga tcggtgtttc cgaggacctt gaatttcttg gagggcacct  5760
tgtactcgtc ggtgatgaca gcccagccga cagagttggt tccaatgtcc aggccgatgg  5820
agtatttctt gtcgaattcc catatggtac cagctgcaga tctcgagctc ggatccttat  5880
cgtcatcgtc gtacagatcc cgacccattt gctgtccacc agtcatgcta gccataccat  5940
gatgatgatg atgatgagaa ccccccatgg ttaattcctc ctgttagccc aaaaaacggg  6000
tatggagaaa cagtagagag ttgcgataaa aagcgtcagg taggatccgc taatcttatg  6060
gataaaaatg ctatggcata gcaaagtgtg acgccgtgca aataatcaat gtggactttt  6120
ctgccgtgat tatagacact tttgttacgc gtttttgtca tggctttggt cccgctttgt  6180
tacagaatgc ttttaataag cggggttacc ggtttggtta gcgagaagag ccagtaaaag  6240
acgcagtgac ggcaatgtct gatgcaatat ggacaattgg tttcttctct gaatggcggg  6300
agtatgaaaa gtatggctga agcgcaaaat gatcccctgc tgccgggata ctcgtttaat  6360
gcccatctgg tggcgggttt aacgccgatt gaggccaacg gttatctcga tttttttatc  6420
gaccgaccgc tgggaatgaa aggttatatt ctcaatctca ccattcgcgg tcagggggtg  6480
gtgaaaaatc agggacgaga atttgtttgc cgaccgggtg atattttgct gttcccgcca  6540
ggagagattc atcactacgg tcgtcatccg gaggctcgcg aatggtatca ccagtgggtt  6600
tactttcgtc cgcgcgccta ctggcatgaa tggcttaact ggccgtcaat atttgccaat  6660
acggggttct ttcgcccgga tgaagcgcac cagccgcatt tcagcgacct gtttgggcaa  6720
atcattaacg ccgggcaagg ggaagggcgc tattcggagc tgctggcgat aaatctgctt  6780
gagcaattgt tactgcggcg catggaagcg attaacgagt cgctccatcc accgatggat  6840
aatcgggtac gcgaggcttg tcagtacatc agcgatcacc tggcagacag caattttgat  6900
atcgccagcg tcgcacagca tgtttgcttg tcgccgtcgc gtctgtcaca tcttttccgc  6960
cagcagttag ggattagcgt cttaagctgg cgcgaggacc aacgtatcag ccaggcgaag  7020
ctgcttttga gcaccacccg gatgcctatc gccaccgtcg gtcgcaatgt tggttttgac  7080
gatcaactct atttctcgcg ggtatttaaa aaatgcaccg gggccagccc gagcgagttc  7140
cgtgccggtt gtgaagaaaa agtgaatgat gtagccgtca agttgtcata attggtaacg  7200
aatcagacaa ttgacggccg tcccctggat tagctcgagc cgaacctccg ggaaaagttc  7260
gcgaaaagct ttaatgacct ctggcaagct ataacgtgcc tgagtatgcg tcgttgcaat  7320
agtgagaacg ccagacgtat cgttggtaaa caggtctgca agccgacgaa cattactggc  7380
ttcattcaga atacgttctg caatgaccag taatgctttg cccggttcag tcatgcccag  7440
cagtcgctta cctcgtcgaa caaatatttc gatgccaagt tcatcctcca gttcccgaat  7500
atgacggctg acgcctgact gtgaggtaaa aagcatattc gcaacctctg tcaggttgta  7560
atcctgacgt gcagcctcgc ggattatctt tagttgttgg aaattcacgg taaactccgg  7620
gcagttcaga tttcccgtta ttgttaaagt ctaatgcccg gcataacaaa taataaaaac  7680
ccgcatctta ttccatcccg atataacact tagctcacga agttcatgtt gcctccggtt  7740
tttaagaatc ggcccaagtg ccgccattac ttacaaccag attgcaagat gcttgccagt  7800
tttattttgg tgttgatgta caagctaacc aactgtcaaa taagagatta tgatagattc  7860
gtcatttgct cctttaatca gctgtcgcgt tcccctgccc tataaaagga gggtatgcac  7920
```

```
cacgatggtt cattacccaa taagattgaa agctcaccac tttgttgaaa ttgacagcaa  7980
acaaacaaaa aaatgcattt caccctttga catcaccatg cactgccatt aatatgcgcc  8040
ccgttcacac gattcctctg tagttcagtc ggtagaacgg cggactgtta atccgtatgt  8100
cactggttcg agtccagtca gaggagccaa attcaaaaaa gcctgctttc tagcaggctt  8160
tttgctttct aattaccaac gctcttaaaa catctgtctt gaaccagaac taatttgcaa  8220
gaatcataaa aaatttattt gctttcagga aaatttttct gtataataga ttcatatgca  8280
atacttcagc agccgtttta gagctagaaa tagcaagtta aaataaggct agtccgttat  8340
caacttgaaa aagtggcacc gagtcggtgc gactcctgtt gatagatcca gtaatgacct  8400
cagaactcca tctggatttg ttcagaacgc tcggttgccg ccgggcgttt tttattggtg  8460
agaatggttt attgactacc ggaagcagtg tgaccgtgtg cttctcaaat gcctcaggct  8520
gtctatgtgt gactgttgag ctgtaacaag ttgtctcagg tgttcaattt catgttctag  8580
ttgctttgtt ttactggttt cacctgttct attaggtgtt acatgctgtt catctgttac  8640
attgtcgatc tgttcatggt gaacagcttt aaatgcacca aaaactcgta aaagctctga  8700
tgtatctatc ttttttacac cgttttcatc tgtgcatatg gacagttttc cctttgatat  8760
ctaacggtga acagttgttc tacttttgtt tgttagtctt gatgcttcac tgatagatac  8820
aagagccata agaacctcag atccttccgt atttagccag tatgttctct agtgtggttc  8880
gttgtttttg cgtgagccat gagaacgaac cattgagatc atgcttactt tgcatgtcac  8940
tcaaaaattt tgcctcaaaa ctggtgagct gaatttttgc agttaaagca tcgtgtagtg  9000
tttttcttag tccgttacgt aggtaggaat ctgatgtaat ggttgttggt attttgtcac  9060
cattcatttt tatctggttg ttctcaagtt cggttacgag atccatttgt ctatctagtt  9120
caacttggaa aatcaacgta tcagtcgggc ggcctcgctt atcaaccacc aatttcatat  9180
tgctgtaagt gtttaaatct ttacttattg gtttcaaaac ccattggtta agccttttaa  9240
actcatggta gttattttca agcattaaca tgaacttaaa ttcatcaagg ctaatctcta  9300
tatttgcctt gtgagttttc ttttgtgtta gttcttttaa taaccactca taaatcctca  9360
tagagtattt gttttcaaaa gacttaacat gttccagatt atattttatg aatttttta  9420
actggaaaag ataaggcaat atctcttcac taaaaactaa ttctaatttt tcgcttgaga  9480
acttggcata gtttgtccac tggaaaatct caaagccttt aaccaaagga ttcctgattt  9540
ccacagttct cgtcatcagc tctctggttg ctttagctaa tacaccataa gcattttccc  9600
tactgatgtt catcatctga gcgtattggt tataagtgaa cgataccgtc cgttctttcc  9660
ttgtagggtt ttcaatcgtg gggttgagta gtgccacaca gcataaaatt agcttggttt  9720
catgctccgt taagtcatag cgactaatcg ctagttcatt tgctttgaaa acaactaatt  9780
cagacataca tctcaattgg tctaggtgat tttaatcact ataccaattg agatgggcta  9840
gtcaatgata attactagtc cttttccttt gagttgtggg tatctgtaaa ttctgctaga  9900
cctttgctgg aaaacttgta aattctgcta gaccctctgt aaattccgct agacctttgt  9960
gtgttttttt tgtttatatt caagtggtta taatttatag aataaagaaa gaataaaaaa  10020
agataaaaag aatagatccc agccctgtgt ataactcact actttagtca gttccgcagt  10080
attacaaaag gatgtcgcaa acgctgtttg ctcctctaca aaacagacct taaaacccta  10140
aaggcttaag tagcaccctc gcaagctcgg gcaaatcgct gaatattcct tttgtctccg  10200
accatcaggc acctgagtcg ctgtcttttt cgtgacattc agttcgctgc gctcacggct  10260
ctggcagtga atgggggtaa atggcactac aggcgccttt tatggattca tgcaaggaaa  10320
ctacccataa tacaagaaaa gcccgtcacg ggcttctcag ggcgttttat ggcgggtctg  10380
ctatgtggtg ctatctgact ttttgctgtt cagcagttcc tgccctctga ttttccagtc  10440
tgaccacttc ggattatccc gtgacaggtc attcagactg gctaatgcac ccagtaaggc  10500
agcggtatca tcaacaggct tacccgtctt actgtcggat cgacgctctc ccttatgcga  10560
ctcctgcat                                                         10569

SEQ ID NO: 116          moltype = DNA  length = 10569
FEATURE                 Location/Qualifiers
misc_feature            1..10569
                        note = pRF861-nacETsite2 plasmid
source                  1..10569
                        mol_type = other DNA
                        organism = synthetic construct
SEQUENCE: 116
ccctttcgtc ttcgaataaa tacctgtgac ggaagatcac ttcgcagaat aaataaatcc  60
tggtgtccct gttgataccg ggaagccctg ggccaacttt tggcgaaaat gagacgttga  120
tcggcacgta agaggttcca actttcacca taatgaaata agatcactac cgggcgtatt  180
ttttgagtta tcgagatttt caggagctaa ggaagctaaa atggagaaaa aaatcactgg  240
atataccacc gttgatatat cccaatggca tcgtaaagaa cattttgagg catttcagtc  300
agttgctcaa tgtacctata accagaccgt tcagctggat attacggcct ttttaaagac  360
cgtaaagaaa aataagcaca agttttatcc ggcctttatt cacattcttg cccgcctgat  420
gaatgctcat ccggaattcc gtatggcaat gaaagacggt gagctggtga tatgggatag  480
tgttcaccct tgttacaccg ttttccatga gcaaactgaa acgttttcat cgctctggag  540
tgaataccac gacgatttcc ggcagtttct acacatatat tcgcaagatg tggcgtgtta  600
cggtgaaaac ctggcctatt tccctaaagg gtttattgag aatatgtttt tcgtctcagc  660
caatccctgg gtgagtttca ccagttttga tttaaacgtg gccaatatgg acaacttctt  720
cgcccccgtt ttcaccatgg gcaaatatta tacgcaaggc gacaaggtgc tgatgccgct  780
ggcgattcag gttcatcatg ccgtttgtga tggcttccat gtcggcagaa tgcttaatga  840
attacaacag tactgcgatg agtggcaggg cggggcgtaa tttttttaag gcagttattg  900
gtgcccttaa acgcctggtg ctacgcctga ataagtgata ataagcggat gaatggcaga  960
aattcgaaag caaattcgac ccggtcgtcg gttcagggca gggtcgttaa atagccgctt  1020
atgtctattg ctggtttatc ggtacccccc aactgatctt cagcatcttt tactttcacc  1080
agcgtttctg ggtgagcaaa aacaggaagg caaaatgccg caaaaaaggg aataagggcg  1140
acacggaaat gttgaatact catactcttc ctttttcaat attattgaag catttatcag  1200
ggttattgtc tcatgagcgg atacatattt gaatgtattt agaaaaataa acaaaagagt  1260
ttgtagaaac gcaaaaaggc catccgtcag gatggccttc tgcttaattt gatgcctggc  1320
agtttatggc gggcgtcctg cccgccaccc tccgggccgt tgcttcgcaa cgttcaaatc  1380
cgctcccggc ggatttgtcc tactcaggag agcgttcacc gacaaacaac agataaaacg  1440
aaaggcccag tctttcgact gagcctttcg ttttatttga tgcctggcag ttccctactc  1500
```

-continued

```
tcgcatgggg agaccccaca ctaccatcgg cgctacggcg tttcacttct gagttcggca 1560
tggggtcagg tgggaccacc gcgctactgc cgccaggcaa attctgtttt atcagaccgc 1620
ttctgcgttc tgatttaatc tgtatcaggc tgaaaatctt ctctcatccg ccaaaacagc 1680
caagcttagc ggccgcttag acctttcgct ttttcttggg atcggctctg gagtcgccac 1740
caagctgaga caggtcgatt cggtctcgt acaggccagt gatggactgg tgaatcaggg 1800
tggcatcgag aacctccttg gtggatgtgt accgctttcg gtcgatagtg gtatcgaagt 1860
acttgaaagc tgcaggagca cccaggttgg taagagtaaa caggtgaatg atgttctccg 1920
cctgttctcg aatgggtttg tcccgatgct tgttgtaggc agagagcacc ttgtccaagt 1980
tggcatcagc caggatgact cgcttcgaaa actcggaaat ctgctcgata atctcgtcga 2040
ggtaatgttt gtgctgctca acgaagagtt gcttctgttc gttgtcctcg ggagaaccct 2100
tgagcttctc gtagtgagaa gccagataga gaaagttgac gtacttcgaa ggcaaggcaa 2160
gctcgtttcc cttctgcagc tcgccagcgg aggcgagcat acgctttcga ccgttctcca 2220
gttcgaacag agagtacttg ggcagcttga taatgaggtc tttcttgacc tccttgtaac 2280
ccttggcttc caagaagtcg atgggattct tctcgaagct cgatcgctcc atgatggtaa 2340
ttccgagcag ctccttgacg gacttgagct tttggactt gcccttctcg accttcgcaa 2400
cgacaagcac ggaataggcg acggtaggag aatcgaagcc accgtatttc ttgggatccc 2460
agtctttctt tcgagcgatg agcttgtcgg agtttcgctt gggcagaatc gactccttgg 2520
agaatccgcc agtctgaacc tcggttttct tgacgatgtt gacctgaggc atcgacagaa 2580
cctttcgcac ggttgcaaag tctcgaccct tgtcccacac gatctctcca gtttcgccgt 2640
tggtctcgat aagtggtctc tttcgaatct ctccgttggc caaggtgatc tcggtcttga 2700
aaaagttcat gatgttggag taaaagaagt acttggcagt agccttgcca atctcctgtt 2760
cggacttggc aatcatcttt cgaacgtcgt agaccttgta atcgccgtaa acgaactcgc 2820
tttcgagctt ggggtatttc ttgatgagcg cagtgccaac gacggcgttg aggtaagcat 2880
cgtgggcatg gtggtaattg ttgatctctc gcaccttgta gaactgaaag tcctttcgga 2940
aatcggagac cagtttggac ttgagagtaa tcaccttgac ctctcggatg agcttgtcgt 3000
tctcgtcgta cttggtgttc atccgagaat cgagaatctg tgcgacgtgc tttgtgatct 3060
gtctggtctc gacgagttga cgcttgatga agccagcctt gtcgagctcg gacagaccgc 3120
ctcgctcggc cttggtaaga ttgtcgaact ttcgctgggt aatgagcttg gcgttgagca 3180
gctgtcgcca gtagttcttc atctttttga ccacctcttc gctgggaacg ttgtccgact 3240
tgcctctgtt cttgtcggat cgtgtaagga ccttgttgtc gatagaatcg tccttgagaa 3300
aggattgagg gacaatgtgg tccacatcgt agtcgctgag acgattgatg tccagttcct 3360
gatccacgta catgtctcga ccattctgca gatagtagag atacagcttc tcgttctgca 3420
gttgagtgtt ctcgacggga tgctccttga gaatctggga tcccagctcc ttgatgcctt 3480
cctcgattcg cttcatccgc tctcgcgagt tttctgacc cttttgagtt gtctggttct 3540
ctctggccat ctcgatcaca atgttctcgg gcttgtgacg tcccatgacc ttcaccagct 3600
cgtcgacaac cttgacagtc tggagaatgc ctttcttgat ggctggcgaa ccagccaggt 3660
tggcaatatg ttcgtgcaag ctgtcgccct gaccggacac ttgtgccttc tggatgtcct 3720
ccttgaaggt aagagaatcg tcgtgaatga gctgcatgaa gtttcggttg gcaaagccat 3780
cggacttgag aaagtccaga atggtctttc cggactgctt gtctctgatg ccgttgatga 3840
gctttcgcga aagtcttccc cagccggtgt atctacgtcg cttgagttgt ttcatgacct 3900
tgtcgtcgaa caggtgagcg tatgtcttga gtcgttcctc gatcatctcc cgatcttcga 3960
acagggtaag agtgagcacg atgtcctcca gaatgtcctc gttttcctcg ttgtcgagaa 4020
aatccttgtc cttgataatc ttgagcagat cgtgataggt gcccaaagag gcgttgaatc 4080
ggtcctcaac tccggaaatc tcgacgctgt cgaaacactc gattttcttg aagtagtcct 4140
ccttgagctg cttaacagtg acctttcggt tggtcttgaa caggagatcg acaatggctt 4200
tcttctgttc gccagacaag aaggcaggct ttcgcattcc ctcggtaacg tacttgactt 4260
tggtgagttc gttgtagact gtaaagtact cgtagagcag cgaatgcttg ggaagaacct 4320
tctcgttggg cagattcttg tcgaagttgg tcattcgctc gatgaaggac tgtgcagagg 4380
caccttgtc cacgacttcc tcgaagttcc agggagtgat ggtttcctcg gactttcgag 4440
tcatccaagc aaatcgagag tttcctctgg caagaggacc aacatagtag gggattcgaa 4500
aggtaagaat cttctcgatc ttctctcggt tgtccttgag aaaggggtag aagtcttcct 4560
gacgtcgaag aatggcgtgc agctcaccga ggtggatctg atgaggaatg ctgccgttgt 4620
cgaaggttcg ttgcttccga agcagatcct ctcgattgag cttgacaagc agttcctcgg 4680
ttccgtccat cttctcgaga attggcttga tgaacttgta gaactcttcc tgagaggctc 4740
cgccgtcgat gtatccagcg tagccgttct tcgactgatc gaaaaagatc tccttgtact 4800
tctcgggcag ttgctgtcgg acaagagcct tgagcagtgt gagatcctga tggtgctcgt 4860
cgtatcgctt gatcatggag gcagaaaggg gagcctttgt gatctcggtg ttgactcgca 4920
gaatgtcaga caagagaata gcatccgaaa ggttcttggc agcgagaaac aggtcggcgt 4980
actgatcgcc aatctgtgca agcaggttgt cgaggtcatc gtcgtaggtg tccttggaca 5040
gctggagctt ggcgtcctcc gccagatcga agttggactt gaagttgggt gtgagaccaa 5100
gagaaagggc aatgaggttg ccaaacagtc cgttcttttt ctcgccagga agttgggcaa 5160
tgaggttctc cagtcgtctg ctcttcgaga gtcgagcaga caagatggcc tttgcatcga 5220
ctccggaggc attgatgggg ttttcctcga acagctggtt gtaggtctga acgagctgaa 5280
tgaacagctt gtccacatcg ctgttgtcgg gattgagatc gccctcgatg aggaaatgac 5340
ctcgaaactt gatcatgtgt gccagagcga gatggataag tctgagatcc gccttgtcgg 5400
tggaatcgac gagtttcttt cgcaggtggt agatggtagg atacttctcg tggtaagcaa 5460
cctcgtccac aatgttgcca aagatgggat gacgctcgtg tttcttgtct tcctcgacga 5520
ggaaggattc ctccagtcga tgaaagaacg aatcgtccac cttggccatc tcgttggaaa 5580
agatctcctg caggtagcag attcggttct tccgtcgggt gtaacgtcgc cgagcagttc 5640
gcttgagtct ggtagcttcg gcagtctcgc cagaatcgaa caacagggca ccaatgaggt 5700
ttttcttgat ggagtgtcga tcggtgtttc cgaggacctt gaatttcttg gagggcacct 5760
tgtactcgtc ggtgatgaca gcccagccga cagagttggt tccaatgtcc aggccgatgg 5820
agtatttctt gtcgaattcc catatggtac cagctgcaga tctcgagctc ggatccttat 5880
cgtcatcgtc gtacagatcc cgacccattt gctgtccacc agtcatgcta gccataccat 5940
gatgatgatg atgatgagaa ccccccatgg ttaattcctc ctgttagccc aaaaaacggg 6000
tatggagaaa cagtagagag ttgcgataaa aagcgtcagg taggatccgc taatcttatg 6060
gataaaaatg ctatggcata gcaaagtgtg acgccgtgca aataatcaat gtggactttt 6120
ctgccgtgat tatagacact tttgttacgc gtttttgtca tggctttggt cccgctttgt 6180
tacagaatgc ttttaataag cggggttacc ggtttggtta gcgagaagag ccagtaaaag 6240
```

```
acgcagtgac ggcaatgtct gatgcaatat ggacaattgg tttcttctct gaatggcggg  6300
agtatgaaaa gtatggctga agcgcaaaat gatcccctgc tgccgggata ctcgtttaat  6360
gcccatctgg tggcgggttt aacgccgatt gaggccaacg gttatctcga tttttttatc  6420
gaccgaccgc tgggaatgaa aggttatatt ctcaatctca ccattcgcgg tcagggggtg  6480
gtgaaaaatc agggacgaga atttgtttgc cgaccgggtg atattttgct gttcccgcca  6540
ggagagattc atcactacgg tcgtcatccg gaggctcgcg aatggtatca ccagtgggtt  6600
tactttcgtc cgcgcgccta ctggcatgaa tggcttaact ggccgtcaat atttgccaat  6660
acggggttct ttcgcccgga tgaagcgcac cagccgcatt tcagcgacct gtttgggcaa  6720
atcattaacg ccgggcaagg ggaagggcgc tattcggagc tgctggcgat aaatctgctt  6780
gagcaattgt tactgcggcg catggaagcg attaacgagt cgctccatcc accgatggat  6840
aatcgggtac gcgaggcttg tcagtacatc agcgatcacc tggcagacag caattttgat  6900
atcgccagcg tcgcacagca tgtttgcttg tcgccgtcgc gtctgtcaca tcttttccgc  6960
cagcagttag ggattagcgt cttaagctgg cgcgaggacc aacgtatcag ccaggcgaag  7020
ctgcttttga gcaccacccg gatgcctatc gccaccgtcg gtcgcaatgt tggttttgac  7080
gatcaactct atttctcgcg ggtatttaaa aaatgcaccg gggccagccc gagcgagttc  7140
cgtgccggtt gtgaagaaaa agtgaatgat gtagccgtca agttgtcata attggtaacg  7200
aatcagacaa ttgacggccg tcccctggat tagctcgagc cgaacctccg ggaaaagttc  7260
gcgaaaagct ttaatgacct ctggcaagct ataacgtgcc tgagtatgcg tcgttgcaat  7320
agtgagaacg ccagacgtat cgttggtaaa caggtctgca agccgacgaa cattactggc  7380
ttcattcaga atacgttctg caatgaccag taatgctttg cccggttcag tcatgcccag  7440
cagtcgctta cctcgtcgaa caaatatttc gatgccaagt tcatcctcca gttcccgaat  7500
atgacggctg acgcctgact gtgaggtaaa aagcatattc gcaacctctg tcaggttgta  7560
atcctgacgt gcagcctcgc ggattatctt tagttgttgg aaattcacgg taaactccgg  7620
gcagttcaga tttcccgtta ttgttaaagt ctaatgcccg gcataacaaa taataaaaac  7680
ccgcatctta ttccatcccg atataacact tagctcacga agttcatgtt gcctccggtt  7740
tttaagaatc ggcccaagtg ccgccattac ttacaaccag attgcaagat gcttgccagt  7800
tttattttgg tgttgatgta caagctaacc aactgtcaaa taagagatta tgatagattc  7860
gtcatttgct cctttaatca gctgtcgcgt tcccctgccc tataaaagga gggtatgcac  7920
cacgatggtt cattacccaa taagattgaa agctcaccac tttgttgaaa ttgacagcaa  7980
acaaacaaaa aaatgcattt caccctttga catcaccatg cactgccatt aatatgcgcc  8040
ccgttcacac gattcctctg tagttcagtc ggtagaacgg cggactgtta atccgtatgt  8100
cactggttcg agtccagtca gaggagccaa attcaaaaaa gcctgctttc tagcaggctt  8160
tttgctttct aattaccaac gctcttaaaa catctgtctt gaaccagaac taatttgcaa  8220
gaatcataaa aaatttattt gctttcagga aaatttttct gtataataga ttcaacaacc  8280
agcgctcagc cagcgtttta gagctagaaa tagcaagtta aaataaggct agtccgttat  8340
caacttgaaa aagtggcacc gagtcggtgc gactcctgtt gatagatcca gtaatgacct  8400
cagaactcca tctggatttg ttcagaacgc tcggttgccg ccgggcgttt tttattggtg  8460
agaatggttt attgactacc ggaagcagtg tgaccgtgtg cttctcaaat gcctcaggct  8520
gtctatgtgt gactgttgag ctgtaacaag ttgtctcagg tgttcaattt catgttctag  8580
ttgctttgtt ttactggttt cacctgttct attaggtgtt acatgctgtt catctgttac  8640
attgtcgatc tgttcatggt gaacagcttt aaatgcacca aaaactcgta aaagctctga  8700
tgtatctatc ttttttacac cgttttcatc tgtgcatatg gacagttttc cctttgatat  8760
ctaacggtga acagttgttc tacttttgtt tgttagtctt gatgcttcac tgatagatac  8820
aagagccata agaacctcag atccttccgt atttagccag tatgttctct agtgtggttc  8880
gttgtttttg cgtgagccat gagaacgaac cattgagatc atgcttactt tgcatgtcac  8940
tcaaaaattt tgcctcaaaa ctggtgagct gaatttttgc agttaaagca tcgtgtagtg  9000
tttttcttag tccgttacgt aggtaggaat ctgatgtaat ggttgttggt attttgtcac  9060
cattcatttt tatctggttg ttctcaagtt cggttacgag atccatttgt ctatctagtt  9120
caacttggaa aatcaacgta tcagtcgggc ggcctcgctt atcaaccacc aatttcatat  9180
tgctgtaagt gtttaaatct ttacttattg gtttcaaaac ccattggtta agccttttaa  9240
actcatggta gttattttca agcattaaca tgaacttaaa ttcatcaagg ctaatctcta  9300
tatttgcctt gtgagttttc ttttgtgtta gttcttttaa taaccactca taaatcctca  9360
tagagtattt gttttcaaaa gacttaacat gttccagatt atattttatg aatttttttta  9420
actggaaaag ataaggcaat atctcttcac taaaaactaa ttctaatttt tcgcttgaga  9480
acttggcata gtttgtccac tggaaaatct caaagccttt aaccaaagga ttcctgattt  9540
ccacagttct cgtcatcagc tctctggttg ctttagctaa tacaccataa gcattttccc  9600
tactgatgtt catcatctga gcgtattggt tataagtgaa cgataccgtc cgttctttcc  9660
ttgtagggtt ttcaatcgtg gggttgagta gtgccacaca gcataaaatt agcttggttt  9720
catgctccgt taagtcatag cgactaatcg ctagttcatt tgctttgaaa acaactaatt  9780
cagacataca tctcaattgg tctaggtgat tttaatcact ataccaattg agatgggcta  9840
gtcaatgata attactagtc cttttccttt gagttgtggg tatctgtaaa ttctgctaga  9900
cctttgctgg aaaacttgta aattctgcta gaccctctgt aaattccgct agacctttgt  9960
gtgttttttt tgtttatatt caagtggtta taatttatag aataaagaaa gaataaaaaa  10020
agataaaaag aatagatccc agccctgtgt ataactcact actttagtca gttccgcagt  10080
attacaaaag gatgtcgcaa acgctgtttg ctcctctaca aaacagacct taaaacccta  10140
aaggcttaag tagcaccctc gcaagctcgg gcaaatcgct gaatattcct tttgtctccg  10200
accatcaggc acctgagtcg ctgtcttttt cgtgacattc agttcgctgc gctcacggct  10260
ctggcagtga atgggggtaa atggcactac aggcgccttt tatggattca tgcaaggaaa  10320
ctacccataa tacaagaaaa gcccgtcacg ggcttctcag ggcgttttat ggcgggtctg  10380
ctatgtggtg ctatctgact ttttgctgtt cagcagttcc tgccctctga ttttccagtc  10440
tgaccacttc ggattatccc gtgacaggtc attcagactg gctaatgcac ccagtaaggc  10500
agcggtatca tcaacaggct tacccgtctt actgtcggat cgacgctctc ccttatgcga  10560
ctcctgcat                                                         10569
```

```
SEQ ID NO: 117          moltype = DNA  length = 1958
FEATURE                 Location/Qualifiers
source                  1..1958
                        mol_type = unassigned DNA
                        organism = Streptococcus pyogenes
```

```
SEQUENCE: 117
caatgtcgca atttcctgtg gcgtcccctg gattagctcg agccgaacct ccgggaaaag  60
ttcgcgaaaa gctttaatga cctctggcaa gctataacgt gcctgagtat gcgtcgttgc  120
aatagtgaga acgccagacg tatcgttggt aaacaggtct gcaagccgac gaacattact  180
ggcttcattc agaatacgtt ctgcaatgac cagtaatgct ttgcccggtt cagtcatgcc  240
cagcagtcgc ttacctcgtc gaacaaatat ttcgatgcca agttcatcct ccagttcccg  300
aatatgacgg ctgacgcctg actgtgaggt aaaaagcata ttcgcaacct ctgtcaggtt  360
gtaatcctga cgtgcagcct cgcggattat ctttagttgt tggaaattca cggtaaactc  420
cgggcagttc agatttcccg ttattgttaa agtctaatgc ccggcataac aaataataaa  480
aacccgcatc ttattccatc ccgatataac acttagctca ccaattgcca ctgccttttt  540
tccatcactg gagaactaat cactgacatt aacaactctt tcactgcctg tgcctgtggc  600
gataagttcg ctctggcggg taaatttaat gacaaagaga gactcatgga aggagtggta  660
atgcgtgaca tccacccatt tactgcgcca cataacgaac gcgcggccga ttcgggtaat  720
actgcaacgc ccatgccgct ggcaatcgct gcggtaagcg tggcaataga ctcaatttca  780
ccaataactt ttgccgtgag tcgccgtagg gaaaaagcct catcaacacg aagtctaata  840
gcactgtaat cactggggag aaagaggttc atttgcgcaa tagcattcac atcaacgctt  900
tgccccgggc aatcttgagt tcctaccaga aaaagatctt ctttcagcaa agcctgactg  960
gatacaccag ccacagggga atgctcataa atcaccgcca tatcgagttg gtgatttatc  1020
aatttttcgt taagcactgc accactattt tcatgaagat agataacgat ctccggaaat  1080
tcagcgcgaa ccgcctgtaa taagggcatg gtgatggatg acgcagcggt tcctggtgca  1140
aagccaatcg agacttgccc cgataatgcc tgaccaacgt tatgcaccgc cagttgggcc  1200
tgttcacact gacgtaaaat ggcccgcgca tgggtataga gaatttttcc ggcgtctgtt  1260
ggtgtaacgc cccgctttgt acggatcaaa agttgttgat ttaactcacc ttccagtgtg  1320
gcaacctgct ggctgagcgc tggttgtgcg atatgcaata cttcagcagc ctgggtcagg  1380
ctaccaatat ctacaatttt tacgaagtat ttcaggcgtc tgaagttcat gttgcctccg  1440
gtttttaaga atcggcccaa gtgccgccat tacttacaac cagattgcaa gatgcttgcc  1500
agttttattt tggtgttgat gtacaagcta accaactgtc aaataagaga ttatgataga  1560
ttcgtcattt gctcctttaa tcagctgtcg cgttcccctg ccctataaaa ggagggtatg  1620
caccacgatg gttcattacc caataagatt gaaagctcac cactttgttg aaattgacag  1680
caaacaaaca aaaaaatgca tttcaccctt tgacatcacc atgcactgcc attaatatgc  1740
gccccgttca cacgattcct ctgtagttca gtcggtagaa cggcggactg ttaatccgta  1800
tgtcactggt tcgagtccag tcagaggagc caaattcaaa aaagcctgct ttctagcagg  1860
ctttttgctt tctaattacc aacgctctta aaacatctgt cttgaaccag aactaatttg  1920
cacaggcatt cccgatcgac gttgcaacgc agcatttg                         1958

SEQ ID NO: 118         moltype = DNA  length = 1058
FEATURE                Location/Qualifiers
misc_feature           1..1058
                       note = edited nac locus
source                 1..1058
                       mol_type = other DNA
                       organism = synthetic construct
SEQUENCE: 118
caatgtcgca atttcctgtg gcgtcccctg gattagctcg agccgaacct ccgggaaaag  60
ttcgcgaaaa gctttaatga cctctggcaa gctataacgt gcctgagtat gcgtcgttgc  120
aatagtgaga acgccagacg tatcgttggt aaacaggtct gcaagccgac gaacattact  180
ggcttcattc agaatacgtt ctgcaatgac cagtaatgct ttgcccggtt cagtcatgcc  240
cagcagtcgc ttacctcgtc gaacaaatat ttcgatgcca agttcatcct ccagttcccg  300
aatatgacgg ctgacgcctg actgtgaggt aaaaagcata ttcgcaacct ctgtcaggtt  360
gtaatcctga cgtgcagcct cgcggattat ctttagttgt tggaaattca cggtaaactc  420
cgggcagttc agatttcccg ttattgttaa agtctaatgc ccggcataac aaataataaa  480
aacccgcatc ttattccatc ccgatataac acttagctca cgaagttcat gttgcctccg  540
gtttttaaga atcggcccaa gtgccgccat tacttacaac cagattgcaa gatgcttgcc  600
agttttattt tggtgttgat gtacaagcta accaactgtc aaataagaga ttatgataga  660
ttcgtcattt gctcctttaa tcagctgtcg cgttcccctg ccctataaaa ggagggtatg  720
caccacgatg gttcattacc caataagatt gaaagctcac cactttgttg aaattgacag  780
caaacaaaca aaaaaatgca tttcaccctt tgacatcacc atgcactgcc attaatatgc  840
gccccgttca cacgattcct ctgtagttca gtcggtagaa cggcggactg ttaatccgta  900
tgtcactggt tcgagtccag tcagaggagc caaattcaaa aaagcctgct ttctagcagg  960
ctttttgctt tctaattacc aacgctctta aaacatctgt cttgaaccag aactaatttg  1020
cacaggcatt cccgatcgac gttgcaacgc agcatttg                         1058

SEQ ID NO: 119         moltype = DNA  length = 20
FEATURE                Location/Qualifiers
misc_feature           1..20
                       note = primer
source                 1..20
                       mol_type = other DNA
                       organism = synthetic construct
SEQUENCE: 119
caatgtcgca atttcctgtg                                             20

SEQ ID NO: 120         moltype = DNA  length = 19
FEATURE                Location/Qualifiers
misc_feature           1..19
                       note = primer
source                 1..19
                       mol_type = other DNA
                       organism = synthetic construct
```

```
SEQUENCE: 120
caaatgctgc gttgcaacg                                              19

SEQ ID NO: 121          moltype = DNA  length = 4104
FEATURE                 Location/Qualifiers
source                  1..4104
                        mol_type = unassigned DNA
                        organism = Streptococcus pyogenes
SEQUENCE: 121
atggataaaa aatacagcat tggtctggat atcggaacca acagcgttgg gtgggcagta  60
ataacagatg aatacaaagt gccgtcaaaa aaatttaagg ttctggggaa tacagatcgc  120
cacagcataa aaaagaatct gattggggca ttgctgtttg attcgggtga gacagctgag  180
gccacgcgtc tgaaacgtac agcaagaaga cgttacacac gtcgtaaaaa tcgtatttgc  240
tacttacagg aaattttttc taacgaaatg gccaaggtag atgatagttt cttccatcgt  300
ctcgaagaat cttttctggt tgaggaagat aaaaaacacg aacgtcaccc tatctttggc  360
aatatcgtgg atgaagtggc ctatcatgaa aaataccct a cgatttatca tcttcgcaag  420
aagttggttg atagtacgga caaagcggat ctgcgtttaa tctatcttgc gttagcgcac  480
atgatcaaat ttcgtggtca tttcttaatt gaaggtgatc tgaatcctga taactctgat  540
gtggacaaat tgtttataca attagtgcaa acctataatc agctgttcga ggaaaacccc  600
attaatgcct ctggagttga tgccaaagcg attttaagcg cgagactttc taagtcccgg  660
cgtctggaga atctgatcgc ccagttacca ggggaaaaga aaaatggtct gtttggtaat  720
ctgattgccc tcagtctggg gcttaccccg aacttcaaat ccaattttga cctggctgag  780
gacgcaaagc tgcagctgag caaagatact tatgatgatg acctcgacaa tctgctcgcc  840
cagattggtg accaatatgc ggatctgttt ctggcagcga agaatctttc ggatgctatc  900
ttgctgtcgg atattctgcg tgttaatacc gaaatcacca aagcgcctct gtctgcaagt  960
atgatcaaga gatacgacga gcaccaccag gacctgactc ttcttaaggc actggtacgc  1020
caacagcttc cggagaaata caaagaaata ttcttcgacc agtccaagaa tggttacgcg  1080
ggctacatcg atggtggtgc atcacaggaa gagttctata aatttattaa accaatcctt  1140
gagaaaatgg atggcacgga agagttactt gttaaactta accgcgaaga cttgcttaga  1200
aagcaacgta cattcgacaa cggctccatc ccacaccaga ttcatttagg tgaacttcac  1260
gccatcttgc gcagacaaga agatttctat cccttcttaa aagacaatcg ggagaaaatc  1320
gagaagatcc tgacgttccg cattccctat tatgtcggtc ccctggcacg tggtaattct  1380
cggtttgcct ggatgacgcg caaaagtgag gaaaccatca ccccttggaa ctttgaagaa  1440
gtcgtggata aaggtgctag cgcgcagtct tttatagaaa gaatgacgaa cttcgataaa  1500
aacttgccca acgaaaaagt cctgcccaag cactctcttt tatatgagta ctttactgtg  1560
tacaacgaac tgactaaagt gaaatacgtt acggaaggta tgcgcaaacc tgcctttctt  1620
agtggcgagc agaaaaaagc aattgtcgat cttctcttta aaacgaatcg caaggtaact  1680
gtaaaacagc tgaaggaaga ttatttcaaa aagatcgaat gctttgattc tgtcgagatc  1740
tcgggtgtcg aagatcgttt caacgcttcc ttagggacct atcatgattt gctgaagata  1800
ataaaagaca aagactttct cgacaatgaa gaaaatgaag atattctgga ggatattgtt  1860
ttgaccttga ccttattcga agatagagag atgatcgagg agcgcttaaa aacctatgcc  1920
cacctgtttg atgacaaagt catgaagcaa ttaaagcgcc gcagatatac ggggtggggc  1980
cgcttgagcc gcaagttgat taacggtatt agagacaagc agagcggaaa aactatcctg  2040
gatttcctca aatctgacgg atttgcgaac cgcaatttta tgcagcttat acatgatgat  2100
tcgcttacat tcaaagagga tattcagaag gctcaggtgt ctgggcaagg tgattcactc  2160
cacgaacata tagcaaattt ggccggctct cctgcgatta agaaggggat cctgcaaaca  2220
gttaaagttg tggatgaact tgtaaaagta atgggccgcc acaagccgga gaatatcgtg  2280
atagaaatgg cgcgcgagaa tcaaacgaca caaaaaggtc aaaagaactc aagagagaga  2340
atgaagcgca ttgaggaggg gataaaggaa cttggatctc aaattctgaa agaacatcca  2400
gttgaaaaca ctcagctgca aaatgaaaaa ttgtacctgt actacctgca gaatggaaga  2460
gacatgtacg tggatcagga attggatatc aatagactct cggactatga cgtagatcac  2520
attgtccctc agagcttcct caaggatgat tctatagata ataaagtact tacgagatcg  2580
gacaaaaatc gcggtaaatc ggataacgtc ccatcggagg aagtcgttaa aaagatgaaa  2640
aactattggc gtcaactgct gaacgccaag ctgatcacac agcgtaagtt tgataatctg  2700
actaaagccg aacgcggtgg tcttagtgaa ctcgataaag caggatttat aaaacggcag  2760
ttagtagaaa cgcgccaaat tacgaaacac gtggctcaga tcctcgattc tagaatgaat  2820
acaaagtacg atgaaaacga taaactgatc cgtgaagtaa aagtcattac cttaaaatct  2880
aaacttgtgt ccgatttccg caaagatttt cagttttaca aggtccggga aatcaataac  2940
tatcaccatg cacatgatgc atatttaaat gcggttgtag gcacggccct tattaagaaa  3000
taccctaaac tcgaaagtga gtttgtttat ggggattata aagtgtatga cgttcgcaaa  3060
atgatcgcga aatcagaaca ggaaatcggt aaggctaccg ctaaatactt tttttattcc  3120
aacattatga atttttttaa gaccgaaata actctcgcga atggtgaaat ccgtaaacgg  3180
cctcttatag aaaccaatgg tgaaacggga gaaatcgttt gggataaagg tcgtgacttt  3240
gccaccgttc gtaaagtcct ctcaatgccg caagttaaca ttgtcaagaa gacggaagtt  3300
caaacagggg gattctccaa agaatctatc ctgccgaagc gtaacagtga taaacttatt  3360
gccagaaaaa aagattggga tccaaaaaaa tacggaggct ttgattcccc taccgtcgcg  3420
tatagtgtgc tggtggttgc taaagtcgag aaagggaaaa gcaagaaatt gaaatcagtt  3480
aaagaactgc tgggtattac aattatggaa agatcgtcct ttgagaaaaa tccgatcgac  3540
tttttagagg ccaaggggta taaggaagtg aaaaaagatc tcatcatcaa attaccgaag  3600
tatagtcttt ttgagctgga aaacggcaga aaaagaatgc tggcctccgc gggcgagtta  3660
cagaagggaa atgagctggc gctgccttcc aaatatgtta attttctgta ccttgccagt  3720
cattatgaga aactgaaggg cagccccgaa gataacgaac agaaacaatt attcgtggaa  3780
cagcataagc actatttaga tgaaattata gagcaaatta gtgaattttc taagcgcgtt  3840
atcctcgcgg atgctaattt agacaaagta ctgtcagctt ataataaaca tcgggataag  3900
ccgattagag aacaggccga aaatatcatt catttgttta ccttaaccaa ccttggagca  3960
ccagctgcct tcaaatattt cgataccaca attgatcgta aacggtatac aagtacaaaa  4020
gaagtcttgg acgcaaccct cattcatcaa tctattactg gattatatga gacacgcatt  4080
gatctttcac agctgggcgg agac                                        4104
```

```
SEQ ID NO: 122          moltype = DNA  length = 4104
FEATURE                 Location/Qualifiers
misc_feature            1..4104
                        note = synthesized Cas9 Y155H DNA
source                  1..4104
                        mol_type = other DNA
                        organism = synthetic construct
SEQUENCE: 122
atggataaaa aatacagcat tggtctggat atcggaacca acagcgttgg gtgggcagta  60
ataacagatg aatacaaagt gccgtcaaaa aaatttaagg ttctggggaa tacagatcgc  120
cacagcataa aaaagaatct gattggggca ttgctgtttg attcgggtga gacagctgag  180
gccacgcgtc tgaaacgtac agcaagaaga cgttacacac gtcgtaaaaa tcgtatttgc  240
tacttacagg aaattttttc taacgaaatg gccaaggtag atgatagttt cttccatcgt  300
ctcgaagaat cttttctggt tgaggaagat aaaaaacacg aacgtcaccc tatctttggc  360
aatatcgtgg atgaagtggc ctatcatgaa aaataccccta cgatttatca tcttcgcaag  420
aagttggttg atagtacgga caaagcggat ctgcgtttaa tccatcttgc gttagcgcac  480
atgatcaaat ttcgtggtca tttcttaatt gaaggtgatc tgaatcctga taactctgat  540
gtggacaaat tgtttataca attagtgcaa acctataatc agctgttcga ggaaaacccc  600
attaatgcct ctggagttga tgccaaagcg attttaagcg cgagactttc taagtcccgg  660
cgtctggaga atctgatcgc ccagttacca ggggaaaaga aaaatggtct gtttggtaat  720
ctgattgccc tcagtctggg gcttaccccg aacttcaaat ccaattttga cctggctgag  780
gacgcaaagc tgcagctgag caaagatact tatgatgatg acctcgacaa tctgctcgcc  840
cagattggtg accaatatgc ggatctgttt ctggcagcga agaatctttc ggatgctatc  900
ttgctgtcgg atattctgcg tgttaatacc gaaatcacca aagcgcctct gtctgcaagt  960
atgatcaaga gatacgacga gcaccaccag gacctgactc ttcttaaggc actggtacgc  1020
caacagcttc cggagaaata caaagaaata ttcttcgacc agtccaagaa tggttacgcg  1080
ggctacatcg atggtggtgc atcacaggaa gagttctata aatttattaa accaatcctt  1140
gagaaaatgg atggcacgga agagttactt gttaaactta accgcgaaga cttgcttaga  1200
aagcaacgta cattcgacaa cggctccatc ccacaccaga ttcatttagg tgaacttcac  1260
gccatcttgc gcagacaaga agatttctat cccttcttaa aagacaatcg ggagaaaatc  1320
gagaagatcc tgacgttccg cattccctat tatgtcggtc ccctggcacg tggtaattct  1380
cggtttgcct ggatgacgcg caaaagtgag gaaaccatca ccccttggaa ctttgaagaa  1440
gtcgtggata aaggtgctag cgcgcagtct tttatagaaa gaatgacgaa cttcgataaa  1500
aacttgccca acgaaaaagt cctgcccaag cactctcttt tatatgagta ctttactgtg  1560
tacaacgaac tgactaaagt gaaatacgtt acggaaggta tgcgcaaacc tgcctttctt  1620
agtggcgagc agaaaaaagc aattgtcgat cttctcttta aaacgaatcg caaggtaact  1680
gtaaaacagc tgaaggaaga ttatttcaaa aagatcgaat gctttgattc tgtcgagatc  1740
tcgggtgtcg aagatcgttt caacgcttcc ttagggacct atcatgattt gctgaagata  1800
ataaaagaca aagactttct cgacaatgaa gaaaatgaag atattctgga ggatattgtt  1860
ttgaccttga ccttattcga agatagagag atgatcgagg agcgcttaaa aacctatgcc  1920
cacctgtttg atgacaaagt catgaagcaa ttaaagcgcc gcagatatac ggggtggggc  1980
cgcttgagcc gcaagttgat taacggtatt agagacaagc agagcggaaa aactatcctg  2040
gatttcctca aatctgacgg atttgcgaac cgcaatttta tgcagcttat acatgatgat  2100
tcgcttacat tcaaagagga tattcagaag gctcaggtgt ctgggcaagg tgattcactc  2160
cacgaacata tagcaaattt ggccggctct cctgcgatta agaaggggat cctgcaaaca  2220
gttaaagttg tggatgaact tgtaaaagta atgggccgcc acaagccgga gaatatcgtg  2280
atagaaatgg cgcgcgagaa tcaaacgaca caaaaaggtc aaaagaactc aagagagaga  2340
atgaagcgca ttgaggaggg gataaaggaa cttggatctc aaattctgaa agaacatcca  2400
gttgaaaaca ctcagctgca aaatgaaaaa ttgtacctgt actacctgca gaatggaaga  2460
gacatgtacg tggatcagga attggatatc aatagactct cggactatga cgtagatcac  2520
attgtccctc agagcttcct caaggatgat tctatagata ataaagtact tacgagatcg  2580
gacaaaaatc gcggtaaatc ggataacgtc ccatcggagg aagtcgttaa aaagatgaaa  2640
aactattggc gtcaactgct gaacgccaag ctgatcacac agcgtaagtt tgataatctg  2700
actaaagccg aacgcggtgg tcttagtgaa ctcgataaag caggatttat aaaacggcag  2760
ttagtagaaa cgcgccaaat tacgaaacac gtggctcaga tcctcgattc tagaatgaat  2820
acaaagtacg atgaaaacga taaactgatc cgtgaagtaa aagtcattac cttaaaatct  2880
aaacttgtgt ccgatttccg caaagatttt cagttttaca aggtccggga aatcaataac  2940
tatcaccatg cacatgatgc atatttaaat gcggttgtag gcacggccct tattaagaaa  3000
taccctaaac tcgaaagtga gtttgtttat ggggattata aagtgtatga cgttcgcaaa  3060
atgatcgcga aatcagaaca ggaaatcggt aaggctaccg ctaaatactt tttttattcc  3120
aacattatga attttttttaa gaccgaaata actctcgcga atggtgaaat ccgtaaacgg  3180
cctcttatag aaaccaatgg tgaaacggga gaaatcgttt gggataaagg tcgtgacttt  3240
gccaccgttc gtaaagtcct ctcaatgccg caagttaaca ttgtcaagaa gacggaagtt  3300
caaacagggg gattctccaa agaatctatc ctgccgaagc gtaacagtga taaacttatt  3360
gccagaaaaa aagattggga tccaaaaaaa tacggaggct ttgattcccc taccgtcgcg  3420
tatagtgtgc tggtggttgc taaagtcgag aaagggaaaa gcaagaaatt gaaatcagtt  3480
aaagaactgc tgggtattac aattatggaa agatcgtcct ttgagaaaaa tccgatcgac  3540
tttttagagg ccaaggggta taaggaagtg aaaaaagatc tcatcatcaa attaccgaag  3600
tatagtcttt ttgagctgga aaacggcaga aaaagaatgc tggcctccgc gggcgagtta  3660
cagaagggaa atgagctggc gctgccttcc aaatatgtta attttctgta ccttgccagt  3720
cattatgaga aactgaaggg cagccccgaa gataacgaac agaaacaatt attcgtggaa  3780
cagcataagc actatttaga tgaaattata gagcaaatta gtgaattttc taagcgcgtt  3840
atcctcgcgg atgctaattt agacaaagta ctgtcagctt ataataaaca tcgggataag  3900
ccgattagag aacaggccga aaatatcatt catttgttta ccttaaccaa ccttggagca  3960
ccagctgcct tcaaatattt cgataccaca attgatcgta aacggtatac aagtacaaaa  4020
gaagtcttgg acgcaaccct cattcatcaa tctattactg gattatatga gacacgcatt  4080
gatctttcac agctgggcgg agac                                          4104

SEQ ID NO: 123          moltype = AA  length = 1368
```

```
FEATURE                 Location/Qualifiers
REGION                  1..1368
                        note = synthesized Cas9 Y155N variant
source                  1..1368
                        mol_type = protein
                        organism = synthetic construct
SEQUENCE: 123
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLINLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 124          moltype = DNA  length = 4104
FEATURE                 Location/Qualifiers
misc_feature            1..4104
                        note = synthesized Cas9 Y155N
source                  1..4104
                        mol_type = other DNA
                        organism = synthetic construct
SEQUENCE: 124
atggataaaa aatacagcat tggtctggat atcggaacca acagcgttgg gtgggcagta  60
ataacagatg aatacaaagt gccgtcaaaa aaatttaagg ttctggggaa tacagatcgc  120
cacagcataa aaaagaatct gattggggca ttgctgtttg attcgggtga gacagctgag  180
gccacgcgtc tgaaacgtac agcaagaaga cgttacacac gtcgtaaaaa tcgtatttgc  240
tacttacagg aaattttttc taacgaaatg gccaaggtag atgatagttt cttccatcgt  300
ctcgaagaat cttttctggt tgaggaagat aaaaaacacg aacgtcaccc tatctttggc  360
aatatcgtgg atgaagtggc ctatcatgaa aaatacccta cgatttatca tcttcgcaag  420
aagttggttg atagtacgga caaagcggat ctgcgtttaa tcaatcttgc gttagcgcac  480
atgatcaaat ttcgtggtca tttcttaatt gaaggtgatc tgaatcctga taactctgat  540
gtggacaaat tgtttataca attagtgcaa acctataatc agctgttcga ggaaaacccc  600
attaatgcct ctggagttga tgccaaagcg attttaagcg cgagactttc taagtcccgg  660
cgtctggaga atctgatcgc ccagttacca ggggaaaaga aaaatggtct gtttggtaat  720
ctgattgccc tcagtctggg gcttaccccg aacttcaaat ccaattttga cctggctgag  780
gacgcaaagc tgcagctgag caaagatact tatgatgatg acctcgacaa tctgctcgcc  840
cagattggtg accaatatgc ggatctgttt ctggcagcga agaatctttc ggatgctatc  900
ttgctgtcgg atattctgcg tgttaatacc gaaatcacca aagcgcctct gtctgcaagt  960
atgatcaaga gatacgacga gcaccaccag gacctgactc ttcttaaggc actggtacgc  1020
caacagcttc cggagaaata caaagaaata ttcttcgacc agtccaagaa tggttacgcg  1080
ggctacatcg atggtggtgc atcacaggaa gagttctata aatttattaa accaatcctt  1140
gagaaaatgg atggcacgga agagttactt gttaaactta accgcgaaga cttgcttaga  1200
aagcaacgta cattcgacaa cggctccatc ccacaccaga ttcatttagg tgaacttcac  1260
gccatcttgc gcagacaaga agatttctat cccttcttaa aagacaatcg ggagaaaatc  1320
gagaagatcc tgacgttccg cattccctat tatgtcggtc ccctggcacg tggtaattct  1380
cggtttgcct ggatgacgcg caaaagtgag gaaaccatca ccccttggaa ctttgaagaa  1440
gtcgtggata aaggtgctag cgcgcagtct tttatagaaa gaatgacgaa cttcgataaa  1500
aacttgccca acgaaaaagt cctgcccaag cactctcttt tatatgagta ctttactgtg  1560
tacaacgaac tgactaaagt gaaatacgtt acggaaggta tgcgcaaacc tgcctttctt  1620
agtggcgagc agaaaaaagc aattgtcgat cttctcttta aaacgaatcg caaggtaact  1680
gtaaaacagc tgaaggaaga ttatttcaaa aagatcgaat gctttgattc tgtcgagatc  1740
tcgggtgtcg aagatcgttt caacgcttcc ttagggacct atcatgattt gctgaagata  1800
ataaaagaca aagactttct cgacaatgaa gaaaatgaag atattctgga ggatattgtt  1860
ttgaccttga ccttattcga agatagagag atgatcgagg agcgcttaaa aacctatgcc  1920
cacctgtttg atgacaaagt catgaagcaa ttaaagcgcc gcagatatac ggggtggggc  1980
cgcttgagcc gcaagttgat taacggtatt agagacaagc agagcggaaa aactatcctg  2040
gatttcctca aatctgacgg atttgcgaac cgcaatttta tgcagcttat acatgatgat  2100
tcgcttacat tcaaagagga tattcagaag gctcaggtgt ctgggcaagg tgattcactc  2160
cacgaacata tagcaaattt ggccggctct cctgcgatta agaaggggat cctgcaaaca  2220
gttaaagttg tggatgaact tgtaaaagta atgggccgcc acaagccgga gaatatcgtg  2280
atagaaatgg cgcgcgagaa tcaaacgaca caaaaaggtc aaaagaactc aagagagaga  2340
atgaagcgca ttgaggaggg gataaaggaa cttggatctc aaattctgaa agaacatcca  2400
```

```
gttgaaaaca ctcagctgca aaatgaaaaa ttgtacctgt actacctgca gaatggaaga  2460
gacatgtacg tggatcagga attggatatc aatagactct cggactatga cgtagatcac  2520
attgtccctc agagcttcct caaggatgat tctatagata ataaagtact tacgagatcg  2580
gacaaaaatc gcggtaaatc ggataacgtc ccatcggagg aagtcgttaa aaagatgaaa  2640
aactattggc gtcaactgct gaacgccaag ctgatcacac agcgtaagtt tgataatctg  2700
actaaagccg aacgcggtgg tcttagtgaa ctcgataaag caggatttat aaaacggcag  2760
ttagtagaaa cgcgccaaat tacgaaacac gtggctcaga tcctcgattc tagaatgaat  2820
acaaagtacg atgaaaacga taaactgatc cgtgaagtaa aagtcattac cttaaaatct  2880
aaacttgtgt ccgatttccg caaagatttt cagttttaca aggtccggga aatcaataac  2940
tatcaccatg cacatgatgc atatttaaat gcggttgtag gcacggccct tattaagaaa  3000
taccctaaac tcgaaagtga gtttgtttat ggggattata aagtgtatga cgttcgcaaa  3060
atgatcgcga aatcagaaca ggaaatcggt aaggctaccg ctaaatactt tttttattcc  3120
aacattatga attttttttaa gaccgaaata actctcgcga atggtgaaat ccgtaaacgg  3180
cctcttatag aaaccaatgg tgaaacggga gaaatcgttt gggataaagg tcgtgacttt  3240
gccaccgttc gtaaagtcct ctcaatgccg caagttaaca ttgtcaagaa gacggaagtt  3300
caaacagggg gattctccaa agaatctatc ctgccgaagc gtaacagtga taaacttatt  3360
gccagaaaaa aagattggga tccaaaaaaa tacggaggct ttgattcccc taccgtcgcg  3420
tatagtgtgc tggtggttgc taaagtcgag aaagggaaaa gcaagaaatt gaaatcagtt  3480
aaagaactgc tgggtattac aattatggaa agatcgtcct ttgagaaaaa tccgatcgac  3540
tttttagagg ccaaggggta taaggaagtg aaaaaagatc tcatcatcaa attaccgaag  3600
tatagtcttt ttgagctgga aaacggcaga aaaagaatgc tggcctccgc gggcgagtta  3660
cagaagggaa atgagctggc gctgccttcc aaatatgtta attttctgta ccttgccagt  3720
cattatgaga aactgaaggg cagcccccgaa gataacgaac agaaacaatt attcgtggaa  3780
cagcataagc actatttaga tgaaattata gagcaaatta gtgaattttc taagcgcgtt  3840
atcctcgcgg atgctaattt agacaaagta ctgtcagctt ataataaaca tcgggataag  3900
ccgattagag aacaggccga aaatatcatt catttgttta ccttaaccaa ccttggagca  3960
ccagctgcct tcaaatattt cgataccaca attgatcgta aacggtatac aagtacaaaa  4020
gaagtcttgg acgcaaccct cattcatcaa tctattactg gattatatga gacacgcatt  4080
gatctttcac agctgggcgg agac                                          4104

SEQ ID NO: 125         moltype = AA  length = 1368
FEATURE                Location/Qualifiers
REGION                 1..1368
                       note = synthesized Cas9 Y155E
source                 1..1368
                       mol_type = protein
                       organism = synthetic construct
SEQUENCE: 125
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIELALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD               1368

SEQ ID NO: 126         moltype = DNA  length = 4104
FEATURE                Location/Qualifiers
misc_feature           1..4104
                       note = synthesized Cas9 Y155E
source                 1..4104
                       mol_type = other DNA
                       organism = synthetic construct
SEQUENCE: 126
atggataaaa aatacagcat tggtctggat atcggaacca acagcgttgg gtgggcagta  60
ataacagatg aatacaaagt gccgtcaaaa aaatttaagg ttctggggaa tacagatcgc  120
cacagcataa aaaagaatct gattggggca ttgctgtttg attcgggtga gacagctgag  180
gccacgcgtc tgaaacgtac agcaagaaga cgttacacac gtcgtaaaaa tcgtatttgc  240
tacttacagg aaatttttc taacgaaatg gccaaggtag atgatagttt cttccatcgt  300
ctcgaagaat cttttctggt tgaggaagat aaaaaacacg aacgtcaccc tatctttggc  360
aatatcgtgg atgaagtggc ctatcatgaa aaataccta cgatttatca tcttcgcaag  420
aagttggttg atagtacgga caaagcggat ctgcgtttaa tcgagcttgc gttagcgcac  480
atgatcaaat ttcgtggtca tttcttaatt gaaggtgatc tgaatcctga taactctgat  540
```

```
gtggacaaat tgtttataca attagtgcaa acctataatc agctgttcga ggaaaacccc  600
attaatgcct ctggagttga tgccaaagcg attttaagcg cgagactttc taagtcccgg  660
cgtctggaga atctgatcgc ccagttacca ggggaaaaga aaaatggtct gtttggtaat  720
ctgattgccc tcagtctggg gcttaccccg aacttcaaat ccaattttga cctggctgag  780
gacgcaaagc tgcagctgag caaagatact tatgatgatg acctcgacaa tctgctcgcc  840
cagattggtg accaatatgc ggatctgttt ctggcagcga agaatctttc ggatgctatc  900
ttgctgtcgg atattctgcg tgttaatacc gaaatcacca aagcgcctct gtctgcaagt  960
atgatcaaga gatacgacga gcaccaccag gacctgactc ttcttaaggc actggtacgc  1020
caacagcttc cggagaaata caaagaaata ttcttcgacc agtccaagaa tggttacgcg  1080
ggctacatcg atggtggtgc atcacaggaa gagttctata aatttattaa accaatcctt  1140
gagaaaatgg atggcacgga agagttactt gttaaactta accgcgaaga cttgcttaga  1200
aagcaacgta cattcgacaa cggctccatc ccacaccaga ttcatttagg tgaacttcac  1260
gccatcttgc gcagacaaga agatttctat cccttcttaa aagacaatcg ggagaaaatc  1320
gagaagatcc tgacgttccg cattccctat tatgtcggtc ccctggcacg tggtaattct  1380
cggtttgcct ggatgacgcg caaaagtgag gaaaccatca ccccttggaa ctttgaagaa  1440
gtcgtggata aaggtgctag cgcgcagtct tttatagaaa gaatgacgaa cttcgataaa  1500
aacttgccca acgaaaaagt cctgcccaag cactctcttt tatatgagta ctttactgtg  1560
tacaacgaac tgactaaagt gaaatacgtt acggaaggta tgcgcaaacc tgcctttctt  1620
agtggcgagc agaaaaaagc aattgtcgat cttctcttta aaacgaatcg caaggtaact  1680
gtaaaacagc tgaaggaaga ttatttcaaa aagatcgaat gctttgattc tgtcgagatc  1740
tcgggtgtcg aagatcgttt caacgcttcc ttagggacct atcatgattt gctgaagata  1800
ataaaagaca aagacttttct cgacaatgaa gaaaatgaag atattctgga ggatattgtt  1860
ttgaccttga ccttattcga agatagagag atgatcgagg agcgcttaaa aacctatgcc  1920
cacctgtttg atgacaaagt catgaagcaa ttaaagcgcc gcagatatac ggggtggggc  1980
cgcttgagcc gcaagttgat taacggtatt agagacaagc agagcggaaa aactatcctg  2040
gatttcctca aatctgacgg atttgcgaac cgcaatttta tgcagcttat acatgatgat  2100
tcgcttacat tcaaagagga tattcagaag gctcaggtgt ctgggcaagg tgattcactc  2160
cacgaacata tagcaaattt ggccggctct cctgcgatta agaaggggat cctgcaaaca  2220
gttaaagttg tggatgaact tgtaaaagta atgggccgcc acaagccgga gaatatcgtg  2280
atagaaatgg cgcgcgagaa tcaaacgaca caaaaaggtc aaaagaactc aagagagaga  2340
atgaagcgca ttgaggaggg gataaaggaa cttggatctc aaattctgaa agaacatcca  2400
gttgaaaaca ctcagctgca aaatgaaaaa ttgtacctgt actacctgca gaatggaaga  2460
gacatgtacg tggatcagga attggatatc aatagactct cggactatga cgtagatcac  2520
attgtccctc agagcttcct caaggatgat tctatagata ataaagtact tacgagatcg  2580
gacaaaaatc gcggtaaatc ggataacgtc ccatcggagg aagtcgttaa aaagatgaaa  2640
aactattggc gtcaactgct gaacgccaag ctgatcacac agcgtaagtt tgataatctg  2700
actaaagccg aacgcggtgg tcttagtgaa ctcgataaag caggatttat aaaacggcag  2760
ttagtagaaa cgcgccaaat tacgaaacac gtggctcaga tcctcgattc tagaatgaat  2820
acaaagtacg atgaaaacga taaactgatc cgtgaagtaa aagtcattac cttaaaatct  2880
aaacttgtgt ccgatttccg caaagatttt cagttttaca aggtccggga aatcaataac  2940
tatcaccatg cacatgatgc atatttaaat gcggttgtag gcacggccct tattaagaaa  3000
taccctaaac tcgaaagtga gtttgtttat ggggattata aagtgtatga cgttcgcaaa  3060
atgatcgcga aatcagaaca ggaaatcggt aaggctaccg ctaaatactt tttttattcc  3120
aacattatga atttttttaa gaccgaaata actctcgcga atggtgaaat ccgtaaacgg  3180
cctcttatag aaaccaatgg tgaaacggga gaaatcgttt gggataaagg tcgtgacttt  3240
gccaccgttc gtaaagtcct ctcaatgccg caagttaaca ttgtcaagaa gacggaagtt  3300
caaacagggg gattctccaa agaatctatc ctgccgaagc gtaacagtga taaacttatt  3360
gccagaaaaa aagattggga tccaaaaaaa tacggaggct ttgattcccc taccgtcgcg  3420
tatagtgtgc tggtggttgc taaagtcgag aaagggaaaa gcaagaaatt gaaatcagtt  3480
aaagaactgc tgggtattac aattatggaa agatcgtcct ttgagaaaaa tccgatcgac  3540
tttttagagg ccaaggggta taaggaagtg aaaaaagatc tcatcatcaa attaccgaag  3600
tatagtcttt ttgagctgga aaacggcaga aaaagaatgc tggcctccgc gggcgagtta  3660
cagaagggaa atgagctggc gctgccttcc aaatatgtta atttctgta ccttgccagt  3720
cattatgaga aactgaaggg cagccccgaa gataacgaac agaaacaatt attcgtggaa  3780
cagcataagc actatttaga tgaaattata gagcaaatta gtgaattttc taagcgcgtt  3840
atcctcgcgg atgctaattt agacaaagta ctgtcagctt ataataaaca tcgggataag  3900
ccgattagag aacaggccga aaatatcatt catttgttta ccttaaccaa ccttggagca  3960
ccagctgcct tcaaatattt cgataccaca attgatcgta aacggtatac aagtacaaaa  4020
gaagtcttgg acgcaaccct cattcatcaa tctattactg gattatatga gacacgcatt  4080
gatctttcac agctgggcgg agac                                        4104
```

```
SEQ ID NO: 127          moltype = AA  length = 1368
FEATURE                 Location/Qualifiers
REGION                  1..1368
                        note = synthesized Cas9 Y155F
source                  1..1368
                        mol_type = protein
                        organism = synthetic construct
SEQUENCE: 127
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIFLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
```

```
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 128          moltype = DNA  length = 4104
FEATURE                 Location/Qualifiers
misc_feature            1..4104
                        note = synthesized Cas9 Y155F
source                  1..4104
                        mol_type = other DNA
                        organism = synthetic construct
SEQUENCE: 128
atggataaaa aatacagcat tggtctggat atcggaacca acagcgttgg gtgggcagta  60
ataacagatg aatacaaagt gccgtcaaaa aaatttaagg ttctggggaa tacagatcgc  120
cacagcataa aaaagaatct gattggggca ttgctgtttg attcgggtga gacagctgag  180
gccacgcgtc tgaaacgtac agcaagaaga cgttacacac gtcgtaaaaa tcgtatttgc  240
tacttacagg aaattttttc taacgaaatg gccaaggtag atgatagttt cttccatcgt  300
ctcgaagaat cttttctggt tgaggaagat aaaaaacacg aacgtcaccc tatctttggc  360
aatatcgtgg atgaagtggc ctatcatgaa aaatacccta cgatttatca tcttcgcaag  420
aagttggttg atagtacgga caaagcggat ctgcgtttaa tctttcttgc gttagcgcac  480
atgatcaaat ttcgtggtca tttcttaatt gaaggtgatc tgaatcctga taactctgat  540
gtggacaaat tgtttataca attagtgcaa acctataatc agctgttcga ggaaaacccc  600
attaatgcct ctggagttga tgccaaagcg attttaagcg cgagactttc taagtcccgg  660
cgtctggaga atctgatcgc ccagttacca ggggaaaaga aaaatggtct gtttggtaat  720
ctgattgccc tcagtctggg gcttaccccg aacttcaaat ccaattttga cctggctgag  780
gacgcaaagc tgcagctgag caaagatact tatgatgatg acctcgacaa tctgctcgcc  840
cagattggtg accaatatgc ggatctgttt ctggcagcga agaatctttc ggatgctatc  900
ttgctgtcgg atattctgcg tgttaatacc gaaatcacca aagcgcctct gtctgcaagt  960
atgatcaaga gatacgacga gcaccaccag gacctgactc ttcttaaggc actggtacgc  1020
caacagcttc cggagaaata caaagaaata ttcttcgacc agtccaagaa tggttacgcg  1080
ggctacatcg atggtggtgc atcacaggaa gagttctata aatttattaa accaatcctt  1140
gagaaaatgg atggcacgga agagttactt gttaaactta accgcgaaga cttgcttaga  1200
aagcaacgta cattcgacaa cggctccatc ccacaccaga ttcatttagg tgaacttcac  1260
gccatcttgc gcagacaaga agatttctat ccctteftaa aagacaatcg ggagaaaatc  1320
gagaagatcc tgacgttccg cattccctat tatgtcggtc ccctggcacg tggtaattct  1380
cggtttgcct ggatgacgcg caaaagtgag gaaaccatca ccccttggaa ctttgaagaa  1440
gtcgtggata aggtgctagc cgcgcagtct tttatagaaa gaatgacgaa cttcgataaa  1500
aacttgccca acgaaaaagt cctgcccaag cactctcttt tatatgagta ctttactgtg  1560
tacaacgaac tgactaaagt gaaatacgtt acggaaggta tgcgcaaacc tgcctttctt  1620
agtggcgagc agaaaaaagc aattgtcgat cttctcttta aaacgaatcg caaggtaact  1680
gtaaaacagc tgaaggaaga ttatttcaaa aagatcgaat gctttgattc tgtcgagatc  1740
tcgggtgtcg aagatcgttt caacgcttcc ttagggacct atcatgattt gctgaagata  1800
ataaaagaca aagactttct cgacaatgaa gaaaatgaag atattctgga ggatattgtt  1860
ttgaccttga ccttattcga agatagagag atgatcgagg agcgcttaaa aacctatgcc  1920
cacctgtttg atgacaaagt catgaagcaa ttaaagcgcc gcagatatac ggggtggggc  1980
cgcttgagcc gcaagttgat taacggtatt agagacaagc agagcggaaa aactatcctg  2040
gatttcctca aatctgacgg atttgcgaac cgcaatttta tgcagcttat acatgatgat  2100
tcgcttacat tcaaagagga tattcagaag gctcaggtgt ctgggcaagg tgattcactc  2160
cacgaacata tagcaaattt ggccggctct cctgcgatta agaaggggat cctgcaaaca  2220
gttaaagttg tggatgaact tgtaaaagta atgggccgcc acaagccgga gaatatcgtg  2280
atagaaatgg cgcgcgagaa tcaaacgaca caaaaaggtc aaaagaactc aagagagaga  2340
atgaagcgca ttgaggaggg gataaaggaa cttggatctc aaattctgaa agaacatcca  2400
gttgaaaaca ctcagctgca aaatgaaaaa ttgtacctgt actacctgca gaatggaaga  2460
gacatgtacg tggatcagga attggatatc aatagactct cggactatga cgtagatcac  2520
attgtccctc agagcttcct caaggatgat tctatagata ataaagtact tacgagatcg  2580
gacaaaaatc gcggtaaatc ggataacgtc ccatcggagg aagtcgttaa aaagatgaaa  2640
aactattggc gtcaactgct gaacgccaag ctgatcacac agcgtaagtt tgataatctg  2700
actaaagccg aacgcggtgg tcttagtgaa ctcgataaag caggatttat aaaacggcag  2760
ttagtagaaa cgcgccaaat tacgaaacac gtggctcaga tcctcgattc tagaatgaat  2820
acaaagtacg atgaaaacga taaactgatc cgtgaagtaa aagtcattac cttaaaatct  2880
aaacttgtgt ccgatttccg caaagatttt cagttttaca aggtccggga aatcaataac  2940
tatcaccatg cacatgatgc atatttaaat gcggttgtag gcacggccct tattaagaaa  3000
taccctaaac tcgaaagtga gtttgtttat ggggattata aagtgtatga cgttcgcaaa  3060
atgatcgcga aatcagaaca ggaaatcggt aaggctaccg ctaaatactt tttttattcc  3120
aacattatga attttttaa gaccgaaata actctcgcga atggtgaaat ccgtaaacgg  3180
cctcttatag aaaccaatgg tgaaacggga gaaatcgttt gggataaagg tcgtgacttt  3240
gccaccgttc gtaaagtcct ctcaatgccg caagttaaca ttgtcaagaa gacggaagtt  3300
caaacagggg gattctccaa agaatctatc ctgccgaagc gtaacagtga taaacttatt  3360
gccagaaaaa aagattggga tccaaaaaaa tacggaggct ttgattcccc taccgtcgcg  3420
```

```
tatagtgtgc tggtggttgc taaagtcgag aaagggaaaa gcaagaaatt gaaatcagtt  3480
aaagaactgc tgggtattac aattatggaa agatcgtcct ttgagaaaaa tccgatcgac  3540
tttttagagg ccaaggggta taaggaagtg aaaaaagatc tcatcatcaa attaccgaag  3600
tatagtcttt ttgagctgga aaacggcaga aaaagaatgc tggcctccgc gggcgagtta  3660
cagaagggaa atgagctggc gctgccttcc aaatatgtta attttctgta ccttgccagt  3720
cattatgaga aactgaaggg cagccccgaa gataacgaac agaaacaatt attcgtggaa  3780
cagcataagc actatttaga tgaaattata gagcaaatta gtgaattttc taagcgcgtt  3840
atcctcgcgg atgctaattt agacaaagta ctgtcagctt ataataaaca tcgggataag  3900
ccgattagag aacaggccga aaatatcatt catttgttta ccttaaccaa ccttggagca  3960
ccagctgcct tcaaatattt cgataccaca attgatcgta aacggtatac aagtacaaaa  4020
gaagtcttgg acgcaaccct cattcatcaa tctattactg gattatatga gacacgcatt  4080
gatctttcac agctgggcgg agac                                          4104
```

```
SEQ ID NO: 129          moltype = AA  length = 1368
FEATURE                 Location/Qualifiers
REGION                  1..1368
                        note = synthesized Cas9 F86A F98A variant
source                  1..1368
                        mol_type = protein
                        organism = synthetic construct
SEQUENCE: 129
MDKKYSIGLD IGTNSVGWAV ITDEYKVPSK KFKVLGNTDR HSIKKNLIGA LLFDSGETAE  60
ATRLKRTARR RYTRRKNRIC YLQEIASNEM AKVDDSAFHR LEESFLVEED KKHERHPIFG  120
NIVDEVAYHE KYPTIYHLRK KLVDSTDKAD LRLIHLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368
```

```
SEQ ID NO: 130          moltype = DNA  length = 498
FEATURE                 Location/Qualifiers
misc_feature            1..498
                        note = synthesized F86A F98A synthetic fragment
source                  1..498
                        mol_type = other DNA
                        organism = synthetic construct
SEQUENCE: 130
cacgtcgtaa aaatcgtatt tgctacttac aggaaattgc gtctaacgaa atggccaagg  60
tagatgatag tgcgttccat cgtctcgaag aatctttttct ggttgaggaa gataaaaaac  120
acgaacgtca ccctatcttt ggcaatatcg tggatgaagt ggcctatcat gaaaaatacc  180
ctacgattta tcatcttcgc aagaagttgg ttgatagtac ggacaaagcg gatctgcgtt  240
taatccatct tgcgttagcg cacatgatca aatttcgtgg tcatttctta attgaaggtg  300
atctgaatcc tgataactct gatgtggaca aattgtttat acaattagtg caaacctata  360
atcagctgtt cgaggaaaac cccattaatg cctctggagt tgatgccaaa gcgattttaa  420
gcgcgagact ttctaagtcc cggcgtctgg agaatctgat cgcccagtta ccaggggaaa  480
agaaaaatgg tctgtttg                                                 498
```

```
SEQ ID NO: 131          moltype = DNA  length = 9266
FEATURE                 Location/Qualifiers
misc_feature            1..9266
                        note = plasmid pRF801 backbone for F86A-F98A
source                  1..9266
                        mol_type = other DNA
                        organism = synthetic construct
SEQUENCE: 131
aaagaaaaat ggtctgtttg gtaatctgat tgccctcagt ctggggctta ccccgaactt  60
caaatccaat tttgacctgg ctgaggacgc aaagctgcag ctgagcaaag atacttatga  120
tgatgacctc gacaatctgc tcgcccagat tggtgaccaa tatgcggatc tgtttctggc  180
agcgaagaat ctttcggatg ctatcttgct gtcggatatt ctgcgtgtta ataccgaaat  240
caccaaagcg cctctgtctg caagtatgat caagagatac gacgagcacc accaggacct  300
gactcttctt aaggcactgg tacgccaaca gcttccggag aaatacaaag aaatattctt  360
cgaccagtcc aagaatggtt acgcgggcta catcgatggt ggtgcatcac aggaagagtt  420
ctataaattt attaaaccaa tccttgagaa aatggatggc acggaagagt tacttgttaa  480
```

```
acttaaccgc gaagacttgc ttagaaagca acgtacattc gacaacggct ccatcccaca  540
ccagattcat ttaggtgaac ttcacgccat cttgcgcaga caagaagatt tctatccctt  600
cttaaaagac aatcgggaga aaatcgagaa gatcctgacg ttccgcattc cctattatgt  660
cggtcccctg gcacgtggta attctcggtt tgcctggatg acgcgcaaaa gtgaggaaac  720
catcacccct tggaactttg aagaagtcgt ggataaaggt gctagcgcgc agtcttttat  780
agaaagaatg acgaacttcg ataaaaactt gcccaacgaa aaagtcctgc ccaagcactc  840
tcttttatat gagtacttta ctgtgtacaa cgaactgact aaagtgaaat acgttacgga  900
aggtatgcgc aaacctgcct ttcttagtgg cgagcagaaa aaagcaattg tcgatcttct  960
ctttaaaacg aatcgcaagg taactgtaaa acagctgaag gaagattatt tcaaaaagat  1020
cgaatgcttt gattctgtcg agatctcggg tgtcgaagat cgtttcaacg cttccttagg  1080
gacctatcat gatttgctga agataataaa agacaaagac tttctcgaca atgaagaaaa  1140
tgaagatatt ctggaggata ttgttttgac cttgacctta ttcgaagata gagagatgat  1200
cgaggagcgc ttaaaaacct atgcccacct gtttgatgac aaagtcatga agcaattaaa  1260
gcgccgcaga tatacggggt ggggccgctt gagccgcaag ttgattaacg gtattagaga  1320
caagcagagc ggaaaaacta tcctggattt cctcaaatct gacggatttg cgaaccgcaa  1380
ttttatgcag cttatacatg atgattcgct tacattcaaa gaggatattc agaaggctca  1440
ggtgtctggg caaggtgatt cactccacga acatatagca aatttggccg gctctcctgc  1500
gattaagaag gggatcctgc aaacagttaa agttgtggat gaacttgtaa aagtaatggg  1560
ccgccacaag ccggagaata tcgtgataga aatggcgcgc gagaatcaaa cgacacaaaa  1620
aggtcaaaag aactcaagag agagaatgaa gcgcattgag gaggggataa aggaacttgg  1680
atctcaaatt ctgaaagaac atccagttga aaacactcag ctgcaaaatg aaaaattgta  1740
cctgtactac ctgcagaatg gaagagacat gtacgtggat caggaattgg atatcaatag  1800
actctcggac tatgacgtag atcacattgt ccctcagagc ttcctcaagg atgattctat  1860
agataataaa gtacttacga gatcggacaa aaatcgcggt aaatcggata acgtcccatc  1920
ggaggaagtc gttaaaaaga tgaaaaacta ttggcgtcaa ctgctgaacg ccaagctgat  1980
cacacagcgt aagtttgata atctgactaa agccgaacgc ggtggtctta gtgaactcga  2040
taaagcagga tttataaaac ggcagttagt agaaacgcgc caaattacga aacacgtggc  2100
tcagatcctc gattctagaa tgaatacaaa gtacgatgaa aacgataaac tgatccgtga  2160
agtaaaagtc attaccttaa aatctaaact tgtgtccgat ttccgcaaag attttcagtt  2220
ttacaaggtc cgggaaatca ataactatca ccatgcacat gatgcatatt taaatgcggt  2280
tgtaggcacg gcccttatta agaaataccc taaactcgaa agtgagtttg tttatgggga  2340
ttataaagtg tatgacgttc gcaaaatgat cgcgaaatca gaacaggaaa tcggtaaggc  2400
taccgctaaa tacttttttt attccaacat tatgaatttt tttaagaccg aaataactct  2460
cgcgaatggt gaaatccgta aacggcctct tatagaaacc aatggtgaaa cgggagaaat  2520
cgtttgggat aaaggtcgtg actttgccac cgttcgtaaa gtcctctcaa tgccgcaagt  2580
taacattgtc aagaagacgg aagttcaaac agggggattc tccaaagaat ctatcctgcc  2640
gaagcgtaac agtgataaac ttattgccag aaaaaaagat tgggatccaa aaaaatacgg  2700
aggctttgat tcccctaccg tcgcgtatag tgtgctggtg gttgctaaag tcgagaaagg  2760
gaaaagcaag aaattgaaat cagttaaaga actgctgggt attacaatta tggaaagatc  2820
gtcctttgag aaaaatccga tcgacttttt agaggccaag gggtataagg aagtgaaaaa  2880
agatctcatc atcaaattac cgaagtatag tctttttgag ctggaaaacg gcagaaaaag  2940
aatgctggcc tccgcgggcg agttacagaa gggaaatgag ctggcgctgc cttccaaata  3000
tgttaatttt ctgtaccttg ccagtcatta tgagaaactg aagggcagcc ccgaagataa  3060
cgaacagaaa caattattcg tggaacagca taagcactat ttagatgaaa ttatagagca  3120
aattagtgaa ttttctaagc gcgttatcct cgcggatgct aatttagaca aagtactgtc  3180
agcttataat aaacatcggg ataagccgat tagagaacag gccgaaaata tcattcattt  3240
gtttacctta accaaccttg gagcaccagc tgccttcaaa tatttcgata ccacaattga  3300
tcgtaaacgg tatacaagta caaaagaagt cttggacgca accctcattc atcaatctat  3360
tactggatta tatgagacac gcattgatct ttcacagctg ggcggagaca agaagaaaaa  3420
actgaaactg caccatcatc accatcatca tcaccatcat tgataactcg agaaagctta  3480
cataaaaaac cggccttggc cccgccggtt ttttattatt tttcttcctc cgcatgttca  3540
atccgctcca taatcgacgg atggctccct ctgaaaattt taacgagaaa cggcgggttg  3600
acccggctca gtcccgtaac ggccaagtcc tgaaacgtct caatcgccgc ttcccggttt  3660
ccggtcagct caatgccgta acggtcggcg gcgttttcct gataccggga gacggcattc  3720
gtaatcgggt gaagtggtca agacctcact aggcacctta aaaatagcgc accctgaaga  3780
agatttattt gaggtagccc ttgcctacct agcttccaag aaagatatcc taacagcaca  3840
agagcggaaa gatgttttgt tctacatcca gaacaacctc tgctaaaatt cctgaaaaat  3900
tttgcaaaaa gttgttgact ttatctacaa ggtgtggcat aatgtgtgga ctcgacttcg  3960
aatacatcca gttttagagc tagaaatagc aagttaaaat aaggctagtc cgttatcaac  4020
ttgaaaaagt ggcaccgagt cggtgcgact cctgttgata gatccagtaa tgacctcaga  4080
actccatctg gatttgttca gaacgctcgg ttgccgccgg gcgtttttta ttggtgagaa  4140
tgtcgacctc gagagttacg ctagggataa cagggtaata taggagctcc agtcggctta  4200
aaccagtttt cgctggtgcg aaaaaagagt gtcttgtgac acctaaattc aaaatctatc  4260
ggtcagattt ataccgattt gattttatat attcttgaat aacatacgcc gagttatcac  4320
ataaaagcgg gaaccaatca taaaatttaa acttcattgc ataatccatt aaactcttaa  4380
attctacgat tccttgttca tcaataaact caatcatttc tttaattaat ttatatctat  4440
ctgttgttgt tttctttaat aattcattaa catctacacc gccataaact atcatatctt  4500
ctttttgata tttaaattta ttaggatcgt ccatgtgaag catatatctc acaagacctt  4560
tcacacttcc tgcaatctgc ggaatagtcg cattcaattc ttctgttaat tatttttatc  4620
tgttcataag atttattacc ctcatacatc actagaatat gataatgctc tttttttcatc  4680
ctaccttctg tatcagtatc cctatcatgt aatggagaca ctacaaattg aatgtgtaac  4740
tcttttaaat actctaacca ctcggctttt gctgattctg gatataaaac aaatgtccaa  4800
ttacgtcctc ttgaattttt cttgttttca gtttctttta ttacattttc gctcatgata  4860
taataacggt gctaatacac ttaacaaaat ttagtcatag ataggcagca tgccagtgct  4920
gtctatcttt ttttgtttaa aatgcaccgt attcctcctt tgcatatttt tttattagaa  4980
taccggttgc atctgatttg ctaatattat atttttcttt gattctattt aatatctcat  5040
tttcttctgt tgtaagtctt aaagtaacag caactttttt ctcttctttt ctatctacaa  5100
ctatcactgt acctcccaac atctgttttt ttcactttaa cataaaaaac aacctttttaa  5160
cattaaaaac ccaatattta tttatttgtt tggacaatgg acactggaca cctagggggg  5220
```

```
aggtcgtagt accccccctat gttttctccc ctaaataacc ccaaaaatct aagaaaaaaa  5280
gacctcaaaa aggtctttaa ttaacatctc aaatttcgca tttattccaa tttccttttt  5340
gcgtgtgatg cgagctcatc ggctccgtcg atactatgtt atacgccaac tttcaaaaca  5400
actttgaaaa agctgttttc tggtatttaa ggttttagaa tgcaaggaac agtgaattgg  5460
agttcgtctt gttataatta gcttcttggg gtatctttaa atactgtaga aaagaggaag  5520
gaaataataa atggctaaaa tgagaatatc accggaattg aaaaaactga tcgaaaaata  5580
ccgctgcgta aaagatacgg aaggaatgtc tcctgctaag gtatataagc tggtgggaga  5640
aaatgaaaac ctatatttaa aaatgacgga cagccggtat aaagggacca cctatgatgt  5700
ggaacgggaa aaggacatga tgctatggct ggaaggaaag ctgcctgttc caaaggtcct  5760
gcactttgaa cggcatgatg gctggagcaa tctgctcatg agtgaggccg atggcgtcct  5820
ttgctcggaa gagtatgaag atgaacaaag ccctgaaaag attatcgagc tgtatgcgga  5880
gtgcatcagg ctctttcact ccatcgacat atcggattgt ccctatacga atagcttaga  5940
cagccgctta gccgaattgg attacttact gaataacgat ctggccgatg tggattgcga  6000
aaactgggaa gaagacactc catttaaaga tccgcgcgag ctgtatgatt ttttaaagac  6060
ggaaaagccc gaagaggaac ttgtcttttc ccacggcgac ctgggagaca gcaacatctt  6120
tgtgaaagat ggcaaagtaa gtggctttat tgatcttggg agaagcggca gggcggacaa  6180
gtggtatgac attgccttct gcgtccggtc gatcagggag gatatcgggg aagaacagta  6240
tgtcgagcta ttttttgact tactggggat caagcctgat tgggagaaaa taaaatatta  6300
tattttactg gatgaattgt tttagtgact gcagtgagat ctggtaatga ctctctagct  6360
tgaggcatca aataaaacga aaggctcagt cgaaagactg ggcctttcgt tttatctgtt  6420
gtttgtcggt gaacgctctc ctgagtagga caaatccgcc gctctagcta agcagaaggc  6480
catcctgacg gatggccttt ttgcgtttct acaaactctt gttaactcta gagctgcctg  6540
ccgcgtttcg gtgatgaaga tcttcccgat gattaattaa ttcagaacgc tcggttgccg  6600
ccgggcgttt tttatgaagc ttcgttgctg gcgtttttcc ataggctccg ccccccctgac  6660
gagcatcaca aaaatcgacg ctcaagtcag aggtggcgaa acccgacagg actataaaga  6720
taccaggcgt ttccccctgg aagctccctc gtgcgctctc ctgttccgac cctgccgctt  6780
accggatacc tgtccgcctt tctcccttcg ggaagcgtgg cgctttctca tagctcacgc  6840
tgtaggtatc tcagttcggt gtaggtcgtt cgctccaagc tgggctgtgt gcacgaaccc  6900
cccgttcagc ccgaccgctg cgccttatcc ggtaactatc gtcttgagtc caacccggta  6960
agacacgact tatcgccact ggcagcagcc actggtaaca ggattagcag agcgaggtat  7020
gtaggcggtg ctacagagtt cttgaagtgg tggcctaact acggctacac tagaaggaca  7080
gtatttggta tctgcgctct gctgaagcca gttaccttcg gaaaaagagt tggtagctct  7140
tgatccggca aacaaaccac cgctggtagc ggtggttttt ttgtttgcaa gcagcagatt  7200
acgcgcagaa aaaaaggatc tcaagaagat cctttgatct tttctacggg gtctgacgct  7260
cagtggaacg aaaactcacg ttaagggatt ttggtcatga gattatcaaa aaggatcttc  7320
acctagatcc ttttaaatta aaaatgaagt tttaaatcaa tctaaagtat atatgagtaa  7380
acttggtctg acaaatggtt ctttccccctg tcctaaacaa aaaacccgct ttattgaaaa  7440
agcggggctg ttttacagac aggtcaaata aacgtttgaa aatgttcatt tcaaaacgcg  7500
cggaacctcc atcttctccc atccagacta tactgtcggc ttcggaatcg caccgaatcc  7560
tgcccataaa aaggctcgcg ggcttagagc gcttgctcat caccgccggt agggaatttc  7620
accctgcccc gaagattgat cttatttatt tttaatactg atattattat aaattaattg  7680
tgaaaaaatg tacaggtgca aagcttattg cgctgttttg ggacatcctg cacgatattt  7740
cggtaaactc actttttccg catactaaaa accgcacatt cacagttatt tcatttttaa  7800
ttttcgtctt tccgcgtgaa actcattgac actctttatg gaatatggta aattatcaga  7860
tatttatgac gcttatttag gaggaaatct tacacagaag ctgcggaacc tgaaaagaat  7920
tcctttcagg ttccgttttt tttaggaatt ctccctgatc tcaagcatct ggcggggata  7980
aatccgctct cctttcaaat cgttccattc tttgaggcgc tgtacagtta cgcccatttt  8040
ttcggcgata tgatgaagcg tatccccttt ccgcactaca tatgtaccgg tcttcgattc  8100
atcgtcatga aggcggagtg tttggccggc cttgagattt gaatgtttca acccgtttat  8160
tctcatgatc tcctcgatgg atataccgct atccttgctg attctccaga gcgtgtcccc  8220
tttttgaacg gtcaccgcac cgctcattgt cccggcgttt tgataaacgt ggatagaatt  8280
ttgccggaac gcctcctcac gaagcaccgt cagcggattg attgcatatc ttttatcttc  8340
agtccatgaa ccgtgatgca tttcaaaatg caggtgggtt ccggtcgata ttcgaattcc  8400
tccattttct tctgctatca aaataacaga ctcgtgattt tccaaacgag ctttcaaaaa  8460
agcctctgcc ccttgcaaat cggatgcctg tctataaaat tcccgatatt ggttaaacag  8520
cggcgcaatg gcggccgcat ctgatgtctt tgcttggcga atgttcatct tatttcttcc  8580
tccctctcaa taatttttc attctatccc ttttctgtaa agtttatttt tcagaatact  8640
tttatcatca tgctttgaaa aaatatcacg ataatatcca ttgttctcac ggaagcacac  8700
gcaggtcatt tgaacgaatt ttttcgacag gaatttgccg ggactcagga gcatttaacc  8760
taaaaaagca tgacatttca gcataatgaa catttactca tgtctatttt cgttcttttc  8820
tgtatgaaaa tagttatttc gagtctctac ggaaatagcg agagatgata tacctaaata  8880
gagataaaat catctcaaaa aaatgggtct actaaaatat tattccatct attacaataa  8940
attcacagaa tagtctttta agtaagtcta ctctgaattt ttttaaaagg agagggtaac  9000
tagtggcccc aaaaaagaaa cgcaaggtta tggataaaaa atacagcatt ggtctggata  9060
tcggaaccaa cagcgttggg tgggcagtaa taacagatga atacaaagtg ccgtcaaaaa  9120
aatttaaggt tctggggaat acagatcgcc acagcataaa aaagaatctg attggggcat  9180
tgctgtttga ttcgggtgag acagctgagg ccacgcgtct gaaacgtaca gcaagaagac  9240
gttacacacg tcgtaaaaat cgtatt                                        9266
```

SEQ ID NO: 132    moltype = DNA  length = 20
FEATURE    Location/Qualifiers
misc_feature    1..20
    note = primer pRF801 backbone forward
source    1..20
    mol_type = other DNA
    organism = synthetic construct
SEQUENCE: 132

```
aaagaaaaat ggtctgtttg                                               20
```

```
SEQ ID NO: 133          moltype = DNA  length = 20
FEATURE                 Location/Qualifiers
misc_feature            1..20
                        note = primer pRF801 backbone reverse
source                  1..20
                        mol_type = other DNA
                        organism = synthetic construct
SEQUENCE: 133
aatacgattt ttacgacgtg                                             20

SEQ ID NO: 134          moltype = DNA  length = 20
FEATURE                 Location/Qualifiers
misc_feature            1..20
                        note = primer F86A F98A synthetic forward
source                  1..20
                        mol_type = other DNA
                        organism = synthetic construct
SEQUENCE: 134
cacgtcgtaa aaatcgtatt                                             20

SEQ ID NO: 135          moltype = DNA  length = 20
FEATURE                 Location/Qualifiers
misc_feature            1..20
                        note = primer F86A F98A synthetic reverse
source                  1..20
                        mol_type = other DNA
                        organism = synthetic construct
SEQUENCE: 135
caaacagacc atttttcttt                                             20

SEQ ID NO: 136          moltype = DNA  length = 9724
FEATURE                 Location/Qualifiers
misc_feature            1..9724
                        note = plasmid pRF866
source                  1..9724
                        mol_type = other DNA
                        organism = synthetic construct
SEQUENCE: 136
gggtgaagtg gtcaagacct cactaggcac cttaaaaata gcgcaccctg aagaagattt  60
atttgaggta gcccttgcct acctagcttc caagaaagat atcctaacag cacaagagcg  120
gaaagatgtt ttgttctaca tccagaacaa cctctgctaa aattcctgaa aaattttgca  180
aaaagttgtt gactttatct acaaggtgtg gcataatgtg tggactcgac ttcgaataca  240
tccagtttta gagctagaaa tagcaagtta aaataaggct agtccgttat caacttgaaa  300
aagtggcacc gagtcggtgc gactcctgtt gatagatcca gtaatgacct cagaactcca  360
tctggatttg ttcagaacgc tcggttgccg ccgggcgttt tttattggtg agaatgtcga  420
cctcgagagt tacgctaggg ataacagggt aatataggag ctccagtcgg cttaaaccag  480
ttttcgctgg tgcgaaaaaa gagtgtcttg tgacacctaa attcaaaatc tatcggtcag  540
atttataccg atttgatttt atatattctt gaataacata cgccgagtta tcacataaaa  600
gcgggaacca atcataaaat ttaaacttca ttgcataatc cattaaactc ttaaattcta  660
cgattccttg ttcatcaata aactcaatca tttctttaat taatttatat ctatctgttg  720
ttgttttctt taataattca ttaacatcta caccgccata aactatcata tcttcttttt  780
gatatttaaa tttattagga tcgtccatgt gaagcatata tctcacaaga cctttcacac  840
ttcctgcaat ctgcggaata gtcgcattca attcttctgt taattatttt tatctgttca  900
taagatttat taccctcata catcactaga atatgataat gctctttttt catcctacct  960
tctgtatcag tatccctatc atgtaatgga gacactacaa attgaatgtg taactctttt  1020
aaatactcta accactcggc ttttgctgat tctggatata aaacaaatgt ccaattacgt  1080
cctcttgaat tttcttgtt ttcagtttct tttattacat tttcgctcat gatataataa  1140
cggtgctaat acacttaaca aaatttagtc atagataggc agcatgccag tgctgtctat  1200
cttttttgt ttaaaatgca ccgtattcct cctttgcata ttttttttatt agaataccgg  1260
ttgcatctga tttgctaata ttatattttt ctttgattct atttaatatc tcattttctt  1320
ctgttgtaag tcttaaagta acagcaactt ttttctcttc ttttctatct acaactatca  1380
ctgtacctcc caacatctgt ttttttcact ttaacataaa aaacaacctt ttaacattaa  1440
aaacccaata tttatttatt tgtttggaca atggacactg gacacctagg ggggaggtcg  1500
tagtaccccc ctatgtttc tcccctaaat aaccccaaaa atctaagaaa aaaagacctc  1560
aaaaaggtct ttaattaaca tctcaaattt cgcatttatt ccaatttcct ttttgcgtgt  1620
gatgcgagct catcggctcc gtcgatacta tgttatacgc caactttcaa aacaactttg  1680
aaaaagctgt tttctggtat ttaaggtttt agaatgcaag gaacagtgaa ttggagttcg  1740
tcttgttata attagcttct tggggtatct ttaaatactg tagaaaagag gaaggaaata  1800
ataaatggct aaaatgagaa tatcaccgga attgaaaaaa ctgatcgaaa aataccgctg  1860
cgtaaaagat acggaaggaa tgtctcctgc taaggtatat aagctggtgg gagaaaatga  1920
aaacctatat ttaaaaatga cggacagccg gtataaaggg accacctatg atgtggaacg  1980
ggaaaaggac atgatgctat ggctggaagg aaagctgcct gttccaaagg tcctgcactt  2040
tgaacggcat gatggctgga gcaatctgct catgagtgag gccgatggcg tcctttgctc  2100
ggaagagtat gaagatgaac aaagccctga aaagattatc gagctgtatg cggagtgcat  2160
caggctcttt cactccatcg acatatcgga ttgtccctat acgaatagct tagacagccg  2220
cttagccgaa ttggattact tactgaataa cgatctggcc gatgtggatt gcgaaaactg  2280
ggaagaagac actccattta aagatccgcg cgagctgtat gattttttaa agacggaaaa  2340
gcccgaagag gaacttgtct tttcccacgg cgacctggga gacagcaaca tctttgtgaa  2400
agatggcaaa gtaagtggct ttattgatct tgggagaagc ggcagggcgg acaagtggta  2460
```

```
tgacattgcc ttctgcgtcc ggtcgatcag ggaggatatc ggggaagaac agtatgtcga  2520
gctatttttt gacttactgg ggatcaagcc tgattgggag aaaataaaat attatatttt  2580
actggatgaa ttgttttagt gactgcagtg agatctggta atgactctct agcttgaggc  2640
atcaaataaa acgaaaggct cagtcgaaag actgggcctt tcgttttatc tgttgtttgt  2700
cggtgaacgc tctcctgagt aggacaaatc cgccgctcta gctaagcaga aggccatcct  2760
gacggatggc ctttttgcgt ttctacaaac tcttgttaac tctagagctg cctgccgcgt  2820
ttcggtgatg aagatcttcc cgatgattaa ttaattcaga acgctcggtt gccgccgggc  2880
gtttttttatg aagcttcgtt gctggcgttt ttccataggc tccgcccccc tgacgagcat  2940
cacaaaaatc gacgctcaag tcagaggtgg cgaaacccga caggactata aagataccag  3000
gcgtttcccc ctggaagctc cctcgtgcgc tctcctgttc cgaccctgcc gcttaccgga  3060
tacctgtccg cctttctccc ttcgggaagc gtggcgcttt ctcatagctc acgctgtagg  3120
tatctcagtt cggtgtaggt cgttcgctcc aagctgggct gtgtgcacga accccccgtt  3180
cagcccgacc gctgcgcctt atccggtaac tatcgtcttg agtccaaccc ggtaagacac  3240
gacttatcgc cactggcagc agccactggt aacaggatta gcagagcgag gtatgtaggc  3300
ggtgctacag agttcttgaa gtggtggcct aactacggct acactagaag gacagtattt  3360
ggtatctgcg ctctgctgaa gccagttacc ttcggaaaaa gagttggtag ctcttgatcc  3420
ggcaaacaaa ccaccgctgg tagcggtggt ttttttgttt gcaagcagca gattacgcgc  3480
agaaaaaaag gatctcaaga agatcctttg atcttttcta cggggtctga cgctcagtgg  3540
aacgaaaact cacgttaagg gattttggtc atgagattat caaaaaggat cttcacctag  3600
atccttttaa attaaaaatg aagttttaaa tcaatctaaa gtatatatga gtaaacttgg  3660
tctgacaaat ggttctttcc cctgtcctaa acaaaaaacc cgctttattg aaaaagcggg  3720
gctgttttac agacaggtca aataaacgtt tgaaaatgtt catttcaaaa cgcgcggaac  3780
ctccatcttc tcccatccag actatactgt cggcttcgga atcgcaccga atcctgccca  3840
taaaaaggct cgcgggctta gagcgcttgc tcatcaccgc cggtagggaa tttcaccctg  3900
ccccgaagat tgatcttatt tatttttaat actgatatta ttataaatta attgtgaaaa  3960
aatgtacagg tgcaaagctt attgcgctgt tttgggacat cctgcacgat atttcggtaa  4020
actcactttt tccgcatact aaaaaccgca cattcacagt tatttcattt ttaattttcg  4080
tctttccgcg tgaaactcat tgacactctt tatggaatat ggtaaattat cagatattta  4140
tgacgcttat ttaggaggaa atcttacaca gaagctgcgg aacctgaaaa gaattccttt  4200
caggttccgt tttttttagg aattctccct gatctcaagc atctggcggg gataaatccg  4260
ctctcctttc aaatcgttcc attctttgag gcgctgtaca gttacgccca tttttcggc  4320
gatatgatga agcgtatccc ctttccgcac tacatatgta ccggtcttcg attcatcgtc  4380
atgaaggcgg agtgtttggc cggccttgag atttgaatgt ttcaacccgt ttattctcat  4440
gatctcctcg atggatatac cgctatcctt gctgattctc cagagcgtgt ccccttttg  4500
aacggtcacc gcaccgctca ttgtcccggc gttttgataa acgtggatag aattttgccg  4560
gaacgcctcc tcacgaagca ccgtcagcgg attgattgca tatcttttat cttcagtcca  4620
tgaaccgtga tgcatttcaa aatgcaggtg ggttccggtc gatattcgaa ttcctccatt  4680
ttcttctgct atcaaaataa cagactcgtg attttccaaa cgagctttca aaaaagcctc  4740
tgccccttgc aaatcggatg cctgtctata aaattcccga tattggttaa acagcggcgc  4800
aatggcggcc gcatctgatg tctttgcttg gcgaatgttc atcttatttc ttcctccctc  4860
tcaataattt tttcattcta tcccttttct gtaaagttta tttttcagaa tacttttatc  4920
atcatgcttt gaaaaaatat cacgataata tccattgttc tcacggaagc acacgcaggt  4980
catttgaacg aattttttcg acaggaattt gccgggactc aggagcattt aacctaaaaa  5040
agcatgacat ttcagcataa tgaacattta ctcatgtcta ttttcgttct tttctgtatg  5100
aaaatagtta tttcgagtct ctacggaaat agcgagagat gatataccta aatagagata  5160
aaatcatctc aaaaaaatgg gtctactaaa atattattcc atctattaca ataaattcac  5220
agaatagtct tttaagtaag tctactctga attttttttaa aaggagaggg taactagtgg  5280
ccccaaaaaa gaaacgcaag gttatggata aaaaatacag cattggtctg gatatcggaa  5340
ccaacagcgt tgggtgggca gtaataacag atgaatacaa agtgccgtca aaaaaattta  5400
aggttctggg gaatacagat cgccacagca taaaaaagaa tctgattggg gcattgctgt  5460
ttgattcggg tgagacagct gaggccacgc gtctgaaacg tacagcaaga agacgttaca  5520
cacgtcgtaa aaatcgtatt tgctacttac aggaaattgc gtctaacgaa atggccaagg  5580
tagatgatag tgcgttccat cgtctcgaag aatcttttct ggttgaggaa gataaaaaac  5640
acgaacgtca ccctatcttt ggcaatatcg tggatgaagt ggcctatcat gaaaaatacc  5700
ctacgattta tcatcttcgc aagaagttgg ttgatagtac ggacaaagcg gatctgcgtt  5760
taatccatct tgcgttagcg cacatgatca aatttcgtgg tcatttctta attgaaggtg  5820
atctgaatcc tgataactct gatgtggaca aattgtttat acaattagtg caaacctata  5880
atcagctgtt cgaggaaaac cccattaatg cctctggagt tgatgccaaa gcgattttaa  5940
gcgcgagact ttctaagtcc cggcgtctgg agaatctgat cgcccagtta ccagggggaaa  6000
agaaaaatgg tctgtttggt aatctgattg ccctcagtct ggggcttacc ccgaacttca  6060
aatccaattt tgacctggct gaggacgcaa agctgcagct gagcaaagat acttatgatg  6120
atgacctcga caatctgctc gcccagattg gtgaccaata tgcggatctg tttctggcag  6180
cgaagaatct ttcggatgct atcttgctgt cggatattct gcgtgttaat accgaaatca  6240
ccaaagcgcc tctgtctgca agtatgatca agagatacga cgagcaccac caggacctga  6300
ctcttcttaa ggcactggta cgccaacagc ttccggagaa atacaaagaa atattcttcg  6360
accagtccaa gaatggttac gcgggctaca tcgatggtgg tgcatcacag gaagagttct  6420
ataaatttat taaaccaatc cttgagaaaa tggatggcac ggaagagtta cttgttaaac  6480
ttaaccgcga agacttgctt agaaagcaac gtacattcga caacggctcc atcccacacc  6540
agattcattt aggtgaactt cacgccatct tgcgcagaca agaagatttc tatcccttct  6600
taaaagacaa tcgggagaaa atcgagaaga tcctgacgtt ccgcattccc tattatgtcg  6660
gtcccctggc acgtggtaat tctcggtttg cctggatgac gcgcaaaagt gaggaaacca  6720
tcacccccttg gaactttgaa gaagtcgtgg ataaaggtgc tagcgcgcag tcttttatag  6780
aaagaatgac gaacttcgat aaaaacttgc ccaacgaaaa agtcctgccc aagcactctc  6840
ttttatatga gtactttact gtgtacaacg aactgactaa agtgaaatac gttacggaag  6900
gtatgcgcaa acctgccttt cttagtggcg agcagaaaaa agcaattgtc gatcttctct  6960
ttaaaacgaa tcgcaaggta actgtaaaac agctgaagga agattatttc aaaaagatcg  7020
aatgctttga ttctgtcgag atctcgggtg tcgaagatcg tttcaacgct tccttaggga  7080
cctatcatga tttgctgaag ataataaaag acaaagactt tctcgacaat gaagaaaatg  7140
aagatattct ggaggatatt gttttgacct tgaccttatt cgaagataga gagatgatcg  7200
```

```
aggagcgctt aaaaacctat gcccacctgt ttgatgacaa agtcatgaag caattaaagc  7260
gccgcagata tacggggtgg ggccgcttga gccgcaagtt gattaacggt attagagaca  7320
agcagagcgg aaaaactatc ctggatttcc tcaaatctga cggatttgcg aaccgcaatt  7380
ttatgcagct tatacatgat gattcgctta cattcaaaga ggatattcag aaggctcagg  7440
tgtctgggca aggtgattca ctccacgaac atatagcaaa tttggccggc tctcctgcga  7500
ttaagaaggg gatcctgcaa acagttaaag ttgtggatga acttgtaaaa gtaatgggcc  7560
gccacaagcc ggagaatatc gtgatagaaa tggcgcgcga gaatcaaacg acacaaaaag  7620
gtcaaaagaa ctcaagagag agaatgaagc gcattgagga ggggataaag gaacttggat  7680
ctcaaattct gaaagaacat ccagttgaaa acactcagct gcaaaatgaa aaattgtacc  7740
tgtactacct gcagaatgga agagacatgt acgtggatca ggaattggat atcaatagac  7800
tctcggacta tgacgtagat cacattgtcc ctcagagctt cctcaaggat gattctatag  7860
ataataaagt acttacgaga tcggacaaaa atcgcggtaa atcggataac gtcccatcgg  7920
aggaagtcgt taaaaagatg aaaaactatt ggcgtcaact gctgaacgcc aagctgatca  7980
cacagcgtaa gtttgataat ctgactaaag ccgaacgcgg tggtcttagt gaactcgata  8040
aagcaggatt tataaaacgg cagttagtag aaacgcgcca aattacgaaa cacgtggctc  8100
agatcctcga ttctagaatg aatacaaagt acgatgaaaa cgataaactg atccgtgaag  8160
taaaagtcat taccttaaaa tctaaacttg tgtccgattt ccgcaaagat tttcagtttt  8220
acaaggtccg ggaaatcaat aactatcacc atgcacatga tgcatattta aatgcggttg  8280
taggcacggc ccttattaag aaatacccta aactcgaaag tgagtttgtt tatggggatt  8340
ataaagtgta tgacgttcgc aaaatgatcg cgaaatcaga acaggaaatc ggtaaggcta  8400
ccgctaaata cttttttat tccaacatta tgaatttttt taagaccgaa ataactctcg  8460
cgaatggtga aatccgtaaa cggcctctta tagaaaccaa tggtgaaacg ggagaaatcg  8520
tttgggataa aggtcgtgac tttgccaccg ttcgtaaagt cctctcaatg ccgcaagtta  8580
acattgtcaa gaagacggaa gttcaaacag gggattctc caaagaatct atcctgccga  8640
agcgtaacag tgataaactt attgccagaa aaaaagattg ggatccaaaa aaatacggag  8700
gctttgattc ccctaccgtc gcgtatagtg tgctggtggt tgctaaagtc gagaaaggga  8760
aaagcaagaa attgaaatca gttaaagaac tgctgggtat tacaattatg gaaagatcgt  8820
cctttgagaa aaatccgatc gactttttag aggccaaggg gtataaggaa gtgaaaaaag  8880
atctcatcat caaattaccg aagtatagtc tttttgagct ggaaaacggc agaaaaagaa  8940
tgctggcctc cgcgggcgag ttacagaagg gaaatgagct ggcgctgcct tccaaatatg  9000
ttaattttct gtaccttgcc agtcattatg agaaactgaa gggcagcccc gaagataacg  9060
aacagaaaca attattcgtg gaacagcata agcactattt agatgaaatt atagagcaaa  9120
ttagtgaatt ttctaagcgc gttatcctcg cggatgctaa tttagacaaa gtactgtcag  9180
cttataataa acatcgggat aagccgatta gagaacaggc cgaaaatatc attcatttgt  9240
ttaccttaac caaccttgga gcaccagctg ccttcaaata tttcgatacc acaattgatc  9300
gtaaacggta tacaagtaca aaagaagtct tggacgcaac cctcattcat caatctatta  9360
ctggattata tgagacacgc attgatcttt cacagctggg cggagacaag aagaaaaaac  9420
tgaaactgca ccatcatcac catcatcatc accatcattg ataactcgag aaagcttaca  9480
taaaaaaccg gccttggccc cgccggtttt ttattatttt tcttcctccg catgttcaat  9540
ccgctccata atcgacggat ggctccctct gaaaatttta acgagaaacg gcgggttgac  9600
ccggctcagt cccgtaacgg ccaagtcctg aaacgtctca atcgccgctt cccggtttcc  9660
ggtcagctca atgccgtaac ggtcggcggc gttttcctga taccgggaga cggcattcgt  9720
aatc                                                              9724
```

```
SEQ ID NO: 137          moltype = DNA  length = 5042
FEATURE                 Location/Qualifiers
misc_feature            1..5042
                        note = Bacillus F86A-F98A expression cassette
source                  1..5042
                        mol_type = other DNA
                        organism = synthetic construct
SEQUENCE: 137
attcctccat tttcttctgc tatcaaaata acagactcgt gattttccaa acgagctttc  60
aaaaaagcct ctgccccttg caaatcggat gcctgtctat aaaattcccg atattggtta  120
aacagcggcg caatggcggc cgcatctgat gtctttgctt ggcgaatgtt catcttattt  180
cttcctccct ctcaataatt ttttcattct atccctttc tgtaaagttt atttttcaga  240
atacttttat catcatgctt tgaaaaaata tcacgataat atccattgtt ctcacggaag  300
cacacgcagg tcatttgaac gaatttttc gacaggaatt tgccgggact caggagcatt  360
taacctaaaa aagcatgaca tttcagcata atgaacattt actcatgtct attttcgttc  420
ttttctgtat gaaaatagtt atttcgagtc tctacggaaa tagcgagaga tgatatacct  480
aaatagagat aaaatcatct caaaaaaatg ggtctactaa aatattattc catctattac  540
aataaattca cagaatagtc ttttaagtaa gtctactctg aattttttta aaaggagagg  600
gtaactagtg gccccaaaaa agaaacgcaa ggttatggat aaaaaataca gcattggtct  660
ggatatcgga accaacagcg ttgggtgggc agtaataaca gatgaataca aagtgccgtc  720
aaaaaaattt aaggttctgg ggaatacaga tcgccacagc ataaaaaaga atctgattgg  780
ggcattgctg tttgattcgg gtgagacagc tgaggccacg cgtctgaaac gtacagcaag  840
aagacgttac acacgtcgta aaaatcgtat ttgctactta caggaaattg cgtctaacga  900
aatggccaag gtagatgata gtgcgttcca tcgtctcgaa gaatcttttc tggttgagga  960
agataaaaaa cacgaacgtc accctatctt tggcaatatc gtggatgaag tggcctatca  1020
tgaaaaatac cctacgattt atcatcttcg caagaagttg gttgatagta cggacaaagc  1080
ggatctgcgt ttaatccatc ttgcgttagc gcacatgatc aaatttcgtg gtcatttctt  1140
aattgaaggt gatctgaatc ctgataactc tgatgtggac aaattgttta tacaattagt  1200
gcaaacctat aatcagctgt tcgaggaaaa ccccattaat gcctctggag ttgatgccaa  1260
agcgatttta agcgcgagac tttctaagtc ccggcgtctg gagaatctga tcgcccagtt  1320
accaggggaa aagaaaaatg gtctgtttgg taatctgatt gccctcagtc tggggcttac  1380
cccgaacttc aaatccaatt ttgacctggc tgaggacgca aagctgcagc tgagcaaaga  1440
tacttatgat gatgacctcg acaatctgct cgcccagatt ggtgaccaat atgcggatct  1500
gtttctggca gcgaagaatc tttcggatgc tatcttgctg tcggatattc tgcgtgttaa  1560
taccgaaatc accaaagcgc ctctgtctgc aagtatgatc aagagatacg acgagcacca  1620
```

```
ccaggacctg actcttctta aggcactggt acgccaacag cttccggaga aatacaaaga  1680
aatattcttc gaccagtcca agaatggtta cgcgggctac atcgatggtg gtgcatcaca  1740
ggaagagttc tataaattta ttaaaccaat ccttgagaaa atggatggca cggaagagtt  1800
acttgttaaa cttaaccgcg aagacttgct tagaaagcaa cgtacattcg acaacggctc  1860
catcccacac cagattcatt taggtgaact tcacgccatc ttgcgcagac aagaagattt  1920
ctatcccttc ttaaaagaca atcgggagaa aatcgagaag atcctgacgt tccgcattcc  1980
ctattatgtc ggtcccctgg cacgtggtaa ttctcggttt gcctggatga cgcgcaaaag  2040
tgaggaaacc atcacccctt ggaactttga agaagtcgtg gataaaggtg ctagcgcgca  2100
gtcttttata gaaagaatga cgaacttcga taaaaacttg cccaacgaaa aagtcctgcc  2160
caagcactct cttttatatg agtactttac tgtgtacaac gaactgacta aagtgaaata  2220
cgttacggaa ggtatgcgca aacctgcctt tcttagtggc gagcagaaaa aagcaattgt  2280
cgatcttctc tttaaaacga atcgcaaggt aactgtaaaa cagctgaagg aagattattt  2340
caaaaagatc gaatgctttg attctgtcga gatctcgggt gtcgaagatc gtttcaacgc  2400
ttccttaggg acctatcatg atttgctgaa gataataaaa gacaaagact ttctcgacaa  2460
tgaagaaaat gaagatattc tggaggatat tgttttgacc ttgaccttat tcgaagatag  2520
agagatgatc gaggagcgct taaaaaccta tgcccacctg tttgatgaca aagtcatgaa  2580
gcaattaaag cgccgcagat atacggggtg gggccgcttg agccgcaagt tgattaacgg  2640
tattagagac aagcagagcg gaaaaactat cctggatttc ctcaaatctg acggatttgc  2700
gaaccgcaat tttatgcagc ttatacatga tgattcgctt acattcaaag aggatattca  2760
gaaggctcag gtgtctgggc aaggtgattc actccacgaa catatagcaa atttggccgg  2820
ctctcctgcg attaagaagg ggatcctgca aacagttaaa gttgtggatg aacttgtaaa  2880
agtaatgggc cgccacaagc cggagaatat cgtgatagaa atggcgcgcg agaatcaaac  2940
gacacaaaaa ggtcaaaaga actcaagaga gagaatgaag cgcattgagg aggggataaa  3000
ggaacttgga tctcaaattc tgaaagaaca tccagttgaa aacactcagc tgcaaaatga  3060
aaaattgtac ctgtactacc tgcagaatgg aagagacatg tacgtggatc aggaattgga  3120
tatcaataga ctctcggact atgacgtaga tcacattgtc cctcagagct tcctcaagga  3180
tgattctata gataataaag tacttacgag atcggacaaa aatcgcggta aatcggataa  3240
cgtcccatcg gaggaagtcg ttaaaaagat gaaaaactat tggcgtcaac tgctgaacgc  3300
caagctgatc acacagcgta agtttgataa tctgactaaa gccgaacgcg gtggtcttag  3360
tgaactcgat aaagcaggat ttataaaacg gcagttagta gaaacgcgcc aaattacgaa  3420
acacgtggct cagatcctcg attctagaat gaatacaaag tacgatgaaa acgataaact  3480
gatccgtgaa gtaaaagtca ttaccttaaa atctaaactt gtgtccgatt tccgcaaaga  3540
ttttcagttt tacaaggtcc gggaaatcaa taactatcac catgcacatg atgcatattt  3600
aaatgcggtt gtaggcacgg cccttattaa gaaataccct aaactcgaaa gtgagtttgt  3660
ttatggggat tataaagtgt atgacgttcg caaaatgatc gcgaaatcag aacaggaaat  3720
cggtaaggct accgctaaat actttttttta ttccaacatt atgaattttt ttaagaccga  3780
aataactctc gcgaatggtg aaatccgtaa acggcctctt atagaaacca atggtgaaac  3840
gggagaaatc gtttgggata aaggtcgtga ctttgccacc gttcgtaaag tcctctcaat  3900
gccgcaagtt aacattgtca agaagacgga agttcaaaca ggggggattct ccaaagaatc  3960
tatcctgccg aagcgtaaca gtgataaact tattgccaga aaaaaagatt gggatccaaa  4020
aaaatacgga ggctttgatt cccctaccgt cgcgtatagt gtgctggtgg ttgctaaagt  4080
cgagaaaggg aaaagcaaga aattgaaatc agttaaagaa ctgctgggta ttacaattat  4140
ggaaagatcg tcctttgaga aaaatccgat cgacttttta gaggccaagg ggtataagga  4200
agtgaaaaaa gatctcatca tcaaattacc gaagtatagt ctttttgagc tggaaaacgg  4260
cagaaaaaga atgctggcct ccgcgggcga gttacagaag ggaaatgagc tggcgctgcc  4320
ttccaaatat gttaattttc tgtaccttgc cagtcattat gagaaactga agggcagccc  4380
cgaagataac gaacagaaac aattattcgt ggaacagcat aagcactatt tagatgaaat  4440
tatagagcaa attagtgaat tttctaagcg cgttatcctc gcggatgcta atttagacaa  4500
agtactgtca gcttataata aacatcggga taagccgatt agagaacagg ccgaaaatat  4560
cattcatttg tttaccttaa ccaaccttgg agcaccagct gccttcaaat atttcgatac  4620
cacaattgat cgtaaacggt atacaagtac aaaagaagtc ttggacgcaa ccctcattca  4680
tcaatctatt actggattat atgagacacg cattgatctt tcacagctgg gcggagacaa  4740
gaagaaaaaa ctgaaactgc accatcatca ccatcatcat caccatcatt gataaacata  4800
aaaaaccggc cttggccccg ccggtttttt attattttc ttcctccgca tgttcaatcc  4860
gctccataat cgacggatgg ctccctctga aaattttaac gagaaacggc gggttgaccc  4920
ggctcagtcc cgtaacggcc aagtcctgaa acgtctcaat cgccgcttcc cggtttccgg  4980
tcagctcaat gccgtaacgg tcggcggcgt tttcctgata ccgggagacg gcattcgtaa  5040
tc                                                                 5042
```

```
SEQ ID NO: 138          moltype = DNA  length = 54
FEATURE                 Location/Qualifiers
misc_feature            1..54
                        note = primer
source                  1..54
                        mol_type = other DNA
                        organism = synthetic construct
SEQUENCE: 138
aaagaaatat atagagagat actcttatca atgatggtga tgatgatggt gatg        54
```

```
SEQ ID NO: 139          moltype = DNA  length = 58
FEATURE                 Location/Qualifiers
misc_feature            1..58
                        note = primer
source                  1..58
                        mol_type = other DNA
                        organism = synthetic construct
SEQUENCE: 139
acacgtattt atttgtccaa ttaccatggc cccaaaaaag aaacgcaagg ttatggat    58
```

```
SEQ ID NO: 140          moltype = DNA  length = 767
FEATURE                 Location/Qualifiers
misc_feature            1..767
                        note = synthesized RNR2p promoter
source                  1..767
                        mol_type = other DNA
                        organism = synthetic construct
SEQUENCE: 140
gccaatctaa agcgttgtct tcctcgttcc tcgcgcacgc gattttgcgt tctgcatagg  60
aagccgaagt cgaacaagaa gcaggcaaag tttagagcac tgcccctccg cactcaaaaa  120
agaaaaaact aggaggaaaa taaaattctc aaccacacaa acacataaac acatacaaat  180
acaaatacaa gcttatttac ttgacatcgc gcgatcttcc actattcagc gccgtccgcc  240
ctctctcgtg ttttttgttt acgcgacaac tatgcgaaat ccggagcaac gggcaaccgt  300
ttggggaaag accacaccca cgcgcgatcg ccatggcaac gaggtcgcac acgccccaca  360
cccagacctc cctgcgagcg ggcatgggta caatgtcccc gttgccacag agaccacttc  420
gtagcacagc gcagagcgta gcgtgttgtt gctgctgaca aaagaaaatt tttcttagca  480
aagcaaagga ggggaagcac gggcagatag caccgtacca taccccttgga aactcgaaat  540
gaacgaagca ggaaatgaga gaatgagagt tttgtaggta tatatagcgg tagtgtttgc  600
gcgttaccat catcttctgg atctatctat tgttcttttc ctcatcactt tcccctttt  660
cgctcttctt cttgtctttt atttctttct tttttttaat tgttccctcg attggctatc  720
taccaaagaa tccaaactta atacacgtat ttatttgtcc aattacc                767

SEQ ID NO: 141          moltype = DNA  length = 1346
FEATURE                 Location/Qualifiers
misc_feature            1..1346
                        note = synthesized 2-micron replication origin 1
source                  1..1346
                        mol_type = other DNA
                        organism = synthetic construct
SEQUENCE: 141
aacgaagcat ctgtgcttca ttttgtagaa caaaaatgca acgcgagagc gctaattttt  60
caaacaaaga atctgagctg catttttaca gaacagaaat gcaacgcgaa agcgctattt  120
taccaacgaa gaatctgtgc ttcatttttg taaaacaaaa atgcaacgcg agagcgctaa  180
tttttcaaac aaagaatctg agctgcattt ttacagaaca gaaatgcaac gcgagagcgc  240
tattttacca acaaagaatc tatacttctt ttttgttcta caaaaatgca tcccgagagc  300
gctatttttc taacaaagca tcttagatta cttttttttct cctttgtgcg ctctataatg  360
cagtctcttg ataacttttt gcactgtagg tccgttaagg ttagaagaag gctactttgg  420
tgtctatttt ctcttccata aaaaaagcct gactccactt cccgcgttta ctgattacta  480
gcgaagctgc gggtgcattt tttcaagata aaggcatccc cgattatatt ctataccgat  540
gtggattgcg catactttgt gaacagaaag tgatagcgtt gatgattctt cattggtcag  600
aaaattatga acggtttctt ctattttgtc tctatatact acgtatagga aatgtttaca  660
ttttcgtatt gttttcgatt cactctatga atagttctta ctacaatttt tttgtctaaa  720
gagtaatact agagataaac ataaaaaatg tagaggtcga gtttagatgc aagttcaagg  780
agcgaaaggt ggatgggtag gttatatagg gatatagcac agagatatat agcaaagaga  840
tacttttgag caatgtttgt ggaagcggta ttcgcaatat tttagtagct cgttacagtc  900
cggtgcgttt ttggtttttt gaaagtgcgt cttcagagcg cttttggttt tcaaaagcgc  960
tctgaagttc ctatactttc tagagaatag gaacttcgga ataggaactt caaagcgttt  1020
ccgaaaacga gcgcttccga aaatgcaacg cgagctgcgc acatacagct cactgttcac  1080
gtcgcaccta tatctgcgtg ttgcctgtat atatatatac atgagaagaa cggcatagtg  1140
cgtgtttatg cttaaatgcg tacttatatg cgtctattta tgtaggatga aaggtagtct  1200
agtacctcct gtgatattat cccattccat gcggggtatc gtatgcttcc ttcagcacta  1260
ccctttagct gttctatatg ctgccactcc tcaattggat tagtctcatc cttcaatgct  1320
atcatttcct ttgatattgg atcata                                       1346

SEQ ID NO: 142          moltype = DNA  length = 1705
FEATURE                 Location/Qualifiers
misc_feature            1..1705
                        note = KanMX expression cassette
source                  1..1705
                        mol_type = other DNA
                        organism = synthetic construct
SEQUENCE: 142
ctagggattc ataaccattt tctcaatcga attacacaga acacaccgta caaacctctc  60
tatcataact acttaatagt cacacacgta ctcgtctaaa tacacatcat cgtcctacaa  120
gttcatcaaa gtgttggaca gacaactata ccagcatgga tctcttgtat cggttctttt  180
ctcccgctct ctcgcaataa caatgaacac tgggtcaatc atagcctaca caggtgaaca  240
gagtagcgtt tatacagggt ttatacggtg attcctacgg caaaaatttt tcatttctaa  300
aaaaaaaaag aaaaattttt ctttccaacg ctagaaggaa aagaaaaatc taattaaatt  360
gatttggtga ttttctgaga gttccctttt tcatatatcg aattttgaat ataaaaggag  420
atcgaaaaaa tttttctatt caatctgttt tctggtttta tttgatagtt tttttgtgta  480
ttattattat ggattagtac tggtttatat gggtttttct gtataacttc tttttatttt  540
agtttgttta atcttatttt gagttacatt atagttccct aactgcaaga gaagtaacat  600
taaaactcga gatgggtaag gaaaagactc acgtttcgag gccgcgatta aattccaaca  660
tggatgctga tttatatggg tataaatggg ctcgcgataa tgtcgggcaa tcaggtgcga  720
caatctatcg attgtatggg aagcccgatg cgccagagtt gtttctgaaa catggcaaag  780
gtagcgttgc caatgatgtt acagatgaga tggtcagact aaactggctg acggaattta  840
tgcctcttcc gaccatcaag cattttatcc gtactcctga tgatgcatgg ttactcacca  900
ctgcgatccc cggcaaaaca gcattccagg tattagaaga atatcctgat tcaggtgaaa  960
atattgttga tgcgctggca gtgttcctgc gccggttgca ttcgattcct gtttgtaatt  1020
```

```
gtccttttaa cagcgatcgc gtatttcgtc tggctcaggc gcaatcacga atgaataacg  1080
gtttggttga tgcgagtgat tttgatgacg agcgtaatgg ctggcctgtt gaacaagtct  1140
ggaaagaaat gcataagctt ttgccattct caccggattc agtcgtcact catggtgatt  1200
tctcacttga taaccttatt tttgacgagg ggaaattaat aggttgtatt gatgttggac  1260
gagtcggaat cgcagaccga taccaggatc ttgccatcct atggaactgc ctcggtgagt  1320
tttctccttc attacagaaa cggctttttc aaaaatatgg tattgataat cctgatatga  1380
ataaattgca gtttcatttg atgctcgatg agtttttcta agtttaactt gatactacta  1440
gatttttctc ttcatttata aaatttttgg ttataattga agctttagaa gtatgaaaaa  1500
atcctttttt ttcattcttt gcaaccaaaa taagaagctt cttttattca ttgaaatgat  1560
gaatataaac ctaacaaaag aaaaagactc gaatatcaaa cattaaaaaa aaataaaaga  1620
ggttatctgt tttcccattt agttggagtt tgcatttttct aatagataga actctcaatt  1680
aatgtggatt tagtttctct gttcg                                     1705

SEQ ID NO: 143          moltype = DNA  length = 299
FEATURE                 Location/Qualifiers
misc_feature            1..299
                        note = synthesized SNR52p promoter
source                  1..299
                        mol_type = other DNA
                        organism = synthetic construct
SEQUENCE: 143
ccctcactaa agggaacaaa agctggagct tctttgaaaa gataatgtat gattatgctt  60
tcactcatat ttatacagaa acttgatgtt ttctttcgag tatatacaag gtgattacat  120
gtacgtttga agtacaactc tagattttgt agtgccctct tgggctagcg ggaaaggtgc  180
gcattttttc acaccctaca atgttctgtt caaaagattt tggtcaaacg ctgtagaagt  240
gaaagttggt gcgcatgttt cggcgttcga aacttctccg cagtgaaaga taaatgatc   299

SEQ ID NO: 144          moltype = DNA  length = 11555
FEATURE                 Location/Qualifiers
misc_feature            1..11555
                        note = pSE087 plasmid
source                  1..11555
                        mol_type = other DNA
                        organism = synthetic construct
SEQUENCE: 144
gatcctctag tttctcggta ctatgcatat gatccaatat caaaggaaat gatagcattg  60
aaggatgaga ctaatccaat tgaggagtgg cagcatatag aacagctaaa gggtagtgct  120
gaaggaagca tacgataccc cgcatggaat gggataatat cacaggaggt actagactac  180
ctttcatcct acataaatag acgcatataa gtacgcattt aagcataaac acgcactatg  240
ccgttcttct catgtatata tatatacagg caacacgcag atataggtgc gacgtgaaca  300
gtgagctgta tgtgcgcagc tcgcgttgca ttttcggaag cgctcgtttt cggaaacgct  360
ttgaagttcc tattccgaag ttcctattct ctagaaagta taggaacttc agagcgcttt  420
tgaaaaccaa aagcgctctg aagacgcact ttcaaaaaac caaaaacgca ccggactgta  480
acgagctact aaaatattgc gaataccgct tccacaaaca ttgctcaaaa gtatctcttt  540
gctatatatc tctgtgctat atccctatat aacctaccca tccacctttc gctccttgaa  600
cttgcatcta aactcgacct ctacattttt tatgtttatc tctagtatta ctctttagac  660
aaaaaaattg tagtaagaac tattcataga gtgaatcgaa aacaatacga aaatgtaaac  720
atttcctata cgtagtatat agagacaaaa tagaagaaac cgttcataat tttctgacca  780
atgaagaatc atcaacgcta tcactttctg ttcacaaagt atgcgcaatc cacatcggta  840
tagaatataa tcggggatgc ctttatcttg aaaaaatgca cccgcagctt cgctagtaat  900
cagtaaacgc gggaagtgga gtcaggcttt ttttatggaa gagaaaatag acaccaaagt  960
agccttcttc taaccttaac ggacctacag tgcaaaaagt tatcaagaga ctgcattata  1020
gagcgcacaa aggagaaaaa aagtaatcta agatgctttg ttagaaaaat agcgctctcg  1080
ggatgcattt ttgtagaaca aaaaagaagt atagattctt tgttggtaaa atagcgctct  1140
cgcgttgcat ttctgttctg taaaaatgca gctcagattc tttgtttgaa aaattagcgc  1200
tctcgcgttg catttttgtt ttacaaaaat gaagcacaga ttcttcgttg gtaaaatagc  1260
gctttcgcgt tgcatttctg ttctgtaaaa atgcagctca gattctttgt ttgaaaaatt  1320
agcgctctcg cgttgcattt ttgttctaca aaatgaagca cagatgcttc gttaacaaag  1380
atatgctatt gaagtgcaag atggaaacgc agaaaatgaa ccggggatgc gacgtgcaag  1440
attacctatg caatagatgc aatagtttcg gcatgccgaa cagagaaact aaatccacat  1500
taattgagag ttctatctat tagaaaatgc aaactccaac taaatgggaa aacagataac  1560
ctcttttatt tttttttaat gtttgatatt cgagtctttt tcttttgtta ggtttatatt  1620
catcatttca atgaataaaa gaagcttctt attttggttg caaagaatga aaaaaaagga  1680
ttttttcata cttctaaagc ttcaattata accaaaaatt ttataaatga agagaaaaat  1740
ctagtagtat caagttaaac ttagaaaaac tcatcgagca tcaaatgaaa ctgcaattta  1800
ttcatatcag gattatcaat accatatttt tgaaaaagcc gtttctgtaa tgaaggagaa  1860
aactcaccga ggcagttcca taggatggca agatcctggt atcggtctgc gattccgact  1920
cgtccaacat caatacaacc tattaatttc ccctcgtcaa aaataaggtt atcaagtgag  1980
aaatcaccat gagtgacgac tgaatccggt gagaatggca aaagcttatg catttctttc  2040
cagacttgtt caacaggcca gccattacgc tcgtcatcaa aatcactcgc atcaaccaaa  2100
ccgttattca ttcgtgattg cgcctgagcc agacgaaata cgcgatcgct gttaaaagga  2160
caattacaaa caggaatcga atgcaaccgg cgcaggaaca ctgccagcgc atcaacaata  2220
ttttcacctg aatcaggata ttcttctaat acctggaatg ctgttttgcc ggggatcgca  2280
gtggtgagta accatgcatc atcaggagta cggataaaat gcttgatggt cggaagaggc  2340
ataaattccg tcagccagtt tagtctgacc atctcatctg taacatcatt ggcaacgcta  2400
cctttgccat gtttcagaaa caactctggc gcatcgggct tcccatacaa tcgatagatt  2460
gtcgcacctg attgcccgac attatcgcga gcccatttat acccatataa atcagcatcc  2520
atgttggaat ttaatcgcgg cctcgaaacg tgagtctttt ccttacccat ctcgagtttt  2580
aatgttactt ctcttgcagt tagggaacta taatgtaact caaaataaga ttaaacaaac  2640
```

```
taaaataaaa agaagttata cagaaaaacc catataaacc agtactaatc cataataata  2700
atacacaaaa aaactatcaa ataaaaccag aaaacagatt gaatagaaaa attttttcga  2760
tctcctttta tattcaaaat tcgatatatg aaaaagggaa ctctcagaaa atcaccaaat  2820
caatttaatt agatttttct tttccttcta gcgttggaaa gaaaaatttt tcttttttt  2880
tttagaaatg aaaaattttt gccgtaggaa tcaccgtata aaccctgtat aaacgctact  2940
ctgttcacct gtgtaggcta tgattgaccc agtgttcatt gttattgcga gagagcggga  3000
gaaaagaacc gatacaagag atccatgctg gtatagttgt ctgtccaaca ctttgatgaa  3060
cttgtaggac gatgatgtgt atttagacga gtacgtgtgt gactattaag tagttatgat  3120
agagaggttt gtacggtgtg ttctgtgtaa ttcgattgag aaaatggtta tgaatcccta  3180
gacccgggaa tctctaagta aatgcatgta tactaaactc acaaattaga gcttcaattt  3240
aattatatca gttattaccc gggttacgcc aagcgcgcaa ttaaccctca ctaaagggaa  3300
caaaagctgg agctcccctc actaaaggga acaaaagctg gagcttcttt gaaaagataa  3360
tgtatgatta tgctttcact catatttata cagaaacttg atgttttctt tcgagtatat  3420
acaaggtgat tacatgtacg tttgaagtac aactctagat tttgtagtgc cctcttgggc  3480
tagcgggaaa ggtgcgcatt ttttcacacc ctacaatgtt ctgttcaaaa gattttggtc  3540
aaacgctgta gaagtgaaag ttggtgcgca tgtttcggcg ttcgaaactt ctccgcagtg  3600
aaagataaat gatcggagac ggatacgttc tctatggagg agttttagag ctagaaatag  3660
caagttaaaa taaggctagt ccgttatcaa cttgaaaaag tggcaccgag tcggtggtgc  3720
ttttttctg gccgtctcta agggcccggt acccaattcg ccctatagtg agtcgtatta  3780
cgccagctgc attaatgaat cggccaacgc gcggggagag gcggtttgcg tattgggcgc  3840
tcttccgctt cctcgctcac tgactcgctg cgctcggtcg ttcggctgcg gcgagcggta  3900
tcagctcact caaaggcggt aatacggtta tccacagaat caggggataa cgcaggaaag  3960
aacatgtgag caaaaggcca gcaaaaggcc aggaaccgta aaaaggccgc gttgctggcg  4020
tttttccata ggctccgccc ccctgacgag catcacaaaa atcgacgctc aagtcagagg  4080
tggcgaaacc cgacaggact ataaagatac caggcgtttc cccctggaag ctccctcgtg  4140
cgctctcctg ttccgaccct gccgcttacc ggatacctgt ccgcctttct cccttcggga  4200
agcgtggcgc tttctcatag ctcacgctgt aggtatctca gttcggtgta ggtcgttcgc  4260
tccaagctgg gctgtgtgca cgaacccccc gttcagcccg accgctgcgc cttatccggt  4320
aactatcgtc ttgagtccaa cccggtaaga cacgacttat cgccactggc agcagccact  4380
ggtaacagga ttagcagagc gaggtatgta ggcggtgcta cagagttctt gaagtggtgg  4440
cctaactacg gctacactag aagaacagta tttggtatct gcgctctgct gaagccagtt  4500
accttcggaa aaagagttgg tagctcttga tccggcaaac aaaccaccgc tggtagcggt  4560
ggtttttttg tttgcaagca gcagattacg cgcagaaaaa aaggatctca agaagatcct  4620
ttgatctttt ctacggggtc tgacgctcag tggaacgaaa actcacgtta agggattttg  4680
gtcatgagat tatcaaaaag gatcttcacc tagatccttt taaattaaaa atgaagtttt  4740
aaatcaatct aaagtatata tgagtaaact tggtctgaca gttaccaatg cttaatcagt  4800
gaggcaccta tctcagcgat ctgtctattt cgttcatcca tagttgcctg actccccgtc  4860
gtgtagataa ctacgatacg ggagggctta ccatctggcc ccagtgctgc aatgataccg  4920
cgagacccac gctcaccggc tccagattta tcagcaataa accagccagc cggaagggcc  4980
gagcgcagaa gtggtcctgc aactttatcc gcctccatcc agtctattaa ttgttgccgg  5040
gaagctagag taagtagttc gccagttaat agtttgcgca acgttgttgc cattgctaca  5100
ggcatcgtgg tgtcacgctc gtcgtttggt atggcttcat tcagctccgg ttcccaacga  5160
tcaaggcgag ttacatgatc ccccatgttg tgcaaaaaag cggttagctc cttcggtcct  5220
ccgatcgttg tcagaagtaa gttggccgca gtgttatcac tcatggttat ggcagcactg  5280
cataattctc ttactgtcat gccatccgta agatgctttt ctgtgactgg tgagtactca  5340
accaagtcat tctgagaata gtgtatgcgg cgaccgagtt gctcttgccc ggcgtcaata  5400
cgggataata ccgcgccaca tagcagaact ttaaaagtgc tcatcattgg aaaacgttct  5460
tcggggcgaa aactctcaag gatcttaccg ctgttgagat ccagttcgat gtaacccact  5520
cgtgcaccca actgatcttc agcatctttt actttcacca gcgtttctgg gtgagcaaaa  5580
acaggaaggc aaaatgccgc aaaaaaggga ataagggcga cacggaaatg ttgaatactc  5640
atactcttcc tttttcaata ttattgaagc atttatcagg gttattgtct catgagcgga  5700
tacatatttg aatgtattta gaaaaataaa caaatagggg ttccgcgcac atttccccga  5760
aaagtgccac ctgacgtcgg cgcgccattt aaatagatcc ggtccgctcg agctgtaccg  5820
cagatgggac ctcttatgaa agtagacatc cttaagtgat gtaggggtat gtccgagtag  5880
ttcgttcaac tatttttaaa gacacatcgt tccaggttta tattcatata catatgtatg  5940
tattgtatag gtttttttat tttttatttt ttattttttt tttttttttt ttcaattttt  6000
ttaagctttt cttacttttc cgatgccctt tccactttaa tcaatatacg tatgaaattc  6060
agccgaagtt tccgtttgat aatatattag attcaatata aaaaaaagtt tatatgattc  6120
agtgtatata tatatatata aataagaggt gcgaaagccc acataaagag attgaagaga  6180
ctgcgtaaaa agaaatatat agagagatac tcttaactag acctttcttt tcttctttgg  6240
gtcggctctg gagtcgccac ccaattgaga taagtcaatt ctagtttcgt acaaaccagt  6300
aatagattga tggatcaagg tggcgtccaa gacttccttg gtagaggtgt aacgcttacg  6360
gtcaatagtg gtgtcgaagt acttgaaggc agcaggagca cccaaattgg tcaaagtgaa  6420
caagtgaatg atgttttcag cttgttctct gattggcttg tctctgtgct tgttgtaggc  6480
ggacaaaacc ttgtccaagt tagcgtcagc caaaatgact ctcttggaga actcggagat  6540
ttgttcaatg atttcgtcca agtagtgctt gtgttgttcg acgaatagtt gctttgttc  6600
gttgtcttct ggactaccct tcaactttc gtagtgagaa gccaagtata ggaagttaac  6660
gtacttgctt ggcaaggcca attcgttacc cttttgcaat tcaccagcgg aagccaacat  6720
tctctttcta ccgttttcca attcgaacaa tgagtacttt ggcaacttta tgatcaagtc  6780
tttcttgact tccttgtaac ccttagcttc taggaagtcg attgggttct tttcgaaaga  6840
acttctttcc atgatggtaa tacctaacaa ttccttgacg ctcttcaatt tcttagactt  6900
acccttttca accttagcga caaccaaaac gctgtaggca acggtaggag agtcgaagcc  6960
accgtatttc tttgggtccc aatctttctt tctagcgatc aacttatcag agtttctctt  7020
tggtaagata gattccttag agaagccacc agtttggact tcggttttct tgacgatgtt  7080
gacttgtggc atagacaaaa cctttctaac ggtagcgaaa tcacgaccct tgtcccaaac  7140
aatttcacct gtttcaccgt ttgtttcgat caatggtctc tttctgattt caccgttagc  7200
caaggtgatt tcggtcttaa agaagttcat aatgttagag taaaagaagt acttagcagt  7260
ggccttaccg atttcttgtt cagacttagc gatcatcttt ctgacatcgt agaccttgta  7320
atcaccgtag acaaattcag attctagctt tgggtatttc ttgattagag cggtacccac  7380
```

```
gacagcgttc aagtaagcat cgtgagcatg gtggtaattg ttgatttctc taaccttgta  7440
gaattggaag tcctttctga agtcagaaac caacttggac ttcaaagtga tgaccttgac  7500
ttctctaatc aacttatcat tttcgtcgta cttggtgttc atacgggaat ctaggatttg  7560
ggcaacgtgc ttggtgattt gtctggtttc gaccaattgt ctcttgatga agccagcctt  7620
atccaattcg gacaatccac ctctttcagc cttagttagg ttatcgaact ttctttgagt  7680
gattagctta gcgtttagca attgtctcca gtagttcttc atctttttca cgacctcttc  7740
ggatggaacg ttgtcagact tacctctgtt cttgtcggat ctggtcaaaa ccttgttgtc  7800
aatagaatcg tccttcaaga aagattgtgg gacgatgtgg tcaacgtcgt agtcggataa  7860
tctgttgata tctaattctt ggtcaacgta catatctcta ccgttttgca agtagtacaa  7920
gtataacttt tcgttttgta gttgggtgtt ttcaacgggg tgttccttca agatttgaga  7980
acccaattcc ttgataccct cttcgattct cttcattctt tctctagagt tcttttgacc  8040
cttttgtgta gtttgatttt ctctagccat ttctatgacg atgttttctg gcttgtgtct  8100
acccataacc ttaactagtt cgtctacaac cttgacagtt tgtagaatac ctttctttat  8160
ggctggggaa ccagccaagt tagcgatgtg ttcgtgcaag gaatcacctt gaccagaaac  8220
ttgagccttt tggatatctt ccttgaaggt caaagaatcg tcgtggatca attgcatgaa  8280
gtttctgttg gcgaaaccat cggacttcaa gaaatccaag atggtcttac cagattgctt  8340
gtctctgata ccgttaatca actttcttga caatctaccc caaccagtgt acctacgtct  8400
tttcaattgc ttcataacct tgtcatcaaa caagtgggcg taggtcttca atctctcttc  8460
gatcatttct ctgtcttcga acaaggttaa agttaggaca atgtcttcca aaatgtcttc  8520
gttctcttcg ttatccaaga agtccttgtc cttaatgatc tttagtaagt cgtggtaggt  8580
acccaaagaa gcgttgaatc tatcttcaac accagagatt tcaacagaat cgaaacattc  8640
gattttcttg aagtagtctt cctttagttg cttaacagtg acctttctgt ttgtcttgaa  8700
taacaagtca acgatagctt tcttttgttc gccagacaag aaggctggct ttctcatacc  8760
ttcagtaacg tacttgacct tggtcaattc gttgtaaaca gtgaagtatt cgtataacaa  8820
ggaatgcttt ggcaagacct tttcgtttgg caagtttttg tcgaagttgg tcattctttc  8880
gatgaaagat tgagcggaag caccctaatc tacgacctct tcgaaattcc aaggggtgat  8940
ggtctcttcg gactttctgg tcatccaagc gaatctggag ttacctctag ctagaggacc  9000
gacgtagtat gggattctaa aagttaggat cttttcaatc ttttctctgt tgtccttcaa  9060
gaatgggtag aagtcttctt gccttctcaa gatagcgtgt agttcaccta agtggatttg  9120
gtgtggaatg gaaccgttgt cgaaggttct ttgctttctt aacaagtctt ctctattcaa  9180
cttaactagc aactcttcgg taccgtccat cttttccaag attggcttga tgaacttgta  9240
gaactcttct tgactagctc caccgtcgat gtaaccagcg taaccgttct tagattgatc  9300
aaagaagatt tccttgtact tttcgggcaa ttgttgtcta accaaagcct tcaatagagt  9360
caagtcttga tggtgttcgt cgtatctctt aatcatggaa gcagacaatg gagccttagt  9420
gatttcagtg ttaactctca aaatgtcaga tagcaaaatg gcatcagaca agttcttggc  9480
agccaagaac aagtcagcgt attggtcacc aatttgggct aacaagttat ctaaatcgtc  9540
atcgtaagtg tccttggaca attgcaactt agcatcttca gccaaatcga agttagactt  9600
gaagtttgga gtcaaaccca aagacaaagc aatcaagtta ccgaacaaac cgtttttctt  9660
ttcacctggt aattgggcaa tcaagttttc caaacgtctg gacttggata atctagcgga  9720
caaaatggcc ttagcgtcaa caccagaggc gttgatagga ttctcttcga acaattggtt  9780
gtaagtttga accaattgga tgaacaactt atcgacgtca gagttgtctg ggttcaagtc  9840
accttcgatt aggaagtgac cacggaactt gatcatgtgg gccaaagcca agtagatcaa  9900
tctcaagtca gccttgtcgg tggagtcaac caatttcttt ctcaagtggt agatagttgg  9960
gtacttttcg tggtaagcga cttcgtcaac gatgttaccg aagattgggt gtctttcgtg  10020
ctttttgtcc tcttcgacca agaaagactc ttccaatctg tgaaagaaag aatcgtcaac  10080
cttagccatt tcattagaga agatttcttg caagtaacag attctgttct tacgtctagt  10140
gtaacgtcta cgggctgttc tcttcaatct agtagcttcg gcagtttcac cagagtcgaa  10200
taacaaagca ccgattaggt ttttcttgat ggagtgtcta tcggtgttac ccaagacctt  10260
gaatttctta gatgggacct tgtattcgtc agtaatgaca gcccaaccaa cagagttggt  10320
accgatgtcc aaaccgatag agtatttctt gtccatggta attggacaaa taaatacgtg  10380
tattaagttt ggattctttg gtagatagcc aatcgaggga acaattaaaa aaaagaaaga  10440
aataaaagac aagaagaaga gcgaaaaagg ggaaagtgat gaggaaaaga acaatagata  10500
gatccagaag atgatggtaa cgcgcaaaca ctaccgctat atatacctac aaaactctca  10560
ttctctcatt tcctgctcg ttcatttcga gtttccaagg gtatggtacg gtgctatctg  10620
cccgtgcttc ccctcctttg ctttgctaag aaaaatttc ttttgtcagc agcaacaaca  10680
cgctacgctc tgcgctgtgc tacgaagtgg tctctgtggc aacggggaca ttgtacccat  10740
gcccgctcgc agggaggtct gggtgtgggg cgtgtgcgac ctcgttgcca tggcgatcgc  10800
gcgtgggtgt ggtctttccc caaacggttg cccgttgctc cggatttcgc atagttgtcg  10860
cgtaaacaaa aaacacgaga gagggcggac ggcgctgaat agtggaagat cgcgcgatgt  10920
caagtaaata agcttgtatt tgtatttgta tgtgtttatg tgtttgtgtg gttgagaatt  10980
ttattttcct cctagttttt tctttttga gtgcggaggg gcagtgctct aaactttgcc  11040
tgcttcttgt tcgacttcgg cttcctatgc agaacgcaaa atcgcgtgcg cgaggaacga  11100
ggaagacaac gctttagatt ggcgcggccg cccgcaaatt aaagccttcg agcgtcccaa  11160
aaccttctca agcaaggttt tcagtataat gttacatgcg tacacgcgtc tgtacagaaa  11220
aaaaagaaaa atttgaaata taaataacgt tcttaatact aacataacta taaaaaaata  11280
aatagggacc tagacttcag gttgtctaac tccttccttt tcggttagag cggatgtggg  11340
gggagggcgt gaatgtaagc gtgacataac taattacatg attaatctag taacaaggct  11400
aagatatcag cctgaaataa agggtggtga agtaataatt aaatcatccg tataaaccta  11460
tacacatata tgaggaaaaa taatacaaaa gtgttttaaa tacagataca tacatgaaca  11520
tatgcacgta tagcgcccaa atgtcggtaa tggga                            11555
```

```
SEQ ID NO: 145          moltype = DNA  length = 57
FEATURE                 Location/Qualifiers
misc_feature            1..57
                        note = primer
source                  1..57
                        mol_type = other DNA
                        organism = synthetic construct
SEQUENCE: 145
```

```
ctccgcagtg aaagataaat gatcgcccaa aatttgttta ctaaaaacac atgtgga     57

SEQ ID NO: 146         moltype = DNA  length = 58
FEATURE                Location/Qualifiers
misc_feature           1..58
                       note = primer
source                 1..58
                       mol_type = other DNA
                       organism = synthetic construct
SEQUENCE: 146
gaattgggta ccgggccctt agagtaaaaa attgtacttg gcggataatg cctttagc    58

SEQ ID NO: 147         moltype = DNA  length = 106
FEATURE                Location/Qualifiers
misc_feature           1..106
                       note = synthesized targeting sgRNA + T(6) terminator
source                 1..106
                       mol_type = other DNA
                       organism = synthetic construct
SEQUENCE: 147
gatacgttct ctatggagga gttttagagc tagaaatagc aagttaaaat aaggctagtc  60
cgttatcaac ttgaaaaagt ggcaccgagt cggtggtgct tttttt                 106

SEQ ID NO: 148         moltype = DNA  length = 50
FEATURE                Location/Qualifiers
misc_feature           1..50
                       note = synthesized 50 bp upstream homology arm
source                 1..50
                       mol_type = other DNA
                       organism = synthetic construct
SEQUENCE: 148
cccaaaattt gtttactaaa aacacatgtg gatatcttga ctgatttttc             50

SEQ ID NO: 149         moltype = DNA  length = 106
FEATURE                Location/Qualifiers
misc_feature           1..106
                       note = synthesized URA3 targeting sgRNA + T(6) terminator
source                 1..106
                       mol_type = other DNA
                       organism = synthetic construct
SEQUENCE: 149
tatcttgact gatttttcca gttttagagc tagaaatagc aagttaaaat aaggctagtc  60
cgttatcaac ttgaaaaagt ggcaccgagt cggtggtgct tttttt                 106

SEQ ID NO: 150         moltype = DNA  length = 50
FEATURE                Location/Qualifiers
misc_feature           1..50
                       note = synthesized 50 bp downstream homology arm
source                 1..50
                       mol_type = other DNA
                       organism = synthetic construct
SEQUENCE: 150
gcacagttaa gccgctaaag gcattatccg ccaagtacaa tttttactc              50

SEQ ID NO: 151         moltype = DNA  length = 57
FEATURE                Location/Qualifiers
misc_feature           1..57
                       note = primer
source                 1..57
                       mol_type = other DNA
                       organism = synthetic construct
SEQUENCE: 151
ccgccaagta caatttttta ctctaagggc ccggtaccca attcgcccta tagtgag     57

SEQ ID NO: 152         moltype = DNA  length = 57
FEATURE                Location/Qualifiers
misc_feature           1..57
                       note = primer
source                 1..57
                       mol_type = other DNA
                       organism = synthetic construct
SEQUENCE: 152
catcatcacc atcattgata agagtatctc tctatatatt tctttttacg cagtctc     57

SEQ ID NO: 153         moltype = DNA  length = 566
FEATURE                Location/Qualifiers
misc_feature           1..566
                       note = synthesized 2-micron replication origin 2
source                 1..566
```

```
                         mol_type = other DNA
                         organism = synthetic construct
SEQUENCE: 153
gtaatctgct gcttgcaaac aaaaaaacca ccgctaccag cggtggtttg tttgccggat  60
caagagctac caactctttt tccgaaggta actggcttca gcagagcgca gataccaaat  120
actgttcttc tagtgtagcc gtagttaggc caccacttca agaactctgt agcaccgcct  180
acatacctcg ctctgctaat cctgttacca gtggctgctg ccagtggcga taagtcgtgt  240
cttaccgggt tggactcaag acgatagtta ccggataagg cgcagcggtc gggctgaacg  300
gggggttcgt gcacacagcc cagcttggag cgaacgacct acaccgaact gagataccta  360
cagcgtgagc tatgagaaag cgccacgctt cccgaaggga gaaaggcgga caggtatccg  420
gtaagcggca gggtcggaac aggagagcgc acgagggagc ttccaggggg aaacgcctgg  480
tatctttata gtcctgtcgg gtttcgccac ctctgacttg agcgtcgatt tttgtgatgc  540
tcgtcagggg ggcggagcct atggaa                                      566

SEQ ID NO: 154           moltype = DNA  length = 859
FEATURE                  Location/Qualifiers
misc_feature             1..859
                         note = synthesized ampicillin resistant gene
source                   1..859
                         mol_type = other DNA
                         organism = synthetic construct
SEQUENCE: 154
atgagtattc aacatttccg tgtcgccctt attccctttt ttgcggcatt ttgccttcct  60
gtttttgctc acccagaaac gctggtgaaa gtaaaagatg ctgaagatca gttgggtgca  120
cgagtgggtt acatcgaact ggatctcaac agcggtaaga tccttgagag ttttcgcccc  180
gaagaacgtt ttccaatgat gagcactttt aaagttctgc tatgtggcgc ggtattatcc  240
cgtattgacg ccgggcaaga gcaactcggt cgccgcatac actattctca gaatgacttg  300
gttgagtact caccagtcac agaaaagcat cttacggatg gcatgacagt aagagaatta  360
tgcagtgctg ccataaccat gagtgataac actgcggcca acttacttct gacaacgatc  420
ggaggaccga aggagctaac cgcttttttg cacaacatgg gggatcatgt aactcgcctt  480
gatcgttggg aaccggagct gaatgaagcc ataccaaacg acgagcgtga caccacgatg  540
cctgtagcaa tggcaacaac gttgcgcaaa ctattaactg gcgaactact tactctagct  600
tcccggcaac aattaataga ctggatggag gcggataaag ttgcaggacc acttctgcgc  660
tcggcccttc cggctggctg gtttattgct gataaatctg gagccggtga gcgtgggtct  720
cgcggtatca ttgcagcact ggggccagat ggtaagccct cccgtatcgt agttatctac  780
acgacgggga gtcaggcaac tatggatgaa cgaaatagac agatcgctga gataggtgcc  840
tcactgatta agcattggt                                              859

SEQ ID NO: 155           moltype = DNA  length = 400
FEATURE                  Location/Qualifiers
misc_feature             1..400
                         note = synthesized RNR2 terminator
source                   1..400
                         mol_type = other DNA
                         organism = synthetic construct
SEQUENCE: 155
gagtatctct ctatatattt ctttttacgc agtctcttca atctctttat gtgggctttc  60
gcacctctta tttatatata tatatataca ctgaatcata taaacttttt tttatattga  120
atctaatata ttatcaaacg gaaacttcgg ctgaatttca tacgtatatt gattaaagtg  180
gaaagggcat cggaaaagta agaaaagctt aaaaaaattg aaaaaaaaaa aaaaaaaaat  240
aaaaaataaa aaataaaaaa acctatacaa tacatacata tgtatatgaa tataaacctg  300
gaacgatgtg tctttaaaaa tagttgaacg aactactcgg acatacccct acatcactta  360
aggatgtcta ctttcataag aggtcccatc tgcggtacag                        400

SEQ ID NO: 156           moltype = DNA  length = 56
FEATURE                  Location/Qualifiers
misc_feature             1..56
                         note = primer
source                   1..56
                         mol_type = other DNA
                         organism = synthetic construct
SEQUENCE: 156
ccttgcgttt ctttttgggg gccatggtaa ttggacaaat aaatacgtgt attaag      56

SEQ ID NO: 157           moltype = DNA  length = 56
FEATURE                  Location/Qualifiers
misc_feature             1..56
                         note = primer
source                   1..56
                         mol_type = other DNA
                         organism = synthetic construct
SEQUENCE: 157
tgtttttagt aaacaaattt tgggcgatca tttatctttc actgcggaga agtttc      56
```

CAS9 VARIANTS AND METHODS OF USE

This application is a Divisional of U.S. application Ser. No. 16/772,910, filed Jun. 15, 2020, which is a 371 of International Application No. PCT/US18/64955, filed Dec. 11, 2018, which claims the benefit of U.S. Provisional Application No. 62/599,176 filed Dec. 15, 2017, all are incorporated herein in their entirety by reference.

FIELD

The present disclosure relates to the field of molecular biology, in particular, to compositions of guide polynucleotide/Cas endonuclease systems and compositions and methods thereof for modifying the genome of a cell.

REFERENCE TO SEQUENCE LISTING SUBMITTED ELECTRONICALLY

The official copy of the sequence listing is submitted electronically via Patent Center as an XML formatted sequence listing with a file named 20230828_NB41317-US-PCD_SeqLst created on Aug. 28, 2023 and having a size of 508,309 bytes and is filed concurrently with the specification. The sequence listing contained in this XML formatted document is part of the specification and is herein incorporated by reference in its entirety.

BACKGROUND

Recombinant DNA technology has made it possible to insert DNA sequences at targeted genomic locations and/or modify specific endogenous chromosomal sequences. Site-specific integration techniques, which employ site-specific recombination systems, as well as other types of recombination technologies, have been used to generate targeted insertions of genes of interest in a variety of organism. Given the site-specific nature of Cas systems, genome modification/engineering techniques based on these systems have been described, including in mammalian cells (see, e.g., Hsu et al., 2014). Cas-based genome engineering, when functioning as intended, confers the ability to target virtually any specific location within a complex genome, by designing a recombinant crRNA (or equivalently functional guide polynucleotide) in which the DNA-targeting region (i.e., the variable targeting domain) of the crRNA is homologous to a desired target site in the genome, and combining the crRNA with a Cas endonuclease (through any convenient and conventional means) into a functional complex in a host cell.

Although Cas-based genome engineering techniques have been applied to a number of different host cell types, these techniques have known limitations. For example, the efficiency of transforming certain host cells, such as but not limiting to *Bacillus* species, remains low and costly.

Therefore, there remains a need for developing more effective, efficient or otherwise more robust or flexible Cas-based genome modification methods and compositions thereof for modifying/altering a genomic target site in a prokaryotic or eukaryotic cell.

BRIEF SUMMARY

Compositions and methods are provided for variant Cas systems and elements comprising such systems, including, but not limiting to, Cas endonuclease variants, guide polynucleotides, guide polynucleotide/Cas endonuclease complexes, guide RNA/Cas endonuclease systems, in particular, to Cas9 endonuclease variants comprising at least one amino acid modification located outside of its HNH and RuvC domain, and optionally wherein the Cas9 endonuclease variant has at least one improved property, when compared to its parent Cas9 endonuclease that does not have the at least one amino acid modification.

Compositions and methods are also provided for direct delivery of Cas9 endonuclease variants, guide polynucleotides and guide polynucleotide/Cas endonuclease systems comprising at least one Cas9 endonuclease variant and at least one guide RNA, as well as for genome modification of a target sequence in the genome of a prokaryotic or eukaryotic cell, for gene editing and for inserting or deleting a polynucleotide of interest into or from the genome of an organism.

In one embodiment of the disclosure, the Cas9 endonuclease variant is a Cas9 endonuclease variant, or an active fragment thereof, having at least 80% amino acid identity to a parent Cas9 polypeptide set forth in SEQ ID NO: 2 and having at least one amino acid substitution at a position selected from the group consisting of position 86, position 98, position 155 and a combination thereof, wherein the amino acid positions of the variant are numbered by correspondence with the amino acid sequence of said parent Cas9 polypeptide, wherein said Cas9 endonuclease variant has endonuclease activity. Said Cas9 endonuclease variant can have at least one amino acid substitution selected from the group consisting of Y155H, Y155N, Y155E, Y155F (at position 155), F86A (at position 86) and F98A (at position 98). The Cas9 endonuclease variant can have at least one improved property selected from the group consisting of improved transformation efficiency and improved editing efficiency, when compared to its parent Cas9 endonuclease. The Cas9 endonuclease variant, or active fragment thereof, can have at least 1, 2, 3, 4, 5, 6, 7, 8, 9, 10 amino acid substitutions when compared to its parent Cas9 endonuclease.

In one embodiment of the disclosure, the Cas9 endonuclease variant is a Cas9 endonuclease variant, or active fragment thereof, wherein said variant comprises an amino acid sequence having 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 2.

In one embodiment of the disclosure, the Cas9 endonuclease variant is a Cas9 endonuclease variant, wherein the improved property is improved transformation efficiency and wherein said variant, or active fragment thereof, also has an improved editing efficiency.

In one embodiment of the disclosure, the composition is a composition comprising a Cas9 endonuclease variant disclosed herein, or a functional fragment thereof. The composition can be selected from the group consisting of a guide polynucleotide/Cas9 endonuclease complex, a guide RNA/Cas9 endonuclease complex, and a fusion protein comprising said Cas9 endonuclease variant.

In one embodiment of the disclosure, the polynucleotide is a polynucleotide comprising a nucleic acid sequence encoding any one Cas9 endonuclease variant disclosed herein.

In one embodiment of the disclosure, the guide polynucleotide/Cas endonuclease complex (PGEN) is a PGEN comprising at least one guide polynucleotide and at least one Cas9 endonuclease variant described herein, wherein said guide polynucleotide is a chimeric non-naturally occurring guide polynucleotide, wherein said guide polynucleotide/Cas endonuclease complex is capable of recognizing, binding to, and optionally nicking, unwinding, or cleaving all or part of a target sequence In one embodiment of the disclosure, the method comprises a method for modifying a target site in the genome of a cell, the method comprising introducing into a cell at least one PGEN comprising at least one guide polynucleotide and at least one Cas9 endonuclease variant described herein, and identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

In one embodiment of the disclosure, the method comprises a method for editing a nucleotide sequence in the genome of a cell, the method comprising introducing into at least one PGEN comprising at least one guide polynucleotide and at least one Cas9 endonuclease variant described herein and a polynucleotide modification template, wherein said polynucleotide modification template comprises at least one nucleotide modification of said nucleotide sequence In one embodiment of the disclosure, the method comprises a method for modifying a target site in the genome of a cell, the method comprising introducing into a cell at least one PGEN comprising at least one guide polynucleotide and at least one Cas9 endonuclease variant described herein and at least one donor DNA, wherein said donor DNA comprises a polynucleotide of interest.

In one embodiment of the disclosure, the method comprises a method for improving at least one property of a Cas9 endonuclease variant, said method comprising introducing at least one amino acid modification in a parent Cas9 endonuclease, wherein said at least one amino acid modification is located outside the RuvC and HNH domain of the parent Cas9 endonuclease, thereby creating said Cas9 endonuclease variant, wherein said Cas9 endonuclease variant shows an improvement in at least one property when compared to said parent Cas9 endonuclease. The at least one amino acid modification can be an amino acid substitution at a position selected from the group consisting of position 86, position 98, position 155 and a combination thereof, wherein the amino acid positions of the variant are numbered by correspondence with the amino acid sequence of said parent Cas9 endonuclease. The at least one amino acid substitution can be selected from the group consisting of Y155H, Y155N, Y155E, Y155F (at position 155), F86A (at position 86) and F98A (at position 98).

Also provided are expression cassettes, recombinant DNAs, nucleic acid constructs, prokaryotic and eukaryotic cells having a modified target sequence or having a modification at a nucleotide sequence in the genome of the prokaryotic and eukaryotic cells produced by the methods described herein. Additional embodiments of the methods and compositions of the present disclosure are shown herein.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

FIG. 1 depicts a schematic representation of a Cas9 polypeptide and its Cas9 protein domains. Shown in black fill is the RuvC nuclease domain, cross hatch indicates the bridge helix, diagonal dash fill indicates the REC I domain, medium gray fill indicates the REC II domain, light gray fill indicates the HNH nuclease domain, ball fill indicates the PAM recognition domain. (Adapted from Jinek M., Jiang F., Taylor D. W. et al. 2014, Science 343, 1247997). The Y155 modification of the Cas9 endonuclease variant described herein is located in the REC1 domain.

Figure 1:
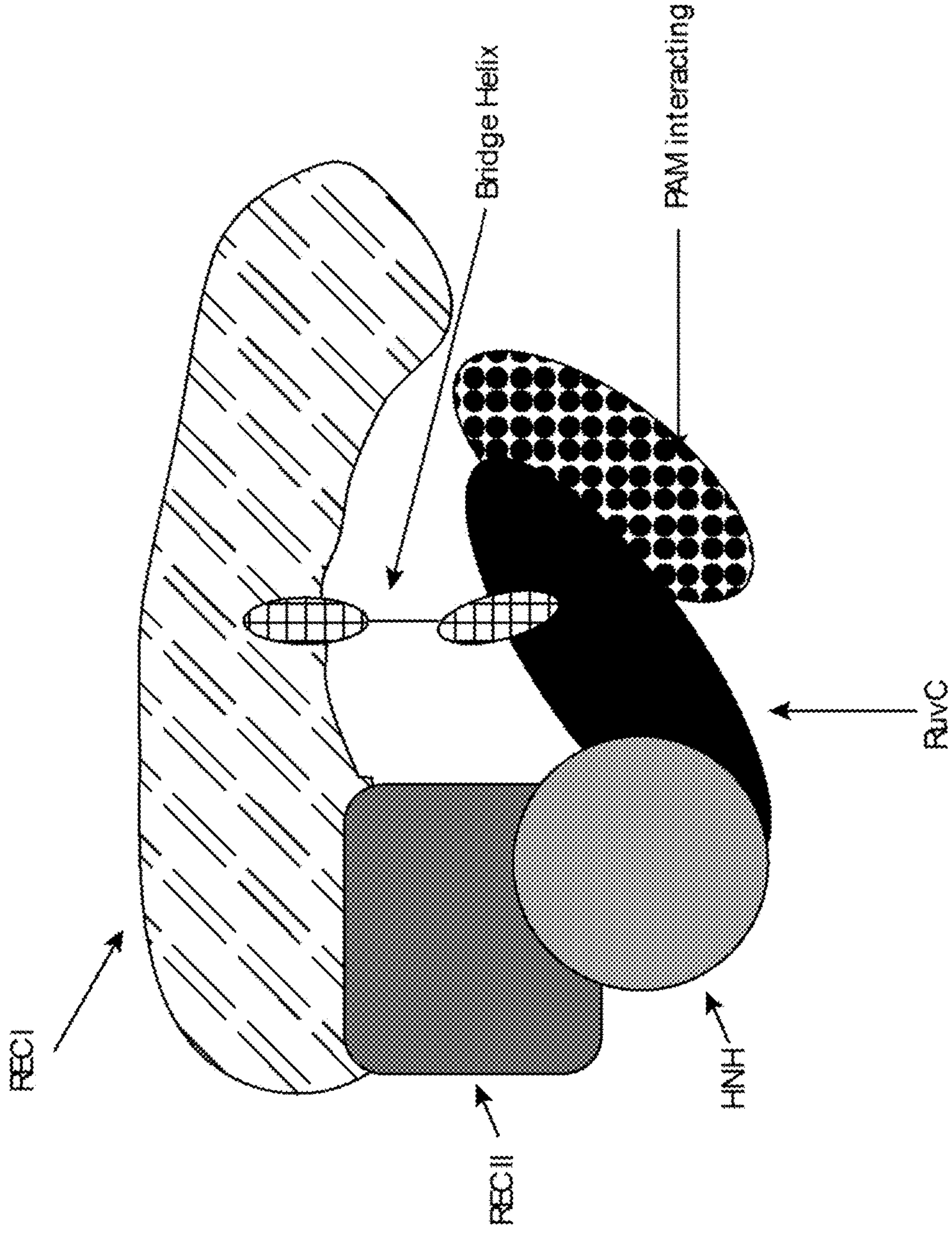
Figure 2:
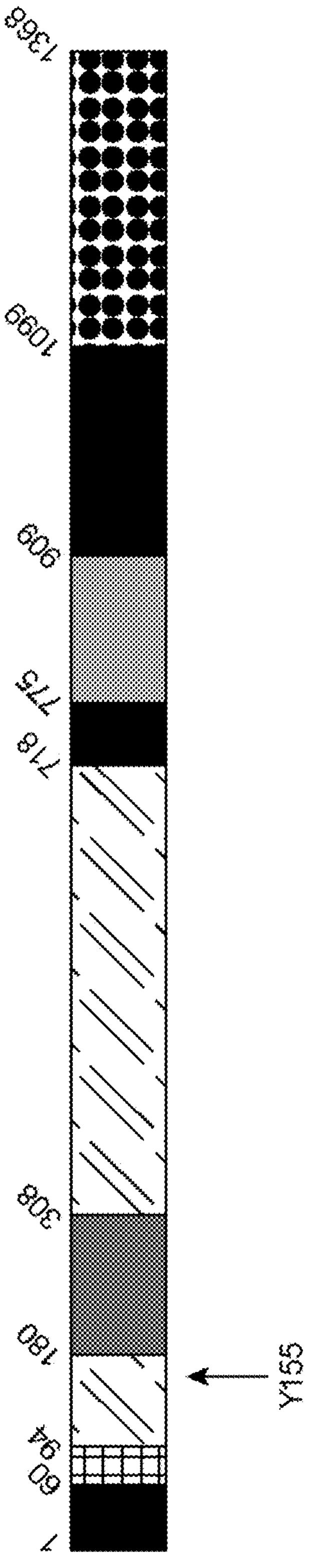
FIG. 2 depicts the domain architecture mapped onto the primary amino acid structure of a Cas9 endonuclease. The location of the Y155 modification of the Cas9 Y155 endonuclease variant (in the REC1 domain) described herein is indicated by an arrow.
Figure 3:
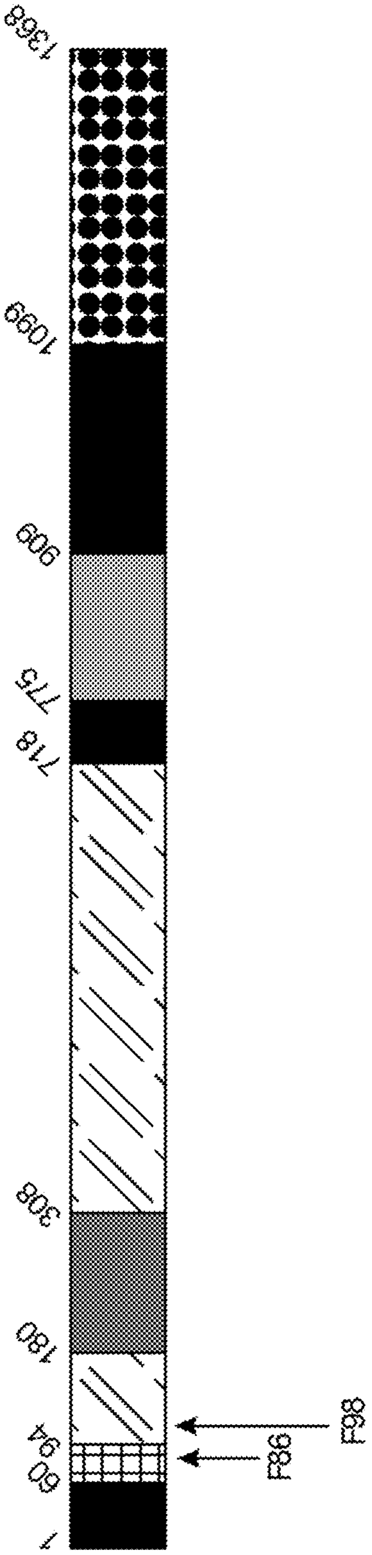
FIG. 3 depicts the domain architecture mapped onto the primary amino acid structure of a Cas9 endonuclease. The location of the F86 and F98 modifications of the Cas9 endonuclease F86-F98 variant described herein are indicated by an arrow.

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NO:1 sets forth the amino acid sequence of *Streptococcus pyogenes* Cas9.

SEQ ID NO:2 sets forth the nucleotide sequence of *Bacillus* codon optimized Cas9 gene, encoding the wild type Cas9 protein of *Streptococcus pyogenes* Cas9.

SEQ ID NO:3 sets forth the amino acid sequence of N-terminal NLS.

SEQ ID NO:4 sets forth the amino acid sequence of C-terminal NLS.

SEQ ID NO:5 sets forth the amino acid sequence of deca-Histidine tag.

SEQ ID NO:6 sets forth the nucleotide sequence of 6 aprE promoter.

SEQ ID NO:7 sets forth the nucleotide sequence of terminator.

SEQ ID NOs: 8-9, 12-13, 38-39, 41-42, 50-51, 54-55, 59-60, 67-68, 71-72, 79-80, 88-89, 91-92, 111-112, 119-120, 138-139, 145-146, 151-152, 156-157 set forth the nucleotide sequence of a primer.

SEQ ID NO: 10 sets forth the nucleotide sequence of the pKB320 backbone.

SEQ ID NO: 11 sets forth the nucleotide sequence of pKB320.

SEQ ID NO: 14 sets forth the nucleotide sequence of plasmid RSP1.

SEQ ID NO: 15 sets forth the nucleotide sequence of plasmid RSP2.

SEQ ID NOs: 16-27 sets forth the nucleotide sequence of plasmids FSP1, FSP2, FSP3, FSP4, FSP5, FSP6, FSP7, RSP3, FSP8, pRF694, pRF801 and pRF806, respectively.

SEQ ID NO: 28 sets forth the nucleotide sequence of target site 1 of *Bacillus licheniformis.*

SEQ ID NO: 29 sets forth the nucleotide sequence of target site 1 of *Bacillus licheniformis.*

SEQ ID NO: 30 sets forth the nucleotide sequence of serA1 open reading frame.

SEQ ID NO: 31 sets forth the nucleotide sequence of target site 1+PAM of *Bacillus licheniformis.*

SEQ ID NO: 32 sets forth the nucleotide sequence of DNA encoding variable targeting domain 1 SEQ ID NO: 33 sets forth the nucleotide sequence of DNA encoding CER domain.

SEQ ID NO: 34 sets forth the nucleotide sequence of gRNA targeting target site 1.

SEQ ID NO: 35 sets forth the nucleotide sequence of spac promoter.

SEQ ID NO: 36 sets forth the nucleotide sequence of t0 terminator SEQ ID NO: 37 sets forth the nucleotide sequence of serA1 homology arm 1 of *Bacillus licheniformis.*

SEQ ID NO: 40 sets forth the nucleotide sequence of serA1 homology arm 2 of *Bacillus licheniformis.*

SEQ ID NO: 43 sets forth the nucleotide sequence of DNA encoding ts1 gRNA expression cassette.

SEQ ID NO: 44 sets forth the nucleotide sequence of serA1 deletion editing template.

SEQ ID NO: 45 sets forth the nucleotide sequence of rghR1 open reading frame of *Bacillus licheniformis.*

SEQ ID NO: 46 sets forth the nucleotide sequence of target site 2 of *Bacillus* 20 *licheniformis.*

SEQ ID NO: 47 sets forth the nucleotide sequence of target site 2+PAM of *Bacillus licheniformis.*

SEQ ID NO: 48 sets forth the nucleotide sequence of DNA encoding variable targeting domain 2.

SEQ ID NO: 49 sets forth the nucleotide sequence of the guide RNA (gRNA) targeting target site 2.

SEQ ID NO: 50 sets forth the nucleotide sequence of homology arm 1 of rghR1 from *Bacillus licheniformis.*

SEQ ID NO: 53 sets forth the nucleotide sequence of homology arm 2 of rghR1 from *Bacillus licheniformis.*

SEQ ID NO: 56 sets forth the nucleotide sequence of DNA encoding ts2 expression cassette.

SEQ ID NO: 57 sets forth the nucleotide sequence of rghR1 deletion editing template.

SEQ ID NO: 58 sets forth the amino acid sequence of Cas9 Y155H variant.

SEQ ID NO: 61 sets forth the nucleotide sequence of pRF827.

SEQ ID NO: 62 sets forth the nucleotide sequence of Cas9 Y155H variant expression cassette.

SEQ ID NO: 63 sets forth the nucleotide sequence of pRF856, SEQ ID NO: 64 sets forth the nucleotide sequence of pBL.comK-syn.

SEQ ID NO: 65 sets forth the nucleotide sequence of the target site 1 locus from *Bacillus licheniformis.*

SEQ ID NO: 66 sets forth the nucleotide sequence of the target site 1 edited locus.

SEQ ID NO: 69 sets forth the nucleotide sequence of the target site 2 locus from *Bacillus licheniformis.*

SEQ ID NO: 70 sets forth the nucleotide sequence of the target site 2 edited locus.

SEQ ID NO: 73 sets forth the nucleotide sequence of *Yarrowia* codon optimized Cas9.

SEQ ID NO: 74 sets forth the nucleotide sequence of SV40 NLS.

SEQ ID NO: 75 sets forth the nucleotide sequence of *Yarrowia* FBA1 promoter.

SEQ ID NO: 76 sets forth the nucleotide sequence of *Yarrowia* Cas9 expression cassette.

SEQ ID NO: 77 sets forth the nucleotide sequence of pZufCas9.

SEQ ID NO: 78 sets forth the nucleotide sequence of Cas9-SV40 fusion.

SEQ ID NO: 81 sets forth the nucleotide sequence of Cas9-SV40 PCR product.

SEQ ID NOs: 82-83 sets forth the nucleotide sequence of pBAD/HisB and pRF48, respectively.

SEQ ID NO: 84 sets forth the nucleotide sequence of the *E. coli* optimized Cas9 expression cassette, SEQ ID NO: 85-86 sets forth the nucleotide sequence of pKO3 and pRF97, respectively.

SEQ ID NO: 87 sets forth the nucleotide sequence of the Cas9 Y155H encoding synthetic fragment;

SEQ ID NO: 90 sets forth the nucleotide sequence of pRF97-Y155H fragment.

SEQ ID NO: 93 sets forth the nucleotide sequence of pRF861 SEQ ID NO: 94 sets forth the nucleotide sequence of the nac gene from *E. coli.*

SEQ ID NO: 95 sets forth the nucleotide sequence of nac target site 1.

SEQ ID NO: 96 sets forth the nucleotide sequence of nac target site 1+PAM *E. coli.*

SEQ ID NO: 97 sets forth the nucleotide sequence of nac target site 1.

SEQ ID NO: 98 sets forth the nucleotide sequence of nac target site 1+PAM.

SEQ ID NO: 99 sets forth the nucleotide sequence of N25 phage promoter SEQ ID NO: 100 sets forth the nucleotide sequence of nac target site 1 gRNA expression cassette.

SEQ ID NO: 101 sets forth the nucleotide sequence of nac target site 2 gRNA expression cassette.

SEQ ID NO: 102 sets forth the nucleotide sequence of nac upstream deletion arm.

SEQ ID NO: 103 sets forth the nucleotide sequence of nac downstream deletion arm.

SEQ ID NO: 104 sets forth the nucleotide sequence of nac deletion editing template.

SEQ ID NO: 105 sets forth the nucleotide sequence of 5' pRF97 or pRF861 identity.

SEQ ID NO: 106 sets forth the nucleotide sequence of 3' pRF97 or pRF861 identity.

SEQ ID NO: 107 sets forth the nucleotide sequence of nacETsite1.

SEQ ID NO: 108 sets forth the nucleotide sequence of nacETsite2.

SEQ ID NO: 109 sets forth the nucleotide sequence of pRF97-cassette.

SEQ ID NO: 110 sets forth the nucleotide sequence of pRF861-cassette.

SEQ ID NO: 113 sets forth the nucleotide sequence of pRF97-nacETsite1.

SEQ ID NO: 114 sets forth the nucleotide sequence of pRF97-nacETsite2.

SEQ ID NO: 115 sets forth the nucleotide sequence of pRF861-nacETsite1.

SEQ ID NO: 116 sets forth the nucleotide sequence of pRF861-nacETsite2.

SEQ ID NO: 117 sets forth the nucleotide sequence of the wild type (WT) nac locus from *E. coli.*

SEQ ID NO: 118 sets forth the nucleotide sequence of the edited nac locus.

SEQ ID NO: 121 sets forth the nucleotide sequence of *Streptococcus pyogenes* Cas9.

SEQ ID NO: 122 sets forth the nucleotide sequence encoding the Cas9 Y155H variant.

SEQ ID NO: 123 sets forth the amino acid sequence of the Cas9 Y155N variant.

SEQ ID NO: 124 sets forth the nucleotide sequence encoding the Cas9 Y155N variant.

SEQ ID NO: 125 sets forth the amino acid sequence of the Cas9 Y155E variant.

SEQ ID NO: 126 sets forth the nucleotide sequence encoding the Cas9 Y155E variant.

SEQ ID NO: 127 sets forth the amino acid sequence of the Cas9 Y155F variant.

SEQ ID NO: 128 sets forth the nucleotide sequence encoding the Cas9 Y155F variant.

SEQ ID NO: 129 sets forth the amino acid sequence of the Cas9 F86A-F98A variant.

SEQ ID NO: 130 sets forth the nucleotide sequence of the F86A-F98A synthetic fragment.

SEQ ID NO: 131 sets forth the nucleotide sequence of pRF801 backbone for F86A F98A.

SEQ ID NO: 132 sets forth the nucleotide sequence of pRF801 backbone forward.

SEQ ID NO: 133 sets forth the nucleotide sequence of pRF801 backbone reverse

SEQ ID NO: 134 sets forth the nucleotide sequence of F86A-F98A synthetic forward.

SEQ ID NO: 135 sets forth the nucleotide sequence of F86A-F98A synthetic reverse.

SEQ ID NO: 136 sets forth the nucleotide sequence of *Bacillus* F86A F98A expression cassette.

SEQ ID NO: 137 sets forth the nucleotide sequence of pRF866.

SEQ ID NO: 140 sets forth the nucleotide sequence of RNR2p promoter.

SEQ ID NO: 141 sets forth the nucleotide sequence of 2-micron replication origin 1.

SEQ ID NO: 142 sets forth the nucleotide sequence of KanMX expression cassette.

SEQ ID NO: 143 sets forth the nucleotide sequence of SNR52p promoter.

SEQ ID NO: 144 sets forth the nucleotide sequence of pSE087 plasmid.

SEQ ID NO: 147 sets forth the nucleotide sequence of targeting sgRNA+T(6) terminator.

SEQ ID NO: 148 sets forth the nucleotide sequence of 50 bp upstream homology arm.

SEQ ID NO: 149 sets forth the nucleotide sequence of URA3 targeting sgRNA+T(6) terminator.

SEQ ID NO: 150 sets forth the nucleotide sequence of 50 bp downstream homology arm.

SEQ ID NO: 153 sets forth the nucleotide sequence of 2-micron replication origin 2.

SEQ ID NO: 154 sets forth the nucleotide sequence of 154 ampicillin resistant gene.

SEQ ID NO: 155 sets forth the nucleotide sequence of RNR2 terminator.

DETAILED DESCRIPTION

Compositions and methods are provided for variant Cas systems and elements comprising such systems, including, but not limiting to, Cas endonuclease variants, guide polynucleotide/Cas endonuclease complexes comprising Cas endonuclease variants, as well as guide polynucleotides and guide RNA elements that can interact with Cas endonuclease variants. Compositions and methods are also provided for direct delivery of Cas endonucleases variants, guide RNAs and guide RNA/Cas endonucleases complexes. The present disclosure further includes compositions and methods for genome modification of a target sequence in the genome of a cell, for gene editing, and for inserting a polynucleotide of interest into the genome of a cell.

The present document is organized into a number of sections for ease of reading; however, the reader will appreciate that statements made in one section may apply to other sections. In this manner, the headings used for different sections of the disclosure should not be construed as limiting.

The headings provided herein are not limitations of the various aspects or embodiments of the present compositions and methods which can be had by reference to the specification as a whole. Accordingly, the terms defined immediately below are more fully defined by reference to the specification as a whole.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

Cas Genes and Proteins

CRISPR (clustered regularly interspaced short palindromic repeats) loci refers to certain genetic loci encoding components of DNA cleavage systems, for example, used by bacterial and archaeal cells to destroy foreign DNA (Horvath and Barrangou, 2010, Science 327:167-170; WO2007/025097, published Mar. 1, 2007). A CRISPR locus can consist of a CRISPR array, comprising short direct repeats (CRISPR repeats) separated by short variable DNA sequences (called 'spacers'), which can be flanked by diverse Cas (CRISPR-associated) genes. The number of CRISPR-associated genes at a given CRISPR locus can vary between species. Multiple CRISPR/Cas systems have been described including Class 1 systems, with multisubunit effector complexes (comprising type I, type III and type IV subtypes), and Class 2 systems, with single protein effectors (comprising type II and type V subtypes, such as but not limiting to Cas9, Cpf1, C2c1, C2c2, C2c3). Class 1 systems (Makarova et al. 2015, Nature Reviews; Microbiology Vol. 13:1-15; Zetsche et al., 2015, Cell 163, 1-13; Shmakov et al., 2015, Molecular_Cell 60, 1-13; Haft et al., 2005, Computational Biology, PLoS Comput Biol 1(6): e60. doi:10.1371/journal.pcbi. 0010060 and WO 2013/176772 A1 published on Nov. 23, 2013 incorporated by reference herein). The type II CRISPR/Cas system from bacteria employs a crRNA (CRISPR RNA) and tracrRNA (trans-activating CRISPR RNA) to guide the Cas endonuclease to its DNA target. The crRNA contains a spacer region complementary to one strand of the double strand DNA target and a region that base pairs with the tracrRNA (trans-activating CRISPR RNA) forming a RNA duplex that directs the Cas endonuclease to cleave the DNA target. Spacers are acquired through a not fully understood process involving Cas1 and Cas2 proteins. All type II CRISPR/Cas loci contain cas1 and cas2 genes in addition to the cas9 gene (Chylinski et al., 2013, RNA Biology 10:726-737; Makarova et al. 2015, Nature Reviews Microbiology Vol. 13:1-15). Type II CRISPR-Cas loci can encode a tracrRNA, which is partially complementary to the repeats within the respective CRISPR array, and can comprise other proteins such as Csn1 and Csn2. The presence of cas9 in the vicinity of Cas 1 and cas2 genes is the hallmark of type II loci (Makarova et al. 2015, Nature Reviews Microbiology Vol. 13:1-15). Type I CRISPR-Cas (CRISPR-associated) systems consist of a complex of proteins, termed Cascade (CRISPR-associated complex for antiviral defense), which function together with a single CRISPR RNA (crRNA) and Cas3 to defend against invading viral DNA (Brouns, S. J. J. et al. Science 321:960-964; Makarova et al. 2015, Nature Reviews; Microbiology Vol. 13:1-15, which are incorporated in their entirety herein).

The term "Cas gene" herein refers to a gene that is generally coupled, associated or close to, or in the vicinity of flanking CRISPR loci. The terms "Cas gene", "cas gene", "CRISPR-associated (Cas) gene" and "Clustered Regularly Interspaced Short Palindromic Repeats-associated gene" are used interchangeably herein.

The term "Cas protein" or "Cas polypeptide" refers to a polypeptide encoded by a Cas (CRISPR-associated) gene. A Cas protein includes a Cas endonuclease.

A Cas protein may be a bacterial or archaeal protein. Type I-III CRISPR Cas proteins herein are typically prokaryotic in origin; type I and III Cas proteins can be derived from bacterial or archaeal species, whereas type II Cas proteins (i.e., a Cas9) can be derived from bacterial species, for example. In other aspects, Cas proteins include one or more of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. A Cas protein includes a Cas9 protein, a Cpf1 protein, a C2c1 protein, a C2c2 protein, a C2c3 protein, Cas3, Cas3-HD, Cas 5, Cas7, Cas8, Cas10, or combinations or complexes of these.

The term "Cas endonuclease" refers to a Cas polypeptide (Cas protein) that, when in complex with a suitable polynucleotide component, is capable of recognizing, binding to, and optionally nicking or cleaving all or part of a specific DNA target sequence. A Cas endonuclease is guided by the guide polynucleotide to recognize, bind to, and optionally nick or cleave all or part of a specific target site in double stranded DNA (e.g., at a target site in the genome of a cell). A Cas endonuclease described herein comprises one or more nuclease domains. The Cas endonucleases employed in donor DNA insertion methods described herein are endonucleases that introduce single or double-strand breaks into the DNA at the target site. Alternatively, a Cas endonuclease may lack DNA cleavage or nicking activity, but can still specifically bind to a DNA target sequence when complexed with a suitable RNA component.

As used herein, a polypeptide referred to as a "Cas9" (formerly referred to as Cas5, Csn1, or Csx12) or a "Cas9 endonuclease" or having "Cas9 endonuclease activity" refers to a Cas endonuclease that forms a complex with a crNucleotide and a tracrNucleotide, or with a single guide polynucleotide, for specifically binding to, and optionally nicking or cleaving all or part of a DNA target sequence. A Cas9 endonuclease comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Makarova et al. 2015, Nature Reviews Microbiology Vol. 13:1-15, Hsu et al, 2013, Cell 157:1262-1278). Cas9 endonucleases are typically derived from a type II CRISPR system, which includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA (Makarova et al. 2015, Nature Reviews Microbiology Vol. 13:1-15).

A "functional fragment", "fragment that is functionally equivalent" and "functionally equivalent fragment" of a Cas endonuclease are used interchangeably herein, and refer to a portion or subsequence of the Cas endonuclease in which the ability to recognize, bind to, and optionally unwind, nick or cleave (introduce a single or double-strand break in) the target site is retained.

The terms "functional variant", "variant that is functionally equivalent" and "functionally equivalent variant" of a Cas endonuclease of the present disclosure, are used interchangeably herein, and refer to a variant of the Cas endonuclease of the present disclosure in which the ability to recognize, bind to, and optionally unwind, nick or cleave all or part of a target sequence is retained.

Determining binding activity and/or endonucleolytic activity of a Cas protein herein toward a specific target DNA sequence may be assessed by any suitable assay known in the art, such as disclosed in U.S. Pat. No. 8,697,359, which is disclosed herein by reference. A determination can be made, for example, by expressing a Cas protein and suitable RNA component in host cell/organism, and then examining the predicted DNA target site for the presence of an indel (a Cas protein in this particular assay would have endonucleolytic activity [single or double-strand cleaving activity]). Examining for the presence of an indel at the predicted target site could be done via a DNA sequencing method or by inferring indel formation by assaying for loss of function of the target sequence, for example. In another example, Cas protein activity can be determined by expressing a Cas protein and suitable RNA component in a host cell/organism that has been provided a donor DNA comprising a sequence homologous to a sequence in at or near the target site. The presence of donor DNA sequence at the target site (such as would be predicted by successful HR between the donor and target sequences) would indicate that targeting occurred.

A variant of a Cas endonuclease, also referred to as "Cas endonuclease variant", refers to a variant of a parent Cas endonuclease wherein the Cas endonuclease variant retains the ability to recognize, bind to, and optionally unwind, nick or cleave all or part of a DNA target sequence, when associated with a crNucleotide and a tracrNucleotide, or with a single guide polynucleotide, (such as a guide polynucleotide described herein). A Cas endonuclease variant includes a Cas endonuclease variant described herein, where the Cas endonuclease variant differs from the parent Cas endonuclease, in such a manner that the Cas endonuclease variant (when in complex with a guide polynucleotide to form a polynucleotide-guided endonuclease complex capable of modifying a target site) has at least one improved property such as, but not limited to, increased transformation efficiency increased DNA editing efficiency, reduced off target cleavage, or any combination thereof, when compared to the parent Cas endonuclease (in complex with the same guide polynucleotide to form a polynucleotide-guided endonuclease complex capable of modifying the same target site).

As used herein, the term "transformation efficiency" is defined by diving the number of transformed cells obtained when a Cas9 variant is used in combination with a guide polynucleotide to form a polynucleotide-guided endonuclease PGEN complex capable of modifying a target site, with the number of transformed cells obtained when the parent (wild type) Cas9 is used in combination with the same guide polynucleotide to form a PGEN complex as the Cas endonuclease component of a PGEN capable of modifying the same target site. This number can be multiplied by 100 to express it as a %.

$$\text{Transformation efficiency} = \frac{(\text{number of transformed cells with } Cas9 \text{ variant})}{(\text{number of transformed cells with parent WT } Cas9)}$$

A transformation efficiency of 1 (or 100%) indicates that the number of transformed cells obtained when a Cas9 variant is used is about the same or identical to the number of number of transformed cells obtained when a WT Cas9 variant. In this case the Cas9 variant would not have an improved property when compared to its parent Cas9 endonuclease. In contrast, a transformation efficiency of greater than 1 indicates that the number of transformed cells obtained when a Cas9 variant is used is greater than the number of transformed cells obtained when a WT Cas9 variant. In this case the Cas9 variant does have an improved property, e.g. an improved transformation efficiency, when compared to the parent Cas9 endonuclease.

As used herein, the term "editing efficiency" or "DNA editing efficiency" is used interchangeably herein and is defined by diving the number of cells comprising a DNA edit (edited cell) obtained when a Cas9 variant is used in combination with a guide polynucleotide to form a polynucleotide-guided endonuclease PGEN complex capable of modifying a target site, with the number of edited cells obtained when the parent (wild type) Cas9 is used in combination with the same guide polynucleotide to form a PGEN complex as the Cas endonuclease component of a PGEN capable of modifying the same target site. This number can be multiplied by 100 to express it as a %.

$$\text{Editing efficiency} = \frac{(\text{number of cells comprising a DNA edit made by } Cas9 \text{ variant})}{(\text{number of cells comprising a DNA edit made by parent } Cas9)}$$

A DNA editing efficiency of 1 (or 100%) indicates that the number of edited cells obtained when a Cas9 variant is used is about the same or identical to the number of number of edited cells obtained when a WT Cas9 variant is used. In this case the Cas9 variant would not have an improved property when compared to its parent cas9 endonuclease. In contrast, a DNA editing efficiency of greater than 1 indicates that the number of transformed cells obtained when a Cas9 variant is used is greater than the number of transformed cells obtained when a parent (WT) Cas9 variant is used. In this case the Cas9 variant does have an improved property, e.g. an improved editing efficiency, when compared to the parent Cas9 endonuclease.

A Cas endonuclease variant may comprise an amino acid sequence that is at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the parent Cas endonuclease.

A variant Cas endonuclease gene (variant cas gene) may comprise a nucleotide sequence that is at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the parent Cas endonuclease nucleotide sequence.

Non limiting examples of parent Cas endonucleases herein can be Cas endonucleases from any of the following genera: Aeropyrum, *Pyrobaculum, Sulfolobus, Archaeoglobus, Haloarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Streptococcus, Treponema, Francisella*, or *Thermotoga*. Furthermore, a parent Cas endonuclease herein can be encoded, for example, by any of SEQ ID NOs:462-465, 467-472, 474-477, 479-487, 489-492, 494-497, 499-503, 505-508, 510-516, or 517-521 as disclosed in U.S. Appl. Publ. No. 2010/0093617, which is incorporated herein by reference.

Furthermore, a parent Cas9 endonuclease herein may be derived from a *Streptococcus* (e.g., *S. pyogenes, S. pneumoniae, S. thermophilus, S. agalactiae, S. parasanguinis, S. oralis, S. salivarius, S. macacae, S. dysgalactiae, S. anginosus, S. constellatus, S. pseudoporcinus, S. mutans*), *Listeria* (e.g., *L. innocua*), *Spiroplasma* (e.g., *S. apis, S. syrphidicola*), *Peptostreptococcaceae, Atopobium, Porphyromonas* (e.g., *P. catoniae*), *Prevotella* (e.g., *P. intermedia*), *Veillonella, Treponema* (e.g., *T. socranskii, T. denticola*), *Capnocytophaga, Finegoldia* (e.g., *F. magna*), *Coriobacteriaceae* (e.g., *C. bacterium*), *Olsenella* (e.g., *O. profusa*), *Haemophilus* (e.g., *H. sputorum, H. pittmaniae*), *Pasteurella* (e.g., *P. bettyae*), *Olivibacter* (e.g., *O. sitiensis*), *Epilithonimonas* (e.g., *E. tenax*), *Mesonia* (e.g., *M. mobilis*), *Lactobacillus* (e.g., *L. plantarum*), *Bacillus* (e.g., *B. cereus*), *Aquimarina* (e.g., *A. muelleri*), *Chryseobacterium* (e.g., *C. palustre*), *Bacteroides* (e.g., *B. graminisolvens*), *Neisseria* (e.g., *N. meningitidis*), *Francisella* (e.g., *F. novicida*), or *Flavobacterium* (e.g., *F. frigidarium, F. soli*) *species, for example. In* one aspect a *S. pyogenes* parent Cas9 endonuclease is described herein. As another example, a parent Cas9 endonuclease can be any of the Cas9 proteins disclosed in Chylinski et al. (RNA Biology 10:726-737), which is incorporated herein by reference.

The sequence of a parent Cas9 endonuclease herein can comprise, for example, any of the Cas9 amino acid sequences disclosed in GenBank Accession Nos. G3ECR1 (*S. thermophilus*), WP_026709422, WP_027202655, WP_027318179, WP_027347504, WP_027376815, WP_027414302, WP_027821588, WP_027886314, WP_027963583, WP_028123848, WP_028298935, Q03J16 (*S. thermophilus*), EGP66723, EGS38969, EGV05092, EH165578 (*S. pseudoporcinus*), EIC75614 (*S. oralis*), EID22027 (*S. constellatus*), EIJ69711, EJP22331 (*S. oralis*), EJP26004 (*S. anginosus*), EJP30321, EPZ44001 (*S. pyogenes*), EPZ46028 (*S. pyogenes*), EQL78043 (*S. pyogenes*), EQL78548 (*S. pyogenes*), ERL10511, ERL12345, ERL19088 (*S. pyogenes*), ESA57807 (*S. pyogenes*), ESA59254 (*S. pyogenes*), ESU85303 (*S. pyogenes*), ETS96804, UC75522, EGR87316 (*S. dysgalactiae*), EGS33732, EGV01468 (*S. oralis*), EHJ52063 (*S. macacae*), EID26207 (*S. oralis*), EID33364, EIG27013 (*S. parasanguinis*), EJF37476, EJO19166 (*Streptococcus* sp. BS35b), EJU16049, EJU32481, YP_006298249, ERF61304, ERK04546, ETJ95568 (*S. agalactiae*), TS89875, ETS90967 (*Streptococcus* sp. SR4), ETS92439, EUB27844 (*Streptococcus* sp. BS21), AFJ08616, EUC82735 (*Streptococcus* sp. CM6), EWC92088, EWC94390, EJP25691, YP_008027038, YP_008868573, AGM26527, AHK22391, AHB36273, Q927P4, G3ECR1, or Q99ZW2 (*S. pyogenes*), which are incorporated by reference. Alternatively, a Cas9 protein herein can be encoded by any of SEQ ID NOs:462 (*S. thermophilus*), 474 (*S. thermophilus*), 489 (*S. agalactiae*), 494 (*S. agalactiae*), 499 (*S. mutans*), 505 (*S. pyogenes*), or 518 (*S. pyogenes*) as disclosed in U.S. Appl. Publ. No. 2010/0093617 (incorporated herein by reference), for example.

Given that certain amino acids share similar structural and/or charge features with each other (i.e., conserved), the amino acid at each position in a Cas9 can be as provided in the disclosed sequences or substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

Fragments and variants can be obtained via methods such as site-directed mutagenesis and synthetic construction. Methods for measuring endonuclease activity are well known in the art such as, but not limiting to, PCT/US13/39011, filed May 1, 2013, PCT/US16/32073 filed May 12, 2016, PCT/US16/32028 filed May 12, 2016, incorporated by reference herein).

In one embodiment, the Cas endonuclease variant is a Cas9 endonuclease variant described herein. As used herein, a "Cas9 endonuclease variant" or "Cas9 variant" refers to a variant of a parent Cas9 endonuclease wherein the Cas9 endonuclease variant retains the ability to recognize, bind to, and optionally unwind, nick or cleave all or part of a DNA target sequence, when associated with a crNucleotide and a tracrNucleotide, or with a single guide polynucleotide (such as a guide polynucleotide described herein. A Cas9 endonuclease variant includes a Cas9 endonuclease variant described herein, where the Cas endonuclease variant differs from the parent Cas9 endonuclease, in such a manner that the Cas9 endonuclease variant (when in complex with a guide polynucleotide to form a polynucleotide-guided endonuclease complex capable of modifying a target site) has at least one improved property such as, but not limited to, increased transformation efficiency increased DNA editing efficiency, reduced off target cleavage, or any combination thereof, when compared to the parent Cas9 endonuclease (in complex with the same guide polynucleotide to form a polynucleotide-guided endonuclease complex capable of modifying the same target site).

A Cas9 endonuclease variant described herein includes a variant that can bind to and nick a double strand DNA target site when associated with a crNucleotide and a tracrNucleotide, or with a single guide polynucleotide, whereas the parent Cas endonuclease can bind to and make a double strand break (cleave) at the target site, when associated with a crNucleotide and a tracrNucleotide, or with a single guide polynucleotide.

As described herein, it has been found surprisingly and unexpectedly that a Cas9 endonuclease variant having at least one an amino acid modification outside its HNH and RuvC domain (when in complex with a guide polynucleotide to form a polynucleotide-guided endonuclease complex capable of modifying a target site) can have at least one improved property such as, but not limited to, an increased transformation efficiency, an increased DNA editing efficiency, or a combination thereof, when compared to its parent Cas9 endonuclease (in complex with the same guide polynucleotide to form a polynucleotide-guided endonuclease complex capable of modifying the same target site).

In one aspect the Cas9 endonuclease variant described herein comprises a RuvC nuclease domain and an HNH (H—N—H) nuclease domain, and at least one amino acid modification (deletion, substitution or insertion of at least one amino acid) located outside the HNH and RuvC domain.

In one aspect the Cas9 endonuclease variant described herein, or an active fragment thereof, comprises at least 1, 2, 3, 4, 5, 6, 7, 8, 9, 10 amino acid substitutions when compared to the parent Cas9 endonuclease.

In one aspect the Cas9 endonuclease variant described herein has an amino acid modification outside its HNH and RuvC domain, wherein said Cas9 endonuclease has increased transformation efficiency and/or DNA editing efficiency when compared to a parent Cas9 endonuclease that does not comprises said amino acid modification, wherein said guide polynucleotide and Cas9 endonuclease variant can form a complex capable of recognizing, binding to, and optionally nicking, unwinding, or cleaving all or part of said target sequence.

In one aspect, the Cas9 endonuclease variant described herein has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to a parent Cas9 polypeptide set forth in SEQ ID NO: 1 and has at least one amino acid substitution at position 155, wherein the amino acid positions of the variant are numbered by correspondence with the amino acid sequence of the parent Cas9 polypeptide, wherein said Cas9 endonuclease variant has endonuclease activity.

The Cas9 endonuclease variant substitution at position 155 can be selected from the group consisting of Y155H, Y155 N, Y 155 E, Y155 F resulting in a Cas9 Y155H variant (SEQ ID NO: 58), Cas9 Y155N variant (SEQ ID NO: 123), Cas9 Y155E variant (SEQ ID NO: 125 and Cas9 Y155F variant (SEQ ID NO: 127), respectively. DNA sequences encoding the Cas9 Y155 variants can be optimized for expression in a particular host organism as is well known in the art. Examples of DNA sequences encoding Cas9Y155 variant proteins are set forth in SEQ ID NOs: 122, 124, 126 and 128.

In one aspect, the Cas9 endonuclease variant described herein has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to a parent Cas9 polypeptide set forth in SEQ ID NO: 1 and has at least two amino acid substitutions, one at position 86 and another one at position 98, wherein the amino acid positions of the variant are numbered by correspondence with the amino acid sequence of the parent Cas9 polypeptide, wherein said Cas9 endonuclease variant has endonuclease activity.

The Cas9 endonuclease variant substitution at position 86 can be an F86A substitution resulting in a Cas9 F86A variant.

The Cas9 endonuclease variant substitution at position 89 can be an F98A substitution resulting in a Cas9 F98A variant.

The Cas9 endonuclease variant can comprise at least two substitutions, a first substitution at position 86, such as a F86A substitution and a second substitution at position 98 such as a F98A substitution, resulting in a Cas9 F86A-F98A variant set forth in SEQ ID NO: 129

The Cas9 endonuclease variant can comprise at least three substitutions wherein the at least three substitutions comprise a first substitution at position 86, such as a F86A substitution, a second substitution at position 98 such as a F98A substitution, and a third substitution a selected from the group consisting of a Y155H, Y155 N, Y 155 E, Y155 F.

DNA sequences encoding the Cas9 Y155 variants can be optimized for expression in a particular host organism as is well known in the art. Examples of DNA sequences encoding Cas9Y155 variant proteins are set forth in SEQ ID NOs: 122, 124, 126 and 128. Examples of a DNA sequence encoding the Cas9F86A-F98A variant protein is set forth in SEQ ID NO: 130.

The Cas9 endonuclease variant comprising at least one, at least two, or at least three substitutions selected form the group consisting of positions 86, 98 and 155, or any combination thereof, when in complex with a guide polynucleotide to form a polynucleotide-guided endonuclease complex capable of modifying a target site) can have at least one improved property such as, but not limited to, an increased transformation efficiency, an increased DNA editing efficiency, or a combination thereof, when compared to its parent Cas9 endonuclease (in complex with the same guide polynucleotide to form a polynucleotide-guided endonuclease complex capable of modifying the same target site).

The at least one, at least two, or at least three substitutions selected form the group consisting of positions 86, 98 and 155 (or any combination) thereof can be combined with any other amino acid modification known to one skilled in the art. In one aspect, any one of the substitutions (or any one combination thereof) selected form the group consisting of positions 86, 98 and 155 described herein can be combined with any amino acid substitution located in the HNH and RuvC domain known to one skilled in the art to cause a Cas9 endonuclease to act as a nickase (Trevino A. E. and Feng Zhang, 2014, Methods in Enzymology, volume 546 pg 161-174). A "nickase" Cas9 (Cas9n) can be generated by alanine substitution at key catalytic residues within the HNH or RuvC domains-SpCas9 D10A inactivates RuvC (Jinek, M, et al, 2012, Science, 337(6096), 816-821), while N863A has been found to inactivate HNH (Nishimasu et al., 2014; Shen et al 2014 Nature Methods 11, 399-402). A H840A mutation (Shen et al 2014 Nature Methods 11, 399-402) was also reported to convert Cas9 into a nicking enzyme, however, this mutant had reduced levels of activity in mammalian cells compared with N863A (Nishimasu et al. 2014, Cell, 156(5), 935-949.)

In one aspect, Cas9(N863A), Cas9(D10A) and/or Cas9 (H840A) can be further modified to include the at least one substitution selected form the group consisting of positions 86, 98 and 155 (or any combination) described herein, optionally resulting in an improved property of the modified Cas9(N863A), Cas9(D10A) and/or Cas9(H840A), respectively.

In one aspect, any one of the substitutions selected form the group consisting of positions 86, 98 and 155 (or any combination thereof) described herein can be combined with the amino acid substitutions selected from the group consisting of D10A, H840A or N863A and H840A.

In one aspect, a Cas9 endonuclease variant having at least one amino acid substitution at position 155, wherein the amino acid positions of the variant are numbered by correspondence with the amino acid sequence of the parent Cas9 polypeptide, has at least one improved property selected from an increased transformation efficiency, an increased DNA editing efficiency, or a combination thereof when compared to said parent Cas9 endonuclease.

In one aspect, a Cas9 endonuclease variant having a Y155H substitution at position 155, wherein the amino acid positions of the variant are numbered by correspondence with the amino acid sequence of the parent Cas9 polypeptide, has an increased transformation efficiency, when compared to said parent Cas9 endonuclease. In one aspect this increased transformation efficiency is observed in a prokaryotic host cell, such as but not limiting to a *Bacillus* species or *Escherichia coli* (*E. coli*) host cell.

In one aspect, a Cas9 endonuclease variant having a Y155H substitution at position 155, wherein the amino acid positions of the variant are numbered by correspondence with the amino acid sequence of the parent Cas9 polypeptide, has an increased transformation efficiency and an increased DNA editing efficiency, when compared to said parent Cas9 endonuclease. In one aspect this increased transformation efficiency and increased DNA editing efficiency is observed in a prokaryotic host cell, such as but not limiting to a *Bacillus* species or *Escherichia coli* (*E. coli*) host cell.

The improved property of a Cas9 variant described herein includes increased transformation efficiency, wherein the transformation efficiency, when compared to the parent Cas endonuclease is increased by at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 110,120, 130, 140, 150,160, 170, 180, 190, 200, 210, 220, 230, 240, 250, 260, 270, 280, 290, 300, 310, 320, 330, 340, 350, 360, 370, 380, 390,400, 410, 420, 430, 440, 440, 450, 460, 470, 480, 490, or up to 500 fold, when compared to the parent Cas endonuclease.

The improved property of a Cas9 variant described herein includes increased DNA editing efficiency, wherein the DNA editing efficiency, when compared to the parent Cas endonuclease is increased by at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, 110%, 120%, 130%, 140%, 150%, 160%, 170%, 180%, 190%, 200%, 210%, 220%, 230%, or 250%, or at least about 2, 3, 4, 5, 6, 7, 8, 9, up to 10 fold, when compared to the parent Cas endonuclease.

Cas endonuclease variants described herein, can be used for genome modification of prokaryotic and eukaryotic cells and organisms as further described herein.

The Cas endonuclease, or functional fragment or variant thereof, for use in the disclosed methods, can be isolated from a recombinant source where the genetically modified host cell (e.g. a bacterial cell, an insect cell, a fungal cell, a yeast cell or human-derived cell line) is modified to express the nucleic acid sequence encoding the Cas protein. Alternatively, the Cas protein can be produced using cell free protein expression systems or be synthetically produced.

The Cas endonuclease, including the Cas9 Y155 endonuclease variant described herein, can comprise a modified form of the Cas polypeptide. The modified form of the Cas polypeptide can include an amino acid change (e.g., deletion, insertion, or substitution) that reduces the naturally-occurring nuclease activity of the Cas protein. For example, in some instances, the modified form of the Cas protein, including the Cas9 Y155 endonuclease variant described herein, has less than 50%, less than 40%, less than 30%, less than 20%, less than 10%, less than 5%, or less than 1% of the nuclease activity of the corresponding wild-type Cas polypeptide (US patent application US20140068797 A1, published on Mar. 6, 2014). In some cases, the modified form of the Cas polypeptide has no substantial nuclease activity and is referred to as catalytically "inactivated Cas" or "deactivated Cas (dCas)." An inactivated Cas/deactivated Cas includes a deactivated Cas endonuclease (dCas). A catalytically inactive Cas, including one originating from the Cas9 Y155 endonuclease variant described herein can be fused to a heterologous sequence as described herein.

Recombinant DNA constructs expressing the Cas endonuclease and guide polynucleotides described herein (including functional fragments thereof, bacterial-, fungal-, plant-, microbe-, or mammalian-codon optimized Cas proteins) can be stably integrated into the genome of an organism. For example, microorganisms can be produced that comprise a Cas gene stably integrated in the microbe's genome.

The Cas endonuclease described herein (such as but not limited to the Cas9 endonuclease Y155 variant described herein) can be expressed and purified by methods known in the art (such as those described in Example 2 of WO2016/186946, published Nov. 24, 2016 and incorporated herein by reference).

Cas Protein Fusions

A Cas endonuclease, or Cas endonuclease variant described herein, can be part of a fusion protein comprising one or more heterologous protein domains (e.g., 1, 2, 3, or more domains in addition to the Cas polypeptide). Such a fusion protein may comprise any additional protein sequence, and optionally a linker sequence between any two domains, such as between Cas polypeptide and a first heterologous domain. Examples of protein domains that may be fused to a Cas polypeptide include, without limitation, epitope tags (e.g., histidine [His], V5, FLAG, influenza hemagglutinin [HA], myc, VSV-G, thioredoxin [Trx]), reporters (e.g., glutathione-5-transferase [GST], horseradish peroxidase [HRP], chloramphenicol acetyltransferase [CAT], beta-galactosidase, beta-glucuronidase [GUS], luciferase, green fluorescent protein [GFP], HcRed, DsRed, cyan fluorescent protein [CFP], yellow fluorescent protein [YFP], blue fluorescent protein [BFP]), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas endonuclease can also be in fusion with a protein that binds DNA molecules or other molecules, such as maltose binding protein (MBP), S-tag, Lex A DNA binding domain (DBD), GAL4A DNA binding domain, and herpes simplex virus (HSV) VP16.

A Cas endonuclease can comprise a heterologous regulatory element such as a nuclear localization sequence (NLS). A heterologous NLS amino acid sequence may be of sufficient strength to drive accumulation of a Cas endonuclease in a detectable amount in the nucleus of a cell herein. An NLS may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NLS may be operably linked to the N-terminus or C-terminus of a Cas protein herein, for example. Two or more NLS sequences can be linked to a Cas protein, for example, such as on both the N- and C-termini of a Cas protein. The Cas gene can be operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region. Non-limiting examples of suitable NLS sequences herein include those disclosed in U.S. Pat. Nos. 6,660,830 and 7,309,576, which are both incorporated by reference herein. A heterologous NLS amino acid sequence include plant, viral and mammalian nuclear localization signals.

A catalytically active and/or inactive Cas endonuclease, can be fused to a heterologous sequence (US patent application US20140068797 A1, published on Mar. 6, 2014). Suitable fusion partners include, but are not limited to, a polypeptide that provides an activity that indirectly increases transcription by acting directly on the target DNA or on a polypeptide (e.g., a histone or other DNA-binding protein) associated with the target DNA. Additional suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. Further suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). A catalytically inactive Cas9 endonuclease can also be fused to a FokI nuclease to generate double-strand breaks (Guilinger et al. Nature biotechnology, volume 32, number 6, June 2014).

Guide Polynucleotides

As used herein, the term "guide polynucleotide", relates to a polynucleotide sequence that can form a complex with a Cas endonuclease, and enables the Cas endonuclease to recognize, bind to, and optionally nick or cleave a DNA target site. The guide polynucleotide can be a single molecule or a double molecule. The guide polynucleotide sequence can be a RNA sequence, a DNA sequence, or a combination thereof (a RNA-DNA combination sequence).

Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA".

The guide polynucleotide can be a double molecule (also referred to as duplex guide polynucleotide) comprising a crNucleotide sequence and a tracrNucleotide sequence. The crNucleotide includes a first nucleotide sequence domain (referred to as Variable Targeting domain or VT domain) that can hybridize to a nucleotide sequence in a target DNA and a second nucleotide sequence (also referred to as a tracr mate sequence) that is part of a Gas endonuclease recognition (CER) domain. The tracr mate sequence can hybridized to a tracrNucleotide along a region of complementarity and together form the Gas endonuclease recognition domain or CER domain. The CER domain is capable of interacting with a Cas endonuclease polypeptide. The crNucleotide and the tracrNucleotide of the duplex guide polynucleotide can be RNA, DNA, and/or RNA-DNA-combination sequences. (U.S. Patent Application US20150082478, published on Mar. 19, 2015 and US20150059010, published on Feb. 26, 2015, both are herein incorporated by reference). In some embodiments, the crNucleotide molecule of the duplex guide polynucleotide is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. The size of the fragment of the crRNA naturally occurring in Bacteria and Archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the tracrNucleotide is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In certain embodiments, the RNA that guides the RNA/Cas9 endonuclease complex is a duplexed RNA comprising a duplex crRNA-tracrRNA.

In one aspect, the guide polynucleotide is a guide polynucleotide capable of forming a PGEN comprising at least one guide polynucleotide and at least one Cas9 endonuclease variant described herein, wherein said guide polynucleotide comprises a first nucleotide sequence domain (VT domain) that is complementary to a nucleotide sequence in a target DNA, and a second nucleotide sequence domain that interacts with said Cas endonuclease polypeptide.

In one aspect, the guide polynucleotide is a guide polynucleotide described herein, wherein the first nucleotide sequence domain (VT domain) and the second nucleotide sequence domain is selected from the group consisting of a DNA sequence, a RNA sequence, and a combination thereof.

In one aspect, the guide polynucleotide is a guide polynucleotide described herein, wherein the first nucleotide sequence and the second nucleotide sequence domain is selected from the group consisting of RNA backbone modifications that enhance stability, DNA backbone modifications that enhance stability, and a combination thereof (see Kanasty et al., 2013, Common RNA-backbone modifications, Nature Materials 12:976-977;)

The guide polynucleotide includes a dual RNA molecule comprising a chimeric non-naturally occurring crRNA (non-covalently) linked to at least one tracrRNA. A chimeric non-naturally occurring crRNA includes a crRNA that comprises regions that are not found together in nature (i.e., they are heterologous with each other). For example, a non-naturally occurring crRNA is a crRNA wherein the naturally occurring spacer sequence is exchanged for a heterologous Variable Targeting domain. A non-naturally occurring crRNA comprises a first nucleotide sequence domain (referred to as Variable Targeting domain or VT domain) that can hybridize to a nucleotide sequence in a target DNA, linked to a second nucleotide sequence (also referred to as a tracr mate sequence) such that the first and second sequence are not found linked together in nature.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double-strand break) the target site.

The term "variable targeting domain" or "VT domain" is used interchangeably herein and includes a nucleotide sequence that can hybridize (is complementary) to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable targeting domain can be at least 12, 13, 14, 15, 16, 17, 18, 19, 20, 21, 22, 23, 24, 25, 26, 27, 28, 29 or 30 nucleotides in length.

The variable targeting domain can comprises a contiguous stretch of 12 to 30, 12 to 29, 12 to 28, 12 to 27, 12 to 26, 12 to 25, 12 to 26, 12 to 25, 12 to 24, 12 to 23, 12 to 22, 12 to 21, 12 to 20, 12 to 19, 12 to 18, 12 to 17, 12 to 16, 12 to 15, 12 to 14, 12 to 13, 13 to 30, 13 to 29, 13 to 28, 13 to 27, 13 to 26, 13 to 25, 13 to 26, 13 to 25, 13 to 24, 13 to 23, 13 to 22, 13 to 21, 13 to 20, 13 to 19, 13 to 18, 13 to 17, 13 to 16, 13 to 15, 13 to 14, 14 to 30, 14 to 29, 14 to 28, 14 to 27, 14 to 26, 14 to 25, 14 to 26, 14 to 25, 14 to 24, 14 to 23, 14 to 22, 14 to 21, 14 to 20, 14 to 19, 14 to 18, 14 to 17, 14 to 16, 14 to 15, 15 to 30, 15 to 29, 15 to 28, 15 to 27, 15 to 26, 15 to 25, 15 to 26, 15 to 25, 15 to 24, 15 to 23, 15 to 22, 15 to 21, 15 to 20, 15 to 19, 15 to 18, 15 to 17, 15 to 16, 16 to 30, 16 to 29, 16 to 28, 16 to 27, 16 to 26, 16 to 25, 16 to 24, 16 to 23, 16 to 22, 16 to 21, 16 to 20, 16 to 19, 16 to 18, 16 to 17, 17 to 30, 17 to 29, 17 to 28, 17 to 27, 17 to 26, 17 to 25, 17 to 24, 17 to 23, 17 to 22, 17 to 21, 17 to 20, 17 to 19, 17 to 18, 18 to 30, 18 to 29, 18 to 28, 18 to 27, 18 to 26, 18 to 25, 18 to 24, 18 to 23, 18 to 22, 18 to 21, 18 to 20, 18 to 19, 19 to 30, 19 to 29, 19 to 28, 19 to 27, 19 to 26, 19 to 25, 19 to 24, 19 to 23, 19 to 22, 19 to 21, 19 to 20, 20 to 30, 20 to 29, 20 to 28, 20 to 27, 20 to 26, 20 to 25, 20 to 24, 20 to 23, 20 to 22, 20 to 21, 21 to 30, 21 to 29, 21 to 28, 21 to 27, 21 to 26, 21 to 25, 21 to 24, 21 to 23, 21 to 22, 22 to 30, 22 to 29, 22 to 28, 22 to 27, 22 to 26, 22 to 25, 22 to 24, 22 to 23, 23 to 30, 23 to 29, 23 to 28, 23 to 27, 23 to 26, 23 to 25, 23 to 24, 24 to 30, 24 to 29, 24 to 28, 24 to 27, 24 to 26, 24 to 25, 25 to 30, 25 to 29, 25 to 28, 25 to 27, 25 to 26, 26 to 30, 26 to 29, 26 to 28, 26 to 27, 27 to 30, 27 to 29, 27 to 28, 28 to 30, 28 to 29, or 29 to 30 nucleotides.

The variable targeting domain can be composed of a DNA sequence, a RNA sequence, a modified DNA sequence, a modified RNA sequence, or any combination thereof. The VT domain can be complementary to target sequences derived from prokaryotic or eukaryotic DNA.

The term "Cas endonuclease recognition domain" or "CER domain" (of a guide polynucleotide) is used interchangeably herein and includes a nucleotide sequence that interacts with a Cas endonuclease polypeptide. A CER domain comprises a tracrNucleotide mate sequence followed by a tracrNucleotide sequence. The CER domain can be composed of a DNA sequence, a RNA sequence, a modified DNA sequence, a modified RNA sequence (see for example US 2015-0059010 A1, published on Feb. 26, 2015, incorporated in its entirety by reference herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide (also referred to as "loop") can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. The loop can be 3-4, 3-5, 3-6, 3-7, 3-8, 3-9, 3-10, 3-11, 3-12, 3-13, 3-14, 3-15, 3-20, 3-30, 3-40, 3-50, 3-60, 3-70, 3-80, 3-90, 3-100, 4-5, 4-6, 4-7, 4-8, 4-9, 4-10, 4-11, 4-12, 4-13, 4-14, 4-15, 4-20, 4-30, 4-40, 4-50, 4-60, 4-70, 4-80, 4-90, 4-100, 5-6, 5-7, 5-8, 5-9, 5-10, 5-11, 5-12, 5-13, 5-14, 5-15, 5-20, 5-30, 5-40, 5-50, 5-60, 5-70, 5-80, 5-90, 5-100, 6-7, 6-8, 6-9, 6-10, 6-11, 6-12, 6-13, 6-14, 6-15, 6-20, 6-30, 6-40, 6-50, 6-60, 6-70, 6-80, 6-90, 6-100, 7-8, 7-9, 7-10, 7-11, 7-12, 7-13, 7-14, 7-15, 7-20, 7-30, 7-40, 7-50, 7-60, 7-70, 7-80, 7-90, 7-100, 8-9, 8-10, 8-11, 8-12, 8-13, 8-14, 8-15, 8-20, 8-30, 8-40, 8-50, 8-60, 8-70, 8-80, 8-90, 8-100, 9-10, 9-11, 9-12, 9-13, 9-14, 9-15, 9-20, 9-30, 9-40, 9-50, 9-60, 9-70, 9-80, 9-90, 9-100, 10-20, 20-30, 30-40, 40-50, 50-60, 70-80, 80-90 or 90-100 nucleotides in length.

In another aspect, the nucleotide sequence linking the crNucleotide and the tracrNucleotide of a single guide polynucleotide can comprise a tetraloop sequence, such as, but not limiting to a GAAA tetraloop sequence.

The single guide polynucleotide includes a chimeric non-naturally occurring single guide RNA. The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). A chimeric non-naturally occurring guide RNA comprising regions that are not found together in nature (i.e., they are heterologous with each other). For example, a chimeric non-naturally occurring guide RNA comprising a first nucleotide sequence domain (referred to as Variable Targeting domain or VT domain) that can hybridize to a nucleotide sequence in a target DNA, linked to a second nucleotide sequence that can recognize the Cas endonuclease, such that the first and second nucleotide sequence are not found linked together in nature.

The chimeric non-naturally occurring guide RNA can comprise a crRNA or and a tracrRNA of the type II CRISPR/Cas system that can form a complex with a type II Cas endonuclease, such as the Cas9 endonuclease variant described herein, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site.

Production and Stabilization of Guide Polynucleotides

The guide polynucleotide can be produced by any method known in the art, including chemically synthesizing guide polynucleotides (such as but not limiting to Hendel et al. 2015, Nature Biotechnology 33, 985-989), in vitro generated guide polynucleotides, and/or self-splicing guide RNAs (such as but not limiting to Xie et al. 2015, PNAS 112: 3570-3575).

A method of expressing RNA components such as guide RNA in eukaryotic cells for performing Cas9-mediated DNA targeting has been to use RNA polymerase III (Pol III) promoters, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161). This strategy has been successfully applied in cells of several different species including maize and soybean (US20150082478, published on Mar. 19, 2015). Methods for expressing RNA components that do not have a 5' cap have been described (WO2016/025131, published on Feb. 18, 2016).

In some aspects, a subject nucleic acid (e.g., a guide polynucleotide, a nucleic acid comprising a nucleotide sequence encoding a guide polynucleotide; a nucleic acid encoding Cas protein; a crRNA or a nucleotide encoding a crRNA, a tracrRNA or a nucleotide encoding a tracrRNA, a nucleotide encoding a VT domain, a nucleotide encoding a CPR domain, etc.) comprises a modification or sequence that provides for an additional desirable feature (e.g., modified or regulated stability; subcellular targeting; tracking, e.g., a fluorescent label; a binding site for a protein or protein complex; etc.). Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

The terms “5'-cap” and “7-methylguanylate ($m^7G$) cap” are used interchangeably herein. A 7-methylguanylate residue is located on the 5' terminus of messenger RNA (mRNA) in eukaryotes. RNA polymerase II (Pol II) transcribes mRNA in eukaryotes. Messenger RNA capping occurs generally as follows: The most terminal 5' phosphate group of the mRNA transcript is removed by RNA terminal phosphatase, leaving two terminal phosphates. A guanosine monophosphate (GMP) is added to the terminal phosphate of the transcript by a guanylyl transferase, leaving a 5'-5' triphosphate-linked guanine at the transcript terminus. Finally, the 7-nitrogen of this terminal guanine is methylated by a methyl transferase.

Guided Cas Systems

As used herein, the terms “guide polynucleotide/Cas endonuclease complex”, “guide polynucleotide/Cas endonuclease system”, “guide polynucleotide/Cas complex”, “guide polynucleotide/Cas system” and “guided Cas system” “Polynucleotide-guided endonuclease”, “PGEN” are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double-strand break) the DNA target site. A guide polynucleotide/Cas endonuclease complex herein can comprise Cas protein(s), or fragments and variants thereof, and suitable polynucleotide component(s) of any of the known CRISPR systems (Horvath and Barrangou, 2010, Science 327:167-170; Makarova et al. 2015, Nature Reviews Microbiology Vol. 13:1-15; Zetsche et al., 2015, Cell 163, 1-13; Shmakov et al., 2015, Molecular Cell 60, 1-13). A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component.

A guide polynucleotide/Cas endonuclease complex that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas protein disclosed herein), or a variant thereof retaining some or all activity in each endonuclease domain of the Cas protein, is a suitable example of a Cas endonuclease that can cleave both strands of a DNA target sequence.

A guide polynucleotide/Cas endonuclease complex that can cleave one strand of a DNA target sequence can be characterized herein as having nickase activity (e.g., partial cleaving capability). A Cas nickase typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain. As another example, a Cas9 nickase may comprise (i) a functional RuvC domain (e.g., wild type RuvC domain) and (ii) a mutant, dysfunctional HNH domain.

Non-limiting examples of Cas9 nickases suitable for use herein are disclosed by Gasiunas et al. (*Proc. Natl. Acad. Sci. U.S.A.* 109:E2579-E2586), Jinek et al. (*Science* 337:816-821), Sapranauskas et al. (*Nucleic Acids Res.* 39:9275-9282) and U.S. Patent Appl. Publ. No. 2014/0189896, which is incorporated by reference herein.

For example, a Cas9 nickase herein can comprise an *S. thermophilus* Cas9 having an Asp-31 substitution (e.g., Asp-31-Ala) (an example of a mutant RuvC domain), or a His-865 substitution (e.g., His-865-Ala), Asn-882 substitution (e.g., Asn-882-Ala), or Asn-891 substitution (e.g., Asn-891-Ala) (examples of mutant HNH domains). Also for example, a Cas9 nickase herein can comprise an *S. pyogenes* Cas9 having an Asp-10 substitution (e.g., Asp-10-Ala), Glu-762 substitution (e.g., Glu-762-Ala), or Asp-986 substitution (e.g., Asp-986-Ala) (examples of mutant RuvC domains), or a His-840 substitution (e.g., His-840-Ala), Asn-854 substitution (e.g., Asn-854-Ala), or Asn-863 substitution (e.g., Asn-863-Ala) (examples of mutant HNH domains). Regarding *S. pyogenes* Cas9, the three RuvC subdomains are generally located at amino acid residues 1-59, 718-769 and 909-1098, respectively, and the HNH domain is located at amino acid residues 775-908 (Nishimasu et al., *Cell* 156:935-949).

A Cas9 nickase herein can be used for various purposes in host cells of the disclosed invention. For example, a Cas9 nickase can be used to stimulate HR at or near a DNA target site sequence with a suitable donor polynucleotide. Since nicked DNA is not a substrate for NHEJ processes, but is recognized by HR processes, nicking DNA at a specific target site should render the site more receptive to HR with a suitable donor polynucleotide.

A pair of Cas nickases can be used to increase the specificity of DNA targeting. In general, this can be done by providing two Cas nickases that, by virtue of being associated with RNA components with different guide sequences, target and nick nearby DNA sequences on opposite strands in the region for desired targeting. Such nearby cleavage of each DNA strand creates a double-strand break (i.e., a DSB with single-stranded overhangs), which is then recognized as a substrate for non-homologous-end-joining, NHEJ (prone to imperfect repair leading to mutations) or homologous recombination, HR. Each nick in these embodiments can be at least about 5, 10, 15, 20, 30, 40, 50, 60, 70, 80, 90, or 100 (or any integer between 5 and 100) bases apart from each other, for example. One or two Cas nickase proteins herein can be used in a Cas nickase pair. For example, a Cas9 nickase with a mutant RuvC domain, but functioning HNH domain (i.e., Cas9 HNH+/RuvC−), can be used (e.g., *Streptococcus pyogenes* Cas9 HNH+/RuvC−). Each Cas9 nickase (e.g., Cas9 HNH+/RuvC−) can be directed to specific DNA sites nearby each other (up to 100 base pairs apart) by using suitable RNA components herein with guide RNA sequences targeting each nickase to each specific DNA site.

A guide polynucleotide/Cas endonuclease complex in certain embodiments can bind to a DNA target site sequence, but does not cleave any strand at the target site sequence. Such a complex may comprise a Cas protein in which all of its nuclease domains are mutant, dysfunctional. For example, a Cas9 protein herein that can bind to a DNA target site sequence, but does not cleave any strand at the target site sequence, may comprise both a mutant, dysfunctional RuvC domain and a mutant, dysfunctional HNH domain. Non-limiting examples of such a Cas9 protein comprise any of the RuvC and HNH nuclease domain mutations disclosed above (e.g., an *S. pyogenes* Cas9 with an Asp-10 substitution such as Asp-10-Ala and a His-840 substitution such as His-840-Ala). A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein). For example, a Cas9 comprising an *S. pyogenes* Cas9 with an Asp-10 substitution (e.g., Asp-10-Ala) and a His-840 substitution (e.g., His-840-Ala) can be fused to a VP16 or VP64 transcriptional activator domain.

A guide polynucleotide/Cas endonuclease complex can comprise a Cas endonuclease variant, or active fragment thereof, described herein, wherein said guide polynucleotide is a chimeric non-naturally occurring guide polynucleotide, wherein said guide polynucleotide/Cas endonuclease complex is capable of recognizing, binding to, and optionally nicking, unwinding, or cleaving all or part of a target sequence.

In one aspect the guide polynucleotide/Cas endonuclease complex is a complex of a guide polynucleotide and a Cas9 endonuclease variant described herein, wherein said guide polynucleotide is a chimeric non-naturally occurring guide polynucleotide, wherein said Cas9 endonuclease variant has at least one improved property such as, but not limited to, increased transformation efficiency increased DNA editing efficiency, reduced off target cleavage, or any combination thereof, when compared to a its parent Cas endonuclease (in complex with the same guide polynucleotide to form a polynucleotide-guided endonuclease complex capable of modifying the same target site).

The guide polynucleotide/Cas endonuclease complex can be a complex of a guide polynucleotide and a Cas9 endonuclease variant described herein, wherein said guide polynucleotide is a chimeric non-naturally occurring guide polynucleotide, wherein said Cas9 endonuclease variant, or an active fragment thereof, has at least 80% amino acid identity to a parent Cas9 polypeptide described herein and having at least one amino acid substitution at a position outside its HNH and RuVC domain, wherein the amino acid positions of the variant are numbered by correspondence with the amino acid sequence of the parent Cas9 polypeptide, wherein said Cas9 endonuclease variant has endonuclease activity.

The guide polynucleotide/Cas endonuclease complex can be a complex of a guide polynucleotide and a Cas9 endonuclease variant described herein, wherein said guide polynucleotide is a chimeric non-naturally occurring guide polynucleotide, wherein said Cas9 endonuclease variant, or an active fragment thereof, has at least 80% amino acid identity to a parent Cas9 polypeptide set forth in SEQ ID NO: 1 and having at least one amino acid substitution at position 155, wherein the amino acid positions of the variant are numbered by correspondence with the amino acid sequence of the parent Cas9 polypeptide, wherein said Cas9 endonuclease variant has endonuclease activity.

The guide polynucleotide/Cas endonuclease complex can be a complex of a guide polynucleotide and a Cas9 endonuclease variant described herein, wherein said guide polynucleotide is a chimeric non-naturally occurring guide polynucleotide, wherein said Cas9 endonuclease variant, or an active fragment thereof, has at least 80% amino acid identity to a parent Cas9 polypeptide set forth in SEQ ID NO: 1 and having at least two amino acid substitution, a first one at position 86 and a second one at position 98 wherein the amino acid positions of the variant are numbered by correspondence with the amino acid sequence of the parent Cas9 polypeptide, wherein said Cas9 endonuclease variant has endonuclease activity.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease, that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site The guided Cas systems described herein can be expressed in a host cell from one or more expression constructs. In some aspects, the Cas endonuclease variant described herein can be expressed from an expression cassette directing the expression of the Cas protein in a prokaryotic or eukaryotic cell, and the guide polynucleotide can be expressed from a second expression cassette directing the expression of the guide polynucleotide in the prokaryotic or eukaryotic cell.

The present disclosure further provides expression constructs for expressing in a prokaryotic or eukaryotic cell/organism a guide RNA/Cas system that is capable of recognizing, binding to, and optionally nicking, unwinding, or cleaving all or part of a target sequence.

Expression Cassettes and Recombinant DNA Constructs

Polynucleotides disclosed herein can be provided in an expression cassette (also referred to as DNA construct) for expression in an organism of interest. The term "expression", as used herein, refers to the production of a functional end-product (e.g., a crRNA, a tracrRNA, a mRNA, a guide RNA, or a polypeptide (protein) in either precursor or mature form. The term "expression" includes any step involved in the production of a polypeptide including, but not limited to, transcription, post-transcriptional modification, translation, post-translational modification, and secretion.

The expression cassette can include 5' and 3' regulatory sequences operably linked to a polynucleotide as disclosed herein.

"Operably linked" is intended to mean a functional linkage between two or more elements. For example, an operable linkage between a polynucleotide of interest and a regulatory sequence (e.g., a promoter) is a functional link that allows for expression of the polynucleotide of interest (i.e., the polynucleotide of interest is under transcriptional control of the promoter). Operably linked elements may be contiguous or non-contiguous. When used to refer to the joining of two protein coding regions, by operably linked is intended that the coding regions are in the same reading frame.

The expression cassettes disclosed herein may include in the 5-3' direction of transcription, a transcriptional and translational initiation region (i.e., a promoter), a polynucleotide of interest, and a transcriptional and translational termination region (i.e., termination region) functional in the host cell (e.g., a eukaryotic cell). Expression cassettes are also provided with a plurality of restriction sites and/or recombination sites for insertion of the polynucleotide to be under the transcriptional regulation of the regulatory regions described elsewhere herein. The regulatory regions (i.e., promoters, transcriptional regulatory regions, and translational termination regions) and/or the polynucleotide of interest may be native/analogous to the host cell or to each other. Alternatively, the regulatory regions and/or the polynucleotide of interest may be heterologous to the host cell or to each other. As used herein, "heterologous" in reference to a polynucleotide or polypeptide sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, unless otherwise specified, a chimeric polynucleotide comprises a coding sequence operably linked to a transcription initiation region that is heterologous to the coding sequence.

In certain embodiments the polynucleotides disclosed herein can be stacked with any combination of polynucleotide sequences of interest or expression cassettes as disclosed elsewhere herein or known in the art. The stacked polynucleotides may be operably linked to the same promoter as the initial polynucleotide, or may be operably linked to a separate promoter polynucleotide.

Expression cassettes may comprise a promoter operably linked to a polynucleotide of interest, along with a corresponding termination region. The termination region may be native to the transcriptional initiation region, may be native to the operably linked polynucleotide of interest or to the promoter sequences, may be native to the host organism, or may be derived from another source (i.e., foreign or heterologous). Convenient termination regions are available from phage sequences, eg. lambda phage t0 termination region or strong terminators from prokaryotic ribosomal RNA operons. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides of interest may be optimized for increased expression in the transformed or targeted organism. For example, the polynucleotides can be synthesized or altered to use organism-preferred codons for improved expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. 5' leader sequences used interchangeably with 5' untranslated regions could come from well known and well characterized bacterial UTRs such as those from the *Bacillus subtilis* aprE gene or the *Bacillus licheniformis* amyl gene or any bacterial ribosomal protein gene. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Johnson et al. (1986) *Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In some embodiments, a nucleotide sequence encoding a guide nucleotide and/or a Cas protein is operably linked to a control element, e.g., a transcriptional control element, such as a promoter. The transcriptional control element may be functional in either a eukaryotic cell, e.g., a plant, mammalian cell or fungal cell; or a prokaryotic cell (e.g., bacterial or archaeal cell). In some embodiments, a nucleotide sequence encoding a guide nucleotide and/or a Cas protein is operably linked to multiple control elements that allow expression of the nucleotide sequence encoding a guide nucleotide and/or a Cas protein in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. The expression cassette may also contain a ribosome binding site for translation initiation and a transcription terminator. The expression cassette may also contain one or more nuclear localization sequences (NLS sequences) to direct the guide nucleotide and/or a Cas protein to the nucleus in a eukaryotic cell. The expression cassette may also include appropriate sequences for amplifying expression. The expression cassette may also include nucleotide sequences encoding protein tags (e.g., 6× His tag, hemagglutinin tag, green fluorescent protein, etc.) that are fused to the Cas protein, thus resulting in a chimeric polypeptide.

For transcription in a fungal host, non-limiting examples of useful promoters include those derived from the gene encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* glucoamylase, *Rhizomucor miehei* lipase, *Aspergillus oryzae* alkaline protease, *Aspergillus oryzae* triose phosphate isomerase, *Aspergillus nidulans* acetamidase and the like. When a gene encoding a Cas endonuclease is expressed in a bacterial species such as an *E. coli*, a suitable promoter can be selected, for example, from a bacteriophage promoter including a T7 promoter and a phage lambda promoter. Along these lines, examples of suitable promoters for the expression in a yeast species include, but are not limited to, the Gal 1 and Gal 10 promoters of *Saccharomyces cerevisiae* and the *Pichia pastoris* AOX1 or AOX2 promoters. Expression in filamentous fungal host cells often involves cbh1, which is an endogenous, inducible promoter from *T. reesei* or constitutive glycolytic promoters (e.g., pki). For example, see Liu et al. 2008.

Non-limiting examples of promoters for directing the transcription of a DNA sequence (such as but not limiting to DNA sequences encoding a Cas endonuclease variant described herein) in a bacterial host, include the promoter of the lac operon of *E. coli*, the *Streptomyces coelicolor* agarase gene dagA or celA promoters, the promoters of the *Bacillus licheniformis* amylase gene (amyL), the promoters of the *Bacillus stearothermophilus* maltogenic amylase gene (amyM), the promoters of the *Bacillus amyloliquefaciens* amylase (amyQ), the promoters of the *Bacillus subtilis* xy/A and xylB genes, and the like.

Expression cassettes can be comprised in lineair DNA, in circular DNA, in recombinant DNA, in plasmid or in vectors.

As used herein, "recombinant" refers to an artificial combination of two otherwise separated segments of sequence, e.g., by chemical synthesis or by the manipulation of isolated segments of nucleic acids by genetic engineering techniques. The term "recombinant," when used in reference to a biological component or composition (e.g., a cell, nucleic acid, polypeptide/enzyme, vector, etc.) indicates that the biological component or composition is in a state that is not found in nature. In other words, the biological component or composition has been modified by human intervention from its natural state. For example, a recombinant cell encompasses a cell that expresses one or more genes that are not found in its native parent (i.e., non-recombinant) cell, a cell that expresses one or more native genes in an amount that is different than its native parent cell, and/or a cell that expresses one or more native genes under different conditions than its native parent cell. Recombinant nucleic acids may differ from a native sequence by one or more nucleotides, be operably linked to heterologous sequences (e.g., a heterologous promoter, a sequence encoding a non-native or variant signal sequence, etc.), be devoid of intronic sequences, and/or be in an isolated form. Recombinant polypeptides/enzymes may differ from a native sequence by one or more amino acids, may be fused with heterologous sequences, may be truncated or have internal deletions of amino acids, may be expressed in a manner not found in a native cell (e.g., from a recombinant cell that over-expresses the polypeptide due to the presence in the cell of an expression vector encoding the polypeptide), and/or be in an isolated form. It is emphasized that in some embodiments, a recombinant polynucleotide or polypeptide/enzyme has a sequence that is identical to its wild-type counterpart but is in a non-native form (e.g., in an isolated or enriched form).

As used herein, "recombinant DNA construct" or "recombinant DNA" refers to an expression cassette comprising an artificial combination of nucleic acid fragments. The recombinant DNA construct can include 5' and 3' regulatory sequences operably linked to a polynucleotide as disclosed herein.

For example, a recombinant DNA construct may comprise regulatory sequences and coding sequences that are derived from different sources. Such a construct may be used by itself or may be used in conjunction with a vector. If a vector is used, then the choice of vector is dependent upon the method that will be used to introduce the vector into the host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

Standard recombinant DNA and molecular cloning techniques used herein are well known in the art and are described more fully in Sambrook et al., *Molecular Cloning: A Laboratory Manual; Cold Spring Harbor Laboratory*: Cold Spring Harbor, NY (1989).

In one aspect, the recombinant DNA construct includes heterologous 5' and 3' regulatory sequences operably linked to a Cas9 endonuclease variant as disclosed herein. These regulatory sequences include but are not limited to a transcriptional and translational initiation region (i.e., a promoter), a nuclear localization signal, and a transcriptional and translational termination region (i.e., termination region) functional in the host cell (such as bacterial or fungal cell).

In one aspect, the recombinant DNA construct comprises a DNA encoding a Cas9 endonuclease variant described herein, wherein said Cas9 endonuclease variant is operably linked to or comprises a heterologous regulatory element such as a nuclear localization sequence (NLS).

In one aspect, the expression cassette or the recombinant DNA herein comprises a promoter operably linked to a nucleotide sequence encoding a Cas9 endonuclease variant described herein and a promoter operably linked to a guide RNA of the present disclosure. The promoter is capable of driving expression of an operably linked nucleotide sequence in a prokaryotic or eukaryotic cell/organism.

The terms "plasmid" or "vector" refer to a linear or circular extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded polynucleotide, derived from any source, in which a number of nucleotide sequences have been joined or recombined into a unique construction which is capable of introducing a polynucleotide of interest into a cell.

Target Sites

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, a transgenic locus, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave.

The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

The target site for a Cas endonuclease can be very specific and can often be defined to the exact nucleotide position, whereas in some cases the target site for a desired genome modification can be defined more broadly than merely the site at which DNA cleavage occurs, e.g., a genomic locus or region that is to be deleted from the genome. Thus, in certain cases, the genome modification that occurs via the activity of Cas/guide RNA DNA cleavage is described as occurring "at or near" the target site.

Methods for "modifying a target site" and "altering a target site" are used interchangeably herein and refer to methods for producing an altered target site.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by a Cas endonuclease.

Assays to measure the single or double-strand break of a target site by an endonuclease are known in the art and generally measure the overall activity and specificity of the agent on DNA substrates containing recognition sites.

Protospacer Adjacent Motif (PAM)

A "protospacer adjacent motif" (PAM) herein refers to a short nucleotide sequence adjacent to a target sequence (protospacer) that is recognized (targeted) by a guide polynucleotide/Cas endonuclease (PGEN) system. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

A PAM herein is typically selected in view of the type of PGEN being employed. A PAM sequence herein may be one recognized by a PGEN comprising a Cas, such as the Cas9 variants described herein, derived from any of the species disclosed herein from which a Cas can be derived, for example. In certain embodiments, the PAM sequence may be one recognized by an RGEN comprising a Cas9 derived from *S. pyogenes, S. thermophilus, S. agalactiae, N. meningitidis, T. denticola*, or *F. novicida*. For example, a suitable Cas9 derived from *S. pyogenes*, Including the Cas9 Y155 variants described herein, could be used to target genomic sequences having a PAM sequence of NGG; N can be A, C, T, or G). As other examples, a suitable Cas9 could be derived from any of the following species when targeting DNA sequences having the following PAM sequences: *S. thermophilus* (NNAGAA), *S. agalactiae* (NGG), NNAGAAW [W is A or T], NGGNG), *N. meningitidis* (NNNNGATT), *T. denticola* (NAAAAC), or *F. novicida* (NG) (where N's in all these particular PAM sequences are A, C, T, or G). Other examples of Cas9/PAMs useful herein include those disclosed in Shah et al. (RNA Biology 10:891-899) and Esvelt et al. (Nature Methods 10:1116-1121), which are incorporated herein by reference.

Uses of Guided Cas Protein Systems

The compositions and methods provided herein find use in a wide variety of host cells. As used herein, a "host cell," refers to any cell type (such as but not limiting to, an in vivo or in vitro cell, a eukaryotic cell, a prokaryotic cell, or a cell from a multicellular organism (e.g., a cell line) cultured as a unicellular entity), used as recipients for a nucleic acid or for a genome modification system (such as the guide polynucleotide/Cas endonuclease system described herein). The term "host cell" includes the progeny of the original cell which has been transformed, transfected or transduced by the nucleic acid or guide polynucleotide/Cas endonuclease complex described herein. A "recombinant host cell" (also referred to as a "genetically modified host cell") is a host cell into which has been introduced a heterologous nucleic acid, e.g., a recombinant DNA construct, or which has been introduced and comprises a genome modification system such as the guide polynucleotide/Cas endonuclease system described herein. For example, a subject bacterial host cell includes a genetically modified bacterial host cell by virtue of introduction into a suitable bacterial host cell of an exogenous nucleic acid (e.g., a plasmid or recombinant DNA construct) and a subject eukaryotic host cell includes a genetically modified eukaryotic host cell (e.g., a fungal, mammalian germ cell or plant cell), by virtue of introduction into a suitable eukaryotic host cell of an exogenous nucleic acid.

In some embodiments, the host cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, in invertebrate cell, a vertebrate cell, a fish cell, a frog cell, a bird cell, an insect cell, a mammalian cell, a pig cell, a cow cell, a goat cell, a sheep cell, a rodent cell, a rat cell, a mouse cell, a non-human primate cell, and a human cell. In some cases, the cell is in vitro. In some cases, the cell is in vivo.

The guide polynucleotide/Cas systems described herein can be used for gene targeting.

The terms "gene targeting", "targeting", and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with a Cas endonuclease associated with a suitable polynucleotide component. Once a single or double-strand break is induced in the DNA, the cell's DNA repair mechanism is activated to repair the break via nonhomologous end-joining (NHEJ) or Homology-Directed Repair (HDR) processes which can lead to modifications at the target site.

The terms "knock-out", "gene knock-out" and "genetic knock-out" are used interchangeably herein. A knock-out represents a DNA sequence of a cell that has been rendered partially or completely inoperative by targeting with a Cas endonuclease, such as a Cas9 endonuclease variant described herein; such a DNA sequence prior to knock-out could have encoded an amino acid sequence, or could have had a regulatory function (e.g., promoter), for example.

As described herein, a guided Cas endonuclease can recognize, bind to a DNA target sequence and introduce a single strand (nick) or double-strand break. Once a single or double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements (such as chromosomal translocations) are possible (Siebert and Puchta, 2002, Plant Cell 14:1121-31; Pacher et al., 2007, Genetics 175:21-9).

A knock-out may be produced by an indel (insertion or deletion of nucleotide bases in a target DNA sequence through NHEJ), or by specific removal of sequence that reduces or completely destroys the function of sequence at or near the targeting site. The term "indel" herein refers to an insertion or deletion of nucleotide bases in a target DNA sequence in a chromosome or episome. Such an insertion or deletion may be of 1, 2, 3, 4, 5, 6, 7, 8, 9, 10, or more bases, for example. An indel in certain embodiments can be even larger, at least about 20, 30, 40, 50, 60, 70p, 80, 90, or 100 bases If an indel is introduced within an open reading frame (ORF) of a gene, oftentimes the indel disrupts wild type expression of protein encoded by the ORF by creating a frameshift mutation.

In one embodiment, the disclosure describes a method for modifying a target site in the genome of a cell, the method comprising introducing into a cell at least one guide polynucleotide and at least one Cas9 endonuclease variant described herein, wherein said guide polynucleotide is a chimeric non-naturally occurring guide polynucleotide, wherein said guide polynucleotide and Cas9 endonuclease variant can form a complex (PGEN) that is capable of recognizing, binding to, and optionally nicking, unwinding, or cleaving all or part of a target sequence, and identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

The guide polynucleotide/Cas endonuclease system can be used in combination with at least one polynucleotide modification template to allow for editing (modification) of a genomic nucleotide sequence of interest.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment, the disclosure comprises a method for editing a nucleotide sequence in the genome of a cell, the method comprising introducing into a cell at least one guide polynucleotide, at least one Cas9 endonuclease variant described herein, and a polynucleotide modification template, wherein said guide polynucleotide is a chimeric non-naturally occurring guide polynucleotide, wherein said guide polynucleotide and Cas9 endonuclease variant can form a complex (PGEN) that is capable of recognizing, binding to, and optionally nicking, unwinding, or cleaving all or part of a target sequence, wherein said polynucleotide modification template comprises at least one nucleotide modification of said nucleotide sequence, and optionally further comprising selecting at least one cell that comprises the edited nucleotide sequence.

The nucleotide to be edited can be located within or outside a target site recognized and cleaved by a Cas endonuclease. In one embodiment, the at least one nucleotide modification is not a modification at a target site recognized and cleaved by a Cas endonuclease, such as the Cas9 endonuclease variant described herein. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

The method for editing a nucleotide sequence in the genome of a cell can be a method without the use of an exogenous selectable marker by restoring function to a non-functional gene product as described in WO2017/070029, published Apr. 27, 2017 and WO2017/070032, published Apr. 27, 2017.

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (for example by homologous recombination (HR), wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

Various methods and compositions can be employed to obtain a cell or organism having a polynucleotide of interest inserted in a target site for a Cas endonuclease. Such methods can employ homologous recombination (HR) to provide integration of the polynucleotide of Interest at the target site. In one method described herein, a polynucleotide of interest is introduced into the organism cell via a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the cell or organism genome.

The donor DNA can be tethered to the guide polynucleotide. Tethered donor DNAs can allow for co-localizing target and donor DNA, useful in genome editing, gene insertion, and targeted genome regulation, and can also be useful in targeting post-mitotic cells where function of endogenous HR machinery is expected to be highly diminished (Mali et al., 2013, Nature Methods Vol. 10: 957-963).

Episomal DNA molecules can also be ligated into the double-strand break, for example, integration of T-DNAs into chromosomal double-strand breaks (Chilton and Que, (2003) Plant Physiol 133:956-65; Salomon and Puchta, (1998) EMBO J 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., 2004, Plant Cell 16:342-52). Ectopic and/or epigenic DNA sequences may also serve as a DNA repair template for homologous recombination (Puchta, (1999) Genetics 152: 1173-81).

Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem. 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932).

By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also be described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) Current Protocols, (Greene Publishing Associates, Inc. and John Wiley & Sons, Inc.); and, Tijssen (1993) *Laboratory Techniques in Biochemistry and Molecular Biology—Hybridization with Nucleic Acid Probes*, (Elsevier, New York).

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some instances the regions of homology share significant sequence homology to the genomic sequence immediately flanking the target site, it is recognized that the regions of homology can be designed to have sufficient homology to regions that may be further 5' or 3' to the target site. The regions of homology can also have homology with a fragment of the target site along with downstream genomic regions In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) Proc. Natl. Acad. Sci. USA 82:4768-72, Sugawara and Haber, (1992) Mol Cell Biol 12:563-75, Rubnitz and Subramani, (1984) Mol Cell Biol 4:2253-8; Ayares et al., (1986) Proc. Natl. Acad. Sci. USA 83:5199-203; Liskay et al., (1987) Genetics 115:161-7.

Alteration of the genome of a prokaryotic and eukaryotic cell or organism cell, for example, through homologous recombination (HR), is a powerful tool for genetic engineering. Homologous recombination has been demonstrated in plants (Halfter et al., (1992) Mol Gen Genet 231:186-93) and insects (Dray and Gloor, 1997, Genetics 147:689-99). Homologous recombination has also been accomplished in other organisms. For example, at least 150-200 bp of homology was required for homologous recombination in the parasitic protozoan *Leishmania* (Papadopoulou and Dumas, (1997) Nucleic Acids Res 25:4278-86). In the filamentous fungus *Aspergillus nidulans*, gene replacement has been accomplished with as little as 50 bp flanking homology (Chaveroche et al., (2000) Nucleic Acids Res 28:e97). Targeted gene replacement has also been demonstrated in the ciliate *Tetrahymena thermophila* (Gaertig et al., (1994) Nucleic Acids Res 22:5391-8). In mammals, homologous recombination has been most successful in the mouse using pluripotent embryonic stem cell lines (ES) that can be grown in culture, transformed, selected and introduced into a mouse embryo (Watson et al., 1992, Recombinant DNA, 2nd Ed., (Scientific American Books distributed by WH Freeman & Co.).

DNA double-strand breaks appear to be an effective factor to stimulate homologous recombination pathways (Puchta et al., (1995) Plant Mol Biol 28:281-92; Tzfira and White, (2005) Trends Biotechnol 23:567-9; Puchta, (2005) J Exp Bot 56:1-14). Using DNA-breaking agents, a two- to nine-fold increase of homologous recombination was observed between artificially constructed homologous DNA repeats in plants (Puchta et al., (1995) Plant Mol Biol 28:281-92). In maize protoplasts, experiments with linear DNA molecules demonstrated enhanced homologous recombination between plasmids (Lyznik et al., (1991) Mol Gen Genet 230:209-18).

In one aspect, the disclosure comprises a method for modifying a target site in the genome of a cell, the method comprising introducing into a cell at least one guide polynucleotide, at least one Cas9 endonuclease variant described herein, and at least one donor DNA, wherein said guide polynucleotide is a chimeric non-naturally occurring guide polynucleotide, wherein said guide polynucleotide and Cas9 endonuclease variant can form a complex (PGEN) that is capable of recognizing, binding to, and optionally nicking, unwinding, or cleaving all or part of a target sequence, wherein said donor DNA comprises a polynucleotide of interest, and optionally, further comprising identifying at least one cell that said polynucleotide of interest integrated in or near said target site.

In one aspect, the disclosure comprises a method for modifying the genome of a *Bacillus* host cell, said method comprising providing to a *Bacillus* host cell comprising at least one target sequence to be modified, at least one non-naturally occurring guide RNA and at least one Cas9 endonuclease variant described herein wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one *Bacillus* host cell, wherein the at least one genome target sequence has been modified. The modification at said target site can be selected from the group consisting of (i) a replacement of at least one nucleotide, (ii) a deletion of at least one nucleotide, (iii) an insertion of at least one nucleotide, and (iv) any combination of (i)-(iii).

In one aspect, the disclosure comprises a method for modifying the genome of an *E. coli* host cell, said method comprising providing to an *E. coli* host cell comprising at least one target sequence to be modified, at least one non-naturally occurring guide RNA and at least one Cas9 endonuclease variant described herein, wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one *E. coli* host cell, wherein the at least one genome target sequence has been modified.

In one aspect, the disclosure comprises a method for modifying the genome of a *Saccharomyces cerevisiae* host cell, said method comprising providing to a *Saccharomyces cerevisiae* host cell comprising at least one target sequence to be modified, at least one non-naturally occurring guide RNA and at least one Cas9 endonuclease variant described herein, wherein the guide RNA and Cas9 endonuclease variant are capable of forming a complex (PGEN), wherein said complex is capable of recognizing, binding to, and optionally nicking, unwinding, or cleaving all or part of said at least one target sequence; and, identifying at least one *Saccharomyces cerevisiae* host cell, wherein the at least one genome target sequence has been modified.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Multiplexing

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide a guide polynucleotide/Cas endonuclease complex to a unique DNA target site.

The Cas9 endonuclease variants described herein can be used for targeted genome editing (via simplex and multiplex double-strand breaks and nicks) and targeted genome regulation (via tethering of epigenetic effector domains to either the Cas9 or sgRNA. Cas9 endonuclease variants described herein may also be engineered to function as an RNA-guided recombinase, and via RNA tethers could serve as a scaffold for the assembly of multiprotein and nucleic acid complexes (Mali et al. 2013 Nature Methods Vol. 10: 957-963.).

Complex Trait Loci

Polynucleotides of interest and/or traits can be stacked together in a complex trait locus as described in WO2012/129373, published Mar. 14, 2013 and in PCT/US13/22891, published Jan. 24, 2013, both hereby incorporated by reference. The guide polynucleotide/Cas endonuclease system, such as the system comprising a Cas9 endonuclease variant described herein, provides for an efficient system to generate single or double-strand breaks and allows for traits to be stacked in a complex trait locus.

Introduction of Polynucleotides, Polypeptides, Expression Cassettes, Recombinant DNA, or any One Component of a Guided Cas Protein System The polynucleotides, polypeptides, expression cassettes or recombinant DNA disclosed herein can be introduced into an organism using any method known in the art. Any one component of the guide polynucleotide/Cas system, the guide polynucleotide/Cas complex itself, as well as the polynucleotide modification template(s) and/or donor DNA(s), can be introduced into a cell by any method known in the art.

"Introducing" is intended to mean presenting to the organism, such as a cell or organism, the polynucleotide or polypeptide or polynucleotide-protein complex (such as a RGEN or PGEN), in such a manner that the component(s) gains access to the interior of a cell of the organism or to the cell itself. The methods and compositions do not depend on a particular method for introducing a sequence into an organism or cell, only that the polynucleotide or polypeptide gains access to the interior of at least one cell of the organism. Introducing includes reference to the incorporation of a nucleic acid into a eukaryotic or prokaryotic cell where the nucleic acid may be incorporated into the genome of the cell, and includes reference to the transient (direct) provision of a nucleic acid, protein or polynucleotide-protein complex (PGEN, RGEN) to the cell.

Methods for introducing polynucleotides, polypeptides, expression cassettes, recombinant DNA or a polynucleotide-protein complexes (PGEN, RGEN) into cells or organisms are known in the art including, but not limited to, natural competence (as described in WO2017/075195, WO2002/14490 and WO2008/7989), microinjection Crossway et al., (1986) *Biotechniques* 4:320-34 and U.S. Pat. No. 6,300,543), meristem transformation (U.S. Pat. No. 5,736,369), electroporation (Riggs et al., (1986) *Proc. Natl. Acad. Sci. USA* 83:5602-6), stable transformation methods, transient transformation methods, ballistic particle acceleration (particle bombardment) (U.S. Pat. Nos. 4,945,050; 5,879,918; 5,886,244; 5,932,782), whiskers mediated transformation (Ainley et al. 2013, Plant Biotechnology Journal 11:1126-1134; Shaheen A. and M. Arshad 2011 Properties and Applications of Silicon Carbide (2011), 345-358 Editor(s): Gerhardt, Rosario. Publisher: InTech, Rijeka, Croatia. CODEN: 69PQBP; ISBN: 978-953-307-201-2), *Agrobacterium*-mediated transformation (U.S. Pat. Nos. 5,563,055 and 5,981,840), direct gene transfer (Paszkowski et al., (1984) *EMBO J* 3:2717-22), viral-mediated introduction (U.S. Pat. Nos. 5,889,191, 5,889,190, 5,866,785, 5,589,367 and 5,316,931), transfection, transduction, cell-penetrating peptides, mesoporous silica nanoparticle (MSN)-mediated direct protein delivery, topical applications, sexual crossing, sexual breeding, and any combination thereof. Stable transformation is intended to mean that the nucleotide construct introduced into an organism integrates into a genome of the organism and is capable of being inherited by the progeny thereof. Transient transformation is intended to mean that a polynucleotide is introduced (directly or indirectly) into the organism and does not integrate into a genome of the organism or a polypeptide is introduced into an organism. Transient transformation indicates that the introduced composition is only temporarily expressed or present in the organism.

The guide polynucleotide (guide RNA, crNucleotide+tracrNucleotide, guide DNA and/or guide RNA-DNA molecule) can be introduced into a cell directly (transiently) as a single stranded or double stranded polynucleotide molecule. The guide RNA (or crRNA+tracrRNA) can also be introduced into a cell indirectly by introducing a recombinant DNA molecule comprising a heterologous nucleic acid fragment encoding the guide RNA (or crRNA+tracrRNA), operably linked to a specific promoter that is capable of transcribing the guide RNA (crRNA+tracrRNA molecules) in said cell. The specific promoter can be, but is not limited to, a RNA polymerase III promoter, which allow for transcription of RNA with precisely defined, unmodified, 5'- and 3'-ends (Ma et al., 2014, Mol. Ther. Nucleic Acids 3:e161; DiCarlo et al., 2013, Nucleic Acids Res. 41: 4336-4343; WO2015026887, published on Feb. 26, 2015). Any promoter capable of transcribing the guide RNA in a cell can be used and includes a heat shock/heat inducible promoter operably linked to a nucleotide sequence encoding the guide RNA.

A Cas endonuclease herein, can be introduced into a cell by directly introducing the Cas polypeptide itself (referred to as direct delivery of Cas endonuclease), the mRNA encoding the Cas protein, and/or the guide polynucleotide/Cas endonuclease complex itself, using any method known in the art. The Cas endonuclease can also be introduced into a cell indirectly by introducing a recombinant DNA molecule that encodes the Cas endonuclease. The endonuclease can be introduced into a cell transiently or can be incorporated into the genome of the host cell using any method known in the art. Uptake of the endonuclease and/or the guided polynucleotide into the cell can be facilitated with a Cell Penetrating Peptide (CPP) as described in WO2016/073433, published May 12, 2016. Any promoter capable of expressing the Cas endonuclease variant herein in a cell can be used and includes a heat shock/heat inducible promoter operably linked to a nucleotide sequence encoding the Cas endonuclease.

Direct delivery of a polynucleotide modification template into cells can be achieved through particle mediated delivery, and any other direct method of delivery, such as but not limiting to, polyethylene glycol (PEG)-mediated transfection to protoplasts, whiskers mediated transformation, electroporation, particle bombardment, cell-penetrating peptides, or mesoporous silica nanoparticle (MSN)-mediated direct protein delivery can be successfully used for delivering a polynucleotide modification template in cells, such as eukaryotic cells.

The donor DNA can be introduced by any means known in the art. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of the Cas endonuclease and the target site, the donor DNA is inserted into the transformed genome of the organism, such as a plant.

Direct delivery of any one of the guided Cas system components described herein can be accompanied by direct delivery (co-delivery) of other mRNAs that can promote the enrichment and/or visualization of cells receiving the guide polynucleotide/Cas endonuclease complex components. For example, direct co-delivery of the guide polynucleotide/Cas endonuclease components (and/or guide polynucleotide/Cas endonuclease complex itself) together with mRNA encoding phenotypic markers (such as but not limiting to transcriptional activators such as CRC (Bruce et al. 2000 The Plant Cell 12:65-79) can enable the selection and enrichment of cells without the use of an exogenous selectable marker by restoring function to a non-functional gene product as described in WO2017/070029, published Apr. 27, 2017 and WO 2017/070032, published Apr. 27, 2017.

Introducing a guide RNA/Cas endonuclease complex (RGEN) as described herein into a cell includes introducing the guide RNA/Cas endonuclease complex as a ribonucleotide-protein into the cell. The ribonucleotide-protein can be assembled prior to being introduced into the cell as described herein. The components comprising the guide RNA/Cas endonuclease ribonucleotide protein can be assembled in vitro or assembles by any means known in the art prior to being introduced into a cell (targeted for genome modification as described herein).

Plants, fungal and bacterial cells differ from human and animal cells in that plant, fungal and bacterial cells contain a cell wall which may act as a barrier to the direct delivery of the RGEN ribonucleoproteins and/or of the direct delivery of the RGEN components.

Direct delivery of the RGEN ribonucleoproteins into plant, fungal and bacterial cells can be achieved through particle mediated delivery (particle bombardment. Based on the experiments described herein, a skilled artesian can now envision that any other direct method of delivery, such as but not limiting to, polyethylene glycol (PEG)-mediated transfection to protoplasts, electroporation, cell-penetrating peptides, or mesoporous silica nanoparticle (MSN)-mediated direct protein delivery, can be successfully used for delivering RGEN ribonucleoproteins into fungal and bacterial cells.

Direct delivery of the RGEN ribonucleoprotein, allows for genome editing at a target site in the genome of a cell which can be followed by rapid degradation of the complex, and only a transient presence of the complex in the cell. This transient presence of the RGEN complex may lead to reduced off-target effects. In contrast, delivery of RGEN components (guide RNA, Cas9 endonuclease) via plasmid DNA sequences can result in constant expression of RGENs from these plasmids which can intensify off target effects (Cradick, T. J. et al (2013) Nucleic Acids Res 41:9584-9592; Fu, Y et al (2014) Nat. Biotechnol. 31:822-826.

Direct delivery can be achieved by combining any one component of the guide RNA/Cas endonuclease complex (RGEN), described herein, (such as at least one guide RNA, at least one Cas9 endonuclease variant), with a particle delivery matrix comprising a microparticle such as but not limited to of a gold particle, tungsten particle, and silicon carbide whisker particle)(see also WO2017/070029, published Apr. 27, 2017 and WO 2017/070032, published Apr. 27, 2017, which are incorporated herein in their entirety by reference).

In one aspect the guide polynucleotide/Cas endonuclease complex (RGEN), is a complex wherein the guide RNA and Cas9 endonuclease variant described herein forming the guide RNA/Cas endonuclease complex are introduced into the cell as RNA and protein, respectively.

In one aspect the guide polynucleotide/Cas endonuclease complex, is a complex wherein the guide RNA and Cas9 endonuclease variant described herein forming the guide RNA/Cas endonuclease complex are preassembled in vitro and introduced into the cell as a ribonucleotide-protein complex.

Nucleic acids and proteins can be provided to a cell by any method including methods using molecules to facilitate the uptake of anyone or all components of a guided Cas system (protein and/or nucleic acids), such as cell-penetrating peptides and nanocariers (US20110035836, published Feb. 20, 2011), incorporated herein by reference.

Cells, Organisms

The presently disclosed Cas endonuclease variants, polynucleotides, peptides, guide polynucleotides, Cas endonucleases, polynucleotide modification templates, donor DNAs, guide polynucleotide/Cas endonuclease systems and any one combination thereof, can be introduced into a cell.

Cells include, but are not limited to, human, non-human, animal, bacterial, fungal, insect, yeast, non-conventional yeast, microbial, and plant cells as well as plants and seeds produced by the methods described herein.

Microbial cells employed in the methods and compositions disclosed herein may be any fungal host cells, filamentous fungal cells and bacterial cells. As used herein, the term "fungal cell", "fungi", "fungal host cell", and the like, as used herein includes the phyla Ascomycota, Basidiomycota, Chytridiomycota, and Zygomycota (as defined by Hawksworth et al., 1995), as well as the Oomycota (Hawksworth et al., 1995) and all mitosporic fungi (Hawksworth et al., 1995). In certain embodiments, the fungal host cell is a yeast cell, wherein the term "yeast" is meant ascosporogenous yeast (Endomycetales), basidiosporogenous yeast, and yeast belonging to the *Fungi imperfecti* (Blastomycetes). As such, a yeast host cell includes a *Candida, Hansenula, Kluyveromyces, Pichia, Saccharomyces, Schizosaccharomyces*, or *Yarrowia* cell. Species of yeast include, but are not limited to, *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis*, and *Yarrowia lipolytica.*

The term "non-conventional yeast" herein refers to any yeast that is not a *Saccharomyces* (e.g., *S. cerevisiae*) or *Schizosaccharomyces* yeast species. (see Non-Conventional Yeasts in Genetics, *Biochemistry and Biotechnology: Practical Protocols*" (K. Wolf, K. D. Breunig, G. Barth, Eds., Springer-Verlag, Berlin, Germany, 2003). Non-conventional yeast incudes member of a genus selected from the group consisting of *Yarrowia, Pichia, Schwanniomyces, Kluyveromyces, Arxula, Trichosporon, Candida, Ustilago, Torulopsis, Zygosaccharomyces, Trigonopsis, Cryptococcus, Rhodotorula, Phaffia, Sporobolomyces*, and *Pachysolen*. Non-conventional yeast includes yeast that favor non-homologous end-joining (NHEJ) DNA repair processes over repair processes mediated by homologous recombination (HR). Definition of a non-conventional yeast along these lines—preference of NHEJ over HR—is further disclosed by Chen et al. (PLoS ONE 8:e57952), which is incorporated herein by reference. The term "yeast" herein refers to fungal species that predominantly exist in unicellular form. Yeast can alternative be referred to as "yeast cells" herein. A suitable example of a *Yarrowia* species is *Y. lipolytica*. Suitable examples of *Pichia* species include *P. pastoris, P. methanolica, P. stipitis, P. anomala* and *P. angusta*. Suitable examples of *Schwanniomyces* species include *S. castellii, S. alluvius, S. hominis, S. occidentalis, S. capriottii, S. etchellsii, S. polymorphus, S. pseudopolymorphus, S. vanrijiae* and *S. yamadae*. Suitable examples of *Kluyveromyces* species include *K. lactis, K. marxianus, K. fragilis, K. drosophilarum, K. thermotolerans, K. phaseolosporus, K. vanudenii, K. waltii, K. africanus* and *K. polysporus*. Suitable examples of Arxula species include *A. adeninivorans* and *A. terrestre*. Suitable examples of *Trichosporon* species include *T. cutaneum, T. capitatum, T. inkin* and *T. beemeri*. Suitable examples of *Candida* species include *C. albicans, C. ascalaphidarum, C. amphixiae, C. antarctica, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogii, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis* and *C. zemplinina*. Suitable examples of *Ustilago* species include *U. avenae, U. esculenta, U. hordei, U. maydis, U. nuda* and *U. tritici*. Suitable examples of *Torulopsis* species include *T. geochares, T. azyma, T. glabrata* and *T. candida*. Suitable examples of *Zygosaccharomyces* species include *Z. bailii, Z. bisporus, Z. cidri, Z. fermentati, Z. florentinus, Z. kombuchaensis, Z. lentus, Z. mellis, Z. microellipsoides, Z. mrakii, Z. pseudorouxii* and *Z. rouxii*. Suitable examples of Trigonopsis species include *T. variabilis*. Suitable examples of *Cryptococcus* species include *C. laurentii, C. albidus, C. neoformans, C. gattii, C. uniguttulatus, C. adeliensis, C. aerius, C. albidosimilis, C. antarcticus, C. aquaticus, C. ater, C. bhutanensis, C. consortionis, C. curvatus, C. phenolicus, C. skinneri, C. terreus* and *C. vishniacci*. Suitable examples of *Rhodotorula* species include *R. acheniorum, R. tula, R. acuta, R. americana, R. araucariae, R. arctica, R. armeniaca, R. aurantiaca, R. auriculariae, R. bacarum, R. benthica, R. biourgei, R. bogoriensis, R. bronchialis, R. buffonii, R. calyptogenae, R. chungnamensis, R. cladiensis, R. corallina, R. cresolica, R. crocea, R. cycloclastica, R. dairenensis, R. diffluens, R. evergladiensis, R. ferulica, R. foliorum, R. fragaria, R. fujisanensis, R. futronensis, R. gelatinosa, R. glacialis, R. glutinis, R. gracilis, R. graminis, R. grinbergsii, R. himalayensis, R. hinnulea, R. histolytica, R. hylophila, R. incarnata, R. ingeniosa, R. javanica, R. koishikawensis, R. lactosa, R. lamellibrachiae, R. laryngis, R. lignophila, R. lini, R. longissima, R. ludwigii, R. lysinophila, R. marina, R. martyniae-fragantis, R. matritensis, R. meli, R. minuta, R. mucilaginosa, R. nitens, R. nothofagi, R. oryzae, R. pacifica, R. pallida, R. peneaus, R. philyla, R. phylloplana, R. pilatii, R. pilimanae, R. pinicola, R. plicata, R. polymorpha, R. psychrophenolica, R. psychrophila, R. pustula, R. retinophila, R. rosacea, R. rosulata, R. rubefaciens, R. rubella, R. rubescens, R. rubra, R. rubrorugosa, R. rufula, R. rutila, R. sanguinea, R. sanniei, R. sartoryi, R. silvestris, R. simplex, R. sinensis, R. slooffiae, R. sonckii, R. straminea, R. subericola, R. suganii, R. taiwanensis, R. taiwaniana, R. terpenoidalis, R. terrea, R. texensis, R. tokyoensis, R. ulzamae, R. vanillica, R. vuilleminii, R. yarrowii, R. yunnanensis* and *R. zsoltii*. Suitable examples of Phaffia species include *P. rhodozyma*. Suitable examples of Sporobolomyces species include *S. alborubescens, S. bannaensis, S. beijingensis, S. bischofiae, S. clavatus, S. coprosmae, S. coprosmicola, S. corallinus, S. dimmenae, S. dracophylli, S. elongatus, S. gracilis, S. inositophilus, S. johnsonii, S. koalae, S. magnisporus, S. novozealandicus, S. odorus, S. patagonicus, S. productus, S. roseus, S. sasicola, S. shiba-*

*tanus, S. singularis, S. subbrunneus, S. symmetricus, S. syzygii, S. taupoensis, S. tsugae, S. xanthus* and *S. yunnanensis*. Suitable examples of *Pachysolen* species include *P. tannophilus*.

As used herein, the term “filamentous fungal cell” includes all filamentous forms of the subdivision Eumycotina. Suitable cells of filamentous fungal genera include, but are not limited to, cells of *Acremonium, Aspergillus, Aureobasidium, Bjerkandera, Ceriporiopsis, Chrysoporium, Coprinus, Coriolus, Corynascus, Chaertomium, Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*.

Suitable cells of filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei*, and *Trichoderma viride*.

In certain embodiments, the microbial host cells are bacterial cells, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* or a *Streptomyces* such as, e.g., a *Streptomyces lividans* or *Streptomyces murinus* or a gram negative bacterium, such as, e.g., an *E. coli* or a *Pseudomonas* sp.

For the aforementioned species, it is understood that the disclosure and source species would encompass both the perfect and imperfect states of such organisms, and other taxonomic equivalents thereof, e.g., anamorphs, regardless of the species name by which they are known. Those skilled in the art will readily recognize the identity of appropriate equivalents of such source species.

Strains of the above-mentioned species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The Cas9 endonuclease variants described herein can be used in methods for homologous recombination in a microbial cell and/or in methods for genome editing in a microbial cell. Methods employing a guide RNA/Cas endonuclease system for inserting a donor DNA with one or more short homology arms at a target site in the genome of a microbial cell (e.g., a filamentous fungal cell) have been disclosed (WO2017/019867, published Feb. 2, 2017). When modification of the genome of the microbial cell results in a phenotypic effect, a donor DNA is often employed that includes a polynucleotide of interest that is (or encodes) a phenotypic marker. Any convenient phenotypic marker can be used, including any selectable or screenable marker that allows one to identify, or select for or against a fungal cell that contains it, often under particular culture conditions. Thus, in some aspects of the present disclosure, the identification of microbial cells having a desired genome modification includes culturing the microbial population of cells that have received the Cas9 endonuclease variant and guide polynucleotide (and optionally a donor DNA) under conditions to select for cells having the modification at the target site. Any type selection system may be employed, including assessing for the gain or loss of an enzymatic activity in the fungal cell (also referred to as a selectable marker), e.g., the acquisition of antibiotic resistance or gain/loss of an auxotrophic marker.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, by “grain” is intended the mature seed produced by commercial growers for purposes other than growing or reproducing the species. Progeny, variants, and mutants of the regenerated plants are also included within the scope of the disclosure, provided that these parts comprise genomic modifications of the regenerated plant such as those resulting from transformation or genome editing.

Any plant or plant part can be used, including monocot and dicot plants or plant parts.

Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum* species, *Triticum aestivum, Triticum monococcum*), sugarcane (*Saccharum* spp.), oats (*Avena*), barley (*Hordeum*), switchgrass (*Panicum virgatum*), pineapple (*Ananas comosus*), banana (Musa spp.), palm, ornamentals, turfgrasses, and other grasses.

The term “dicotyledonous” or “dicot” refers to the subclass of angiosperm plants also knows as “dicotyledoneae” and includes reference to whole plants, plant organs (e.g., leaves, stems, roots, etc.), seeds, plant cells, and progeny of the same. Examples of dicot plants that can be used include, but are not limited to, soybean (*Glycine max*), *Brassica* species (Canola) (*Brassica napus, B. campestris, Brassica rapa, Brassica. juncea*), alfalfa (*Medicago sativa*),), alfalfa (*Medicago sativa*), tobacco (*Nicotiana tabacum*), *Arabidopsis* (*Arabidopsis thaliana*), sunflower (*Helianthus annuus*), cotton (*Gossypium arboreum, Gossypium barbadense*), and peanut (*Arachis hypogaea*), tomato (*Solanum lycopersicum*), potato (*Solanum tuberosum.*

Plants that can be used include safflower (Carthamus tinctorius), sweet potato (*Ipomoea batatus*), cassava (*Manihot esculenta*), coffee (*Coffea* spp.), coconut (*Cocos nucifera*), citrus trees (*Citrus* spp.), cocoa (*Theobroma*

*cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), *hydrangea* (*Macrophylla hydrangea*), hibiscus (*Hibiscus rosasanensis*), roses (Rosa spp.), tulips (*Tulipa* spp.), daffodils (*Narcissus* spp.), petunias (*Petunia hybrida*), carnation (*Dianthus* caryophyllus), poinsettia (*Euphorbia pulcherrima*), and *chrysanthemum.*

Conifers that may be employed in practicing the present invention include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true first such as silver fir (*Abies amabilis*) and balsam fir (*Abies balsamea*); and cedars such as Western red cedar (*Thuja plicata*) and Alaska yellow cedar (*Chamaecyparis nootkatensis*).

The term "plant" includes whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

As used herein, the term "plant part" refers to plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, as well as the parts themselves. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

A fertile plant is a plant that produces viable male and female gametes and is self-fertile. Such a self-fertile plant can produce a progeny plant without the contribution from any other plant of a gamete and the genetic material contained therein.

Definitions

An "allele" or "allelic variant" is one of several alternative forms of a gene occupying a given locus on a chromosome. When all the alleles present at a given locus on a chromosome are the same, that organism is homozygous at that locus. If the alleles present at a given locus on a chromosome differ, that organism is heterozygous at that locus. An allelic variant of a polypeptide is a polypeptide encoded by an allelic variant of a gene.

"Coding sequence" refers to a polynucleotide sequence which codes for a specific amino acid sequence. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, promoters, translation leader sequences, 5' untranslated sequences, 3' untranslated sequences, introns, polyadenylation target sequences, RNA processing sites, effector binding sites, and stem-loop structures.

A "codon-modified gene" or "codon-preferred gene" or "codon-optimized gene" is a gene having its frequency of codon usage designed to mimic the frequency of preferred codon usage of the host cell. The nucleic acid changes made to codon-optimize a gene are "synonymous", meaning that they do not alter the amino acid sequence of the encoded polypeptide of the parent gene. However, both native and variant genes can be codon-optimized for a particular host cell, and as such no limitation in this regard is intended. Methods are available in the art for synthesizing codon-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a host organism. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given host organism (such as a plant), as calculated by reference to known genes expressed in the host cell. When possible, the sequence is modified to avoid one or more predicted hairpin secondary mRNA structures.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA and/or RNA-DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide (nucleotide (e.g., N can be A, C, T, or G, if referring to a DNA sequence; N can be A, C, U, or G, if referring to an RNA sequence).

The term "increased" as used herein may refer to a quantity or activity that is at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390,400, 410, 420, 430, 440, 440, 450, 460, 470, 480, 490, or 500 fold fold more than the quantity or activity for which the increased quantity or activity is being compared. The terms "increased", "greater than", and "improved" are used interchangeably herein. The term "increased" can be used to characterize the transformation or gene editing efficiency of a protein such as the Cas9 endonuclease variant described herein.

In one aspect the increase is an increase in transformation efficiency of a prokaryotic or eukaryotic cell when a Cas9 variant described herein, such as but not limiting to a Cas9 Y155 variant or a Cas9 F86A+F98A variant, is used as part of a PGEN when compared to the same PGEN but comprising its parent (wild type) Cas9 instead, wherein the increase in transformation efficiency is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390,400, 410, 420, 430, 440, 440, 450, 460, 470, 480, 490, or 500 fold In one aspect the increase is an increase in DNA editing efficiency of a prokaryotic or eukaryotic cell when a Cas9 variant described herein, such as but not limiting to a Cas9 Y155 variant or a Cas9 F86A+F98A variant, is used as part of a PGEN when compared to the same PGEN but comprising its parent (wild type) Cas9 instead, wherein the increase in gene editing efficiency is at least 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%.

"Open reading frame" is abbreviated ORF.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas protein system as disclosed herein. A mutated cell or organism is a cell or organism comprising a mutated gene.

The term "genome" as it applies to a prokaryotic and eukaryotic cell or organism cells encompasses not only chromosomal DNA found within the nucleus, but organelle DNA found within subcellular components (e.g., mitochondria, or plastid) of the cell.

Polynucleotides of interest are further described herein and include polynucleotides reflective of the commercial markets and interests of those involved in the production of enzymes (such as, but not limiting to, through fermentation of bacteria or fungi thereby producing the enzymes or by plants producing the enzymes) and development of the crops.

Crops and markets of interest change, and as developing nations open up world markets, new crops and technologies will emerge also. In addition, as our understanding of agronomic traits and characteristics such as yield and heterosis increase, the choice of genes for genetic engineering will change accordingly. Polynucleotides of interest include, but are not limited to, polynucleotides encoding important traits for agronomics, herbicide-resistance, insecticidal resistance, disease resistance, nematode resistance, herbicide resistance. microbial resistance, fungal resistance, viral resistance, fertility or sterility, grain characteristics, and commercial products.

General categories of polynucleotides of interest include, for example, genes of interest involved in information, such as zinc fingers, those involved in communication, such as kinases, and those involved in housekeeping, such as heat shock proteins. More specific polynucleotides of interest include, but are not limited to, genes involved in crop yield, grain quality, crop nutrient content, starch and carbohydrate quality and quantity as well as those affecting kernel size, sucrose loading, protein quality and quantity, nitrogen fixation and/or utilization, fatty acid and oil composition, genes encoding proteins conferring resistance to abiotic stress (such as drought, nitrogen, temperature, salinity, toxic metals or trace elements, or those conferring resistance to toxins such as pesticides and herbicides), genes encoding proteins conferring resistance to biotic stress (such as attacks by fungi, viruses, bacteria, insects, and nematodes, and development of diseases associated with these organisms).

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in organisms. Methods for suppressing gene expression in organisms using polynucleotides in the sense orientation are known in the art. The methods generally involve transforming an organism with a DNA construct comprising a promoter that drives expression in an organism operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as sulphonylureas, glufosinate ammonium, bromoxynil, imidazolinones, and 2,4-dichlorophenoxyacetate (2,4-D). See for example, Acetolactase synthase (ALS) for resistance to sulfonylureas, imidazolinones, triazolopyrimidine sulfonamides, pyrimidinylsalicylates and sulphonylaminocarbonyl-triazolinones Shaner and Singh, 1997, Herbicide Activity: Toxicol Biochem Mol Biol 69-110); glyphosate resistant 5-enolpyruvylshikimate-3-phosphate (EPSPS) (Saroha et al. 1998, J. Plant Biochemistry & Biotechnology Vol 7:65-72);

Polynucleotides of interest includes genes that can be stacked or used in combination with other traits, such as but not limited to herbicide resistance or any other trait described herein. Polynucleotides of interest and/or traits can be stacked together in a complex trait locus as described in US-2013-0263324-A1, published 3 Oct. 2013 and in PCT/US13/22891, published Jan. 24, 2013, both applications are hereby incorporated by reference.

A variety of methods are available for identifying those cells with insertion into the genome at or near to the target site. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference to the extent necessary for the methods described herein. The method also comprises recovering an organism from the cell comprising a polynucleotide of interest integrated into its genome.

A polypeptide of interest includes any protein or polypeptide that is encoded by a polynucleotide of interest described herein.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid sequences wherein changes in one or more amino acids or nucleotide bases do not affect the function of the molecule, such as the ability to mediate gene expression or to produce a certain phenotype. These terms also refer to modification(s) of nucleic acid sequences that do not substantially alter the functional properties of the resulting nucleic acid relative to the initial, unmodified nucleic acid. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

As used herein, the term "promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. As is well-known in the art, promoters can be categorized according to their strength and/or the conditions under which they are active, e.g., constitutive promoters, strong promoters, weak promoters, inducible/repressible promoters, tissue-specific/developmentally regulated promoters, cell-cycle dependent promoters, etc.

Examples of strong promoters useful herein include those disclosed in U.S. Patent Appl. Publ. Nos. 2012/0252079 (DGAT2), 2012/0252093 (EL1), 2013/0089910 (ALK2), 2013/0089911 (SPS19), 2006/0019297 (GPD and GPM), 2011/0059496 (GPD and GPM), 2005/0130280 (FBA, FBAIN, FBAINm), 2006/0057690 (GPAT) and 2010/0068789 (YAT1), which are incorporated herein by reference. Other examples of suitable strong promoters include those listed in Table 2 of WO2016/025131, published on Feb. 19, 2016, incorporated herein by reference.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, WI). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, WI). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) CAB/OS 5:151-153; Higgins et al., (1992) *Comput Appl Biosci* 8:189-191) and found in the MegAlign™ v6.1 program of the LASERGENE bioinformatics computing suite (DNASTAR Inc., Madison, WI). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, CA) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

As used herein, "RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre-mRNA. "Messenger RNA" or "mRNA" refers to the RNA that is without introns and that can be translated into protein by the cell. "cDNA" refers to a DNA that is complementary to, and synthesized from, an mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

As used herein, a "targeted mutation" is a mutation in a gene (referred to as the target gene), including a native gene, that was made by altering a target sequence within the target gene using any method known to one skilled in the art, including a method involving a guided Cas protein system. Where the Cas protein is a cas endonuclease, a guide polynucleotide/Cas endonuclease induced targeted mutation can occur in a nucleotide sequence that is located within or outside a genomic target site that is recognized and cleaved by the Cas endonuclease.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing target sites.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory or analysis. In some examples a recognition site and/or target site can be contained within an intron, coding sequence, 5' UTRs, 3' UTRs, and/or regulatory regions.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kb" means kilobase(s).

Non-Limiting Examples of Compositions and Methods Disclosed Herein are as Follows 1. A Cas9 endonuclease variant, or an active fragment thereof, having at least 80% amino acid identity to a parent Cas9 polypeptide set forth in SEQ ID NO: 1 and having at least one amino acid substitution at a position selected from the group consisting of position 86, position 98, position 155 and a combination thereof, wherein the amino acid positions of the variant are numbered by correspondence with the amino acid sequence of said parent Cas9 polypeptide, wherein said Cas9 endonuclease variant has endonuclease activity.
2. The Cas9 endonuclease variant of embodiment 1, wherein the at least one amino acid substitution is selected from the group consisting of Y155H, Y155N, Y155E, Y155F (at position 155), F86A (at position 86) and F98A (at position 98).
3. The Cas9 endonuclease variant of embodiment 1, wherein the Cas9 endonuclease variant has at least one improved property selected from the group consisting of improved transformation efficiency and improved editing efficiency, when compared to said parent Cas9 endonuclease.
4. The Cas9 endonuclease variant, or active fragment thereof, of any preceding embodiments, wherein said variant comprises an amino acid sequence having 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 1.
5. The Cas9 endonuclease variant of embodiment 3, wherein the improved property is improved transformation efficiency and wherein said variant, or active fragment thereof, has also an improved editing efficiency.
6. The Cas9 endonuclease variant, or active fragment thereof, of any preceding clams, comprising at least 1, 2, 3, 4, 5, 6, 7, 8, 9, 10 amino acid substitutions when compared to the parent Cas9 endonuclease.
7. A composition comprising the Cas9 endonuclease, or a functional fragment thereof, of any of the preceding embodiments.
8. The composition of embodiment 7, wherein said composition is selected from the group consisting of a guide polynucleotide/Cas9 endonuclease complex, a guide RNA/Cas9 endonuclease complex, and a fusion protein comprising said Cas9 endonuclease variant.
9. A polynucleotide comprising a nucleic acid sequence encoding the Cas9 endonuclease variant of any of the preceding embodiments.
10. A guide polynucleotide/Cas endonuclease complex (PGEN) comprising at least one guide polynucleotide and at least one Cas9 endonuclease variant of any one of embodiments 1-6, wherein said guide polynucleotide is a chimeric non-naturally occurring guide polynucleotide, wherein said guide polynucleotide/Cas endonuclease complex is capable of recognizing, binding to, and optionally nicking, unwinding, or cleaving all or part of a target sequence.
11. A recombinant DNA construct comprising the polynucleotide of embodiment 9.
12. A host cell comprising the Cas9 endonuclease, or functional fragment thereof, of any one of embodiments 1-6.
13. A host cell comprising the polynucleotide of embodiment 9.
14. The host cell of embodiment 13, wherein the cell is a prokaryotic cell or eukaryotic cell.
15. The host cell of embodiment 14, wherein the cell is selected from the group consisting of a human, non-human, animal, bacterial, fungal, insect, yeast, non-conventional yeast, and plant cell.

15b. A kit comprising the PGEN of embodiment 7.

15c. A delivery particle comprising the Cas9 endonuclease variant according to embodiments 1, 2, 3, 4, 5, or 6.

15d. The delivery particle of embodiment 15c, wherein the Cas9 endonuclease variant protein is complexed with a guide polynucleotide.

16. A method for modifying a target site in the genome of a cell, the method comprising introducing into a cell at least one PGEN of embodiment 10, and identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).
17. A method for editing a nucleotide sequence in the genome of a cell, the method comprising introducing into at least one PGEN of embodiment 10 and a polynucleotide modification template, wherein said polynucleotide modification template comprises at least one nucleotide modification of said nucleotide sequence.
18. The method of embodiment 17, further comprising selecting at least one cell that comprises the edited nucleotide sequence.
19. A method for modifying a target site in the genome of a cell, the method comprising introducing into a cell at least one PGEN of embodiment 10 and at least one donor DNA, wherein said donor DNA comprises a polynucleotide of interest.
20. The method of embodiment 19, further comprising identifying at least one cell that said polynucleotide of interest integrated in or near said target site.

21. The method of any one of embodiments 16-21, wherein the cell is selected from the group consisting of a human, non-human, animal, bacterial, fungal, insect, yeast, non-conventional yeast, and plant cell.
22. The methods of embodiments 16-21, wherein in the PGEN is introduced into the cell as a pre-assembled polynucleotide-protein complex.
23. The method of any one of embodiments 16-21, wherein the guide polynucleotide/Cas endonuclease is a guide RNA/Cas endonuclease.
24. The method of embodiment 22 wherein the guide RNA/Cas endonuclease complex is assembled in-vitro prior to being introduced into the cell as a ribonucleotide-protein complex.
25. A method for improving at least one property of a Cas9 endonuclease variant, said method comprising introducing at least one amino acid modification in a parent Cas9 endonuclease, wherein said at least one amino acid modification is located outside the RuVC and HNH domain of the parent Cas9 endonuclease, thereby creating said Cas9 endonuclease variant, wherein said Cas9 endonuclease variant shows an improvement in at least one property when compared to said parent Cas9 endonuclease.
26. The method of embodiment 25, wherein said at least one amino acid modification is an amino acid substitution at a position selected from the group consisting of position 86, position 98, position 155 and a combination thereof, wherein the amino acid positions of the variant are numbered by correspondence with the amino acid sequence of said parent Cas9 endonuclease.
27. The method of embodiment 26, wherein the at least one amino acid substitution is selected from the group consisting of Y155H, Y155N, Y155E, Y155F (at position 155), F86A (at position 86) and F98A (at position 98).
28. The method of embodiment 25, wherein the Cas9 endonuclease variant has at least one improved property selected from the group consisting of improved transformation efficiency and improved editing efficiency, when compared to said parent Cas9 endonuclease.
29. A cas9 endonuclease variant produced by the method of any of embodiments 24-27.
30. A method for modifying the genome of a *Bacillus* host cell, said method comprising
   providing to a *Bacillus* host cell comprising at least one target sequence to be modified, at least one non-naturally occurring guide RNA and at least one Cas9 endonuclease variant of any one of embodiments 1-6, wherein the guide RNA and Cas9 endonuclease variant are capable of forming a complex (PGEN), wherein said complex is capable of recognizing, binding to, and optionally nicking, unwinding, or cleaving all or part of said at least one target sequence; and,
   identifying at least one *Bacillus* host cell, wherein the at least one genome target sequence has been modified.
31. The method of 30, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).
32. The method of 29, wherein the *Bacillus* host cell is selected from the group of *Bacillus* species consisting of *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis.*
33. A method for modifying the genome of an *E. coli* host cell, said method comprising
   providing to an *E. coli* host cell comprising at least one target sequence to be modified, at least one non-naturally occurring guide RNA and at least one Cas9 endonuclease variant of any one of embodiments 1-6, wherein the guide RNA and Cas9 endonuclease variant are capable of forming a complex (PGEN), wherein said complex is capable of recognizing, binding to, and optionally nicking, unwinding, or cleaving all or part of said at least one target sequence; and,
   identifying at least one *E. coli* host cell, wherein the at least one genome target sequence has been modified.
34. A method for modifying the genome of a *Saccharomyces cerevisiae* host cell, said method comprising
   providing to a *Saccharomyces cerevisiae* host cell comprising at least one target sequence to be modified, at least one non-naturally occurring guide RNA and at least one Cas9 endonuclease variant of any one of embodiments 1-6, wherein the guide RNA and Cas9 endonuclease variant are capable of forming a complex (PGEN), wherein said complex is capable of recognizing, binding to, and optionally nicking, unwinding, or cleaving all or part of said at least one target sequence; and,
   identifying at least one *Saccharomyces cerevisiae* host cell, wherein the at least one genome target sequence has been modified.
35. A method for modifying the genome of a fungal host cell, said method comprising
   providing to a fungal host cell comprising at least one target sequence to be modified, at least one non-naturally occurring guide RNA and at least one Cas9 endonuclease variant of any one of embodiments 1-6, wherein the guide RNA and Cas9 endonuclease variant are capable of forming a complex (PGEN), wherein said complex is capable of recognizing, binding to, and optionally nicking, unwinding, or cleaving all or part of said at least one target sequence; and,
   identifying at least one fungal host cell, wherein the at least one genome target sequence has been modified.
36. A Cas9 endonuclease variant for the modification of a target site in a cell, said Cas9 endonuclease variant comprising an amino acid modification outside its HNH domain and RuVC domain, wherein said Cas9 endonuclease has at least one improved property, when compared to a parent Cas9 endonuclease that does not comprises said amino acid modification, wherein Cas9 endonuclease variant can form a complex with a said guide polynucleotide wherein said complex is capable of recognizing, binding to, and optionally nicking, unwinding, or cleaving all or part of said target sequence.
37. The Cas9 endonuclease variant of embodiment 34, wherein the Cas9 endonuclease variant has at least one improved property selected from the group consisting of improved transformation efficiency, improved fold transformation, improved editing efficiency and improved fold editing, when compared to said parent Cas9 endonuclease.

38. A method for modifying an organism or a non-human organism by increasing editing efficiency by using a Cas9 endonuclease variant for the modification of a target site in a genomic locus of interest in a cell, said method comprising providing a non-naturally occurring guide polynucleotide and a Cas9 endonuclease variant to said cell, wherein said Cas9 endonuclease variant comprises an amino acid modification outside its HNH and RuvC domain, wherein said Cas9 endonuclease has increased gene editing efficiency when compared to a parent Cas9 endonuclease that does not comprises said amino acid modification, wherein said guide polynucleotide and Cas9 endonuclease variant can form a complex capable of recognizing, binding to, and optionally nicking, unwinding, or cleaving all or part of said target sequence.

39. A method of expressing a Cas endonuclease variant in a prokaryotic or eukaryotic cell, the method comprising:

(a) introducing into a prokaryotic or eukaryotic cell a recombinant DNA construct of embodiment 11; and, (b) incubating the a prokaryotic or eukaryotic cell of step (a) under conditions permitting expression of said Cas endonuclease variant.

38. A Cas9 endonuclease variant selected from the group of consisting of SEQ ID NO: 58 (CasY155H variant), SEQ ID NO: 123 (CasY155N variant), SEQ ID NO: 125 (Cas9 Y155E variant), SEQ ID NO: 127 (Cas9 Y155F variant), SEQ ID NO: 129 (Cas9 F86A-F98A variant).

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1

Construction of Cas9 Expression Cassettes Targeting Target Site 1 and Target Site 2 in *Bacillus*

The Cas9 protein from *Streptococcus pyogenes* (SEQ ID NO: 1) was codon optimized for expression in *Bacillus* (SEQ ID NO: 2) and with the addition of an N-terminal nuclear localization sequence (NLS; "APKKKRKV"; SEQ ID NO: 3), a C-terminal NLS ("KKKKLK"; SEQ ID NO: 4), a deca-histidine tag ("HHHHHHHHHH"; SEQ ID NO: 5), the aprE promoter from *B. subtilis* (SEQ ID NO: 6) and a terminator sequence (SEQ ID NO: 7) and was amplified using Q5 DNA polymerase (NEB) per manufacturer's instructions with the forward/reverse primer pair set forth below in Table 1.

TABLE 1

| Forward and reverse primer pair | | |
|---|---|---|
| Forward | ATATATGAGTAAACTTGGTCTGACAGAATTCCTCCATTTTCTTCTGCTAT | SEQ ID NO: 8 |
| Reverse | TGCGGCCGCGAATTCGATTACGAATGCCGTCTCCC | SEQ ID NO: 9 |

The backbone (SEQ ID NO: 10) of plasmid pKB320 (SEQ ID NO: 11) was amplified using Q5 DNA polymerase (NEB) per manufacturer's instructions with the forward/reverse primer pair set forth below in Table 2.

TABLE 2

| Forward and reverse primer pair | | |
|---|---|---|
| Forward | *GGGAGACGGCATTCGTAATCGAATTCGCGGCCGCA* | SEQ ID NO: 12 |
| Reverse | ATAGCAGAAGAAAATGGAGGAATTCTGTCAGACCAAGTTTACTCATATAT | SEQ ID NO: 13 |

The PCR products were purified using Zymo clean and concentrate 5 columns per manufacturer's instructions. Subsequently, the PCR products were assembled using prolonged overlap extension PCR (POE-PCR) with Q5 Polymerase (NEB) mixing the two fragments at equimolar ratio. The POE-PCR reactions were cycled: 98° C. for five (5) seconds, 64° C. for ten (10) seconds, 72° C. for four (4) minutes and fifteen (15) seconds for 30 cycles. Five (5) μl of the POE-PCR (DNA) was transformed into Top10 *E. coli* (Invitrogen) per manufacturer's instructions and selected on lysogeny (L) Broth (Miller recipe; 1% (w/v) Tryptone, 0.5% Yeast extract (w/v), 1% NaCl (w/v)), containing fifty (50) μg/ml kanamycin sulfate and solidified with 1.5% Agar. Colonies were allowed to grow for eighteen (18) hours at 37° C. Colonies were picked and plasmid DNA prepared using Qiaprep DNA miniprep kit per manufacturer's instructions and eluted in fifty-five (55) μl of $ddH_2O$. The plasmid DNA was Sanger sequenced to verify correct assembly, using the sequencing primers set forth below in Table 3.

TABLE 3

| Sequencing primers | | |
|---|---|---|
| Reverse | CCGACTGGAGCTCCTATATTACC | SEQ ID NO: 14 |
| Forward | GTCTTTTAAGTAAGTCTACTCT | SEQ ID NO: 16 |
| Forward | CCAAAGCGATTTTAAGCGCG | SEQ ID NO: 17 |
| Forward | CCTGGCACGTGGTAATTCTC | SEQ ID NO: 18 |
| Forward | GGATTTCCTCAAATCTGACG | SEQ ID NO: 19 |
| Forward | GTAGAAACGCGCCAAATTACG | SEQ ID NO: 20 |
| Forward | GCTGGTGGTTGCTAAAGTCG | SEQ ID NO: 21 |
| Forward | GGACGCAACCCTCATTCATC | SEQ ID NO: 22 |
| Reverse | CAGGCATCCGATTTGCAAGG | SEQ ID NO: 23 |
| Forward | GCAAGCAGCAGATTACGCG | SEQ ID NO: 24 |

The correctly assembled plasmid, pRF694 (SEQ ID NO: 25) was used to construct plasmids pRF801 (SEQ ID NO: 26) and pRF806 (SEQ ID NO: 27) for editing the *Bacillus*

*licheniformis* genome at target site 1 (SEQ ID NO: 28) and target site 2 (SEQ ID NO: 29) as described below.

The serA1 open reading frame (SEQ ID NO: 30) of *B. licheniformis* contains a unique target site, target site 1 (SEQ ID NO: 28) in the reverse orientation. The target site lies adjacent to a protospacer adjacent motif (SEQ ID NO: 31) in the reverse orientation. The target site can be converted into the DNA encoding a variable targeting domain (SEQ ID NO: 32). The DNA sequence encoding the VT domain (SEQ ID NO: 32) is operably fused to the DNA sequence encoding the Cas9 endonuclease recognition domain (CER, SEQ ID NO: 33) such that when transcribed by RNA polymerase of the bacterial cell it produces a functional gRNA targeting target site 1 (SEQ ID NO: 34). The DNA encoding the gRNA was operably linked to a promoter operable in *Bacillus* sp. cells (e.g., the spac promoter; SEQ ID NO: 35) and a terminator operable in *Bacillus* sp. cells (e.g., the t0 terminator of phage lambda; SEQ ID NO: 36), such that the promoter was positioned 5' of the DNA encoding the gRNA (SEQ ID NO: 33) and the terminator is positioned 3' of the DNA encoding the gRNA (SEQ ID NO: 33).

A polynucleotide modification template (also referred to as an editing template) to delete the serA1 gene in response to Cas9/gRNA cleavage was created by amplification of two homology arms from *B. licheniformis* genomic DNA (gDNA). The first fragment corresponds to the 500 bp directly upstream of the serA1 open reading frame (SEQ ID NO: 37). This fragment was amplified using Q5 DNA polymerase per the manufacturer's instructions and the primers listed in Table 4 below. The primers incorporate 18 bp homologous to the 5' end of the second fragment on the 3' end of the first fragment and 20 bp homologous to pRF694 to the 5' end of first fragment.

TABLE 4

Forward and reverse primer pair.

| | | |
|---|---|---|
| Forward | TGAGTAAACTTGGTCTGACAAATGGTTCTTTCCCCTGTCC | SEQ ID NO: 38 |
| Reverse | AGGTTCCGCAGCTTCTGTGTAAGATTTCCTCCTAAATAAGCGTCAT | SEQ ID NO: 39 |

The second fragment corresponds to the 500 bp directly downstream of the 3' end of the serA1 open reading frame (SEQ ID NO: 40). This fragment was amplified using Q5 DNA polymerase per manufacturer's instructions and the primers listed in Table 5 below. The primers incorporate 28 bp homologus to the 3' end of the first fragment on the 5' end of the second fragment and 21 bp homologous to pRF694 on the 3' end of the second fragment.

TABLE 5

Forward and reverse primer pair.

| | | |
|---|---|---|
| Forward | ATGACGCTTATTTAGGAGGAAATCTTACACAGAAGCTGCGGAACCT | SEQ ID NO: 41 |
| Reverse | CAGAAGAAAATGGAGGAATTCGAATATCGACCGGAACCCAC | SEQ ID NO: 42 |

The DNA encoding the target site 1 gRNA expression cassette (SEQ ID NO: 43), the first (SEQ ID NO: 37) and second homology arms (SEQ ID NO: 40) were assembled into pRF694 (SEQ ID NO: 25) using standard molecular biology techniques generating pRF801 (SEQ ID NO: 26), an *E. coli-B. licheniformis* shuttle plasmid containing a Cas9 expression cassette (SEQ ID NO: 2), a gRNA expression cassette (SEQ ID NO: 43) encoding a gRNA targeting target site 1 within the serA1 open-reading frame and an editing template (SEQ ID NO: 44) composed of the first (SEQ ID NO: 37) and second (SEQ ID NO: 40) homology arms. The plasmid was verified by Sanger sequencing with the oligos set forth in Table 3.

The rghR1 open reading frame of *B. licheniformis* (SEQ ID NO: 45) contains a unique target site on the reverse strand, target site 2 (SEQ ID NO: 46). The target site lies adjacent to a protospacer adjacent motif (last three basis of SEQ ID NO: 47) on the reverse strand. The target site can be converted into the DNA encoding a variable targeting (VT) domain (SEQ ID NO: 48) of a guide RNA. The DNA sequence encoding the VT domain (SEQ ID NO: 48) is operably fused to the DNA sequence encoding the Cas9 endonuclease recognition domain (CER, SEQ ID NO: 33) such that when transcribed by RNA polymerase of the bacterial cell it produces a functional guideRNA (gRNA) targeting target site 2 (SEQ ID NO: 49). The DNA encoding the gRNA was operably linked to a promoter operable in *Bacillus* sp. cells (e.g., the spac promoter from *B. cutilis*; SEQ ID NO: 35) and a terminator operable in *Bacillus* sp. cells (e.g., the t0 terminator of phage lambda; SEQ ID NO: 36), such that the promoter was positioned 5' of the DNA encoding the gRNA (SEQ ID NO: 43) and the terminator is positioned 3' of the DNA encoding the gRNA (SEQ ID NO: 43).

A polynucleotide modification template (also referred to as an editing template) to modify the rghR1 gene in response to Cas9/gRNA cleavage was created by amplification of two homology arms from *B. licheniformis* genomic DNA (gDNA). The first fragment corresponds to the 500 bp directly upstream of the rghR1 open reading frame (SEQ ID NO: 50). This fragment was amplified using Q5 DNA polymerase per the manufacturer's instructions and the primers listed in Table 6 below. The primers incorporate 23 bp homologous to the 5' end of the second fragment on the 3' end of the first fragment and 20 bp homologous to pRF694 to the 5' end of first fragment.

TABLE 6

Forward and reverse primer pair.

| | | |
|---|---|---|
| Forward | TGAGTAAACTTGGTCTGACATTGATATTCAGCACCCTGCG | SEQ ID NO: 51 |
| Reverse | TGTGCCGCGGAGAAGTATGGCCAAAACCTCGCAATCTC | SEQ ID NO: 52 |

The second fragment corresponds to the 500 bp directly downstream of the 3' end of the rghR1 open reading frame (SEQ ID NO: 53). This fragment was amplified using Q5 DNA polymerase per manufacturer's instructions and the primers listed in Table 7 below. The primers incorporate 20 bp homologous to the 3' end of the first fragment on the 5' end of the second fragment and 21 bp homologous to pRF694 on the 3' end of the second fragment.

TABLE 7

| Forward and reverse primer pair. | | |
|---|---|---|
| Forward | GAGATTGCGAGGTTTTGGCCATACTTCTCCGCGGCACA | SEQ ID NO: 54 |
| Reverse | CAGAAGAAAATGGAGGAATTCATTTCTCGGGTTTAAACAGCCAC | SEQ ID NO: 55 |

The DNA encoding the target site 2 gRNA expression cassette (SEQ ID NO: 56), the first (SEQ ID NO: 50) and second homology arms (SEQ ID NO: 53) were assembled into pRF694 (SEQ ID NO: 25) using standard molecular biology techniques generating pRF806 (SEQ ID NO: 27), an *E. coli-B. licheniformis* shuttle plasmid containing a Cas9 expression cassette (SEQ ID NO: 2), a gRNA expression cassette (SEQ ID NO: 56) encoding a gRNA targeting target site 2 within the rghR1 open-reading frame and an editing template (SEQ ID NO: 57) composed of the first (SEQ ID NO: 50) and second (SEQ ID NO: 53) homology arms. The plasmid was verified by sanger sequence with the oligos set forth in Table 3.

Example 2

Creation of Cas9 Y155 Variants

In the present example, the Y155H variant of *S. pyogenes* Cas9 (referred to as Cas9 Y155H variant, herein, SEQ ID NO: 58) was created in the pRF801 (SEQ ID NO: 26) and pRF806 plasmids (SEQ ID NO: 27). To introduce the Cas9 Y155H variant in the pRF801 plasmid (SEQ ID NO: 26) or the pRF806 plasmid (SEQ ID NO: 27) site-directed mutagenesis was performed using Quikchange mutagenesis kit per the manufacturer's instructions and the oligos in Table 8 below using pRF801 (SEQ ID NO: 26) or pRF806 (SEQ ID NO: 27) as template DNA.

TABLE 8

| Forward and reverse primer pair. | | |
|---|---|---|
| Forward | GATCTGCGTTTAATCCATCTTGCGTTAGCGCAC | SEQ ID NO: 59 |
| Reverse | GTGCGCTAACGCAAGATGGATTAAACGCAGATC | SEQ ID NO: 60 |

The resultant products of the reaction, pRF827 (SEQ ID NO: 61) contained a Cas9 Y155H variant expression cassette (SEQ ID NO: 62), a gRNA expression cassette (SEQ ID NO: 43) encoding a gRNA targeting target site 1 within the serA1 open-reading frame and an editing template (SEQ ID NO: 44) composed of the first (SEQ ID NO: 37) and second (SEQ ID NO: 40) homology arms or pRF856 (SEQ ID NO: 63) which contained a Cas9 Y155H variant expression cassette (SEQ ID NO: 62), a gRNA expression cassette (SEQ ID NO: 56) targeting target site 2 within the rghR1 open reading frame and an editing template (SEQ ID NO: 57) composed of the first (SEQ ID NO: 50) and second (SEQ ID NO: 53) homology arms. The plasmid DNAs were Sanger sequenced to verify correct assembly, using the sequencing primers set forth in Table 3.

Other Cas9 Y155 variants were created in a similar matter as described above. A Cas9 Y155N variant was created and is set forth in SEQ ID NO: 123 (amino acid sequence encoded by SEQ ID NO: 124), a Cas9 Y155E variant was created and is set forth in SEQ ID NO: 125 (amino acid sequence encoded by SEQ ID NO: 126), a Cas9 Y155F variant was created and is set forth in SEQ ID NO: 127 (amino acid sequence encoded by SEQ ID NO: 128).

Example 3

Y155H Variant of *Streptococcus pyogenes* Cas9 (Cas9 Y155H Variant) has Increased Transformation Efficiency and Equal or Increased DNA Editing Efficiency in *Bacillus* Cells Compared to Wild Type *Streptococcus pyogenes* Cas9 (WT Cas9)

In the present example, the pRF694 (SEQ ID NO: 25), pRF801 (SEQ ID NO: 26), pRF806 (SEQ ID NO: 27), pRF827 (SEQ ID NO: 61), and pRF856 (SEQ ID NO: 63) plasmids described above were amplified using rolling circle amplification (Sygnis) for 18 hours according to manufacturer's instructions. The rolling circle amplified plasmids were transformed into competent (parental) *B. licheniformis* cells comprising (harboring) a pBL.comK plasmid (SEQ ID NO: 64) as generally described in International PCR publication Nos. WO2017/075195, WO2002/14490 and WO2008/7989. Cell/DNA transformation mixes were plated onto L-broth (Miller recipe) containing 20 μg/ml of kanamycin and solidified with 1.5% Agar. Colonies were allowed to form at 37° C. Colonies that grew on the L agar plates containing kanamycin were picked and streaked on L agar plates to recover. Colonies from transformations with pRF801 (SEQ ID NO: 26) and pRF827 (SEQ ID NO: 61) were screened for editing by Amplifying the target site 1 locus (SEQ ID NO: 65) using Q5 DNA polymerase according to the manufacturer's instructions and the forward/reverse primer pair set forth below in Table 9. The WT and edited target site 1 locus in *Bacillus* cells can be differentiated based on the size of the amplified locus with the WT amplicon (SEQ ID NO: 65) being larger in size than the edited amplicon (SEQ ID NO: 66).

TABLE 9

| Forward and reverse primer pair. | | |
|---|---|---|
| Forward | TAGAGACGAGACGTCTCACC | SEQ ID NO: 67 |
| Reverse | GTATCAATCCGACTCCTACGG | SEQ ID NO: 68 |

Colonies from the transformation with plasmids pRF806 (SEQ ID NO: 27) or pRF856 (SEQ ID NO: 63) were analyzed for editing efficiency by amplifying the target site 2 locus (SEQ ID NO: 69) using Q5 DNA polymerase according to the manufacturer's instructions and the forward/reverse primer pair set forth below in Table 10. The WT (SEQ ID NO: 69) and edited target site 2 locus (SEQ ID NO: 70) can be differentiated based on the size of the edited locus (SEQ ID NO: 70) with the WT amplicon (SEQ ID NO: 69) being larger in size.

TABLE 10

| Forward and reverse primer pair. | | |
|---|---|---|
| Forward | ATCAAACATGCCATGTTTGC | SEQ ID NO: 71 |
| Reverse | AGGTTGAGCAGGTCTTCG | SEQ ID NO: 72 |

The number of transformants obtained on medium selective for the plasmid (L agar containing 20 $\mu g \cdot ml^{-1}$ kanamycin sulfate) is displayed in Table 11. The transformation efficiency is the ratio of the number of transformants obtained from a given Cas9 variant with a specific gRNA and editing template by the number of transformants from the parent (WT) Cas9 with the same gRNA expression cassette and editing template. The results are displayed in Table 11 demonstrating that the Cas9 Y155H variant increased the transformation efficiency of Cas9 variants (delivered by plasmids) by at least 84 to -402 fold.

TABLE 11

Transformation efficiency and editing frequency at *B. licheniformis* targets.

| Cas9 | Target site | Transformants | Transformation Efficiency (Variant or WT/WT) | Editing Frequency | Editing Efficiency (Variant or WT/WT) |
|---|---|---|---|---|---|
| WT | Site 1 | 1 | 1 | 1.00 | 1.0 |
| Y155H | Site 1 | 402 | 402 | 1.00 | 1.0 |
| WT | Site 2 | 3 | 1 | 0.33 | 1.0 |
| Y155H | Site 2 | 84 | 28 | 0.75 | 2.3 |

The results shown in Table 11 demonstrate that the Cas9 Y155H Variant had an editing efficiency that is at least equal to or at least 2.3 fold (or 230%) greater than the DNA editing efficiency of the WT Cas9.

Example 4

Construction of Cas9 F86A-F98A Variant

In the present example a Cas9 F86A-F98A variant (SEQ ID NO: 129) was constructed in the backbone of the pRF801 plasmid (SEQ ID NO: 26) in order to test the Cas9 F86A-F98A variant for transformation efficiency and editing frequency in *B. licheniformis.*

A synthetic fragment containing a portion of Cas9 including F86A and F98A (SEQ ID NO: 130) was ordered from an external vendor. The backbone of pRF801 (SEQ ID NO: 131) was amplified using the oligos set forth in Table 12 using standard PCR techniques.

TABLE 12

| Forward and reverse primer pair. | | |
|---|---|---|
| Forward | AAAGAAAAATGGTCTGTTTG | SEQ ID NO: 132 |
| Reverse | AATACGATTTTTACGACGTG | SEQ ID NO: 133 |

The synthetic fragment (SEQ ID NO: 130) was amplified using oligos set forth in Table 13 below using standard PCR techniques.

TABLE 13

| Forward and reverse primer pair. | | |
|---|---|---|
| Forward | AAAGAAAAATGGTCTGTTTG | SEQ ID NO: 134 |
| Reverse | AATACGATTTTTACGACGTG | SEQ ID NO: 135 |

The pRF801 backbone fragment (SEQ ID NO: 131) was assembled with the F86A-F98A synthetic fragment using standard molecular biology techniques to create plasmid pRF866 (SEQ ID NO: 137). pRF866 contains the F86A F98A Cas9 expression cassette for *Bacillus* (SEQ ID NO: 136), the DNA encoding the expression cassette for the gRNA targeting serA1 ts1 (SEQ ID NO: 43), and the serA1 deletion editing template (SEQ ID NO: 44).

The plasmid pRF866 was transformed into *B. licheniformis* cells.

Example 5

A Cas9 Variant of *Streptococcus pyogenes* Comprising a First Amino Acid Substitution at F86 and a Second Amino Acid Substitution at F98 has Increased Transformation Efficiency and Equal DNA Editing Efficiency in *Bacillus* Cells Compared to its Parent (Wild Type) *Streptococcus Pyogenes* Cas9 (WT Cas9).

A Cas9 variant (referred to as Cas9 F86-F98 variant) of *Streptococcus pyogenes* comprising a first amino acid substitution at F86 (such as F86A) and a second amino acid substitution at F98 (such as F98A), wherein the amino acid positions of the variant are numbered by correspondence with the amino acid sequence of the parent Cas9 polypeptide set forth in SEQ ID NO 1 (*Streptococcus pyogenes* WT Cas9) was created as described in Example 4. The transformation efficiency and editing efficiency were analyzed as described in Example 3 and shown in Table 14.

TABLE 14

Transformation efficiency and editing frequency at a *B. licheniformis* targets using a Cas9 F86-F98 variant.

| Cas9 | Target site | Transformants | Transformation Efficiency (ratio variant or WT/WT) | Editing Frequency | Editing efficiency (ratio variant or WT/WT) |
|---|---|---|---|---|---|
| WT | Site 1 | 1 | 1 | 1.0 | 1.0 |
| F86A F98A | Site 1 | 248 | 248 | 1.0 | 1.0 |

Table 14 clearly shows that the Cas9 F86-F98A variant increased the transformation efficiency 248 fold (or 24,800%) when compared to the WT Cas9. Colonies transformed with editing plasmids were screened as described in Example 3 for editing efficiency by determining the percentage of screened colonies containing the desired edit. The results shown in Table 14 demonstrate that the Cas9 F86A-F98A variant had an editing efficiency equal to that of the WT Cas9.

Example 6

Construction of an *Escherichia coli* Cas9 Vector

In the present example an inducible Cas9 expression vector for genome editing in *Escherichia coli* (*E. coli*) was constructed. Cas9 expression in response to an inducer was confirmed.

The Cas9 protein from *Streptococcus pyogenes* M1 GAS SF370 (SEQ ID NO: 1) was codon optimized per standard techniques known in the art (SEQ ID NO: 73). In order to localize the Cas9 protein to the nucleus of the cells, Simian virus 40 (SV40) monopartite (MAPKKKRKV, SEQ ID NO: 74) nuclear localization signal was incorporated at the carboxy terminus of the Cas9 open reading frame. The *Yarrowia* codon optimized Cas9 gene was fused to a *Yarrowia* constitutive promoter, FBA1 (SEQ ID NO: 75), by standard molecular biology techniques. An example of a *Yarrowia* codon optimized Cas9 expression cassette (SEQ ID NO: 76) containing the constitutive FBA promoter, *Yarrowia* codon optimized Cas9, and the SV40 nuclear localization signal. The Cas9 expression cassette was cloned into the plasmid pZuf and the new construct called pZufCas9 (SEQ ID NO: 77).

The *Yarrowia* codon optimized Cas9-SV40 fusion gene (SEQ ID NO: 78) was amplified from pZufCas9 using standard molecular biology techniques using the primers from Table 15 below.

TABLE 15

| Forward and reverse primer pair. | | |
|---|---|---|
| Forward | GGGGGAATTCGACAAGAAATACTCCATCGGCCTGG | SEQ ID NO: 79 |
| Reverse | CCCCAAGCTTAGCGGCCGCTTAGACCTTTCG | SEQ ID NO: 80 |

The primers in Table 12 added a 5' EcoRI site and a 3' HindIII site to the fusion. The PCR product (SEQ ID NO: 81) was purified using standard techniques. The purified fragment was cloned into the EcoRI and HindIII sites of pBAD/HisB from life technologies (SEQ ID NO: 82) to create pRF48 (SEQ ID NO: 83).

The *E. coli* Cas9 expression cassette (SEQ ID NO: 84) was inserted into a low copy plasmid pKO3 (SEQ ID NO: 85) to create pRF97 (SEQ ID NO: 86) a low copy *E. coli* plasmid containing a Cas9 expression cassette.

Example 7

Creating the Cas9 Y155H Variant in the *E. coli* Cas9 Plasmid

In the present example the Cas9 Y155H variant was introduced into the Cas9 protein encoded on pRF97 (SEQ ID NO: 86).

A synthetic DNA fragment encoding a portion of the Cas9 protein from pRF97 but containing substitutions encoding the Y155H variant (SEQ ID NO: 87) was produced. The synthetic fragment was amplified using standard PCR conditions and the primers listed in Table 16.

TABLE 16

| Forward and reverse primer pair. | | |
|---|---|---|
| Forward | CTCCAGTCGTCTGCTCTTCG | SEQ ID NO: 88 |
| Reverse | CCAACGAGATGGCCAAGGTG | SEQ ID NO: 89 |

The pRF97 plasmid (SEQ ID NO: 86) was amplified to accept insertion of the Y155H synthetic fragment (SEQ ID NO: 87) using standard PCR techniques and the primers listed below in Table 17 to produce the pRF97-Y155H fragment (SEQ ID NO: 90).

TABLE 17

| Forward and reverse primer pair. | | |
|---|---|---|
| Forward | CACCTTGGCCATCTCGTTGG | SEQ ID NO: 91 |
| Reverse | CGAAGAGCAGACGACTGGAG | SEQ ID NO: 92 |

The Y155H synthetic fragment (SEQ ID NO: 87) and the pRF97-Y155H fragment (SEQ ID NO: 90) were combined to create pRF861 (SEQ ID NO: 93) a low copy plasmid containing an *E. coli* expression cassette for the Cas9 Y155H variant.

Example 8

Deletion of the Nitrogen Assimilation Control Gene of *E. coli* Using a WT Cas9 and a Cas9 Y155H Variant In the present example, the nac gene encoding the nitrogen assimilation control gene of *E. coli* was deleted using either the WT Cas9 or the Cas9 Y155H variant.

The *E. coli* nac gene (SEQ ID NO: 94) contains two target sites; target site 1 (SEQ ID NO: 95) and PAM (last three bases of SEQ ID NO: 96), and target site 2 (SEQ ID NO: 97) and PAM (last three bases of SEQ ID NO: 98). As described in example 1 by adding the DNA encoding the CER domain (SEQ ID NO: 33) to the 3' end of the DNA encoding the target site operably fusing a promoter active in *E. coli* (e.g. The N25 phage promoter (SEQ ID NO: 99)) to the 5' end of the target site and a terminator active in *E. coli* (eg. the lambda phage t0 terminator (SEQ ID NO: 36) to the 3' end of the CER domain an operable gRNA expression cassette can be made for nac site 1 (SEQ ID NO: 100) and nac site 2 (SEQ ID NO: 101). *E. coli* mainly repairs DNA via homology directed repair and for efficiency Cas9 mediated editing requires and editing template.

The 491 bp upstream of the nac start codon and the first three codons (SEQ ID NO: 102) was operably linked to the 491 bp downstream of the nac stop codon and the last three codons of the nac open reading frame (SEQ ID NO: 103) to create an editing template that deletes all but the first three and last three codons of the nac open reading frame (SEQ ID NO: 104).

The site 1 gRNA expression cassette (SEQ ID NO: 100) or the site 2 gRNA expression cassette (SEQ ID NO: 102) was operably linked to the nac deletion editing template (SEQ ID NO: 104) and with 20 bp of identity to pRF97 (SEQ ID NO: 86) and pRF861 (SEQ ID NO: 93) on the 5' end (SEQ ID NO: 105) and 21 bp of identity (SEQ ID NO: 106) to pRF97 (SEQ ID NO: 86) and pRF861 (SEQ ID NO: 93) on the 3' end and ordered as nacETsite1 (SEQ ID NO: 107) and nacETsite2 (SEQ ID NO: 108) synthetic DNA fragments.

pRF97 (SEQ ID NO: 86) or pRF861 (SEQ ID NO: 93) were amplified using standard molecular biology techniques and the primers listed in Table 18 below to create linear fragments pRF97-cassette (SEQ ID NO: 109) or pRF861-cassette (SEQ ID NO: 110).

TABLE 18

| Forward and reverse primer pair. | | |
|---|---|---|
| Forward | GGTTTATTGACTACCGGAAGC | SEQ ID NO: 111 |
| Reverse | GCCGTCAATTGTCTGATTCG | SEQ ID NO: 112 |

The pRF97-cassette (SEQ ID NO: 109) or the pRF861-cassette (SEQ ID NO: 110) was assembled with either the nacETsite1 (SEQ ID NO: 107) or nacETsite1 (SEQ ID NO: 108) using standard molecular biology techniques to create pRF97/nacETsite1 (SEQ ID NO:113), pRF97/nacETsite2 (SEQ ID NO: 114), pRF861/nacETsite1 (SEQ ID NO: 115), and pRF861/nacETsite2 (SEQ ID NO: 116).

MG1655 *E. coli* cells were made electrocompetent as described previously (Short protocols in molecular biology) and transformed with 1 μl of pRF97/nacETsite1 (SEQ ID NO:113), pRF97/nacETsite2 (SEQ ID NO: 114), pRF861/nacETsite1 (SEQ ID NO: 115), or pRF861/nacETsite2 (SEQ ID NO: 116). Cells were plated on L broth solidified with 1.5% $w \cdot v^{-1}$ agar containing 25 $\mu g \cdot ml^{-1}$ chloramphenicol and 0.1% $w \cdot v^{-1}$ L-arabinose (to induce Cas9 expression). Colonies from the transformation were counted after 24 hours of growth at 30° C.

To determine if a colony contained an edited allele up to 8 colonies from each transformation were screened by PCR for the presence of the WT nac locus (SEQ ID NO: 117) or the edited nac locus (SEQ ID NO: 118) by PCR amplification using standard techniques and the primers in Table 19 below.

TABLE 19

| Forward and reverse primer pair. | | |
|---|---|---|
| Forward | GGTTTATTGACTACCGGAAGC | SEQ ID NO: 119 |
| Reverse | GCCGTCAATTGTCTGATTCG | SEQ ID NO: 120 |

Colonies which gave amplification products corresponding to the edited nac locus (SEQ ID NO: 118) which is smaller than the WT nac locus (SEQ ID NO: 117) were counted as edited for the calculation of editing frequency. The editing frequency is the percentage of screened cells that demonstrated the presence of the edited nac locus (SEQ ID NO 118) from PCR. The results in Table 20 show the editing frequency and the transformation efficiency (Transformants/transformants WT Cas9).

TABLE 20

Transformation efficiency and editing frequency of WT Cas9 and Y155H Cas9 in *E. coli*

| Cas9 | Target site | Transformants | Transformation Efficiency | Editing Frequency | Editing Efficiency |
|---|---|---|---|---|---|
| WT | Site 1 | 4 | 1.0 | 75 | 1.00 |
| Y155H | Site 1 | 13 | 3.3 | 86 | 1.15 |
| WT | Site 2 | 11 | 1.0 | 63 | 1.00 |
| Y155H | Site 2 | 8 | 0.7 | 100 | 1.59 |

Table 20 clearly demonstrates the Cas9 Y155H variant is operable in *E. coli* and does show an increase in editing efficiency of at least 15% to 59% when compared to the WTCas9 editing frequency.

Example 9

Construction of Cas9-gRNA Vectors for Editing the *Saccharomyces cerevisiae* Chromosomal URA3 Gene Deletion In order to test the transformation and editing efficiencies of Cas9 Y155H variant vs Cas9 wild type (wt) for editing *Saccharomyces cerevisiae* chromosomal URA3 gene deletion, Cas9 Y155H-gRNA and Cas9 wt-gRNA expressing plasmids with a G-418 resistance gene (KanMX) as a selection marker are made as described below.

Fragment A (Cas9 wt) containing a synthetic polynucleotide encoding the Cas9 wild type protein from *S. pyogenes* (SEQ ID NO: 1), comprising an N-terminal nuclear localization sequence (NLS; "APKKKRKV"; SEQ ID NO: 3), a C-terminal NLS ("KKKKLK"; SEQ ID NO: 4) and a deca-histidine tag ("HHHHHHHHHH"; SEQ ID NO: 5), is amplified from pRF694 plasmid (SEQ ID NO: 25) using Q5 DNA polymerase (NEB) per manufacturer's instructions with the forward/reverse primer pair set forth below in Table 21. Fragment A' (Cas9 Y115H) containing a synthetic polynucleotide encoding the Cas9 Y115H variant (SEQ ID NO: 58), comprising an N-terminal nuclear localization sequence, a C-terminal NLS and a deca-histidine tag, is amplified from pRF827 plasmid (SEQ ID NO: 61) using Q5 DNA polymerase (NEB) per manufacturer's instructions with the forward (SEQ ID NO: 138)/reverse (SEQ ID NO: 138) primer pair set forth below in Table 21.

TABLE 21

| Forward and reverse primer pair. | | |
|---|---|---|
| Forward | AAAAGAAATATATAGAGAGATACTCTTATCAATGATGGTGATGAT GATGGTGATG | SEQ ID NO: 138 |
| Reverse | ACACGTATTTATTTGTCCAATTACCATGGCCCCAAAAAAGAAACG CAAGGTTATGGAT | SEQ ID NO: 139 |

Fragment B containing the RNR2p promoter (SEQ ID NO: 140), 2-micron replication origin 1 (SEQ ID NO: 141), KanMX expression cassette (SEQ ID NO: 142), and SNR52p promoter (SEQ ID NO: 143), is amplified from pSE087 plasmid (SEQ ID NO: 144) using Q5 DNA polymerase (NEB) per manufacturer's instructions with the forward (SEQ ID NO: 145)/reverse (SEQ ID NO: 146) primer pair set forth below in Table 22.

TABLE 22

| Forward and reverse primer pair. | | |
|---|---|---|
| Forward | CTCCGCAGTGAAAGATAAATGATCGCCCAAAATTTGTTTACTAAAAAC ACATGTGGA | SEQ ID NO: 145 |
| Reverse | GAATTGGGTACCGGGCCCTTAGAGTAAAAAATTGTACTTGGCGGATAA TGCCTTTAGC | SEQ ID NO: 146 |

The pSE087 plasmid is a 2µ shuttle vector with a heterologous KanMX expression cassette. The plasmid contains the cas9 gene from *S. pyogenes* under the control of the RNR2 promoter, the SNR52 promoter upstream of stuffer fragment containing the targeting sgRNA+T(6) terminator (SEQ ID NO: 147). The sgRNA is flanked by BsmBI binding sites that are oriented such that the linearization of the plasmid by BsmBI releases the sgRNA stuffer leaving incompatible overhangs on the digested plasmid.

Fragment C containing a synthetic polynucleotide of the 50 bp upstream homology arm (SEQ ID NO: 148), URA3 targeting sgRNA+T(6) terminator (SEQ ID NO: 149), and 50 bp downstream (SEQ ID NO: 150), is amplified using Q5 DNA polymerase (NEB) per manufacturer's instructions with the forward (SEQ ID NO: 151)/reverse (SEQ ID NO: 152) primer pair set forth below in Table 23.

TABLE 23

| Forward and reverse primer pair. | | |
|---|---|---|
| Forward | CCGCCAAGTACAATTTTTTACTCTAAGGGCCCGGTACCCAATTCGCC CTATAGTGAG | SEQ ID NO: 151 |
| Reverse | CATCATCACCATCATTGATAAGAGTATCTCTCTATATATTTCTTTTTACG CAGTCTC | SEQ ID NO: 152 |

Fragment D containing the 2-micron replication origin 2 (SEQ ID NO: 153), ampicillin resistant gene (SEQ ID NO: 154) and RNR2 terminator (SEQ ID NO: 155), is amplified from pSE087 plasmid using Q5 DNA polymerase (NEB) per manufacturer's instructions with the forward (SEQ ID NO: 156)/reverse (SEQ ID NO: 157) primer pair set forth below in Table 24.

TABLE 24

| Forward and reverse primer pair. | | |
|---|---|---|
| Forward | **CCTTGCGTTTCTTTTTTGGGGCCATGGTAATTGGACAAATAAATACG TGTATTAAG** | SEQ ID NO: 156 |
| Reverse | **TGTTTTTAGTAAACAAATTTTGGGCGATCATTTATCTTTCACTGCGGAG AAGTTTC** | SEQ ID NO: 157 |

The PCR fragments are purified using the Qiagen PCR purification kit (QIAGEN, Inc) per manufacturer's instructions. Subsequently, the PCR fragments are assembled on the 2-micron plasmid backbone by gap repair in yeast according to below protocol.

*S. cerevisiae* ura3Δ competent cells are prepared by using Frozen-EZ Yeast Transformation II™ kit (Zymo Research, Inc) per manufacturer's instructions. The 50 µl of *S. cerevisiae* ura3Δ competent cells are mixed with 0.1-0.2 µg DNA of each PCR product of the fragment A, B, C, and D to create pWS572 (Cas9 wt). The 50 µl of *S. cerevisiae* ura3Δ competent cells are mixed with 0.1-0.2 µg DNA of each PCR product of the fragment A', B, C, and D to create pWS573 (Cas9 Y115H). The 500 µl EZ 3 solution that is provided from the kit is added and mixed thoroughly. After incubating the mixture at 30° C. for 45 minutes, 50-150 µl of the transformation mixture spreads on the YPD medium plate supplemented with 200 ug/ml Geneticin (G418) antibiotic. The plates incubated at 30° C. for 2-4 days to allow for growth of transformants.

The resulting plasmids of pWS572 (Cas9 wt) and pWS573 (Cas9 Y155H) are prepared from 1 ml of the transformants grown in the YPD medium supplemented with 200 ug/ml Geneticin (G418) antibiotic by using the ChargeSwitch® Plasmid Yeast Mini kit (Invitrogen, Inc).

Example 10

*Saccharomyces cerevisiae* Chromosomal Ura3 Gene Deletion by Using PWS572 (CAS9 WT) and PWS573 (CAS9 Y155H)

In this example, the transformation and editing efficiencies of pWS573 (Cas9 Y155H) vs pWS572 (Cas9 wt) for *Saccharomyces cerevisiae* chromosomal URA3 gene deletion are compared. *S. cerevisiae* wild type competent cells are prepared by using Frozen-EZ Yeast Transformation II™ kit (Zymo Research, Inc) per manufacturer's instructions, and transformed with 100 ng plasmid DNA of pWS573 (Cas9 Y155H) and pWS572 (Cas9 wt), separately. 50-150 μl of the transformation mixture spreads on the YPD medium plate supplemented with 200 ug/ml Geneticin (G418) antibiotic. The plates incubated at 30° C. for 2-4 days to allow for growth of transformants. The correct ura3A colonies are screened for uracil auxotroph by streaking transformants on the synthetic complete media (1× yeast nitrogen base without amino acids, 1× amino acid mix lacking uracil) supplemented with 2 g/L glucose and incubating cells at 30° C. for 2-4 days to allow for growth of transformants. The deletion of the URA3 gene is confirmed by PCR and sequencing with flanking primers of the URA3 target region. The editing frequency for each plasmid is determined by dividing the number of ura3A colonies by the total number of tested colonies.

What is claimed is:

1. A method for modifying a target site in the genome of a cell, the method comprising introducing into a cell at least one guide polynucleotide/Cas endonuclease complex (PGEN) comprising at least one guide polynucleotide and at least one CRISPR-associated endonuclease (Cas9) variant or an active fragment thereof, having at least 85% amino acid identity to a parent Cas9 polypeptide set forth in SEQ ID NO: 1 and having at least one amino acid substitution at a position selected from the group consisting of position 86, position 98, position 155 and a combination thereof, wherein the amino acid positions of the variant are numbered by correspondence with the amino acid sequence of said parent Cas9 polypeptide, wherein said Cas9 endonuclease variant has endonuclease activity, wherein said guide polynucleotide is a chimeric non-naturally occurring guide polynucleotide, wherein said PGEN is capable of recognizing, binding to, and optionally nicking, unwinding, or cleaving a target sequence, and identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

2. A method for modifying a target site in the genome of a cell, the method comprising introducing into a cell at least one guide polynucleotide/Cas endonuclease complex (PGEN) comprising at least one guide polynucleotide and at least one CRISPR-associated endonuclease (Cas9) variant or an active fragment thereof, having at least 80% amino acid identity to a parent Cas9 polypeptide set forth in SEQ ID NO: 1 and having at least one amino acid substitution at a position selected from the group consisting of position 86, position 98, position 155 and a combination thereof, wherein the amino acid positions of the variant are numbered by correspondence with the amino acid sequence of said parent Cas9 polypeptide, wherein said Cas9 endonuclease variant has endonuclease activity, wherein said guide polynucleotide is a chimeric non-naturally occurring guide polynucleotide, wherein said PGEN is capable of recognizing, binding to, and optionally nicking, unwinding, or cleaving all or part of a target sequence and at least one donor DNA, wherein said donor DNA comprises a polynucleotide of interest.

3. The method of claim 2, further comprising identifying at least one cell that said polynucleotide of interest integrated in or near said target site.

4. The method of claim 1 or claim 2, wherein the cell is selected from the group consisting of a human, non-human, animal, bacterial, fungal, insect, yeast, non-conventional yeast, and plant cell.

5. The method of claim 1 or claim 2, wherein in the PGEN is introduced into the cell as a pre-assembled polynucleotide-protein complex.

6. The method of claim 1 or claim 2, wherein the guide polynucleotide/Cas endonuclease is a guide RNA/Cas endonuclease.

7. The method of claim 6 wherein the guide RNA/Cas endonuclease complex is assembled in-vitro prior to being introduced into the cell as a ribonucleotide-protein complex.

8. The method of claim 1 or claim 2, wherein the cell is a *Bacillus* or an *E. coli* cell.

9. The method of claim 8, wherein the *Bacillus* host cell is selected from the group of *Bacillus* species consisting of *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis*.

* * * * *